US008188246B2

(12) United States Patent
Lollar

(10) Patent No.: US 8,188,246 B2
(45) Date of Patent: *May 29, 2012

(54) NUCLEIC ACID AND AMINO ACID SEQUENCES ENCODING HIGH-LEVEL EXPRESSOR FACTOR VIII POLYPEPTIDES AND METHODS OF USE

(75) Inventor: John S. Lollar, Decatur, GA (US)

(73) Assignee: Expression Therapeutics LLC, Tucker, GA (US)

( * ) Notice: Subject to any disclaimer, the term of this patent is extended or adjusted under 35 U.S.C. 154(b) by 254 days.

This patent is subject to a terminal disclaimer.

(21) Appl. No.: 12/636,424

(22) Filed: Dec. 11, 2009

(65) Prior Publication Data
US 2011/0077203 A1 Mar. 31, 2011

Related U.S. Application Data

(60) Division of application No. 10/813,507, filed on Mar. 30, 2004, now Pat. No. 7,635,763, which is a continuation of application No. PCT/US02/33403, filed on Oct. 7, 2002.

(60) Provisional application No. 60/327,388, filed on Oct. 5, 2001.

(51) Int. Cl.
C07H 21/02 (2006.01)
C07H 21/04 (2006.01)
C12Q 1/68 (2006.01)
C12P 19/34 (2006.01)

(52) U.S. Cl. .................. 536/23.1; 536/24.3; 536/24.33; 435/6; 435/91.1; 435/325; 435/375

(58) Field of Classification Search .................. 536/23.1, 536/24.3, 24.33; 435/6, 91.1, 325, 375
See application file for complete search history.

(56) References Cited

U.S. PATENT DOCUMENTS

| 5,364,771 | A | 11/1994 | Lollar et al. |
| 5,583,209 | A | 12/1996 | Lollar et al. |
| 5,663,060 | A | 9/1997 | Lollar et al. |
| 5,744,446 | A | 4/1998 | Lollar et al. |
| 5,859,204 | A | 1/1999 | Lollar |

(Continued)

FOREIGN PATENT DOCUMENTS
WO    WO 00/71141 A1    11/2000

(Continued)

OTHER PUBLICATIONS

Hemostasis, Thrombosis, and Vascular Biology; "Reduction of the Antigenicity of Factor VIII Toward Complex Inhibitory Antibody Plasmas Using Multiply-Substituted Hybrid Human/Porcine Factor VIII Molecules"; Rachel T. Barrow, John F. Healey, David Gailani, Dorothea Scandella, and Pete Lollar; 2000 by The American Society of Hematology: Blood. Jan. 15, 2000—vol. 95, No. 2.

(Continued)

Primary Examiner — Terra Cotta Gibbs
(74) Attorney, Agent, or Firm — Heather N. Schafer

(57) ABSTRACT

Methods and compositions are provided that allow for high-level expression of a factor VIII polypeptide. More specifically, methods and compositions are provided comprising nucleic acid and amino acid sequences comprising a modified factor VIII that result in high-level expression of the polypeptide. The methods and compositions of the invention find use in the treatment of factor VIII deficiency including, for example, hemophilia A.

11 Claims, 33 Drawing Sheets

```
                        A1 DOMAIN
              HUMAN    1 AIRRYYLGAV ELSWDYMQSD LG-ELPVDAR FPPRVPKSFP FNTSVVYKKT
              PIG        AIRRYYLGAV ELSWDYRQSE LLRELHVDTR FPATAPGALP LGPSVLYKKT
              MOUSE      AIRRYYLGAV ELSWNYIQSD LLSVLHTDSR FLPRMSTSFP FNTSIMYKKT
                         ********** ****  **    *   *   **    *      *  ****

50 LFVEFTDHLF NIAKPRPPWM GLLGPTIQAE VYDTVVITLK NMASHPVSLH
                        VFVEFTDQLF SVARPRPPWM GLLGPTIQAE VYDTVVITLK NMASHPVSLH
                        VFVEYKDQLF NIAKPRPPWM GLLGPTIWTE VHDTVVITLK NMASHPVSLH
                        ***  * **   * ****** *******   * ****  *** **********

100 AVGVSYWKAS EGAEYDDQTS QREKEDDKVF PGGSHTYVWQ VLKENGPMAS
                        AVGVSFWKSS EGAEYEDHTS CREKEDDKVL PGKSQTYVWQ VLKENGPTAS
                        AVGVSYWKAS EGDEYEDQTS CMEKEDDKVF PGESHTYVWQ VLKENGPMAS
                        *****  **  ** **** *  * *******  ** *****  ******* **

SIGNAL PEPTIDE                              150 DPLCLTYSYL SHVDLVKDLN SGLIGALLVC REGSLAKEKT QTLHKPILLF
      HUMAN  -19 MQIELSTCFF LCLLRFCFS             DPPCLTYSYL SHVDLVKDLN SGLIGALLVC RBGSLTRERT QNLHEFVLLF
      PIG        MQLELSTCVF LCLLPLGFS             DPPCLTYSYM SHVDLVKDLN SGLIGALLVC KEGSLSKERT QMLYQFVLLF
      MOUSE      MQIALFACFP LSLFNFCSS             ********** ********** **********    ** **    *  ****
                 **   * ** **  *

200 AVFDEGKSWH SETKNSLMQD RDAASARAWP KMHTVNGYVN RSLPGLIGCH
                                                     AVFDEGKSWH SARNDSWTRA MDPAPARAQP AMHTVNGYVN RSLPGLIGCH
                                                     AVFDEGKSWH SETNDSYTQS MDSASARDWP KMHTVNGYVN RSLPGLIGCH
                                                     **********  *  *     *  * ** * *  ******** **********

250 RKSVYWHVIG MGTTPEVHSI FLEGHTFLVR NHRQASLEIS PITFLTAQTL
                                                     KKSVYWHVIG MGTSPEVHSI FLEGHTFLVR HHRQASLEIS PLTFLTAQTF
                                                     RKSVYWHVIG MGTTPEIHSI FLEGHTPFVR NHRQASLEIS PITFLTAQTL
                                                     *********  *** ** *** ******* ** *********   *******

APC/IXa
                                                 300 LMDLGQPLLF CHISSHQHDG MEAYVKVDSC PEEPQLRMKN NEEABDYDDD
                                                     LMDLGQPLLF CHISSHHHGG MEAHRVESC AEEPQLRRKA DE-EEDYDDN
                                                     LIDLGQPLLF CHISSHKHDG MEAYVKVDSC PEESQWQKKN NN-EEMEDYD
                                                     * ********  ******  * *  *  *   ***   **     *  *  *

IIa/Xa
                                                 350 LTDSEMDVVR FDDDNSPSFI QIR
                                                     LYDSDMDVVR LDGDDVSPFI QIR
                                                     DDLYSEMDMF TLDYDSSPFI QIR
                                                                   **  ***
```

U.S. PATENT DOCUMENTS

| | | | |
|---|---|---|---|
| 5,888,974 | A | 3/1999 | Lollar et al. |
| 5,935,935 | A | 8/1999 | Connelly et al. |
| 6,180,371 | B1 | 1/2001 | Lollar |
| 6,200,560 | B1 | 3/2001 | Couto et al. |
| 6,376,463 | B1 | 4/2002 | Lollar |
| 6,458,563 | B1 | 10/2002 | Lollar |
| 6,642,028 | B1 | 11/2003 | Ill et al. |
| 6,818,439 | B1 | 11/2004 | Jolly et al. |

FOREIGN PATENT DOCUMENTS

| | | |
|---|---|---|
| WO | WO 01/68109 A1 | 9/2001 |

OTHER PUBLICATIONS

The Journal of Biological Chemistry: "*High Level Expression of Recombinant Porcine Coagulation Factor VIII*"; Christopher B. Doering, John F. Healey, Ernest T. Parker, Rachel T. Barrow, and Pete Lollar: From the Winship Cancer Institute, Emory University, Atlanta, Georgia: 2002 by The American Society for Biochemistry and Molecular Biology, Inc.; vol. 277, No. 41, Issue of Oct. 11, pp. 38345-38349, 2002.

Doering, C.B., et al., "High Level Expression of Recombinant Porcine Coagulation Factor VIII," *The Journal of Biological Chemistry*. 2002, pp. 38345-38349, vol. 277, No. 41, The American Society for Biochemistry and Molecular Biology, Inc., USA.

Funk, W.D., et al., "Expression of the Amino-Terminal Half-Molecule of Human Serum Transferrin in Cultured Cells and Characterization of Recombinant Protein," *Biochemistry*, 1990, pp. 1654-1660, vol. 29, No. 6.

Healey, J.F., et al., "Residues Glu2181-Val2243 Contain a Major Determinant of the Inhibitory Epitope in the C2 Domain of Human Factor VIII," *Blood*, 1998, pp. 3701-3709, vol. 92, No. 10.

Healey, J.F., et al., "Residues 484-508 Contain a Major Determinant of the Inhibitory Epitope in the A2 Domain of Human Factor VIII," *The Journal of Biological Chemistry*, 1995, pp. 14505-14509, vol. 270, No. 24.

Kaufman, R.I., et at, "Biosynthesis, Assembly and Secretion of Coagulation Factor VIII," *Blood Coagulation and Fibrinolysis*, 1997, pp. S3-S14, vol. 8 (Suppl 2), Rapid science Publishers.

Lind, P., et al., "Novel Forms of B-Domain-Deleted Recombinant Factor VIII Molecules Construction and Biochemical Characterization," *Eur J. Biochem.*, 1995, pp. 19-27, vol. 232.

Lollar, P., "Mapping factor VIII Inhibitor Epitopes Using Hybrid Human/Porcine Factor VIII Molecules," *Haematologica*, 2000, pp. 26-30, vol. 85 (Suppl. to n. 10).

Lubin, I.M., et al., "Elimination of a Major Inhibitor Epitope in Factor VIII," *The Journal of Biological Chemistry*, 1994, pp. 8639-8641, vol. 269, No. 12, The American Society for Biochemistry and Molecular Biology, Inc., USA.

Prescott, R., et al., "The Inhibitor Antibody Response is More Complex in Hemophilia A Patients Than in Most Nonhemophiliacs with Factor VIII Autoantibodies," *Blood*, 1997, pp. 3663-3671, vol. 89, No. 10.

Vehar, G.A., et al., "Structure of Human Factor VIII," *Nature*, 1984, pp. 337-342, vol. 312.

Zhong, D., et al., "Some Human Inhibitor Antibodies Interfere with Factor VIII Binding to Factor IX," 1998, pp. 136-142, vol. 92, No. 1.

Barrow, R.T., et at, "Antigenicity of Putative Phospholipid Membrane-Binding Residues in Factor VIII," *Blood*, 2001, pp. 169-174, vol. 97 No. 1.

Barrow, R.T., et at, "Reduction of the Antigenicity of Factor VIII Toward Complex Inhibitory Antibody Plasmas Using Multiply-Substituted Hybrid Human/Porcine Factor VIII Molecules," *Blood*, 2000, pp. 564-568, vol. 95, No. 2.

Bowie, E.J., and C.A. Owen, "The Clinical and Laboratory Diagnosis of Hemorrhagic Disorders," *Grune & Stratton, Inc.*, Orlando, 1984, pp. 43-72.

Chang, J., el al., "Changing Residue 338 in Human Factor IX from Arginine to Alanine Causes an Increase in Catalytic Activity," *The Journal of Biological Chemistry*, 1998, pp. 12089-12094, vol. 273, No. 20, The American Society for Biochemistry and Molecular Biology, Inc., USA.

```
SIGNAL PEPTIDE
HUMAN   -19  MQIELSTCFF  LCLLRFCFS
PIG          MQLELSTCVF  LCLLPLGFS
MOUSE        MQIALFACFF  LSLFNFCSS
             **  *  * * * *        *
```

FIG. 1A

```
A1 DOMAIN
HUMAN    1  ATRRYYLGAV  ELSWDYMQSD  LG-ELPVDAR  PPPRVPKSFP  FNTSVVYKKT
PIG         AIRRYYLGAV  ELSWDYRQSE  LLRELHVDTR  PPATAPGALP  LGPSVLYKKT
MOUSE       AIRRYYLGAV  ELSWNYIQSD  LLSVLHTDSR  FLPRMSTSFP  FNTSIMYKKT
            **********  ****  * **     *   * *        *      *  ****

50  LFVEFTDHLF  NIAKPRPPWM  GLLGPTIQAE  VYDTVVITLK  NMASHPVSLH
            VFVEFTDQLF  SVARPRPPWM  GLLGPTIQAE  VYDTVVVTLK  NMASHPVSLH
            VFVEYKDQLF  NIAKPRPPWM  GLLGPTIWTE  VHDTVVITLK  NMASHPVSLH
            ***   * **    * ******  *******     * **** ***  **********

100  AVGVSYWKAS  EGAEYDDQTS  QREKEDDKVF  PGGSHTYVWQ  VLKENGPMAS
            AVGVSFWKSS  EGAEYEDHTS  CREKEDDKVL  PGKSQTYVWQ  VLKENGPTAS
            AVGVSYWKAS  EGDEYEDQTS  QMEKEDDKVF  PGESHTYVWQ  VLKENGPMAS
            *****  **  *   ** ****  **  *******  **  * *****  ****** **

150  DPLCLTYSYL  SHVDLVKDLN  SGLIGALLVC  REGSLAKEKT  QTLHKFILLF
            DPPCLTYSYL  SHVDLVKDLN  SGLIGALLVC  REGSLTRERT  QNLHEFVLLF
            DPPCLTYSYM  SHVDLVKDLN  SGLIGALLVC  KEGSLSKERT  QMLYQFVLLF
            ** ******   **********  **********  ****   *  *   *  * ***

200  AVFDEGKSWH  SETKNSLMQD  RDAASARAWP  KMHTVNGYVN  RSLPGLIGCH
            AVFDEGKSWH  SARNDSWTRA  MDPAPARAQP  AMHTVNGYVN  RSLPGLIGCH
            AVFDEGKSWH  SETNDSYTQS  MDSASARDWP  KMHTVNGYVN  RSLPGLIGCH
            **********   *     *     *  **  *   *********  **********

250  RKSVYWHVIG  MGTTPEVHSI  FLEGHTFLVR  NHRQASLEIS  PITFLTAQTL
            KKSVYWHVIG  MGTSPEVHSI  FLEGHTFLVR  HHRQASLEIS  PLTFLTAQTF
            RKSVYWHVIG  MGTTPEIHSI  FLEGHTFFVR  NHRQASLEIS  PITFLTAQTL
             *********  *** ** ***  *******  **  *********  *********
                                                       APC/IXa       ♦
       300  LMDLGQFLLF  CHISSHQHDG  MEAYVKVDSC  PEEPQLRMKN  NEEAEDYDDD
            LMDLGQFLLF  CHISSHHHGG  MEAHVRVESC  AEEPQLRRKA  DE-EEDYDDN
            LIDLGQFLLF  CHISSHKHDG  MEAYVKVDSC  PEESQWQKKN  NN-EEMEDYD
            * ********  ******  * *  ***  *  **  **  *   *   *    *
                                    IIa/Xa
       350  LTDSEMDVVR  FDDDNSPSFI  QIR
            LYDSDMDVVR  LDGDDVSPFI  QIR
            DDLYSEMDMF  TLDYDSSPFI  QIR
                            **    ***
```

FIG. 1B

```
A2 DOMAIN
HUMAN  373  SVAKKHPKTW  VHYIAAEEED  WDYAPLVLAP  DDRSYKSQYL  NNGPQRIGRK
PIG         SVAKKHPKTW  VHYISAEEED  WDYAPAVPSP  SDRSYKSLYL  NSGPQRIGRK
MOUSE       SVAKKYPKTW  IHYISAEEED  WDYAPSVPTS  DNGSYKSQYL  SNGPHRIGRK
            ***** ****  *** *****   ***** *        **** **    ** *****

423  YKKVRFMAYT  DETFKTREAI  QHESGILGPL  LYGEVGDTLL  IIFKNQASRP
            YKKARFVAYT  DVTFKTRKAI  PYESGILGPL  LYGEVGDTLL  IIFKNKASRP
            YKKVRFIAYT  DETFKTRETI  QHESGILGPL  LYGEVGDTLL  IIFKNQASRP
            *** ** ***  * *****  *  *** ****   **********  ***** ****
                                   A2 INHIBITOR EPITOPE
       473  YNIYPHGITD  VRPLYSRRLP  KGVKHLKDFP  ILPGEIFKYK  WTVTVEDGPT
            YNIYPHGITD  VSALHPGRLL  KGWKHLKDMP  ILPGETFKYK  WTVTVEDGPT
            YNIYPHGITD  VSPLHARRLP  RGIKHVKDLP  IHFGEIFKYK  WTVTVEDGPT
            **********  *    *  **  ** ** ** *  * *** ****  **********
                                              F.IXa BINDING
                                           APC
       523  KSDPRCLTRY  YSSFVNMERD  LASGLIGPLL  ICYKESVDQR  GNQIMSDKRN
            KSDPRCLTRY  YSSSINLEKD  LASGLIGPLL  ICYKESVDQR  GNQMMSDKRN
            KSDPRCLTRY  YSSFINPERD  LASGLIGPLL  ICYKESVDQR  GNQMMSDKRN
            **********  ***   *  *  **********  **********  *** ******

573  VILFSVFDEN  RSWYLTENIQ  RFLPNPAGVQ  LEDPEFQASN  IMHSINGYVF
            VILFSVFDEN  QSWYLAENIQ  RFLPNPDGLQ  PQDPEFQASN  IMHSINGYVF
            VILFSIFDEN  QSWYITENMQ  RFLPNAAKTQ  PQDPGFQASN  IMHSINGYVF
            ***** ****  ***   ** *  *****    *   *  * ****  **********

623  DSLQLSVCLH  EVAYWYILSI  GAQTDFLSVF  FSGYTFKHKM  VYEDTLTLFP
            DSLQLSVCLH  EVAYWYILSV  GAQTDFLSVF  FSGYTFKHKM  VYEDTLTLFP
            DSLELTVCLH  EVAYWHILSV  GAQTDFLSIF  FSGYTFKHKM  VYEDTLTLFP
            *** * ****  ***** ***   ******** *  **********  **********
                                                                   ◆◆
       673  FSGETVFMSM  ENPGLWILGC  HNSDFRNRGM  TALLKVSSCD  KNTGDYYEDS
            FSGETVFMSM  ENPGLWVLGC  HNSDLRNRGM  TALLKVYSCD  RDIGDYYDNT
            FSGETVFMSM  ENPGLWVLGC  HNSDFRKRGM  TALLKVSSCD  KSTSDYYEEI
            **********  **********  ****  ***   **********  *    ***
            ◆                     IIa/Xa/APC
       723  YEDISAYLLS  KNNAIEPR
            YEDIPGFLLS  GKNVIEPR
            YEDIPTQLVN  ENNVIDPR
            ****   *     *  * **
```

FIG. 1C

```
B DOMAIN
HUMAN   741  SFSQNSRHPS  TRQKQFNATT  IPENDIEKTD  PWFAHRTPMP  KIQNVSSSDL
PIG          SFAQNSRPPS  ASQKQFQTIT  SPEDDVE-LD  PQSGERTQAL  EELSVPSGDG
MOUSE        SFFQNTNHPN  TRKKKFKDST  IPKNDMEKIE  PQFEEIAEML  KVQSVSVSDM
             ** **    *      *    *     *   *  **    *            *  *

791  LMLLRQS-PT  PHGLSLSDLQ  EAKYETFSDD  PSPGAIDSNN  SLSEMTHFRP
             SMLLGQN-PA  PHGSSSSDLQ  EARNEA--DD  YLPGARERNT  APSAAARLRP
             LMLLGQSHPT  PHGLFLSDGQ  EAIYEAIHDD  HSPNAIDSNE  GPSKVTQLRP
             *** *       ***   *     **  *   **   *    *     *     * **

840  QLHHSGDMVF  TPESGLQLRL  NEKLGTTAAT  ELKKLDFKVS  ST-SNNLIS-
             ELHHSAERVL  TPEP------  ------  EK  ELKKLDSKMS  SSSDLLKTSP
             ESHHSEKIVF  TPQPGLQLRS  NKSLETTIEV  KWKKLGLQVS  SLPSNLMTT-
              ***        **                      ***        *  *

888  TIPSDNLAAGT  DNTSSLGPPS  MPVHYDSQLD  TTLFGKKSSP  LTESGGPLSL
             TIPSDTLSAET  ERTHSLGPPH  PQVNFRSQLG  AIVLGKNSSH  FIGAGVPLGS
             TILSDNLKATF  EKTDSSGFPD  MPVHSSSKLS  TTAFGKKAYS  LVGSHVPLNA
             ** ** * *     *  *  *    *   *  *    *  * **    *       **

939  SEENNDSKLL  ESGLMNSQES  SWGKNVSSTE  SGRLFKGKRA  HGPALLTKDN
             TEED------  -------HES  SLGENVSPVE  SDGIFEKERA  HGPASLTKDD
             SEENSDSNIL  DSTLMYSQES  LPRDNILSIE  NDRLLREKRF  HGIALLTKDN
             **                 **         *         *      ** * * ****

989  ALFKVSISLL  KTNKTSNNSA  TNRKTHIDGP  SLLIENSPSV  WQNILESDTE
             VLFKVNISLV  KTNKARVYLK  TNRKIHIDDA  ALLTENRAS-  ----------
             TLFKDNVSLM  KTNKTYNHST  TNEKLHTESP  TSIENSTTDL  QDAILKVNSE
              ***  **    ****        ** *  *

1039  FKKVTPLIHD  RMLMDKNATA  LRLNHMSNKT  TSSKNMEMVQ  QKKEGPIPPD
             ----------  ATFMDKNTTA  SGLNHVSN--  ----------  ----------
             IQEVTALIHD  GTLLGKNSTY  LRLNHMLNRT  TSTKNKDIFH  RKDEDPIPQD
                *  ***         **     ***   *

1089  AQNPDMSFFK  MLFLPESARW  IQRTHGKNSL  NSGQGPSPKQ  LVSLGPEKSV
             ----------  ---------W  IKGPLGKNPL  SSERGPSPEL  LTSSGSGKSV
             EENTIMPFSK  MLFLSESSNW  FKKTNGNNSL  NSEQEHSPKQ  LVYLMFKKYV
                          *              * * *    *   **      *    *  *

1139  EGQNFLSEKN  KVVVGKGEFT  KDVGLKEMVF  PSSRNLFLTN  LDNLHENNTH
             KGQSSGQGRI  RVAVEEEELS  KG---KEMML  PNSELTFLTN  SADVQGNDTH
             KNQSFLSEKN  KVTVEQDGFT  KNIGLKDMAF  PHNMSIFLTT  LSNVHENGRH
             *             *  *             *     *     ***      *    *

1189  NQEKKIQEEI  EKKETLIQEN  VVLPQIHTVT  GTKNFMKNLF  LLSTRQNVEG
             SQGKKSREEM  ERREKLVQEK  VDLPQVYTAT  GTKNFLRNIF  HQSTEPSVEG
             NQEKNIQEEI  EK-EALIEEK  VVLPQVHEAT  GSKNFLKDIL  ILGTRQNI--
              *     *    *     *        * ***    *  ***         *

1239  SYDGAYAPVL  QDFRSLNDST  NRTKKHTAHF  SK--KGEEEN  LEGLGNQTKQ
             FDGGSHAPVP  QDSRSLNDSA  ERAETHIAHF  SAIR--EEAP  LEAPGNRT--
             SLYEVHVPVL  QNITSINNST  NTVQIHMEHF  FKRRKDKETN  SEGLVNKTRE
                  * **   *    *  *   * *  * **      *           *    *
```

FIG. 1D-1

```
1287  IVEKYACTTR  ISPNTSQQNF  VTQRSKRALK  QFRLPLEETE  LEKRIIVDDT
      ----------  ---GPGPRSA  VPRRVKQSLK  QIRLPLEEIK  PERGVVLNAT
      MVKNYP----  -----SQKNI  TTQRSKRALG  QFRL------  ----------

1337  STQWSKNMKH  LTPSTLTQID  YNEKEKGAIT  QSPLSDCLTR  SHSIPQANRS
      STRWS-----  ----------  ----------  ----------  ----------
      STQWLKTINC  STQCIIKQID  HSKEMKKFIT  KSSLSDS-SV  IKSTTQTNSS
      **  *

1387  PLPIAKVSSF  PSIRPIYLTR  VLFQDNSSHL  PAASY----R  KKDSGVQESS
      ----------  ----------  ----------  ----------  -------ESS
      DSHIVKTSAF  P---PIDLKR  SPFQNKFSHV  QASSYIYDFK  TKSSRIQESN
                                                         **

1433  HFLQGAKKNN  LSLAILTLEM  TGDQREVGSL  GTSATNSVTY  KKVENTVLPK
      PILQGAKRNN  LSLPFLTLEM  AGGQGKISAL  GKSAAGPLAS  GKLEKAVLSS
      NFLKETKINN  PSLAILPWNM  FIDQGKFTSP  GKSNTNSVTY  KKRENIIFLK
        *   **   **  *   *      *         * *         *  *

1483  PDLPKTSGKV  ELLPKVHIYQ  KDLFPTETSN  GSPGHLDLVE  GSLLQGTEGA
      AGLSEASGKA  EFLPKVRVHR  EDLLPQKTSN  VSCAHGDLGQ  EIFLQKTRGP
      PTLPEESGKI  ELLPQVSIQE  EEILPTETSH  GSPGHLNLMK  EVFLQKIQGP
          ***     **  *         *   *      * *         ***   *

1533  IKWNEANRPG  KVPFLRVATE  SSAKTPSKLL  DPLAWDNHYG  TQIPKEEWKS
      VNLNKVNRPG  ----------  ---RTPSKLL  ---------G  PPMPKE-WES
      TKWNKAKRHG  ESIKGKTES-  -SKNTRSKLL  NHHAWDYHYA  AQIPKDMWKS
        *     *                 * ****                  *   *

1583  QEKSPEKTAF  KKKDTI-LSLN  ACESNHAIAA  INEGQNKPEI  EVTWAKQGRT
      LEKSPKSTAL  RTKDIISLPLD  RHESNHSIAA  KNEGQAETQR  EAAWTKQGGP
      KEKSPEIISI  KQEDTI-LSLR  PHGNSHSIGA  -NEKQNWPQR  ETTWVKQGQT
       ****        *      *    **  ** *                  *  ***

1633  ERLCSONPPY  LKRHQR
      GRLCAPKPPV  LRRHQR
      QRTCSQIPPV  LKRHQR
       *  *      *** * ****
```

FIG. 1D-2

```
LIGHT CHAIN ACTIVATION PEPTIDE
                       ♦                      ♦        IIa/Xa
HUMAN  1649  EITRTTLQSDQEEIDYDDTISVEMKKEDFDIYDEDENQSPR
PIG          DISLPTFQPEEDKMDYDDIFSTETKGEDFDIYGEDENQDPR
MOUSE        EL--SAFQSEQEATDYDDAITIET-IEDFDIYSEDIKQGPR
              *   *   ****  *   ****** ** * **
```

FIG. 1E

A3 DOMAIN

```
                                              IXa  Xa
HUMAN 1690 SFQKKTRHYF IAAVERLWDY GMSSSPHVLR NRAQSGSVPQ FKKVVFQEFT
PIG        SFQKRTRHYF IAAVEQLWDY GMSESPRALR NRAQNGEVPR FKKVVFREFA
MOUSE      SVQQKTRHYF IAAVERLWDY GMSTS-HVLR NRYQSDNVPQ FKKVVFQEFT
           *  * ***** ***** **** ***  *   ** ** *   ** ****** **

1740 DGSFTQPLYR GELNEHLGLL GPYIRAEVED NIMVTFRNQA SRPYSFYSSL
           DGSFTQPSYR GELNKHLGLL GPYIRAEVED NIMVTFKNQA SRPYSFYSSL
           DGSFSQPLYR GELNEHLGLL GPYIRAEVED NIMVTFKNQA SRPYSFYSSL
           ****  *  ** **** ***** ********** ****** *** **********
                                  FACTOR IXa BINDING
      1790 ISYEEDQRQG AEPRKNFVKP NETKTYFWKV QHHMAPTKDE FDCKAWAYFS
           ISYPDDQEQG AEPRHNFVQP NETRTYFWKV QHHMAPTEDE FDCKAWAYFS
           ISYKEDQR-G EEPRRNFVKP NETKIYFWKV QHHMAPTEDE FDCKAWAYFS
           ***  **  *  *** *** * ***  ***** **********  **********

1840 DVDLEKDVHS GLIGPLLVCH TNTLNPAHGR QVTVQEFALF FTIFDETKSW
           DVDLEKDVHS GLIGPLLICR ANTLNAAHGR QVTVQEFALF FTIFDETKSW
           DVDLERDMHS GLIGPLLICH ANTLNPAHGR QVSVQEFALL FTIFDETKSW
           *****  *  ** *******  *    **** ****  **    * **********

1890 YFTENMERNC RAPCNIQMED PTFKENYRFH AINGYIMDTL PGLVMAQDQR
           YFTENVERNC RAPCHLQMED PTLKENYRFH AINGYVMDTL PGLVMAQNQR
           YFTENVKRNC KTPCNFQMED PTLKENYRFH AINGYVMDTL PGLVMAQDQR
           *****  ***   **   **** ** ******* **********  ******  **

1940 IRWYLLSMGS NENIHSIHFS GHVFTVRKKE EYKMALYNLY PGVFETVEML
           IRWYLLSMGS NENIHSIHFS GHVFSVRKKE EYKMAVYNLY PGVFETVEML
           IRWYLLSMGN NENIQSIHFS GHVFTVRKKE EYKMAVYNLY PGVFETLEMI
           *********  **** ***** ****  ***** ****  ****  ******  **
                                 PROTEIN C BINDING
      1990 PSKAGIWRVE CLIGEHLHAG MSTLFLVYSN
           PSKVGIWRIE CLIGEHLQAG MSTTFLVYSK
           PSRAGIWRVE CLIGEHLQAG MSTLFLVYSK
           **  **** * *******  **  *** ******
```

FIG. 1F

```
C1 DOMAIN
HUMAN 2020  KCQTPLGMAS GHIRDFQITA SGQYGQWAPK LARLHYSGSI NAWSTKEPFS
PIG         ECQAPLGMAS GRIRDFQITA SGQYGQWAPK LARLHYSGSI NAWSTKDPHS
MOUSE       QCQIPLGMAS GSIRDFQITA SGHYGQWAPN LARLHYSGSI NAWSTKEPFS
             **  ****** * ********* ** ****** ********** ****** * *

2070  WIKVDLLAPM IIHGIKTQGA RQKFSSLYIS QFIIMYSLDG KKWQTYRGNS
            WIKVDLLAPM IIHGIMTQGA RQKFSSLYIS QFIIMYSLDG RNWQSYRGNS
            WIKVDLLAPM IVHGIKTQGA RQKFSSLYIS QFIIMYSLDG KKWLSYQGNS
            **********  *** **** ********** **********   *  * ***

2120  TGTLMVFFGN VDSSGIKHNI FNPPIIARYI RLHPTHYSIR STLRMELMGCDLN
            TGTLMVFFGN VDASGIKHNI FNPPIVARYI RLHPTHYSIR STLRMELMGCDLN
            TGTLMVFFGN VDSSGIKHNS FNPPIIARYI RLHPTHSSIR STLRMELMGCDLN
            **********  ** ******  ***** **** ****** *** *************
```

FIG. 1G

```
C2 DOMAIN                         INHIBITOR EPITOPE
HUMAN 2173  SCSMPLGMES KAISDAQITA SSYFTNMFAT WSPSKARLHL QGRSNAWRPQ
PIG         SCSMPLGMQN KAISDSQITA SSHLSNIFAT WSPSQARLHL QGRTNAWRPR
MOUSE       SCSIPLGMES KVISDTQITA SSYFTNMFAT WSPSQARLHL QGRTNAWRPQ
            *** ****    * *** **** **   * *** **** ***** *** *****
                                                   C2
      2223  VNNPKEWLQV DFQKTMKVTG VTTQGVKSLL TSMYVKEFLI SSSQDGHQWT
            VSSAEEWLQV DLQKTVKVTG ITTQGVKSLL SSMYVKEFLV SSSQDGRRWT
            VNDPKQWLQV DLQKTMKVTG IITQGVKSLF TMSFVKEFLI SSSQDGHHWT
             *    **** * *** **** ********  ** *****   ******   **
                                                      PHOSPHOLIPID
      2273  LFFQNGKVKV FQGNQDSFTP VVNSLDPPLL TRYLRIHPQS WVHQIALRME
            LFLQDGHTKV FQGNQDSSTP VVNALDPPLF TRYLRIHPTS WAQHIALRLE
            QILYNGKVKV FQGNQDSSTP MMNSLDPPLL TRYLRIHPQI WEHQIALRLE
             *  **     ********** *   ****** ********   *  *****  *
            BINDING
      2323  VLGCEAQDLY
            VLGCEAQDLY
            ILGCEAQQQY
             ******  *
```

FIG. 1H

AMINO ACID SEQUENCE OF HP44/OL

```
   1 MQLELSTCVF LCLLPLGFSA IRRYYLGAVE LSWDYRQSEL LRELHVDTRF
  51 PATAPGALPL GPSVLYKKTV FVEFTDQLFS VARPRPPWMG LLGPTIQAEV
 101 YDTVVVTLKN MASHPVSLHA VGVSFWKSSE GAEYEDHTSQ REKEDDKVLP
 151 GKSQTYVWQV LKENGPTASD PPCLTYSYLS HVDLVKDLNS GLIGALLVCR
 201 EGSLTRERTQ NLHEFVLLFA VFDEGKSWHS ARNDSWTRAM DPAPARAQPA
 251 MHTVNGYVNR SLPGLIGCHK KSVYWHVIGM GTSPEVHSIF LEGHTFLVRH
 301 HRQASLEISP LTFLTAQTFL MDLGQFLLFC HISSHHHGGM EAHVRVESCA
 351 EEPQLRRKAD EEEDYDDNLY DSDMDVVRLD GDDVSPFIQI RSVAKKHPKT
 401 WVHYISAEEE DWDYAPAVPS PSDRSYKSLY LNSGPQRIGR KYKKARFVAY
 451 TDVTFKTRKA IPYESGILGP LLYGEVGDTL LIIFKNKASR PYNIYPHGIT
 501 DVSALHPGRL LKGWKHLKDM PILPGETFKY KWTVTVEDGP TKSDPRCLTR
 551 YYSSSINLEK DLASGLIGPL LICYKESVDQ RGNQMMSDKR NVILFSVFDE
 601 NQSWYLAENI QRFLPNPDGL QPQDPEFQAS NIMHSINGYV FDSLQLSVCL
 651 HEVAYWYILS VGAQTDFLSV FFSGYTFKHK MVYEDTLTLF PFSGETVFMS
 701 MENPGLWVLG CHNSDLRNRG MTALLKVYSC DRDIGDYYDN TYEDIPGFLL
 751 SGKNVIEPRS FAQNSRPPSA SAPKPPVLRR HQRDISLPTF QPEEDKMDYD
 801 DIFSTETKGE DFDIYGEDEN QDPRSFQKRT RHYFIAAVEQ LWDYGMSESP
 851 RALRNRAQNG EVPRFKKVVF REFADGSFTQ PSYRGELNKH LGLLGPYIRA
 901 EVEDNIMVTF KNQASRPYSF YSSLISYPDD QEQGAEPRHN FVQPNETRTY
 951 FWKVQHHMAP TEDEFDCKAW AWFSDVDLEK DVHSGLIGPL LICRANTLNA
1001 AHGRQVTVQE FALFFTIFDE TKSWYFTENV ERNCRAPCHL QMEDPTLKEN
1051 YRFHAINGYV MDTLPGLVMA QNQRIRWYLL SMGSNENIHS IHFSGHVFSV
1101 RKKEEYKMAV YNLYPGVFET VEMLPSKVGI WRIECLIGEH LQAGMSTTFL
1151 VYSKKCQTPL GMASGHIRDF QITASGQYGQ WAPKLARLHY SGSINAWSTK
1201 EPFSWIKVDL LAPMIIHGIK TQGARQKFSS LYISQFIIMY SLDGKKWQTY
1251 RGNSTGTLMV FFGNVDSSGI KHNIFNPPII ARYIRLHPTH YSIRSTLRME
1301 LMGCDLNSCS MPLGMESKAI SDAQITASSY FTNMFATWSP SKARLHLQGR
1351 SNAWRPQVNN PKEWLQVDFQ KTMKVTGVTT QGVKSLLTSM YVKEFLISSS
1401 QDGHQWTLFF QNGKVKVFQG NQDSFTPVVN SLDPPLLTRY LRIHPQSWVH
1451 QIALRMEVLG CEAQDLY*
```

1-19 SIGNAL PEPTIDE
20-391 A1 DOMAIN
392-759 A2 DOMAIN
760-783 OL LINKER
784-1154 ap-A3
1155-1307 C1 DOMAIN
1308-1467 C2 DOMAIN

FIG. 4

HP44/OL NUCLEOTIDE SEQUENCE

```
   1 ATGCAGCTAG AGCTCTCCAC CTGTGTCTTT CTGTGTCTCT TGCCACTCGG
     TACGTCGATC TCGAGAGGTG GACACAGAAA GACACAGAGA ACGGTGAGCC
  51 CTTTAGTGCC ATCAGGAGAT ACTACCTGGG CGCAGTGGAA CTGTCCTGGG
     GAAATCACGG TAGTCCTCTA TGATGGACCC GCGTCACCTT GACAGGACCC
 101 ACTACCGGCA AAGTGAACTC CTCCGTGAGC TGCACGTGGA CACCAGATTT
     TGATGGCCGT TTCACTTGAG GAGGCACTCG ACGTGCACCT GTGGTCTAAA
 151 CCTGCTACAG CGCCAGGAGC TCTTCCGTTG GGCCCGTCAG TCCTGTACAA
     GGACGATGTC GCGGTCCTCG AGAAGGCAAC CCGGGCAGTC AGGACATGTT
 201 AAAGACTGTG TTCGTAGAGT TCACGGATCA ACTTTTCAGC GTTGCCAGGC
     TTTCTGACAC AAGCATCTCA AGTGCCTAGT TGAAAAGTCG CAACGGTCCG
 251 CCAGGCCACC ATGGATGGGT CTGCTGGGTC CTACCATCCA GGCTGAGGTT
     GGTCCGGTGG TACCTACCCA GACGACCCAG GATGGTAGGT CCGACTCCAA
 301 TACGACACGG TGGTCGTTAC CCTGAAGAAC ATGGCTTCTC ATCCCGTTAG
     ATGCTGTGCC ACCAGCAATG GGACTTCTTG TACCGAAGAG TAGGGCAATC
 351 TCTTCACGCT GTCGGCGTCT CCTTCTGGAA ATCTTCCGAA GGCGCTGAAT
     AGAAGTGCGA CAGCCGCAGA GGAAGACCTT TAGAAGGCTT CCGCGACTTA
 401 ATGAGGATCA CACCAGCCAA AGGGAGAAGG AAGACGATAA AGTCCTTCCC
     TACTCCTAGT GTGGTCGGTT TCCCTCTTCC TTCTGCTATT TCAGGAAGGG
 451 GGTAAAAGCC AAACCTACGT CTGGCAGGTC CTGAAAGAAA ATGGTCCAAC
     CCATTTTCGG TTTGGATGCA CACCGTCCAG GACTTTCTTT TACCAGGTTG
 501 AGCCTCTGAC CCACCATGTC TTACCTACTC ATACCTGTCT CACGTGGACC
     TCGGAGACTG GGTGGTACAG AATGGATGAG TATGGACAGA GTGCACCTGG
 551 TGGTGAAAGA CCTGAATTCG GCCTCATTG GAGCCCTGCT GGTTTGTAGA
     ACCACTTTCT GGACTTAAGC CCGGAGTAAC CTCGGGACGA CCAAACATCT
 601 GAAGGGAGTC TGACCAGAGA AAGGACCCAG AACCTGCACG AATTTGTACT
     CTTCCCTCAG ACTGGTCTCT TTCCTGGGTC TTGGACGTGC TTAAACATGA
 651 ACTTTTTGCT GTCTTTGATG AAGGGAAAAG TTGGCACTCA GCAAGAAATG
     TGAAAAACGA CAGAAACTAC TTCCCTTTTC AACCGTGAGT CGTTCTTTAC
 701 ACTCCTGGAC ACGGGCCATG GATCCCGCAC CTGCCAGGGC CCAGCCTGCA
     TGAGGACCTG TGCCCGGTAC CTAGGGCGTG GACGGTCCCG GGTCGGACGT
 751 ATGCACACAG TCAATGGCTA TGTCAACAGG TCTCTGCCAG GTCTGATCGG
     TACGTGTGTC AGTTACCGAT ACAGTTGTCC AGAGACGGTC CAGACTAGCC
 801 ATGTCATAAG AAATCAGTCT ACTGGCACGT GATTGGAATG GGCACCAGCC
     TACAGTATTC TTTAGTCAGA TGACCGTGCA CTAACCTTAC CCGTGGTCGG
 851 CGGAAGTGCA CTCCATTTTT CTTGAAGGCC ACACGTTTCT CGTGAGGCAC
     GCCTTCACGT GAGGTAAAAA GAACTTCCGG TGTGCAAAGA GCACTCCGTG
 901 CATCGCCAGG CTTCCTTGGA GATCTCGCCA CTAACTTTCC TCACTGCTCA
     GTAGCGGTCC GAAGGAACCT CTAGAGCGGT GATTGAAAGG AGTGACGAGT
 951 GACATTCCTG ATGGACCTTG GCCAGTTCCT ACTGTTTTGT CATATCTCTT
     CTGTAAGGAC TACCTGGAAC CGGTCAAGGA TGACAAAACA GTATAGAGAA
1001 CCCACCACCA TGGTGGCATG GAGGCTCACG TCAGAGTAGA AAGCTGCGCC
     GGGTGGTGGT ACCACCGTAC CTCCGAGTGC AGTCTCATCT TTCGACGCGG
1051 GAGGAGCCCC AGCTGCGGAG GAAAGCTGAT GAAGAGGAAG ATTATGATGA
     CTCCTCGGGG TCGACGCCTC CTTTCGACTA CTTCTCCTTC TAATACTACT
1101 CAATTTGTAC GACTCGGACA TGGACGTGGT CCGGCTCGAT GGTGACGACG
     GTTAAACATG CTGAGCCTGT ACCTGCACCA GGCCGAGCTA CCACTGCTGC
1151 TGTCTCCCTT TATCCAAATC CGCTCGGTTG CCAAGAAGCA TCCCAAAACC
     ACAGAGGGAA ATAGGTTTAG GCGAGCCAAC GGTTCTTCGT AGGGTTTTGG
1201 TGGGTGCACT ACATCTCTGC AGAGGAGGAG GACTGGGACT ACGCCCCCGC
     ACCCACGTGA TGTAGAGACG TCTCCTCCTC CTGACCCTGA TGCGGGGGCG
1251 GGTCCCCAGC CCCAGTGACA GAAGTTATAA AAGTCTCTAC TTGAACAGTG
     CCAGGGGTCG GGGTCACTGT CTTCAATATT TTCAGAGATG AACTTGTCAC
1301 GTCCTCAGCG AATTGGTAGG AAATACAAAA AAGCTCGATT CGTCGCTTAC
     CAGGAGTCGC TTAACCATCC TTTATGTTTT TTCGAGCTAA GCAGCGAATG
```

FIG. 5A

```
1351  ACGGATGTAA  CATTTAAGAC  TCGTAAAGCT  ATTCCGTATG  AATCAGGAAT
      TGCCTACATT  GTAAATTCTG  AGCATTTCGA  TAAGGCATAC  TTAGTCCTTA
1401  CCTGGGACCT  TTACTTTATG  GAGAAGTTGG  AGACACACTT  TTGATTATAT
      GGACCCTGGA  AATGAAATAC  CTCTTCAACC  TCTGTGTGAA  AACTAATATA
1451  TTAAGAATAA  AGCGAGCCGA  CCATATAACA  TCTACCCTCA  TGGAATCACT
      AATTCTTATT  TCGCTCGGCT  GGTATATTGT  AGATGGGAGT  ACCTTAGTGA
1501  GATGTCAGCG  CTTTGCACCC  AGGGAGACTT  CTAAAAGGTT  GGAAACATTT
      CTACAGTCGC  GAAACGTGGG  TCCCTCTGAA  GATTTTCCAA  CCTTTGTAAA
1551  GAAAGACATG  CCAATTCTGC  CAGGAGAGAC  TTTCAAGTAT  AAATGGACAG
      CTTTCTGTAC  GGTTAAGACG  GTCCTCTCTG  AAAGTTCATA  TTTACCTGTC
1601  TGACTGTGGA  AGATGGGCCA  ACCAAGTCCG  ATCCTCGGTG  CCTGACCCGC
      ACTGACACCT  TCTACCCGGT  TGGTTCAGGC  TAGGAGCCAC  GGACTGGGCG
1651  TACTACTCGA  GCTCCATTAA  TCTAGAGAAA  GATCTGGCTT  CGGGACTCAT
      ATGATGAGCT  CGAGGTAATT  AGATCTCTTT  CTAGACCGAA  GCCCTGAGTA
1701  TGGCCCTCTC  CTCATCTGCT  ACAAAGAATC  TGTAGACCAA  AGAGGAAACC
      ACCGGGAGAG  GAGTAGACGA  TGTTTCTTAG  ACATCTGGTT  TCTCCTTTGG
1751  AGATGATGTC  AGACAAGAGA  AACGTCATCC  TGTTTTCTGT  ATTCGATGAG
      TCTACTACAG  TCTGTTCTCT  TTGCAGTAGG  ACAAAAGACA  TAAGCTACTC
1801  AATCAAAGCT  GGTACCTCGC  AGAGAATATT  CAGCGCTTCC  TCCCCAATCC
      TTAGTTTCGA  CCATGGAGCG  TCTCTTATAA  GTCGCGAAGG  AGGGGTTAGG
1851  GGATGGATTA  CAGCCCCAGG  ATCCAGAGTT  CCAAGCTTCT  AACATCATGC
      CCTACCTAAT  GTCGGGGTCC  TAGGTCTCAA  GGTTCGAAGA  TTGTAGTACG
1901  ACAGCATCAA  TGGCTATGTT  TTTGATAGCT  TGCAGCTGTC  GGTTTGTTTG
      TGTCGTAGTT  ACCGATACAA  AAACTATCGA  ACGTCGACAG  CCAAACAAAC
1951  CACGAGGTGG  CATACTGGTA  CATTCTAAGT  GTTGGAGCAC  AGACGGACTT
      GTGCTCCACC  GTATGACCAT  GTAAGATTCA  CAACCTCGTG  TCTGCCTGAA
2001  CCTCTCCGTC  TTCTTCTCTG  GCTACACCTT  CAAACACAAA  ATGGTCTATG
      GGAGAGGCAG  AAGAAGAGAC  CGATGTGGAA  GTTTGTGTTT  TACCAGATAC
2051  AAGACACACT  CACCCTGTTC  CCCTTCTCAG  GAGAAACGGT  CTTCATCTCA
      TTCTGTGTGA  GTGGGACAAG  GGGAAGAGTC  CTCTTTGCCA  GAAGTACAGT
2101  ATGGAAAACC  CAGGTCTCTG  GGTCCTTGGG  TGCCACAACT  CAGACTTGCG
      TACCTTTTGG  GTCCAGAGAC  CCAGGAACCC  ACGGTGTTGA  GTCTGAACGC
2151  GAACAGAGGG  ATGACAGCCT  TACTGAAGGT  GTATAGTTGT  GACAGGGACA
      CTTGTCTCCC  TACTGTCGGA  ATGACTTCCA  CATATCAACA  CTGTCCCTGT
2201  TTGGTGATTA  TTATGACAAC  ACTTATGAAG  ATATTCCAGG  CTTCTTGCTC
      AACCACTAAT  AATACTGTTG  TGAATACTTC  TATAAGGTCC  GAAGAACGAC
2251  AGTGGAAAGA  ATGTCATTGA  ACCTAGGAGC  TTTGCCCAGA  ATTCAAGACC
      TCACCTTTCT  TACAGTAACT  TGGATCCTCG  AAACGGGTCT  TAAGTTCTGG
2301  CCCTAGTGCG  AGCGCTCCAA  AGCCTCCGGT  CCTGCGACGG  CATCAGAGGG
      GGGATCACGC  TCGCGAGGTT  TCGGAGGCCA  GGACGCTGCC  GTAGTCTCCC
2351  ACATAAGCCT  TCCTACTTTT  CAGCCGGAGG  AAGACAAAAT  GGACTATGAT
      TGTATTCGGA  AGGATGAAAA  GTCGGCCTCC  TTCTGTTTTA  CCTGATACTA
2401  GATATCTTCT  CAACTGAAAC  GAAGGGAGAA  GATTTTGACA  TTTACGGTGA
      CTATAGAAGA  GTTGACTTTG  CTTCCCTCTT  CTAAAACTGT  AAATGCCACT
2451  CGATGAAAAT  CAGGACCCTC  GCAGCTTTCA  GAAGAGAACC  CGACACTATT
      GCTACTTTTA  GTCCTGGGAG  CGTCGAAAGT  CTTCTCTTGG  GCTGTGATAA
2501  TCATTGCTGC  GGTGGAGCAG  CTCTGGGATT  ACGGGATGAG  CGAATCCCCC
      AGTAACGACG  CCACCTCGTC  GAGACCCTAA  TGCCCTACTC  GCTTAGGGGG
2551  CGGGCGCTAA  GAAACAGGGC  TCAGAACGGA  GAGGTGCCTC  GGTTCAAGAA
      GCCCGCGATT  CTTTGTCCCG  AGTCTTGCCT  CTCCACGGAG  CCAAGTTCTT
2601  GGTGGTCTTC  CGGGAATTTG  CTGACGGCTC  CTTCACGCAG  CCGTCGTACC
      CCACCAGAAG  GCCCTTAAAC  GACTGCCGAG  GAAGTGCGTC  GGCAGCATGG
2651  GCGGGGAACT  CAACAAACAC  TTGGGGCTCT  TGGGACCCTA  CATCAGAGCG
      CGCCCCTTGA  GTTGTTTGTG  AACCCCGAGA  ACCCTGGGAT  GTAGTCTCGC
2701  GAAGTTGAAG  ACAACATCAT  GGTAACTTTC  AAAAACCAGG  CGTCTCGTCC
      CTTCAACTTC  TGTTGTAGTA  CCATTGAAAG  TTTTTGGTCC  GCAGAGCAGG
2751  CTATTCCTTC  TACTCGAGCC  TTATTTCTTA  TCCGGATGAT  CAGGAGCAAG
```

FIG. 5B

```
         GATAAGGAAG ATGAGCTCGG AATAAAGAAT AGGCCTACTA GTCCTCGTTC
2801     GGGCAGAACC TCGACACAAC TTCGTCCAGC CAAATGAAAC CAGAACTTAC
         CCCGTCTTGG AGCTGTGTTG AAGCAGGTCG GTTTACTTTG GTCTTGAATG
2851     TTTTGGAAAG TGCAGCATCA CATGGCACCC ACAGAAGACG AGTTTGACTG
         AAAACCTTTC ACGTCGTAGT GTACCGTGGG TGTCTTCTGC TCAAACTGAC
2901     CAAAGCCTGG GCCTACTTTT CTGATGTTGA CCTGGAAAAA GATGTGCACT
         GTTTCGGACC CGGATGAAAA GACTACAACT GGACCTTTTT CTACACGTGA
2951     CAGGCTTGAT CGGCCCCCTT CTGATCTGCC GCGCCAACAC CCTGAACGCT
         GTCCGAACTA GCCGGGGGAA GACTAGACGG CGCCGTTGTG GGACTTGCGA
3001     GCTCACGGTA GACAAGTGAC CGTGCAAGAA TTTGCTCTGT TTTTCACTAT
         CGAGTGCCAT CTGTTCACTG GCACGTTCTT AAACGAGACA AAAAGTGATA
3051     TTTTGATGAG ACAAAGAGCT GGTACTTCAC TGAAAATGTG GAAAGGAACT
         AAAACTACTC TGTTTCTCGA CCATGAAGTG ACTTTTACAC CTTTCCTTGA
3101     GCCGGGCCCC CTGCCATCTG CAGATGGAGG ACCCCACTCT GAAAGAAAAC
         CGGCCCGGGG GACGGTAGAC GTCTACCTCC TGGGGTGAGA CTTTCTTTTG
3151     TATCGCTTCC ATGCAATCAA TGGCTATGTG ATGGATACAC TCCCTGGCTT
         ATAGCGAAGG TACGTTAGTT ACCGATACAC TACCTATGTG AGGGACCGAA
3201     AGTAATGGCT CAGAATCAAA GGATCCGATG GTATCTGCTC AGCATGGGCA
         TCATTACCGA GTCTTAGTTT CCTAGGCTAC CATAGACGAG TCGTACCCGT
3251     GCAATGAAAA TATCCATTCG ATTCATTTTA GCGGACACGT GTTCAGTGTA
         CGTTACTTTT ATAGGTAAGC TAAGTAAAAT CGCCTGTGCA CAAGTCACAT
3301     CGGAAAAAGG AGGAGTATAA AATGGCCGTG TACAATCTCT ATCCGGGTGT
         GCCTTTTTCC TCCTCATATT TTACCGGCAC ATGTTAGAGA TAGGCCCACA
3351     CTTTGAGACA GTGGAAATGC TACCGTCCAA AGTTGGAATT TGGCGAATAG
         GAAACTCTGT CACCTTTACG ATGGCAGGTT TCAACCTTAA ACCGCTTATC
3401     AATGCCTGAT TGGCGAGCAC CTGCAAGCTC GGATGAGCAC GACTTTCCTG
         TTACGGACTA ACCGCTCGTG GACGTTCGAC CCTACTCGTG CTGAAAGGAC
3451     GTGTACAGCA AGAAGTGTCA GACTCCCCTG GGAATGGCTT CTGGACACAT
         CACATGTCGT TCTTCACAGT CTGAGGGGAC CCTTACCGAA GACCTGTGTA
3501     TAGAGATTTT CAGATTACAG CTTCAGGACA ATATGGACAG TGGGCCCCAA
         ATCTCTAAAA GTCTAATGTC GAAGTCCTGT TATACCTGTC ACCCGGGGTT
3551     AGCTGGCCAG ACTTCATTAT TCCGGATCAA TCAATGCCTG GAGCACCAAG
         TCGACCGGTC TGAAGTAATA AGGCCTAGTT AGTTACGGAC CTCGTGGTTC
3601     GAGCCCTTTT CTTGGATCAA GGTGGATCTG TTGGCACCAA TGATTATTCA
         CTCGGGAAAA GAACCTAGTT CCACCTAGAC AACCGTGGTT ACTAATAAGT
3651     CGGCATCAAG ACCCAGGGTG CCCGTCAGAA GTTCTCCAGC CTCTACATCT
         GCCGTAGTTC TGGGTCCCAC GGGCAGTCTT CAAGAGGTCG GAGATGTAGA
3701     CTCAGTTTAT CATCATGTAT AGTCTTGATG GGAAGAAGTG GCAGACTTAT
         GAGTCAAATA GTAGTACATA TCAGAACTAC CCTTCTTCAC CGTCTGAATA
3751     CGAGGAAATT CCACTGGAAC CTTAATGGTC TTCTTTGCA ATGTGGATTC
         GCTCCTTTAA GGTGACCTTG GAATTACCAG AAGAAACCGT TACACCTAAG
3801     ATCTGGGATA AAACACAATA TTTTTAACCC TCCAATTATT GCTCGATACA
         TAGACCCTAT TTTGTGTTAT AAAAATTGGG AGGTTAATAA CGAGCTATGT
3851     TCCGTTTGCA CCCAACTCAT TATAGCATTC GCAGCACTCT TCGCATGGAG
         AGGCAAACGT GGGTTGAGTA ATATCGTAAG CGTCGTCAGA AGCGTACCTC
3901     TTGATGGGCT GTGATTTAAA TAGTTGCAGC ATGCCATTGG GAATGGAGAG
         AACTACCCGA CACTAAATTT ATCAACGTCG TACGGTAACC CTTACCTCTC
3951     TAAAGCAATA TCAGATGCAC AGATTACTGC TTCATCCTAC TTTACCAATA
         ATTTCGTTAT AGTCTACGTG TCTAATGACG AAGTAGGATG AAATGGTTAT
4001     TGTTTGCCAC CTGGTCTCCT TCAAAGCTC GACTTCACCT CCAAGGGAGG
         ACAAACGGTG GACCAGAGGA AGTTTCGAG CTGAAGTGGA GGTTCCCTCC
4051     AGTAATGCCT GGAGACCTCA GGTGAATAAT CCAAAAGAGT GGCTGCAAGT
         TCATTACGGA CCTCTGGAGT CCACTTATTA GGTTTTCTCA CCGACGTTCA
4101     GGACTTCCAG AAGACAATGA AAGTCACAGG AGTAACTACT CAGGGAGTAA
         CCTGAAGGTC TTCTGTTACT TTCAGTGTCC TCATTGATGA GTCCCTCATT
4151     AATCTCTGCT TACCAGCATG TATGTGAAGG AGTTCCTCAT CTCCAGCAGT
         TTAGAGACGA ATGGTCGTAC ATACACTTCC TCAAGGAGTA GAGGTCGTCA
```

FIG. 5C

```
4201  CAAGATGGCC ATCAGTGGAC TCTCTTTTTT CAGAATGGCA AAGTAAAGGT
      GTTCTACCGG TAGTCACCTG AGAGAAAAAA GTCTTACCGT TTCATTTCCA
4251  TTTTCAGGGA AATCAAGACT CCTTCACACC TGTGGTGAAC TCTCTAGACC
      AAAAGTCCCT TTAGTTCTGA GGAAGTGTGG ACACCACTTG AGAGATCTGG
4301  CACCGTTACT GACTCGCTAC CTTCGAATTC ACCCCAGAG TTGGGTGCAC
      GTGGCAATGA CTGAGCGATG GAAGCTTAAG TGGGGGTCTC AACCCACGTG
4351  CAGATTGCCC TGAGGATGGA GGTTCTGGGC TGCGAGGCAC AGGACCTCTA
      GTCTAACGGG ACTCCTACCT CCAAGACCCG ACGCTCCGTG TCCTGGAGAT
4401  C
      G
```

1-57 SIGNAL PEPTIDE
58-1173 A1 DOMAIN
1174-2277 A2 DOMAIN
2278-2349 OL LINKER
2350-3462 ap-A3 DOMAINS
3463-3921 C1 DOMAIN
3922-4401 C2 DOMAIN

FIG. 5D

AMINO ACID SEQUENCE OF HP46/SQ

```
   1  MQLELSTCVF  LCLLPLGFSA  IRRYYLGAVE  LSWDYRQSEL  LRELHVDTRF
  51  PATAPGALPL  GPSVLYKKTV  FVEFTDQLFS  VARPRPPWMG  LLGPTIQAEV
 101  YDTVVVTLKN  MASHPVSLHA  VGVSFWKSSE  GAEYEDHTSQ  REKEDDKVLP
 151  GKSQTYVWQV  LKENGPTASD  PPCLTYSYLS  HVDLVKDLNS  GLIGALLVCR
 201  EGSLTRERTQ  NLHEFVLLFA  VFDEGKSWHS  ARNDSWTRAM  DPAPARAQPA
 251  MHTVNGYVNR  SLPGLIGCHK  KSVYWHVIGM  GTSPEVHSIF  LEGHTFLVRH
 301  HRQASLEISP  LTFLTAQTFL  MDLGQFLLFC  HISSHHHGGM  EAHVRVESCA
 351  EEPQLRRKAD  EEEDYDDNLY  DSDMDVVRLD  GDDVSPFIQI  RSVAKKHPKT
 401  WVHYIAAEEE  DWDYAPLVLA  PDDRSYKSQY  LNNGPQRIGR  KYKKVRFMAY
 451  TDETFKTREA  IQHESGILGP  LLYGEVGDTL  LIIFKNQASR  PYNIYPHGIT
 501  DVRPLYSRRL  PKGVKHLKDF  PILPGEIFKY  KWTVTVEDGP  TKSDPRCLTR
 551  YYSSFVNMER  DLASGLIGPL  LICYKESVDQ  RGNQIMSDKR  NVILFSVFDE
 601  NRSWYLTENI  QRFLPNPAGV  QLEDPEFQAS  NIMHSINGYV  FDSLQLSVCL
 651  HEVAYWYILS  IGAQTDFLSV  FFSGYTFKHK  MVYEDTLTLF  PFSGETVFMS
 701  MENPGLWILG  CHNSFLRNRG  MTALLKVSSC  DKNTGDYYED  SYEDISAYLL
 751  SKNNAIEPRS  FSQNPPVLKR  HQREITRTTL  QSDQEEIDYD  DTISVEMKKE
 801  DFDIYDEDEN  QSPRSFQKKT  RHYFIAAVER  LWDYGMSSSP  HVLRNRAQSG
 851  SVPQFKKVVF  QEFTDGSFTQ  PLYRGELNEH  LGLLGPYIRA  EVEDNIMVTF
 901  RNQASRPYSF  YSSLISYEED  QRQGAEPRKN  FVKPNETKTY  FWKVQHHMAP
 951  TKDEFDCKAW  AYFSDVDLEK  DVHSGLIGPL  LVCHTNTLNP  AHGRQVTVQE
1001  FALFFTIFDE  TKSWYFTENM  ERNCRAPCNI  QMEDPTFKEN  YRFHAINGYI
1051  MDTLPGLVMA  QDQRIRWYLL  SMGSNENIHS  IHFSGHVFTV  RKKEEYKMAL
1101  YNLYPGVFET  VEMLPSKAGI  WRVECLIGEH  LHAGMSTLFL  VYSNKCQTPL
1151  GMASGHIRDF  QITASGQYGQ  WAPKLARLHY  SGSINAWSTK  EPFSWIKVDL
1201  LAPMIIHGIK  TQGARQKFSS  LYISQFIIMY  SLDGKKWQTY  RGNSTGTLMV
1251  FFGNVDSSGI  KHNIFNPPII  ARYIRLHPTH  YSIRSTLRME  LMGCDLNSCS
1301  MPLGMESKAI  SDAQITASSY  FTNMFATWSP  SKARLHLQGR  SNAWRPQVNN
1351  PKEWLQVDFQ  KTMKVTGVTT  QGVKSLLTSM  YVKEFLISSS  QDGHQWTLFF
1401  QNGKVKVFQG  NQDSFTPVVN  SLDPPLLTRY  LRIHPQSWVH  QIALRMEVLG
1451  CEAQDLY*
```

1-19 SIGNAL PEPTIDE
20-391 A1 DOMAIN
392-759 A2 DOMAIN
760-773 SQ LINKER
774-1144 ap-A3
1145-1297 C1 DOMAIN
1298-1457 C2 DOMAIN

FIG. 6

HP46/SQ NUCLEOTIDE SEQUENCE

```
   1  ATGCAGCTAG AGCTCTCCAC CTGTGTCTTT CTGTGTCTCT TGCCACTCGG
      TACGTCGATC TCGAGAGGTG GACACAGAAA GACACAGAGA ACGGTGAGCC
  51  CTTTAGTGCC ATCAGGAGAT ACTACCTGGG CGCAGTGGAA CTGTCCTGGG
      GAAATCACGG TAGTCCTCTA TGATGGACCC GCGTCACCTT GACAGGACCC
 101  ACTACCGGCA AAGTGAACTC CTCCGTGAGC TGCACGTGGA CACCAGATTT
      TGATGGCCGT TTCACTTGAG GAGGCACTCG ACGTGCACCT GTGGTCTAAA
 151  CCTGCTACAG CGCCAGGAGC TCTTCCGTTG GGCCCGTCAG TCCTGTACAA
      GGACGATGTC GCGGTCCTCG AGAAGGCAAC CCGGGCAGTC AGGACATGTT
 201  AAAGACTGTG TTCGTAGAGT TCACGGATCA ACTTTTCAGC GTTGCCAGGC
      TTTCTGACAC AAGCATCTCA AGTGCCTAGT TGAAAAGTCG CAACGGTCCG
 251  CCAGGCCACC ATGGATGGGT CTGCTGGGTC CTACCATCCA GGCTGAGGTT
      GGTCCGGTGG TACCTACCCA GACGACCCAG GATGGTAGGT CCGACTCCAA
 301  TACGACACGG TGGTCGTTAC CCTGAAGAAC ATGGCTTCTC ATCCCGTTAG
      ATGCTGTGCC ACCAGCAATG GGACTTCTTG TACCGAAGAG TAGGGCAATC
 351  TCTTCACGCT GTCGGCGTCT CCTTCTGGAA ATCTTCCGAA GGCGCTGAAT
      AGAAGTGCGA CAGCCGCAGA GGAAGACCTT TAGAAGGCTT CCGCGACTTA
 401  ATGAGGATCA CACCAGCCAA AGGGAGAAGG AAGACGATAA AGTCCTTCCC
      TACTCCTAGT GTGGTCGGTT TCCCTCTTCC TTCTGCTATT TCAGGAAGGG
 451  GGTAAAAGCC AAACCTACGT CTGGCAGGTC CTGAAAGAAA ATGGTCCAAC
      CCATTTTCGG TTTGGATGCA GACCGTCCAG GACTTTCTTT TACCAGGTTG
 501  AGCCTCTGAC CCACCATGTC TTACCTACTC ATACCTGTCT CACGTGGACC
      TCGGAGACTG GGTGGTACAG AATGGATGAG TATGGACAGA GTGCACCTGG
 551  TGGTGAAAGA CCTGAATTCG GGCCTCATTG GAGCCCTGCT GGTTTGTAGA
      ACCACTTTCT GGACTTAAGC CCGGAGTAAC CTCGGGACGA CCAAACATCT
 601  GAAGGGAGTC TGACCAGAGA AAGGACCCAG AACCTGCACG AATTTGTACT
      CTTCCCTCAG ACTGGTCTCT TTCCTGGGTC TTGGACGTGC TTAAACATGA
 651  ACTTTTTGCT GTCTTTGATG AAGGGAAAAG TTGGCACTCA GCAAGAAATG
      TGAAAAACGA CAGAAACTAC TTCCCTTTTC AACCGTGAGT CGTTCTTTAC
 701  ACTCCTGGAC ACGGGCCATG GATCCCGCAC CTGCCAGGGC CCAGCCTGCA
      TGAGGACCTG TGCCCGGTAC CTAGGGCGTG GACGGTCCCG GGTCGGACGT
 751  ATGCACACAC TCAATGGCTA TGTCAACAGG TCTCTGCCAG GTCTGATCGG
      TACGTGTGTC AGTTACCGAT ACAGTTGTCC AGAGACGGTC CAGACTAGCC
 801  ATGTCATAAG AAATCAGTCT ACTGGCACGT GATTGGAATG GGCACCAGCC
      TACAGTATTC TTTAGTCAGA TGACCGTGCA CTAACCTTAC CCGTGGTCGG
 851  CGGAAGTGCA CTCCATTTTT CTTGAAGGCC ACACGTTTCT CGTGAGGCAC
      GCCTTCACGT GAGGTAAAAA GAACTTCCGG TGTGCAAAGA GCACTCCGTG
 901  CATCGCCAGG CTTCCTTGGA GATCTCGCCA CTAACTTTCC TCACTGCTCA
      GTAGCGGTCC GAAGGAACCT CTAGAGCGGT GATTGAAAGG AGTGACGAGT
 951  GACATTCCTG ATGGACCTTG CCAGTTCCT ACTGTTTTGT CATATCTCTT
      CTGTAAGGAC TACCTGGAAC CGGTCAAGGA TGACAAAACA GTATAGAGAA
1001  CCCACCACCA TGGTGGCATG GAGGCTCACG TCAGAGTAGA AAGCTGCGCC
      GGGTGGTGGT ACCACCGTAC CTCCGAGTGC AGTCTCATCT TTCGACGCGG
1051  GAGGAGCCCC AGCTGCGGAG GAAAGCTGAT GAAGAGGAAG ATTATGATGA
      CTCCTCGGGG TCGACGCCTC CTTTCGACTA CTTCTCCTTC TAATACTACT
1101  CAATTTGTAC GACTCGGACA TGGACGTGGT CCGGCTCGAT GGTGACGACG
      GTTAAACATG CTGAGCCTGT ACCTGCACCA GGCCGAGCTA CCACTGCTGC
1151  TGTCTCCCTT TATCCAAATC CGCTCAGTTG CCAAGAAGCA TCCTAAAACT
      ACAGAGGGAA ATAGGTTTAG GCGAGTCAAC GGTTCTTCGT AGGATTTTGA
1201  TGGGTACATT ACATTGCTGC TGAAGAGGAG GACTGGGACT ATGCTCCCTT
```

FIG. 7A

```
          ACCCATGTAA TGTAACGACG ACTTCTCCTC CTGACCCTGA TACGAGGGAA
     1251 AGTCCTCGCC CCCGATGACA GAAGTTATAA AAGTCAATAT TTGAACAATG
          TCAGGAGCGG GGGCTACTGT CTTCAATATT TTCAGTTATA AACTTGTTAC
     1301 GCCCTCAGCG GATTGGTAGG AAGTACAAAA AAGTCCGATT TATGGCATAC
          CGGGAGTCGC CTAACCATCC TTCATGTTTT TTCAGGCTAA ATACCGTATG
     1351 ACAGATGAAA CCTTTAAGAC GCGTGAAGCT ATTCAGCATG AATCAGGAAT
          TGTCTACTTT GGAAATTCTG CGCACTTCGA TAAGTCGTAC TTAGTCCTTA
     1401 CTTGGGACCT TTACTTTATG GGGAAGTTGG AGACACACTG TTGATTATAT
          GAACCCTGGA AATGAAATAC CCCTTCAACC TCTGTGTGAC AACTAATATA
     1451 TTAAGAATCA AGCAAGCAGA CCATATAACA TCTACCCTCA CGGAATCACT
          AATTCTTAGT TCGTTCGTCT GGTATATTGT AGATGGGAGT GCCTTAGTGA
     1501 GATGTCCGTC CTTTGTATTC AAGGAGATTA CCAAAAGGTG TAAAACATTT
          CTACAGGCAG GAAACATAAG TTCCTCTAAT GGTTTTCCAC ATTTTGTAAA
     1551 GAAGGATTTT CCAATTCTGC CAGGAGAAAT ATTCAAATAT AAATGGACAG
          CTTCCTAAAA GGTTAAGACG GTCCTCTTTA TAAGTTTATA TTTACCTGTC
     1601 TGACTGTAGA AGATGGGCCA ACTAAATCAG ATCCGCGGTG CCTGACCCGC
          ACTGACATCT TCTACCCGGT TGATTTAGTC TAGGCGCCAC GGACTGGGCG
     1651 TATTACTCTA GTTTCGTTAA TATGGAGAGA GATCTAGCTT CAGGACTCAT
          ATAATGAGAT CAAAGCAATT ATACCTCTCT CTAGATCGAA GTCCTGAGTA
     1701 TGGCCCTCTC CTCATCTGCT ACAAAGAATC TGTAGTCCAA AGAGGAAACC
          ACCGGGAGAG GAGTAGACGA TGTTTCTTAG ACATCTAGTT TCTCCTTTGG
     1751 AGATAATGTC AGACAAGAGG AATGTCATCC TGTTTTCTGT ATTTGATGAG
          TCTATTACAG TCTGTTCTCC TTACAGTAGG ACAAAAGACA TAAACTACTC
     1801 AACCGAAGCT GGTACCTCAC AGAGAATATA CAACGCTTTC TCCCCAATCC
          TTGGCTTCGA CCATGGAGTG TCTCTTATAT GTTGCGAAAG AGGGGTTAGG
     1851 AGCTGGAGTA CAGCTTGAGG ATCCAGAGTT CCAAGCCTCC AACATCATGC
          TCGACCTCAT GTCGAACTCC TAGGTCTCAA GGTTCGAAGG TTGTAGTACG
     1901 ACAGCATCAA TGGCTATGTT TTTGATAGTT TGCAGTTGTC AGTTTGTTTC
          TGTCGTAGTT ACCGATACAA AAACTATCAA ACGTCAACAG TCAAACAAAC
     1951 CATGAGGTGG CATACTGGTA CATTCTAAGC ATTGGAGCAC AGACTGACTT
          GTACTCCACC GTATGACCAT GTAAGATTCG TAACCTCGTG TCTGACTGAA
     2001 CCTTTCTGTC TTCTTCTCTG GATATATTCT CAAACACAAA ATGGTCTATG
          GGAAAGACAG AAGAAGAGAC CTATATAAGA GTTTGTGTTT TACCAGATAC
     2051 AAGACACACT CACCCTATTC CCATTCTCAG GAGAAACTGT CTTCATGTCG
          TTCTGTGTGA GTGGGATAAG GGTAAGAGTC CTCTTTGACA GAAGTACAGC
     2101 ATGGAAAACC CAGGTCTATG GATTCTGGGG TGCCACAACT CAGACTTTCG
          TACCTTTTGG GTCCAGATAC CTAAGACCCC ACGGTGTTGA GTCTGAAAGC
     2151 GAACAGAGGC ATGACCGCCT TACTGAAGGT TTCTAGTTGT GACAAGAACA
          CTTGTCTCCG TACTGGCGGA ATGACTTCCA AAGATCAACA CTGTTCTTGT
     2201 CTGGTGATTA TTACGAGGAC AGTTATGAAG ATATTTCAGC ATACTTGCTG
          GACCACTAAT AATGCTCCTG TCAATACTTC TATAAAGTCG TATGAACGAC
     2251 AGTAAAAACA ATGCCATTGA ACCTAGGAGC TTCTCTCAGA ATCCACCAGT
          TCATTTTTGT TACGGTAACT TGGATCCTCG AAGAGAGTCT TAGGTGGTCA
     2301 CTTGAAACGC CATCAACGGG AAATAACTCG TACTACTCTT CAGTCAGATC
          GAACTTTGCG GTAGTTGCCC TTTATTGAGC ATGATGAGAA GTCAGTCTAG
     2351 AAGAGGAAAT TGACTATGAT GATACCATAT CAGTTGAAAT GAAGAAGGAA
          TTCTCCTTTA ACTGATACTA CTATGGTATA GTCAACTTTA CTTCTTCCTT
     2401 GATTTTGACA TTTATGATGA GGATGAAAAT CAGAGCCCCC GCAGCTTTCA
          CTAAAACTGT AAATACTACT CCTACTTTTA GTCTCGGGGG CGTCGAAAGT
     2451 AAAGAAAACA CGACACTATT TTATTGCTGC AGTGGAGAGG CTCTGGGATT
          TTTCTTTTGT GCTGTGATAA AATAACGACG TCACCTCTCC GAGACCCTAA
     2501 ATGGGATGAG TAGCTCCCCA CATGTTCTAA GAAACAGGGC TCAGAGTGGC
```

FIG. 7B

```
      TACCCTACTC ATCGAGGGGT GTACAAGATT CTTTGTCCCG AGTCTCAGCG
2551  AGTGTCCTC  AGTTCAAGAA AGTTGTTTTC CAGGAATTTA CTGATGGCTC
      TCACAGGGAG TCAAGTTCTT TCAACAAAAG GTCCTTAAAT GACTACCGAG
2601  CTTTACTCAG CCCTTATACC GTGGAGAACT AAATGAACAT TTGGGACTCC
      GAAATGAGTC GGGAATATGG CACCTCTTGA TTTACTTGTA AACCCTGAGG
2651  TGGGGCCATA TATAAGAGCA GAAGTTGAAG ATAATATCAT GGTAACTTTC
      ACCCCGGTAT ATATTCTCGT CTTCAACTTC TATTATAGTA CCATTGAAAG
2701  AGAAATCAGG CCTCTCGTCC CTATTCCTTC TATTCTAGCC TTATTTCTTA
      TCTTTAGTCC GGAGAGCAGG GATAAGGAAG ATAAGATCGG AATAAAGAAT
2751  TGAGGAAGAT CAGAGGCAAG GAGCAGAACC TAGAAAAAAC TTTGTCAAGC
      ACTCCTTCTA GTCTCCGTTC CTCGTCTTGG ATCTTTTTTG AAACAGTTCG
2801  CTAATGAAAC CAAAACTTAC TTTTGGAAAG TGCAACATCA TATGGCACCC
      GATTACTTTG GTTTTGAATG AAAACCTTTC ACGTTGTAGT ATACCGTGGG
2851  ACTAAAGATG AGTTTGACTG CAAAGCCTGG GCTTATTTCT CTGATGTTGA
      TGATTTCTAC TCAAACTGAC GTTTCGGACC CGAATAAAGA GACTACAACT
2901  CCTGGAAAAA GATGTGCACT CAGGCCTGAT TGGACCCCTT CTGGTCTGCC
      GGACCTTTTT CTACACGTGA GTCCGGACTA ACCTGGGGAA GACCAGACGG
2951  ACACTAACAC ACTGAACCCT GCTCATGGGA GACAAGTGAC AGTACAGGAA
      TGTGATTGTG TGACTTGGGA CGAGTACCCT CTGTTCACTG TCATGTCATT
3001  TTTGCTCTGT TTTTCACCAT CTTTGATGAG ACCAAAAGCT GGTACTTCAC
      AAACGAGACA AAAAGTGGTA GAAACTACTC TGGTTTTCGA CCATGAAGTG
3051  TGAAAATATG GAAAGAAACT GCAGGGCTCC CTGCAATATC CAGATGGAAG
      ACTTTTATAC CTTTCTTTGA CGTCCCGAGG GACGTTATAG GTCTACCTTC
3101  ATCCCACTTT TAAAGAGAAT TATCGCTTCC ATGCAATCAA TGGCTACATA
      TAGGGTGAAA ATTTCTCTTA ATAGCGAAGG TACGTTAGTT ACCGATGTAT
3151  ATGGATACAC TACCTGGCTT AGTAATGGCT CAGGATCAAA GGATTCGATG
      TACCTATGTG ATGGACCGAA TCATTACCGA GTCCTAGTTT CCTAAGCTAC
3201  GTATCTGCTC AGCATGGGCA GCAATGAAAA CATCCATTCT ATTCATTTCA
      CATAGACGAG TCGTACCCGT CGTTACTTTT GTAGGTAAGA TAAGTAAAGT
3251  GTGGACATGT GTTCACTGTA CGAAAAAAAG AGGAGTATAA AATGGCACTG
      CACCTGTACA CAAGTGACAT GCTTTTTTTC TCCTCATATT TTACCGTGAC
3301  TACAATCTCT ATCCAGGTGT TTTTGAGACA GTGGAAATGT TACCATCCAA
      ATGTTAGAGA TAGGTCCACA AAAACTCTGT CACCTTTACA ATGGTAGGTT
3351  AGCTGGAATT TGGCGGGTGG AATGCCTTAT TGGCAGCAT  CTACATGCTG
      TCGACCTTAA ACCGCCCACC TTACGGAATA ACCGTCGTA  GATGTACGAC
3401  GGATGAGCAC ACTTTTTCTG GTGTACAGCA ATAAGTGTCA GACTCCCCTG
      CCTACTCGTG TGAAAAAGAC CACATGTCGT TATTCACAGT CTGAGGGGAC
3451  GGAATGGCTT CTGGACACAT TAGAGATTTT CAGATTACAG CTTCAGGACA
      CCTTACCGAA GACCTGTGTA ATCTCTAAAA GTCTAATGTC GAAGTCCTGT
3501  ATATGGACAG TGGGCCCCAA AGCTGGCCAG ACTTCATTAT TCCGGATCAA
      TATACCTGTC ACCCGGGGTT TCGACCGGTC TGAAGTAATA AGGCCTAGTT
3551  TCAATGCCTG GAGCACCAAG GAGCCCTTTT CTTGGATCAA GGTGGATCTG
      AGTTACGGAC CTCGTGGTTC CTCGGGAAAA GAACCTAGTT CCACCTAGAC
3601  TTGGCACCAA TGATTATTCA CGGCATCAAG ACCCAGGGTG CCCGTCAGAA
      AACCGTGGTT GCCGTAGTTC GCCGTAGTTC TGGGTCCCAC GGGCAGTCTT
3651  GTTCTCCAGC CTCTACATCT CTCAGTTTAT CATCATGTAT AGTCTTGATG
      CAAGAGGTCG GAGATGTAGA GAGTCAAATA GTAGTACATA TCAGAACTAC
3701  GGAAGAAGTG GCAGACTTAT CGAGGAAATT CCACTGGAAC CTTAATGGTC
      CCTTCTTCAC CGTCTGAATA GCTCCTTTAA GGTGACCTTG GAATTACCAG
3751  TTCTTTGGCA ATGTGGATTC ATCTGGGATA AAACACAATA TTTTTAACCC
      AAGAAACCGT TACACCTAAG TAGACCCTAT TTTGTGTTAT AAAAATTGGG
3801  TCCAATTATT GCTCGATACA TCCGTTTGCA CCCAACTCAT TATAGCATTC
```

FIG. 7C

```
      AGGTTAATAA CGAGCTATGT AGGCAAAGCT GGGTTGAGTA ATATCGTAAG
3851  GCAGCACTCT TCGCATGGAG TTGATGGGCT GTGATTTAAA TAGTTGCAGC
      CGTCGTGAGA AGCGTACCTC AACTACCCGA CACTAAATTT ATCAACGTCG
3901  ATGCCATTGG GAATGGAGAG TAAAGCAATA TCAGATGCAC AGATTACTGC
      TACGGTAACC CTTACCTCTC ATTTCGTTAT AGTCTACGTG TCTAATGACG
3951  TTCATCCTAC TTTACCAATA TGTTTGCCAC CTGGTCTCCT TCAAAAGCTC
      AAGTAGGATG AAATGGTTAT ACAAACGGTG GACCAGAGGA AGTTTTCGAG
4001  GACTTCACCT CCAAGGGAGG AGTAATGCCT GGAGACCTCA GGTGAATAAT
      CTGAAGTGGA GGTTCCCTCC TCATTACGGA CCTCTGGAGT CCACTTATTA
4051  CCAAAAGAGT GGCTGCAAGT GGACTTCCAG AAGACAATGA AAGTCACAGG
      GGTTTTCTCA CCGACGTTCA CCTGAAGGTC TTCTGTTACT TTCAGTGTCC
4101  AGTAACTACT CAGGGAGTAA AATCTCTGCT TACCAGCATG TATGTGAAGG
      TCATTGATGA GTCCCTCATT TTAGAGACGA ATGGTCGTAC ATACACTTCC
4151  AGTTCCTCAT CTCCAGCAGT CAAGATGGCC ATCAGTGGAC TCTCTTTTTT
      TCAAGGAGTA GAGGTCGTCA GTTCTACCGG TAGTCACCTG AGAGAAAAAA
4201  CAGAATGGCA AAGTAAAGGT TTTTCAGGGA AATCAAGACT CCTTCACACC
      GTCTTACCGT TCATTTCCA AAAACTCCCT TTAGTTCTGA GGAAGTGTGG
4251  TGTGGTGAAC TCTCTAGACC CACCGTTACT GACTCGCTAC CTTCGAATTC
      ACACCACTTG AGAGATCTGG GTGGCAATGA CTGAGCGATG GAAGCTTAAG
4301  ACCCCCAGAG TTCGGTGCAC CAGATTGCCC TGAGGATGGA GGTTCTGGGC
      TGGGGGTCTC AACCCACGTG GTCTAACGGG ACTCCTACCT CCAAGACCCG
4351  TGCGAGGCAC AGGACCTCTA C
      ACGCTCCGTG TCCTGGAGAT G 1-57 SIGNAL PEPTIDE
58-1173 A1 DOMAIN
1174-2277 A2 DOMAIN
2278-2319 SQ LINKER
2320-3432 ap-A3 DOMAINS
3433-3891 C1 DOMAIN
3892-4371 C2 DOMAIN
```

FIG. 7D

AMINO ACID SEQUENCE OF HP47/OL

```
   1  MQLELSTCVF LCLLPLGFSA IRRYYLGAVE LSWDYRQSEL LRELHVDTRF
  51  PATAPGALPL GPSVLYKKTV FVEFTDQLFS VARPRPPWMG LLGPTIQAEV
 101  YDTVVVTLKN MASHPVSLHA VGVSFWKSSE GAEYEDHTSQ REKEDDKVLP
 151  GKSQTYVWQV LKENGPTASD PPCLTYSYLS HVDLVKDLNS GLIGALLVCR
 201  EGSLTRERTQ NLHEFVLLFA VFDEGKSWHS ARNDSWTRAM DPAPARAQPA
 251  MHTVNGYVNR SLPGLIGCHK KSVYWHVIGM GTSPEVHSIF LEGHTFLVRH
 301  HRQASLEISP LTFLTAQTFL MDLGQFLLFC HISSHHHGGM EAHVRVESCA
 351  EEPQLRRKAD EEEDYDDNLY DSDMDVVRLD GDDVSPFIQI RSVAKKHPKT
 401  WVHYIAAEEE DWDYAPLVLA PDDRSYKSQY LNNGPQRIGR KYKKVRFMAY
 451  TDETFKTREA IQHESGILGP LLYGEVGDTL LIIFKNQASR PYNIYPHGIT
 501  DVRPLYSRRL PKGVKHLKDF PILPGEIFKY KWTVTVEDGP TKSDPRCLTR
 551  YYSSFVNMER DLASGLIGPL LICYKESVDQ RGNQIMSDKR NVILFSVFDE
 601  NRSWYLTENI QRFLPNPAGV QLEDPEFQAS NIMHSINGYV FDSLQLSVCL
 651  HEVAYWYILS IGAQTDFLSV FFSGYTFKHK MVYEDTLTLF PFSGETVFMS
 701  MENPGLWILG CHNSDFRNRG MTALLKVSSC DKNTGDYYED SYEDISAYLL
 751  SKNNAIEPRS FAQNSRPPSA SAPKPPVLRR HQRDISLPTF QPEEDKMDYD
 801  DIFSTETKGE DFDIYGEDEN QDPRSFQKRT RHYFIAAVEQ LWDYGMSESP
 851  RALRNRAQNG EVPRFKKVVF REFADGSFTQ PSYRGELNKH LGLLGPYIRA
 901  EVEDNIMVTF KNQASRPYSF YSSLISYPDD QEQGAEPRHN FVQPNETRTY
 951  FWKVQHHMAP TEDEFDCKAW AYFSDVDLEK DVHSGLIGPL LICRANTLNA
1001  AHGRQVTVQE FALFFTIFDE TKSWYFTENV ERNCRAPCHL QMEDPTLKEN
1051  YRFHAINGYV MDTLPGLVMA QNQRIRWYLL SMGSNENIHS IHFSGHVFSV
1101  RKKEEYKMAV YNLYPGVFET VEMLPSKVGI WRIECLIGEH LQAGMSTTFL
1151  VYSKKCQTPL GMASGHIRDF QITASGQYGQ WAPKLARLHY SGSINAWSTK
1201  EPFSWIKVDL LAPMIIHGIK TQGARQKFSS LYISQFIIMY SLDGKKWQTY
1251  RGNSTGTLMV FFGNVDSSGI KHNIFNPPII ARYIRLHPTH YSIRSTLRME
1301  LMGCDLNSCS MPLGMESKAI SDAQITASSY FTNMFATWSP SKARLHLQGR
1351  SNAWRPQVNN PKEWLQVDFQ KTMKVTGVTT QGVKSLLTSM YVKEFLISSS
1401  QDGHQWTLFF QNGKVKVFQG NQDSFTPVVN SLDPPLLTRY LRIHPQSWVH
1451  QIALRMEVLG CEAQDLY*
```

1-19 SIGNAL PEPTIDE
20-391 A1 DOMAIN
392-759 A2 DOMAIN
760-783 OL LINKER
784-1154 ap-A3
1155-1307 C1 DOMAIN
1308-1467 C2 DOMAIN

FIG. 8

HP47/OL NUCLEOTIDE SEQUENCE

```
   1  ATGCAGCTAG AGCTCTCCAC CTGTGTCTTT CTGTGTCTCT TGCCACTCGG
      TACGTCGATC TCGAGAGGTG GACACAGAAA GACACAGAGA ACGGTGAGCC
  51  CTTTAGTGCC ATCAGGAGAT ACTACCTGGG CGCAGTGGAA CTGTCCTGGG
      GAAATCACGG TAGTCCTCTA TGATGGACCC GCGTCACCTT GACAGGACCC
 101  ACTACCGGCA AAGTGAACTC CTCCGTGAGC TGCACGTGGA CACCAGATTT
      TGATGGCCGT TTCACTTGAG GAGGCACTCG ACGTGCACCT GTGGTCTAAA
 151  CCTGCTACAG CGCCAGGAGC TCTTCCGTTG GGCCCGTCAG TCCTGTACAA
      GGACGATGTC GCGGTCCTCG AGAAGGCAAC CCGGGCAGTC AGGACATGTT
 201  AAAGACTGTG TTCGTAGAGT TCACGGATCA ACTTTTCAGC GTTGCCAGGC
      TTTCTGACAC AAGCATCTCA AGTGCCTAGT TGAAAAGTCG CAACGGTCCG
 251  CCAGGCCACC ATGGATGGGT CTGCTGGGTC CTACCATCCA GGCTGAGGTT
      GGTCCGGTGG TACCTACCCA GACGACCCAG GATGGTAGGT CCGACTCCAA
 301  TACGACACGG TGGTCGTTAC CCTGAAGAAC ATGGCTTCTC ATCCGTTAG
      ATGCTGTGCC ACCAGCAATG GGACTTCTTG TACCGAAGAG TAGGGCAATC
 351  TCTTCACGCT GTCGGCGTCT CCTTCTGGAA ATCTTCCGAA GGCGCTGAAT
      AGAAGTGCGA CAGCCGCAGA GGAAGACCTT TAGAAGGCTT CCGCGACTTA
 401  ATGAGGATCA CACCAGCCAA AGGGAGAAGG AAGACGATAA AGTCCTTCCC
      TACTCCTAGT GTGGTCGGTT TCCCTCTTCC TTCTGCTATT TCAGGAAGGG
 451  GGTAAAAGCC AAACCTACGT CTGGCAGGTC CTGAAAGAAA ATGGTCCAAC
      CCATTTTCGG TTTGGATGCA GACCGTCCAG GACTTTCTTT TACCAGGTTG
 501  AGCCTCTGAC CCACCATGTC TTACCTACTC ATACCTGTCT CACGTGGACC
      TCGGAGACTG GGTGGTACAG AATGGATGAG TATGGACAGA GTGCACCTGG
 551  TGGTGAAAGA CCTGAATTCG GGCCTCATTG GAGCCCTGCT GGTTTGTAGA
      ACCACTTTCT GGACTTAAGC CCGGAGTAAC CTCGGGACGA CCAAACATCT
 601  GAAGGGAGTC TGACCAGAGA AAGGACCCAG AACCTGCACG AATTTGTACT
      CTTCCCTCAG ACTGGTCTCT TTCCTGGGTC TTGGACGTGC TTAAACATGA
 651  ACTTTTTGCT GTCTTTGATG AAGGGAAAAG TTGGCACTCA GCAAGAAATG
      TGAAAAACGA CAGAAACTAC TTCCCTTTTC AACCGTGAGT CGTTCTTTAC
 701  ACTCCTGGAC ACGGGCCATG GATCCCGCAC CTGCCAGGGC CCAGCCTGCA
      TGAGGACCTG TGCCCGGTAC CTAGGGCGTG GACGGTCCCG GGTCGGACGT
 751  ATGCACACAG TCAATGGCTA TGTCAACAGG TCTCTGCCAG GTCTGATCGG
      TACGTGTGTC AGTTACCGAT ACAGTTGTCC AGAGACGGTC CAGACTAGCC
 801  ATGTCATAAG AAATCAGTCT ACTGGCACGT GATTGGAATG GGCACCAGCC
      TACAGTATTC TTTAGTCAGA TGACCGTGCA CTAACCTTAC CCGTGGTCGG
 851  CGGAAGTGCA CTCCATTTTT CTTGAAGGCC ACACGTTTCT CGTGAGGCAC
      GCCTTCACGT GAGGTAAAAA GAACTTCCGG TGTGCAAAGA GCACTCCGTG
 901  CATCGCCAGG CTTCCTTGGA GATCTCGCCA CTAACTTTCC TCACTGCTCA
      GTAGCGGTCC GAAGGAACCT CTAGAGCGGT GATTGAAAGG AGTGACGAGT
 951  GACATTCCTG ATGGACCTTG GCCAGTTCCT ACTGTTTTGT CATATCTCTT
      CTGTAAGGAC TACCTGGAAC CGGTCAAGGA TGACAAAACA GTATAGAGAA
1001  CCCACCACCA TGGTGGCATG GAGGCTCACG TCAGAGTAGA AAGCTGCGCC
      GGGTGGTGGT ACCACCGTAC CTCCGAGTGC AGTCTCATCT TTCGACGCGG
1051  GAGGAGCCCC AGCTGCGGAG GAAAGCTGAT GAAGAGGAAG ATTATGATGA
      CTCCTCGGGG TCGACGCCTC CTTTCGACTA CTTCTCCTTC TAATACTACT
1101  CAATTTGTAC GACTCGGACA TGGACGTGGT CCGGCTCGAT GGTGACGACG
      GTTAAACATG CTGAGCCTGT ACCTGCACCA GGCCGAGCTA CCACTGCTGC
1151  TGTCTCCCTT TATCCAAATC CGCTCGGTTG CCAAGAAGCA TCCTAAAACT
      ACAGAGGGAA ATAGGTTTAG GCGAGCCAAC GGTTCTTCGT AGGATTTTGA
1201  TGGGTACATT ACATTGCTGC TGAAGAGGAG GACTGGGACT ATGCTCCCTT
```

FIG. 9A

```
           ACCCATGTAA TGTAACGACG ACTTCTCCTC CTGACCCTGA TACGAGGGAA
1251       AGTCCTCGCC CCCGATGACA GAAGTTATAA AAGTCAATAT TTGAACAATG
           TCAGGAGCGG GGGCTACTGT CTTCAATATT TTCAGTTATA AACTTGTTAC
1301       GCCCTCAGCG GATTGGTAGG AAGTACAAAA AAGTCCGATT TATGGCATAC
           CGGGAGTCGC CTAACCATCC TTCATGTTTT TTCAGGCTAA ATACCGTATG
1351       ACAGATGAAA CCTTTAAGAC GCGTGAAGCT ATTCAGCATG AATCAGGAAT
           TGTCTACTTT GGAAATTCTG CGCACTTCGA TAAGTCGTAC TTAGTCCTTA
1401       CTTGGGACCT TTACTTTATG GGGAAGTTGG AGACACACTG TTGATTATAT
           GAACCCTGGA AATGAAATAC CCCTTCAACC TCTGTGTGAC AACTAATATA
1451       TTAAGAATCA AGCAAGCAGA CCATATAACA TCTACCCTCA CGGAATCACT
           AATTCTTAGT TCGTTCGTCT GGTATATTGT AGATGGGAGT GCCTTAGTGA
1501       GATGTCCGTC CTTTGTATTC AAGGAGATTA CCAAAAGGTG TAAAACATTT
           CTACAGGCAG GAAACATAAG TTCCTCTAAT GGTTTTCCAC ATTTTGTAAA
1551       GAAGGATTTT CCAATTCTGC CAGGAGAAAT ATTCAAATAT AAATGGACAG
           CTTCCTAAAA GGTTAAGACG GTCCTCTTTA TAAGTTTATA TTTACCTGTC
1601       TGACTGTAGA AGATGGGCCA ACTAAATCAG ATCCGCGGTG CCTGACCCGC
           ACTGACATCT TCTACCCGGT TGATTTAGTC TAGGCGCCAC GGACTGGGCG
1651       TATTACTCTA GTTTCGTTAA TATGGAGAGA GATCTAGCTT CAGGACTCAT
           ATAATGAGAT CAAAGCAATT ATACCTCTCT CTAGATCGAA GTCCTGAGTA
1701       TGGCCCTCTC CTCATCTGCT ACAAAGAATC TGTAGATCAA AGAGGAAACC
           ACCGGGAGAG GAGTAGACGA TGTTTCTTAG ACATCTAGTT TCTCCTTTGG
1751       AGATAATGTC AGACAAGAGG AATGTCATCC TGTTTTCTGT ATTTGATGAG
           TCTATTACAG TCTGTTCTCC TTACAGTAGG ACAAAAGACA TAAACTACTC
1801       AACCGAAGCT GGTACCTCAC AGAGAATATA CAACGCTTTC TCCCCAATCC
           TTGGCTTCGA CCATGGAGTG TCTCTTATAT GTTGCGAAAG AGGGGTTAGG
1851       AGCTGGAGTG CAGCTTGAGG ATCCAGAGTT CCAAGCCTCC AACATCATGC
           TCGACCTCAC GTCGAACTCC TAGGTCTCAA GGTTCGGAGG TTGTAGTACG
1901       ACAGCATCAA TGGCTATGTT TTTGATAGTT TGCAGTTGTC AGTTTGTTTG
           TGTCGTAGTT ACCGATACAA AAACTATCAA ACGTCAACAG TCAAACAAAC
1951       CATGAGGTGG CATACTGGTA CATTCTAAGC ATTGGAGCAC AGACTGACTT
           GTACTCCACC GTATGACCAT GTAAGATTCG TAACCTCGTG TCTGACTGAA
2001       CCTTTCTGTC TTCTTCTCTG GATATACCTT CAAACACAAA ATGGTCTATG
           GGAAAGACAG AAGAAGAGAC CTATATGGAA GTTTGTGTTT TACCAGATAC
2051       AAGACACACT CACCCTATTC CCATTCTCAG GAGAAACTGT CTTCATGTCG
           TTCTGTGTGA GTGGGATAAG GGTAAGAGTC CTCTTTGACA GAAGTACAGC
2101       ATGGAAAACC CAGGTCTATG GATTCTGGGG TGCCACAACT CAGACTTTCG
           TACCTTTTGG GTCCAGATAC CTAAGACCCC ACGGTGTTGA GTCTGAAAGC
2151       GAACAGAGGC ATGACCGCCT TACTGAAGGT TTCTAGTTGT GACAAGAACA
           CTTGTCTCCG TACTGGCGGA ATGACTTCCA AAGATCAACA CTGTTCTTGT
2201       CTGGTGATTA TTACGAGGAC AGTTATGAAG ATATTTCAGC ATACTTGCTG
           GACCACTAAT TTACGAGGAC TCAATACTTC TATAAAGTCG TATGAACGAC
2251       AGTAAAAACA ATGCCATTGA ACCTAGGAGC TTTGCCCAGA ATTCAAGACC
           TCATTTTTGT TACGGTAACT TGGATCCTCG AAACGGGTCT TAAGTTCTGG
2301       CCCTAGTGCG AGCGCTCCAA AGCCTCCGGT CCTGCGACGG CATCAGAGGG
           GGGATCACGC TCGCGAGGTT TCGGAGGCCA GGACGCTGCC GTAGTCTCCC
2351       ACATAAGCCT TCCTACTTTT CAGCCGGAGG AAGACAAAAT GGACTATGAT
           TGTATTCGGA AGGATGAAAA GTCGGCCTCC TTCTGTTTTA CCTGATACTA
2401       GATATCTTCT CAACTGAAAC GAAGGGAGAA GATTTTGACA TTTACGGTGA
           CTATAGAAGA GTTGACTTTG CTTCCCTCTT CTAAAACTGT AAATGCCACT
2451       GGATGAAAAT CAGGACCCTC GCAGCTTTCA GAAGAGAACC CGACACTATT
           CCTACTTTTA GTCCTGGGAG CGTCGAAAGT CTTCTCTTGG GCTGTGATAA
2501       TCATTGCTGC GGTGGAGCAG CTCTGGGATT ACGGGATGAG CGAATCCCCC
```

FIG. 9B

```
          AGTAACGACG CCACCTCGTC GAGACCCTAA TGCCCTACTC GCTTAGGGGG
2551 CGGGCGCTAA GAAACAGGGC TCAGAACGGA GAGGTGCCTC GGTTCAAGAA
          GCCCGCGATT CTTTGTCCCG AGTCTTGCCT CTCCACGGAG CCAAGTTCTT
2601 GGTGGTCTTC CGGGAATTTG CTGACGGCTC CTTCACGCAG CCGTCGTACC
          CCACCAGAAG GCCCTTAAAC GACTGCCGAG GAAGTGCGTC GGCAGCATGG
2651 GCGGGGAACT CAACAAACAC TTGGGGCTCT TGGGACCCTA CATCAGAGCG
          CGCCCCTTGA GTTGTTTGTG AACCCCGAGA ACCCTGGGAT GTAGTCTCGC
2701 GAAGTTGAAG ACAACATCAT GGTAACTTTC AAAAACCAGG CGTCTCGTCC
          CTTCAACTTC TGTTGTAGTA CCATTGAAAG TTTTTGGTCC GCAGAGCAGG
2751 CTATTCCTTC TACTCGAGCC TTATTTCTTA TCCGGATGAT CAGGAGCAAG
          GATAAGGAAG ATGAGCTCGG AATAAAGAAT AGGCCTACTA GTCCTCGTTC
2801 GGGCAGAACC TCGACACAAC TTCGTCCAGC CAAATGAAAC CAGAACTTAC
          CCCGTCTTGG AGCTGTGTTG AAGCAGGTCG GTTTACTTTG GTCTTGAATG
2851 TTTTGGAAAG TGCAGCATCA CATGGCACCC ACAGAAGACG AGTTTGACTG
          AAAACCTTTC ACGTCGTAGT GTACCGTGGG TGTCTTCTGC TCAAACTGAC
2901 CAAAGCCTGG GCCTACTTTT CTGATGTTGA CCTGGAAAAA GATGTGCACT
          GTTTCGGACC CGGATGAAAA GACTACAACT GGACCTTTTT CTACACGTGA
2951 CAGGCTTGAT CGGCCCCCTT CTGATCTGCC GCGCCAACAC CCTGAACGCT
          GTCCGAACTA GCCGGGGAA GACTAGACGG CGCGGTTGTG GGACTTGCGA
3001 GCTCACGGTA GACAAGTGAC CGTGCAAGAA TTTGCTCTGT TTTTCACTAT
          CGAGTGCCAT CTGTTCACTG GCACGTTCTT AAACGAGACA AAAAGTGATA
3051 TTTTGATGAG ACAAAGAGCT GGTACTTCAC TGAAAATGTG GAAAGGAACT
          AAAACTACTC TGTTTCTCGA CCATGAAGTG ACTTTTACAC CTTTCCTTGA
3101 GCCGGGCCCC CTGCCATCTG CAGATGGAGG ACCCCACTCT GAAAGAAAAC
          CGGCCCGGGG GACGGTAGAC GTCTACCTCC TGGGGTGAGA CTTTCTTTTG
3151 TATCGCTTCC ATGCAATCAA TGGCTATGTG ATGGATACAC TCCCTGGCTT
          ATAGCGAAGG TACGTTAGTT ACCGATACAC TACCTATGTG AGGGACCGAA
3201 AGTAATGGCT CAGAATCAAA GGATCCGATG GTATCTGCTC AGCATGGGCA
          TCATTACCGA GTCTTAGTTT CCTAGGCTAC CATAGACGAG TCGTACCCGT
3251 GCAATGAAAA TATCCATTCG ATTCATTTTA GCGGACACGT GTTCAGTGTA
          CGTTACTTTT ATAGGTAAGC TAAGTAAAAT CGCCTGTGCA CAAGTCACAT
3301 CGGAAAAAGG AGGAGTATAA AATGGCCGTG TACAATCTCT ATCCGGGTGT
          GCCTTTTTCC TCCTCATATT TTACCGGCAC ATGTTAGAGA TAGGCCCACA
3351 CTTTGAGACA GTGGAAATGC TACCGTCCAA AGTTGGAATT TGGCGAATAG
          GAAACTCTGT CACCTTTACG ATGGCAGGTT TCAACCTTAA ACCGCTTATC
3401 AATGCCTGAT TGGCGAGCAC CTGCAAGCTG GGATGAGCAC GACTTCCTG
          TTACGGACTA ACCGCTCGTG GACGTTCGAC CCTACTCGTG CTGAAAGGAC
3451 GTGTACAGCA AGAAGTGTCA GACTCCCCTG GAATGGCTT CTGGACACAT
          CACATGTCGT TCTTCACAGT CTGAGGGGAC CCTTACCGAA GACCTGTGTA
3501 TAGAGATTTT CAGATTACAG CTTCAGGACA ATATGGACAG TGGGCCCCAA
          ATCTCTAAAA GTCTAATGTC GAAGTCCTGT TATACCTGTC ACCCGGGGTT
3551 AGCTGGCCAG ACTTCATTAT TCCGGATCAA TCAATGCCTG GAGCACCAAG
          TCGACCGGTC TGAAGTAATA AGGCCTAGTT AGTTACGGAC CTCGTGGTTC
3601 GAGCCCTTTT CTTGGATCAA GGTGGATCTG TTGGCACCAA TGATTATTCA
          CTCGGGAAAA GAACCTAGTT CCACCTAGAC AACCGTGGTT ACTAATAAGT
3651 CGGCATCAAG ACCCAGGGTG CCCGTCAGAA GTTCTCCAGC CTCTACATCT
          GCCGTAGTTC TGGGTCCCAC GGGCAGTCTT CAAGAGGTCG GAGATGTAGA
3701 CTCAGTTTAT CATCATGTAT AGTCTTGATG GGAAGAAGTG GCAGACTTAT
          GAGTCAAATA GTAGTACATA TCAGAACTAC CCTTCTTCAC CGTCTGAATA
3751 CGAGGAAATT CCACTGGAAC CTTAATGGTC TTCTTTGGCA ATGTGGATTC
          GCTCCTTTAA GGTGACCTTG GAATTACCAG AAGAAACCGT TACACCTAAG
3801 ATCTGGGATA AAACACAATA TTTTTAACCC TCCAATTATT GCTCGATACA
```

FIG. 9C

```
           TAGACCCTAT  TTTGTGTTAT  AAAAATTGGG  AGGTTAATAA  CGAGCTATGT
3851       TCCGTTTGCA  CCCAACTCAT  TATAGCATTC  GCAGCACTCT  TCGCATGGAG
           AGGCAAACGT  GGGTTGAGTA  ATATCGTAAG  CGTCGTGAGA  AGCGTACCTC
3901       TTGATGGGCT  GTGATTTAAA  TAGTTGCAGC  ATGCCATTGG  GAATGGAGAG
           AACTACCCGA  CACTAAATTT  ATCAACGTCG  TACGGTAACC  CTTACCTCTC
3951       TAAAGCAATA  TCAGATGCAC  AGATTACTGC  TTCATCCTAC  TTTACCAATA
           ATTTCGTTAT  AGTCTACGTG  TCTAATGACG  AAGTAGGATG  AAATGGTTAT
4001       TGTTTGCCAC  CTGGTCTCCT  TCAAAAGCTC  GACTTCACCT  CCAAGGGAGG
           ACAAACGGTG  GACCAGAGGA  AGTTTTCGAG  CTGAAGTGGA  GGTTCCCTCC
4051       AGTAATGCCT  GGAGACCTCA  GGTGAATAAT  CCAAAAGAGT  GGCTGCAAGT
           TCATTACGGA  CCTCTGGAGT  CCACTTATTA  GGTTTTCTCA  CCGACGTTCA
4101       GGACTTCCAG  AAGACAATGA  AAGTCACAGG  AGTAACTACT  CAGGGAGTAA
           CCTGAAGGTC  TTCTGTTACT  TTCAGTGTCC  TCATTGATGA  GTCCCTCATT
4151       AATCTCTGCT  TACCAGCATG  TATGTGAAGG  AGTTCCTCAT  CTCCAGCAGT
           TTAGAGACGA  ATGGTCGTAC  ATACACTTCC  TCAAGGAGTA  GAGGTCGTCA
4201       CAAGATGGCC  ATCAGTGGAC  TCTCTTTTTT  CAGAATGGCA  AAGTAAAGGT
           GTTCTACCGG  TAGTCACCTG  AGAGAAAAAA  GTCTTACCGT  TTCATTTCCA
4251       TTTTCAGGGA  AATCAAGACT  CCTTCACACC  TGTGGTGAAC  TCTCTAGACC
           AAAAGTCCCT  TTAGTTCTGA  GGAAGTGTGG  ACACCACTTG  AGAGATCTGG
4301       CACCGTTACT  GACTCGCTAC  CTTCGAATTC  ACCCCAGAG   TTGGGTGCAC
           GTGGCAATGA  CTGAGCGATG  GAAGCTTAAG  TGGGGGTCTC  AACCCACGTG
4351       CAGATTGCCC  TGAGGATGGA  GGTTCTGGGC  TGCGAGGCAC  AGGACCTCTA
           GTCTAACGGG  ACTCCTACCT  CCAAGACCCG  ACGCTCCGTG  TCCTGGAGAT
4401       C
           G
```

FIG. 9D

AMINO ACID SEQUENCE OF HUMAN B DOMAIN-DELETED FACTOR VIII (HSQ)

```
Met Gln Ile Glu Leu Ser Thr Cys Phe Phe Leu Cys Leu Leu Arg Phe
 1            5                    10                  15
Cys Phe Ser Ala Thr Arg Arg Tyr Tyr Leu Gly Ala Val Glu Leu Ser
            20                  25                  30
Trp Asp Tyr Met Gln Ser Asp Leu Gly Glu Leu Pro Val Asp Ala Arg
            35                  40                  45
Phe Pro Pro Arg Val Pro Lys Ser Phe Pro Phe Asn Thr Ser Val Val
    50                  55                  60
Tyr Lys Lys Thr Leu Phe Val Glu Phe Thr Val His Leu Phe Asn Ile
65                  70                  75                  80
Ala Lys Pro Arg Pro Pro Trp Met Gly Leu Leu Gly Pro Thr Ile Gln
                85                  90                  95
Ala Glu Val Tyr Asp Tyr Val Val Ile Thr Leu Lys Asn Met Ala Ser
            100                 105                 110
His Pro Val Ser Leu His Ala Val Gly Val Ser Tyr Trp Lys Ala Ser
            115                 120                 125
Glu Gly Ala Glu Thr Asp Asp Gln Thr Ser Gln Arg Glu Lys Glu Asp
    130                 135                 140
Asp Lys Val Phe Pro Gly Gly Ser His Thr Tyr Val Trp Gln Val Leu
145                 150                 155                 160
Lys Glu Asn Gly Pro Met Ala Ser Asp Pro Leu Cys Leu Thr Tyr Ser
                165                 170                 175
Tyr Leu Ser His Val Asp Leu Val Lys Asp Leu Asn Ser Gly Leu Ile
            180                 185                 190
Gly Ala Leu Leu Val Cys Arg Glu Gly Ser Leu Ala Lys Glu Lys Thr
            195                 200                 205
Gln Thr Leu His Lys Phe Ile Leu Leu Phe Ala Val Phe Asp Glu Gly
    210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
            260                 265                 270
Tyr Trp His Val Ile Gly Met Gly Thr Thr Pro Glu Val His Ser Ile
            275                 280                 285
Phe Leu Glu Gly His Thr Phe Leu Val Arg Asn His Arg Gln Ala Ser
    290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
            340                 345                 350
Gln Leu Arg Met Lys Asn Asn Glu Glu Ala Glu Asp Tyr Asp Asp Asp
            355                 360                 365
Leu Thr Asp Ser Glu Met Asp Val Val Arg Phe Asp Asp Asp Asn Ser
370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Asp Trp Asp Tyr Ala Pro
```

FIG. 10A

```
                         405                        410                        415
Leu Val Leu Ala Pro Asp Asp Arg Ser Tyr Lys Ser Gln Tyr Leu Asn
                420                        425                   430
Asn Gly Pro Gln Arg Ile Gly Arg Lys Tyr Lys Lys Val Arg Phe Met
            435                        440                   445
Ala Tyr Thr Asp Glu Thr Phe Lys Thr Arg Glu Ala Ile Gln His Glu
        450                        455                   460
Ser Gly Ile Leu Gly Pro Leu Leu Tyr Gly Glu Val Gly Asp Thr Leu
465                            470                    475                480
Leu Ile Ile Phe Lys Asn Gln Ala Ser Arg Pro Tyr Asn Ile Tyr Pro
                    485                        490                    495
His Gly Ile Thr Asp Val Arg Pro Leu Tyr Ser Arg Arg Leu Pro Lys
                500                        505                    510
Gly Val Lys His Leu Lys Asp Phe Pro Ile Leu Pro Gly Glu Ile Phe
            515                        520                    525
Lys Tyr Lys Trp Thr Val Thr Val Glu Asp Gly Pro Thr Lys Ser Asp
        530                        535                    540
Pro Arg Cys Leu Thr Arg Tyr Tyr Ser Ser Phe Val Asn Met Glu Arg
545                        550                    555                    560
Asp Leu Ala Ser Gly Leu Ile Gly Pro Leu Leu Ile Cys Tyr Lys Glu
                565                        570                    575
Ser Val Asp Gln Arg Gly Asn Gln Ile Met Ser Asp Lys Arg Asn Val
                580                        585                    590
Ile Leu Phe Ser Val Phe Asp Glu Asn Arg Ser Trp Tyr Leu Thr Glu
                595                        600                    605
Asn Ile Gln Arg Phe Leu Pro Asn Pro Ala Gly Val Gln Leu Glu Asp
            610                        615                    620
Pro Glu Phe Gln Ala Ser Asn Ile Met His Ser Ile Asn Gly Tyr Val
625                        630                    635                    640
Phe Asp Ser Leu Gln Leu Ser Val Cys Leu His Glu Val Ala Tyr Trp
                    645                        650                    655
Tyr Ile Leu Ser Ile Gly Ala Gln Thr Asp Phe Leu Ser Val Phe Phe
                660                        665                    670
Ser Gly Tyr Thr Phe Lys His Lys Met Val Tyr Glu Asp Thr Leu Thr
            675                        680                    685
Leu Phe Pro Phe Ser Gly Glu Thr Val Phe Met Ser Met Glu Asn Pro
    690                        695                        700
Gly Leu Trp Ile Leu Gly Cys His Asn Ser Asp Phe Arg Asn Arg Gly
705                        710                    715                    720
Met Thr Ala Leu Leu Lys Val Ser Ser Cys Asp Lys Asn Thr Gly Asp
                    725                        730                    735
Tyr Tyr Glu Asp Ser Tyr Glu Asp Ile Ser Ala Tyr Leu Leu Ser Lys
                740                        745                    750
Asn Asn Ala Ile Glu Pro Arg Ser Phe Ser Gln Asn Pro Pro Val Leu
            755                        760                    765
Lys Arg His Gln Arg Glu Ile Thr Arg Thr Thr Leu Gln Ser Asp Gln
    770                        775                    780
Glu Glu Ile Asp Tyr Asp Asp Thr Ile Ser Val Glu Met Lys Lys Glu
785                        790                    795                    800
Asp Phe Asp Ile Tyr Asp Glu Asp Glu Asn Gln Ser Pro Arg Ser Phe
                    805                        810                    815
Gln Lys Lys Thr Arg His His Tyr Phe Ile Ala Ala Val Glu Arg Leu Trp
                820                        825                    830
Asp Tyr Gly Met Ser Ser Ser Pro His Val Leu Arg Asn Arg Ala Gln
            835                        840                    845
Ser Gly Ser Val Pro Gln Phe Lys Lys Val Val Phe Gln Glu Phe Thr
        850                        855                    860
```

FIG. 10B

```
Asp Gly Ser Phe Thr Gln Pro Leu Tyr Arg Gly Glu Leu Asn Glu His
865                 870                 875                 880
Leu Gly Leu Leu Gly Pro Tyr Ile Arg Ala Glu Val Glu Asp Asn Ile
            885                 890                     895
Met Val Thr Phe Arg Asn Gln Ala Ser Arg Pro Tyr Ser Phe Tyr Ser
            900                 905             910
Ser Leu Ile Ser Tyr Glu Glu Asp Gln Arg Gln Gly Ala Glu Pro Arg
            915                 920             925
Lys Asn Phe Val Lys Pro Asn Glu Thr Lys Thr Tyr Phe Trp Lys Val
930             935                     940
Gln His His Met Ala Pro Thr Lys Asp Glu Phe Asp Cys Lys Ala Trp
945                 950                 955                 960
Ala Tyr Phe Ser Asp Val Asp Leu Glu Lys Asp Val His Ser Gly Leu
            965             970                     975
Ile Gly Pro Leu Leu Val Cys His Thr Asn Thr Leu Asn Pro Ala His
            980             985                     990
Gly Arg Gln Val Thr Val Gln Glu Phe Ala Leu Phe Phe Thr Ile Phe
            995             1000                1005
Asp Glu Thr Lys Ser Trp Tyr Phe Thr Glu Asn Met Glu Arg Asn Cys
1010                1015                1020
Arg Ala Pro Cys Asn Ile Gln Met Glu Asp Pro Thr Phe Lys Glu Asn
1025                1030                1035                1040
Tyr Arg Phe His Ala Ile Asn Gly Tyr Ile Met Asp Thr Leu Pro Gly
                1045                1050                1055
Leu Val Met Ala Gln Asp Gln Arg Ile Arg Trp Tyr Leu Leu Ser Met
            1060                1065                1070
Gly Ser Asn Glu Asn Ile His Ser Ile His Phe Ser Gly His Val Phe
            1075                1080                1085
Thr Val Arg Lys Lys Glu Glu Tyr Lys Met Ala Leu Tyr Asn Leu Tyr
    1090                1095                1100
Pro Gly Val Phe Glu Thr Val Glu Met Leu Pro Ser Lys Ala Gly Ile
1105                1110                1115                1120
Trp Arg Val Glu Cys Leu Ile Gly Glu His Leu His Ala Gly Met Ser
                1125                1130                1135
Thr Leu Phe Leu Val Tyr Ser Asn Lys Cys Gln Thr Pro Leu Gly Met
                1140                1145                1150
Ala Ser Gly His Ile Arg Asp Phe Gln Ile Thr Ala Ser Gly Gln Tyr
    1155                1160                1165
Gly Gln Trp Ala Pro Lys Leu Ala Arg Leu His Tyr Ser Gly Ser Ile
    1170                1175                1180
Asn Ala Trp Ser Thr Lys Glu Pro Phe Ser Trp Ile Lys Val Asp Leu
1185                1190                1195                1200
Leu Ala Pro Met Ile Ile His Gly Ile Lys Thr Gln Gly Ala Arg Gln
                1205                1210                1215
Lys Phe Ser Ser Leu Tyr Ile Ser Gln Phe Ile Ile Met Tyr Ser Leu
                1220                1225                1230
Asp Gly Lys Lys Trp Gln Thr Tyr Arg Gly Asn Ser Thr Gly Thr Leu
        1235                1240                1245
Met Val Phe Phe Gly Asn Val Asp Ser Ser Gly Ile Lys His Asn Ile
1250                1255                1260
Phe Asn Pro Pro Ile Ile Ala Arg Tyr Ile Arg Leu His Pro Thr His
1265                1270                1275                1280
Tyr Ser Ile Arg Ser Thr Leu Arg Met Glu Leu Met Gly Cys Asp Leu
                1285                1290                1295
Asn Ser Cys Ser Met Pro Leu Gly Met Glu Ser Lys Ala Ile Ser Asp
            1300                1305                1310
Ala Gln Ile Thr Ala Ser Ser Tyr Phe Thr Asn Met Phe Ala Thr Trp
```

FIG. 10C

```
                1315                        1320                       1325
Ser Pro Ser Lys Ala Arg Leu His Leu Gln Gly Arg Ser Asn Ala Trp
    1330                    1335                    1340
Arg Pro Gln Val Asn Asn Pro Lys Glu Trp Leu Gln Val Asp Phe Gln
1345                    1350                    1355                1360
Lys Thr Met Lys Val Thr Gly Val Thr Thr Gln Gly Val Lys Ser Leu
                1365                    1370                    1375
Leu Thr Ser Met Tyr Val Lys Glu Phe Leu Ile Ser Ser Ser Gln Asp
            1380                    1385                    1390
Gly His Gln Trp Thr Leu Phe Phe Gln Asn Gly Lys Val Lys Val Phe
        1395                    1400                    1405
Gln Gly Asn Gln Asp Ser Phe Thr Pro Val Val Asn Ser Leu Asp Pro
    1410                    1415                    1420
Pro Leu Leu Thr Arg Tyr Leu Arg Ile His Pro Gln Ser Trp Val His
1425                    1430                    1435                1440
Gln Ile Ala Leu Arg Met Glu Val Leu Gly Cys Glu Ala Gln Asp Leu
                1445                    1450                    1455
Tyr
```

FIG. 10D

NUCLEOTIDE SEQUENCE OF HUMAN B DOMAIN-DELETED FACTOR VIII(HSQ)

```
   1 ATGCAAATAG AGCTCTCCAC CTGCTTCTTT CTGTGCCTTT TGCGATTCTG
  51 CTTTAGTGCC ACCAGAAGAT ACTACCTGGG TGCAGTGGAA CTGTCATGGG
 101 ACTATATGCA AAGTGATCTC GGTGAGCTGC CTGTGGACGC AAGATTTCCT
 151 CCTAGAGTGC CAAAATCTTT TCCATTCAAC ACCTCAGTCG TGTACAAAAA
 201 GACTCTGTTT GTAGAATTCA CGGTTCACCT TTTCAACATC GCTAAGCCAA
 251 GGCCACCCTG GATGGGTCTG CTAGGTCCTA CCATCCAGGC TGAGGTTTAT
 301 GATACAGTGG TCATTACACT TAAGAACATG GCTTCCCATC CTGTCAGTCT
 351 TCATGCTGTT GGTGTATCCT ACTGGAAAGC TTCTGAGGGA GCTGAATATG
 401 ATGATCAGAC CAGTCAAAGG GAGAAAGAAG ATGATAAAGT CTTCCCTGGT
 451 GGAAGCCATA CATATGTCTG GCAGGTCCTG AAAGAGAATG GTCCAATGGC
 501 CTCTGACCCA CTGTGCCTTA CCTACTCATA TCTTTCTCAT GTGGACCTGG
 551 TAAAAGACTT GAATTCAGGC CTCATTGGAG CCCTACTAGT ATGTAGAGAA
 601 GGGAGTCTGG CCAAGGAAAA GACACAGACC TTGCACAAAT TTATACTACT
 651 TTTTGCTGTA TTTGATGAAG GGAAAAGTTG GCACTCAGAA ACAAAGAACT
 701 CCTTGATGCA GGATAGGGAT GCTGCATCTG CTCGGGCCTG GCCTAAAATG
 751 CACACAGTCA ATGGTTATGT AAACAGGTCT CTGCCAGGTC TGATTGGATG
 801 CCACAGGAAA TCAGTCTATT GGCATGTGAT TGGAATGGGC ACCACTCCTG
 851 AAGTGCACTC AATATTCCTC GAAGGTCACA CATTTCTTGT GAGGAACCAT
 901 CGCCAGGCGT CCTTGGAAAT CTCGCCAATA ACTTTCCTTA CTGCTCAAAC
 951 ACTCTTGATG GACCTTGGAC AGTTTCTACT GTTTTGTCAT ATCTCTTCCC
1001 ACCAACATGA TGGCATGGAA GCTTATGTCA AAGTAGACAG CTGTCCAGAG
1051 GAACCCCAAC TACGAATGAA AAATAATGAA GAAGCGGAAG ACTATGATGA
1101 TGATCTTACT GATTCTGAAA TGGATGTGGT CAGGTTTGAT GATGACAACT
1151 CTCCTTCCTT TATCCAAATT CGCTCAGTTG CCAAGAAGCA TCCTAAAACT
1201 TGGGTACATT ACATTGCTGC TGAAGAGGAG GACTGGGACT ATGCTCCCTT
1251 AGTCCTCGCC CCCGATGACA GAAGTTATAA AAGTCAATAT TTGAACAATG
1301 GCCCTCAGCG GATTGGTAGG AAGTACAAAA AAGTCCGATT TATGGCATAC
1351 ACAGATGAAA CCTTTAAGAC GCGTGAAGCT ATTCAGCATG AATCAGGAAT
1401 CTTGGGACCT TTACTTTATG GGGAAGTTGG AGACACACTG TTGATTATAT
1451 TTAAGAATCA AGCAAGCAGA CCATATAACA TCTACCCTCA CGGAATCACT
1501 GATGTCCGTC CTTTGTATTC AAGGAGATTA CCAAAAGGTG TAAAACATTT
1551 GAAGGATTTT CCAATTCTGC CAGGAGAAAT ATTCAAATAT AAATGGACAG
1601 TGACTGTAGA AGATGGGCCA ACTAAATCAG ATCCGCGGTG CCTGACCCGC
1651 TATTACTCTA GTTTCGTTAA TATGGAGAGA GATCTAGCTT CAGGACTCAT
1701 TGGCCCTCTC CTCATCTGCT ACAAAGAATC TGTAGATCAA AGAGGAAACC
1751 AGATAATGTC AGACAAGAGG AATGTCATCC TGTTTTCTGT ATTTGATGAG
1801 AACCGAAGCT GGTACCTCAC AGAGAATATA CAACGCTTTC TCCCCAATCC
1851 AGCTGGAGTG CAGCTTGAGG ATCCAGAGTT CCAAGCCTCC AACATCATGC
1901 ACAGCATCAA TGGCTATGTT TTTGATAGTT TGCAGTTGTC AGTTTGTTTG
1951 CATGAGGTGG CATACTGGTA CATTCTAAGC ATTGGAGCAC AGACTGACTT
2001 CCTTTCTGTC TTCTTCTCTG GATATACCTT CAAACACAAA ATGGTCTATG
2051 AAGACACACT CACCCTATTC CCATTCTCAG GAGAAACTGT CTTCATGTCG
2100 ATGGAAAACC CAGGTCTATG GATTCTGGGG TGCCACAACT CAGACTTTCG
2151 GAACAGAGGC ATGACCGCCT TACTGAAGGT TTCTAGTTGT GACAAGAACA
2201 CTGGTGATTA TTACGAGGAC AGTTATGAAG ATATTTCAGC ATACTTGCTG
2251 AGTAAAAACA ATGCCATTGA ACCTAGGAGC TTCTCTCAGA ATCCACCAGT
2301 CTTGAAACGC CATCAACGGG AAATAACTCG TACTACTCTT CAGTCAGATC
2351 AAGAGGAAAT TGACTATGAT GATACCATAT CAGTTGAAAT GAAGAAGGAA
2401 GATTTTGACA TTTATGATGA GGATGAAAAT CAGAGCCCCC GCAGCTTTCA
```

FIG. 11A

```
2451  AAAGAAAACA  CGACACTATT  TTATTGCTGC  AGTGGAGAGG  CTCTGGGATT
2501  ATGGGATGAG  TAGCTCCCCA  CATGTTCTAA  GAAACAGGGC  TCAGAGTGGC
2551  AGTGTCCCTC  AGTTCAAGAA  AGTTGTTTTC  CAGGAATTTA  CTGATGGCTC
2601  CTTTACTCAG  CCCTTATACC  GTGGAGAACT  AAATGAACAT  TTGGGACTCC
2651  TGGGGCCATA  TATAAGAGCA  GAAGTTGAAG  ATAATATCAT  GGTAACTTTC
2701  AGAAATCAGG  CCTCTCGTCC  CTATTCCTTC  TATTCTAGCC  TTATTTCTTA
2751  TGAGGAAGAT  CAGAGGCAAG  GAGCAGAACC  TAGAAAAAAC  TTTGTCAAGC
2801  CTAATGAAAC  CAAAACTTAC  TTTTGGAAAG  TGCAACATCA  TATGGCACCC
2851  ACTAAAGATG  AGTTTGACTG  CAAAGCCTGG  GCTTATTTCT  CTGATGTTGA
2901  CCTGGAAAAA  GATGTGCACT  CAGGCCTGAT  TGGACCCCTT  CTGGTCTGCC
2951  ACACTAACAC  ACTGAACCCT  GCTCATGGGA  GACAAGTGAC  AGTACAGGAA
3001  TTTGCTCTGT  TTTTCACCAT  CTTTGATGAG  ACCAAAAGCT  GGTACTTCAC
3051  TGAAAATATG  GAAAGAAACT  GCAGGGCTCC  CTGCAATATC  CAGATGGAAG
3101  ATCCCACTTT  TAAAGAGAAT  TATCGCTTCC  ATGCAATCAA  TGGCTACATA
3151  ATGGATACAC  TACCTGGCTT  AGTAATGGCT  CAGGATCAAA  GGATTCGATG
3201  GTATCTGCTC  AGCATGGGCA  GCAATGAAAA  CATCCATTCT  ATTCATTTCA
3251  GTGGACATGT  GTTCACTGTA  CGAAAAAAAG  AGGAGTATAA  AATGGCACTG
3301  TACAATCTCT  ATCCAGGTGT  TTTTGAGACA  GTGGAAATGT  TACCATCCAA
3351  AGCTGGAATT  TGGCGGGTGG  AATGCCTTAT  TGGCGAGCAT  CTACATGCTG
3401  GGATGAGCAC  ACTTTTTCTG  GTGTACAGCA  ATAAGTGTCA  GACTCCCCTG
3451  GGAATGGCTT  CTGGACACAT  TAGAGATTTT  CAGATTACAG  CTTCAGGACA
3501  ATATGGACAG  TGGGCCCCAA  AGCTGGCCAG  ACTTCATTAT  TCCGGATCAA
3551  TCAATGCCTG  GAGCACCAAG  GAGCCCTTTT  CTTGGATCAA  GGTGGATCTG
3601  TTGGCACCAA  TGATTATTCA  CGGCATCAAG  ACCCAGGGTG  CCCGTCAGAA
3651  GTTCTCCAGC  CTCTACATCT  CTCAGTTTAT  CATCATGTAT  AGTCTTGATG
3701  GAAGAAGTG  GCAGACTTAT  CGAGGAAATT  CCACTGGAAC  CTTAATGGTC
3751  TTCTTTGGCA  ATGTGGATTC  ATCTGGGATA  AAACACAATA  TTTTTAACCC
3801  TCCAATTATT  GCTCGATACA  TCCGTTTGCA  CCCAACTCAT  TATAGCATTC
3851  GCAGCACTCT  TCGCATGGAT  TTGATGGGCT  GTGATTTAAA  TAGTTGCAGC
3901  ATGCCATTGG  GAATGGAGAG  TAAAGCAATA  TCAGATGCAC  AGATTACTGC
3951  TTCATCCTAC  TTTACCAATA  TGTTTGCCAC  CTGGTCTCCT  TCAAAAGCTC
4001  GACTTCACCT  CCAAGGGAGG  AGTAATGCCT  GGAGACCTCA  GGTGAATAAT
4051  CCAAAAGAGT  GGCTGCAAGT  GGACTTCCAG  AAGACAATGA  AAGTCACAGG
4101  AGTAACTACT  CAGGGAGTAA  AATCTCTGCT  TACCAGCATG  TATGTGAAGG
4151  AGTTCCTCAT  CTCCAGCAGT  CAAGATGGCC  ATCAGTGGAC  TCTCTTTTTT
4201  CAGAATGGCA  AAGTAAAGGT  TTTTCAGGGA  AATCAAGACT  CCTTCACACC
4251  TGTGGTGAAC  TCTCTAGACC  CACCGTTACT  GACTCGCTAC  CTTCGAATTC
4301  ACCCCCAGAG  TTGGGTGCAC  CAGATTGCCC  TGAGGATGGA  GGTTCTGGGC
4351  TGCGAGGCAC  AGGACCTCTA  C
```

FIG. 11B

AMINO ACID SEQUENCE OF HP630L

```
   1  MQLELSTCVF LCLLPLGFSA IRRYYLGAVE LSWDYRQSEL LRELHVDTRF
  51  PATAPGALPL GPSVLYKKTV FVEFTDQLFS VARPRPPWMG LLGPTIQAEV
 101  YDTVVVTLKN MASHPVSLHA VGVSFWKSSE GAEYEDHTSQ REKEDDKVLP
 151  GKSQTYVWQV LKENGPTASD PPCLTYSYLS HVDLVKDLNS GLIGALLVCR
 201  EGSLTRERTQ NLHEFVLLFA VFDEGKSWHS ARNDSWTRAM DPAPARAQPA
 251  MHTVNGYVNR SLPGLIGCHK KSVYWHVIGM GTSPEVHSIF LEGHTFLVRH
 301  HRQASLEISP LTFLTAQTFL MDLGQFLLFC HISSHHHGGM EAHVRVESCA
 351  EEPQLRRKAD EEEDYDDNLY DSDMDVVRLD GDDVSPFIQI RSVAKKHPKT
 401  WVHYIAAEEE DWDYAPLVLA PDDRSYKSQY LNNGPQRIGR KYKKVRFMAY
 451  TDETFKTREA IQHESGILGP LLYGEVGDTL LIIFKNQASR PYNIYPHGIT
 501  DVRPLYSRRL PKGVKHLKDF PILPGEIFKY KWTVTVEDGP TKSDPRCLTR
 551  YYSSFVNMER DLASGLIGPL LICYKESVDQ RGNQIMSDKR NVILFSVFDE
 601  NRSWYLTENI QRFLPNPAGV QLEDPEFQAS NIMHSINGYV FDSLQLSVCL
 651  HEVAYWYILS IGAQTDFLSV FFSGYTFKHK MVYEDTLTLF PFSGETVFMS
 701  MENPGLWILG CHNSDFRNRG MTALLKVSSC DKNTGDYYED SYEDISAYLL
 751  SKNNAIEPRS FSQNSRHPST RSQNPPVLKR HQREITRTTL QSDQEEIDYD
 801  DTISVEMKKE DFDIYDEDEN QSPRSFQKRT RHYFIAAVEQ LWDYGMSESP
 851  RALRNRAQNG EVPRFKKVVF REFADGSFTQ PSYRGELNKH LGLLGPYIRA
 901  EVEDNIMVTF KNQASRPYSF YSSLISYPDD QEQGAEPRKN FVKPNETKTY
 951  FWKVQHHMAP TEDEFDCKAW AYFSDVDLEK DVHSGLIGPL LICRANTLNA
1001  AHGRQVTVQE FALFFTIFDE TKSWYFTENV ERNCRAPCHL QMEDPTLKEN
1051  YRFHAINGYV MDTLPGLVMA QNQRIRWYLL SMGSNENIHS IHFSGHVFSV
1101  RKKEEYKMAV YNLYPGVFET VEMLPSKVGI WRNRCLIGEH LQAGMSTTFL
1151  VYSKKCQTPL GMASGHIRDF QITASGQYGQ WAPKLARLHY SGSINAWSTK
1201  EPFSWIKVDL LAPMIIHGIK TQGARQKFSS LYISQFIIMY SLDGKKWQTY
1251  RGNSTGTLMV FFGNVDSSGI KHNIFNPPII ARYIRLHPTH YSIRSTLRME
1301  LMGCDLNSCS MPLGMESKAI SDAQITASSY FTNMFATWSP SKARLHLQGR
1351  SNAWRPQVNN PKEWLQVDFQ KTMKVTGVTT QGVKSLLTSM YVKEFLISSS
1401  QDGHQWTLFF QNGKVKVFQG NQDSFTPVVN SLDPPLLTRY LRIHPQSWVH
1451  QIALRMEVLG CEAQDLY
```

FIG. 13

NUCLEOTIDE SEQUENCE OF HP63/OL

```
   1 ATGCAGCTAG AGCTCTCCAC CTGTGTCTTT CTGTGTCTCT TGCCACTCGG
  51 CTTTAGTGCC ATCAGGAGAT ACTACCTGGG CGCAGTGGAA CTGTCCTGGG
 101 ACTACCGGCA AAGTGAACTC CTCCGTGAGC TGCACGTGGA CACCAGATTT
 151 CCTGCTACAG CGCCAGGAGC TCTTCCGTTG GGCCCGTCAG TCCTGTACAA
 201 AAAGACTGTG TTCGTAGAGT TCACGGATCA ACTTTTCAGC GTTGCCAGGC
 251 CCAGGCCACC ATGGATGGGT CTGCTGGGTC CTACCATCCA GGCTGAGGTT
 301 TACGACACGG TGGTCGTTAC CCTGAAGAAC ATGGCTTCTC ATCCCGTTAG
 351 TCTTCACGCT GTCGGCGTCT CCTTCTGGAA ATCTTCCGAA GGCGCTGAAT
 401 ATGAGGATCA CACCAGCCAA AGGGAGAAGG AAGACGATAA AGTCCTTCCC
 451 GGTAAAAGCC AAACCTACGT CTGGCAGGTC CTGAAAGAAA ATGGTCCAAC
 501 AGCCTCTGAC CCACCATGTC TTACCTACTC ATACCTGTCT CACGTGGACC
 551 TGGTGAAAGA CCTGAATTCG GGCCTCATTG GAGCCCTGCT GGTTTGTAGA
 601 GAAGGGAGTC TGACCAGAGA AAGGACCCAG AACCTGCACG AATTTGTACT
 651 ACTTTTTGCT GTCTTTGATG AAGGGAAAAG TTGGCACTCA GCAAGAAATG
 701 ACTCCTGGAC ACGGGCCATG GATCCGCAC CTGCCAGGGC CCAGCCTGCA
 751 ATGCACACAG TCAATGGCTA TGTCAACAGG TCTCTGCCAG GTCTGATCGG
 801 ATGTCATAAG AAATCAGTCT ACTGGCACGT GATTGGAATG GGCACCAGCC
 851 CGGAAGTGCA CTCCATTTTT CTTGAAGGCC ACACGTTTCT CGTGAGGCAC
 901 CATCGCCAGG CTTCCTTGA GATCTCGCCA CTAACTTTCC TCACTGCTCA
 951 GACATTCCTG ATGGACCTTG CCAGTTCCT ACTGTTTTGT CATATCTCTT
1001 CCCACCACCA TGGTGGCATG GAGGCTCACG TCAGAGTAGA AAGCTGCGCC
1051 GAGGAGCCCC AGCTGCGGAG GAAAGCTGAT GAAGAGGAAG ATTATGATGA
1101 CAATTTGTAC GACTCGGACA TGGACGTGGT CCGGCTCGAT GGTGACGACG
1151 TGTCTCCCTT TATCCAAATC CGCTCAGTTG CCAAGAAGCA TCCTAAAACT
1201 TGGGTACATT ACATTGCTGC TGAAGAGGAG GACTGGGACT ATGCTCCCTT
1251 AGTCCTCGCC CCCGATGACA GAAGTTATAA AAGTCAATAT TTGAACAATG
1301 GCCCTCAGCG GATTGGTAGG AAGTACAAAA AAGTCCGATT TATGGCATAC
1351 ACAGATGAAA CCTTTAAGAC TCGTGAAGCT ATTCAGCATG AATCAGGAAT
1401 CTTGGGACCT TTACTTTATG GGAAGTTGG AGACACACTG TTGATTATAT
1451 TTAAGAATCA AGCAAGCAGA CCATATAACA TCTACCCTCA CGGAATCACT
1501 GATGTCCGTC CTTTGTATTC AAGGAGATTA CCAAAAGGTG TAAAACATTT
1551 GAAGGATTTT CCAATTCTGC CAGGAGAAAT ATTCAAATAT AAATGGACAG
1601 TGACTGTAGA AGATGGGCCA ACTAAATCAG ATCCTCGGTG CCTGACCCGC
1651 TATTACTCTA GTTTCGTTAA TATGGAGAGA GATCTAGCTT CAGGACTCAT
1701 TGGCCCTCTC CTCATCTGCT ACAAAGAATC TGTAGATCAA AGAGGAAACC
1751 AGATAATGTC AGACAAGAGG AATGTCATCC TGTTTTCTGT ATTTGATGAG
1801 AACCGAAGCT GGTACCTCAC AGAGAATATA CAACGCTTTC TCCCCAATCC
1851 AGCTGGAGTG CAGCTTGAGG ATCCAGAGTT CCAAGCCTCC AACATCATGC
1901 ACAGCATCAA TGGCTATGTT TTTGATAGTT TGCAGTTGTC AGTTTGTTTG
1951 CATGAGGTGG CATACTGGTA CATTCTAAGC ATTGGAGCAC AGACTGACTT
2001 CCTTTCTGTC TTCTTCTCTG GATATACCTT CAAACACAAA ATGGTCTATG
2051 AAGACACACT CACCCTATTC CCATTCTCAG GAGAAACTGT CTTCATGTCG
2101 ATGGAAAACC CAGGTCTATG GATTCTGGGG TGCCACAACT CAGACTTTCG
2151 GAACAGAGGC ATGACCGCCT TACTGAAGGT TTCTAGTTGT GACAAGAACA
2201 CTGGTGATTA TTACGAGGAC AGTTATGAAG ATATTTCAGC ATACTTGCTG
2251 AGTAAAAACA ATGCCATTGA ACCTAGGAGC TTCTCCCAGA ATTCAAGACA
2301 CCCTAGCACT AGGTCTCAAA ACCCACCAGT CTTGAAACGC ATCAACGGG
2351 AAATAACTCG TACTACTCTT CAGTCAGATC AAGAGGAAAT TGACTATGAT
```

FIG. 14A

```
2401  GATACCATAT  CAGTTGAAAT  GAAGAAGGAA  GATTTTGACA  TTTATGATGA
2451  GGATGAAAAT  CAGAGCCCCC  GCAGCTTTCA  AAAGAGAACC  CGACACTATT
2501  TCATTGCTGC  GGTGGAGCAG  CTCTGGGATT  ACGGGATGAG  CGAATCCCCC
2551  CGGGCGCTAA  GAAACAGGGC  TCAGAACGGA  GAGGTGCCTC  GGTTCAAGAA
2601  GGTGGTCTTC  CGGGAATTTG  CTGACGGCTC  CTTCACGCAG  CCGTCGTACC
2651  GCGGGGAACT  CAACAAACAC  TTGGGGCTCT  TGGGACCCTA  CATCAGAGCG
2701  GAAGTTGAAG  ACAACATCAT  GGTAACTTTC  AAAAACCAGG  CGTCTCGTCC
2751  CTATTCCTTC  TACTCGAGCC  TTATTTCTTA  TCCGGATGAT  CAGGAGCAAG
2801  GGGCAGAACC  TCGAAAAAAC  TTTGTCAAGC  CTAATGAAAC  CAAAACTTAC
2851  TTTTGGAAAC  TGCAGCATCA  CATGGCACCC  ACAGAAGACG  AGTTTGACTG
2901  CAAAGCCTGG  GCCTACTTTT  CTGATGTTGA  CCTGGAAAAA  GATGTGCACT
2951  CAGGCTTGAT  CGGCCCCCTT  CTGATCTGCC  GCGCCAACAC  CCTGAACGCT
3001  GCTCACGGTA  GACAAGTGAC  CGTGCAAGAA  TTTGCTCTGT  TTTTCACTAT
3051  TTTTGATGAG  ACAAAGAGCT  GGTACTTCAC  TGAAAATGTG  GAAAGGAACT
3101  GCCGGGCCCC  CTGCCATCTG  CAGATGGAGG  ACCCCACTCT  GAAAGAAAAC
3151  TATCGCTTCC  ATGCAATCAA  TGGCTATGTG  ATGGATACAC  TCCCTGGCTT
3201  AGTAATGGCT  CAGAATCAAA  GGATCCGATG  GTATCTGCTC  AGCATGGGCA
3251  GCAATGAAAA  TATCCATTCG  ATTCATTTTA  GCGGACACGT  GTTCAGTGTA
3301  CGGAAAAAGG  AGGAGTATAA  AATGGCCGTG  TACAATCTCT  ATCCGGGTGT
3351  CTTTGAGACA  GTGGAAATGC  TACCGTCCAA  AGTTGGAATT  TGGCGGAATA
3401  GATGCCTGAT  TGGCGAGCAC  CTGCAAGCTG  GGATGAGCAC  GACTTTCCTG
3451  GTGTACAGCA  AGAAGTGTCA  GACTCCCCTG  GGAATGGCTT  CTGGACACAT
3501  TAGAGATTTT  CAGATTACAG  CTTCAGGACA  ATATGGACAG  TGGGCCCCAA
3551  AGCTGGCCAG  ACTTCATTAT  TCCGGATCAA  TCAATGCCTG  GAGCACCAAG
3601  GAGCCCTTTT  CTTGGATCAA  GGTGGATCTG  TTGGCACCAA  TGATTATTCA
3651  CGGCATCAAG  ACCCAGGGTG  CCCGTCAGAA  GTTCTCCAGC  CTCTACATCT
3701  CTCAGTTTAT  CATCATGTAT  AGTCTTGATG  GGAAGAAGTG  GCAGACTTAT
3751  CGAGGAAATT  CCACTGGAAC  CTTAATGGTC  TTCTTTGGCA  ATGTGGATTC
3801  ATCTGGGATA  AAACACAATA  TTTTTAACCC  TCCAATTATT  GCTCGATACA
3851  TCCGTTTGCA  CCCAACTCAT  TATAGCATTC  GCAGCACTCT  TCGCATGGAG
3901  TTGATGGGCT  GTGATTTAAA  TAGTTGCAGC  ATGCCATTGG  GAATGGAGAG
3951  TAAAGCAATA  TCAGATGCAC  AGATTACTGC  TTCATCCTAC  TTTACCAATA
4001  TGTTTGCCAC  CTGGTCTCCT  TCAAAAGCTC  GACTTCACCT  CCAAGGGAGG
4051  AGTAATGCCT  GGAGACCTCA  GGTGAATAAT  CCAAAAGAGT  GGCTGCAAGT
4101  GGACTTCCAG  AAGACAATGA  AAGTCACAGG  AGTAACTACT  CAGGGAGTAA
4151  AATCTCTGCT  TACCAGCATG  TATGTGAAGG  AGTTCCTCAT  CTCCAGCAGT
4201  CAAGATGGCC  ATCAGTGGAC  TCTCTTTTTT  CAGAATGGCA  AAGTAAAGGT
4251  TTTTCAGGGA  AATCAAGACT  CCTTCACACC  TGTGGTGAAC  TCTCTAGACC
4301  CACCGTTACT  GACTCGCTAC  CTTCGAATTC  ACCCCCAGAG  TTGGGTGCAC
4351  CAGATTGCCC  TGAGGATGGA  GGTTCTGGGC  TGCGAGGCAC  AGGACCTCTA
4401  C
```

NUCLEIC ACID AND AMINO ACID SEQUENCES ENCODING HIGH-LEVEL EXPRESSOR FACTOR VIII POLYPEPTIDES AND METHODS OF USE

CROSS-REFERENCE TO RELATED APPLICATIONS

This application is a divisional application of U.S. application Ser. No. 10/813,507, now U.S. Pat. No. 7,635,763, filed Mar. 30, 2004 which is a continuation of PCT Application No. PCT/US02/33403, filed on Oct. 7, 2002, and which claims the benefit of U.S. Provisional Application No. 60/327,388, filed Oct. 5, 2001, all of which are incorporated herein by reference in their entirety.

FEDERALLY SPONSORED RESEARCH OR DEVELOPMENT

This work was supported by National Institute of Health Grant ROI HL40921.

FIELD OF THE INVENTION

The present invention relates the field of recombinant molecular biology, particularly a modified factor VIII polypeptide and methods of use.

BACKGROUND OF THE INVENTION

Factor VIII is a large (~300 kDa) glycoprotein that functions as an integral component of the intrinsic pathway of blood coagulation. It contains a series of domains designated A1-A2-B-ap-A3-C1-C2. The B domain of factor VIII has no known function and can be deleted without loss of coagulant activity. Mutations in the factor VIII gene that result in decreased or defective factor VIII protein give rise to the genetic disease, hemophilia A, which is characterized by recurrent bleeding episodes. Treatment of hemophilia A requires intravenous infusion of either plasma-derived or recombinant factor VIII.

Since the introduction of recombinant factor VIII for the treatment of hemophilia A, supply has struggled to keep up with demand because factor VIII is expressed and recovered at low levels in the heterologous mammalian cell culture systems used for commercial manufacture (Garber et al. (2000) *Nature Biotechnology* 18: 1133). Additionally, factor VIII levels during hemophilia A gene therapy trials indicate that expression levels will be a limiting feature (Roth, et al. (2001) *N. Engl. J. Med.* 344:1735-1742). The importance of this problem has resulted in significant research efforts to overcome the low factor VIII expression barrier. Several factors that limit expression have been identified, including low mRNA levels (Lynch et al. (1993) *Hum. Gene Ther.* 4:259-272; Hoeben et al. (1995) *Blood* 85:2447-2454; Koeberl et al. (1995) *Hum. Gene Ther.* 6:469-479), interaction with protein chaperones and inefficient secretion (Pipe et al. (1998) *J. Biol. Chem.* 273:8537-8544; Tagliavacca et al. (2000) *Biochemistry* 39:1973-1981; Kaufman et al. (1997) *Blood Coagul Fibrinolysis* 8 Suppl 2:S3-14) and rapid decay in the absence of von Willebrand factor (Kaufman et al. (1988) *J. Biol. Chem.* 263:6352-6362 and Kaufman et al. (1989) *Mol. Cell. Biol.* 9:1233-1242). Deletion of the B-domain has been shown to increase factor VIII protein production in heterologous systems (Toole et al. (1986) *Proc. Natl. Acad. Sci. U.S.A.* 83:5939-5942). A B-domain deleted form of human factor VIII (Lind et al. (1995) *Eur. J. Biochem.* 232:19-27) has been approved for clinical use.

Despite these insights into factor VIII regulation, expression continues to be significantly lower than other recombinant proteins in the heterologous systems used in commercial manufacture (Kaufman et al. (1997) *Blood Coagul. Fibrinolysis* 8 Suppl 2:S3-14), as well as in ex-vivo (Roth, et al. (2001) *N. Engl. J. Med.* 344:1735-1742) and in vivo gene therapy applications (Chuah et al. (1995) *Hum. Gene Ther.* 6:1363-1377). Methods and compositions are needed for the increased expression of factor VIII.

SUMMARY OF THE INVENTION

Methods and compositions are provided that allow for high-level expression of a factor VIII polypeptide. More specifically, the present invention provides methods and compositions comprising nucleic acid and amino acid sequences comprising a modified factor VIII that results in high-level expression of the polypeptide. The methods and compositions of the invention find use in the treatment of factor VIII deficiency, including, for example, hemophilia A.

In particular, one embodiment of the present invention provides an isolated polypeptide comprising an amino acid sequence set forth in SEQ ID NO:15, 17, or 19; an amino acid sequence having at least 85%, 90%, 95%, 97%, 98%, or 99% sequence identity to SEQ ID NO:15, 17, or 19, wherein said polypeptide is characterized by high-level expression, or a fragment thereof.

In another embodiment of the invention, isolated nucleic acid molecules are provided comprising a nucleotide sequence set forth in SEQ ID NO:14, 16, or 18; a nucleotide sequence encoding a polypeptide comprising the amino acid sequence set forth in SEQ ID NO: 15, 17, or 19; and, a nucleotide sequence having at least 85%, 90%, 95%, 97%, 98%, or 99% sequence identity to SEQ ID NO:14, 16, or 18, wherein said nucleotide sequence encodes a polypeptide that is characterized by high-level expression. Expression cassettes, vectors, and cells comprising the nucleic acid molecules of the invention are further provided.

Pharmaceutical compositions comprising the nucleic acid molecules and the polypeptides of the invention are also provided.

Methods for the production of a polypeptide are provided. In one embodiment, the method comprises introducing into a cell a nucleic acid molecule comprising a nucleotide sequence encoding a polypeptide comprising the amino acid sequence set forth in SEQ ID NO:15, 17, or 19; a nucleotide sequence comprising the sequence set forth in SEQ ID NO:14, 16, or 18; a nucleotide sequence having at least 85%, 90%, 95%, 97%, 98%, or 99% sequence identity to SEQ ID NO:14, 16, or 18, wherein the nucleotide sequence encodes a polypeptide characterized by high-level expression, or a fragment thereof; and, culturing the cell under conditions that allow expression of the nucleotide sequence.

Also provided are methods for increasing the level of expression of the factor VIII polypeptide. In one embodiment, the method comprises introducing into a cell a nucleic acid molecule comprising a nucleotide sequence encoding a polypeptide comprising the amino acid sequence set forth in SEQ ID NO:15, 17, or 19; a nucleotide sequence comprising the sequence set forth in SEQ ID NO:14, 16, or 18; a nucleotide sequence having at least 85%, 90%, 95%, 97%, 98%, or 99% sequence identity to SEQ ID NO:14, 16, or 18, wherein the nucleotide sequence encodes a polypeptide characterized by high-level expression, or a fragment thereof; and, culturing the cell under conditions that allow expression of the nucleotide sequence.

Also provided is a method for the treatment of factor VIII deficiencies, including, for example, hemophilia A. The method comprises administering to a subject in need thereof a composition comprising a therapeutically effective amount of a polypeptide, where the polypeptide comprises an amino acid sequence set forth in SEQ ID NO:15, 17, or 19, an amino acid sequence having at least 85%, 90%, 95%, 97%, 98%, or 99% sequence identity to SEQ ID NO:15, 17, or 19, wherein said polypeptide is characterized by high-level expression, or a fragment thereof.

Other methods include treating a factor VIII deficiency by administering to a subject in need thereof a composition comprising a therapeutically effective amount of a nucleic acid molecule, where said nucleic acid molecule comprises a nucleotide sequence set forth in SEQ ID NO: 14, 16, or 18; a nucleotide sequence encoding a polypeptide comprising the amino acid sequence set forth in SEQ ID NO: 15, 17, or 19; a nucleotide sequence having at least 85%, 90%, 95%, 97%, 98%, or 99% sequence identity to SEQ ID NO:14, 16, or 18, wherein said nucleic acid molecule encodes a polypeptide characterized by high-level expression, or a fragment thereof.

BRIEF DESCRIPTION OF THE DRAWINGS

FIG. 1A-1H taken together provide an aligned amino acid sequence comparison of the human (SEQ ID NO:6), porcine (SEQ ID NO:2), and mouse (SEQ ID NO:8) factor VIII polypeptide sequences.

FIG. 4 provides the amino acid sequence for the factor VIII$_{SEP}$ polypeptide designated herein as HP44/OL (SEQ ID NO:15).

FIG. 5A-5D provides the nucleotide sequence (SEQ ID NO:14) encoding the factor VIII$_{SEP}$ polypeptide designated herein as HP44/OL.

FIG. 6 provides the amino acid sequence for the factor VIII$_{SEP}$ polypeptide designated herein as HP46/SQ (SEQ ID NO:17).

FIG. 7A-7D provides the nucleotide sequence (SEQ ID NO:16) encoding the factor VIII$_{SEP}$ polypeptide designated herein as HP46/SQ.

FIG. 8 provides the amino acid sequence for the factor VIII$_{SEP}$ polypeptide designated herein as HP47/SQ (SEQ ID NO:19).

FIG. 9A-9D provides the nucleotide sequence (SEQ ID NO:18) encoding the factor VIII$_{SEP}$ polypeptide designated herein as HP47/SQ.

FIG. 10A-10D provides the amino acid sequence for the human factor VIII B-domain deleted polypeptide (SEQ ID NO:13).

FIG. 11A-11B provides the nucleotide sequence (SEQ ID NO:12) encoding the human factor VIII B-domain deleted polypeptide.

FIG. 13 provides the amino acid sequence (SEQ ID NO:21) encoding the factor VIII$_{SEP}$ polypeptide designated herein as HP63/OL.

FIG. 14A-14B provides the nucleotide sequence (SEQ ID NO:20) encoding the factor VIII$_{SEP}$ polypeptide designated herein as HP63/OL.

DETAILED DESCRIPTION OF THE INVENTION

Overview

Figure 2:
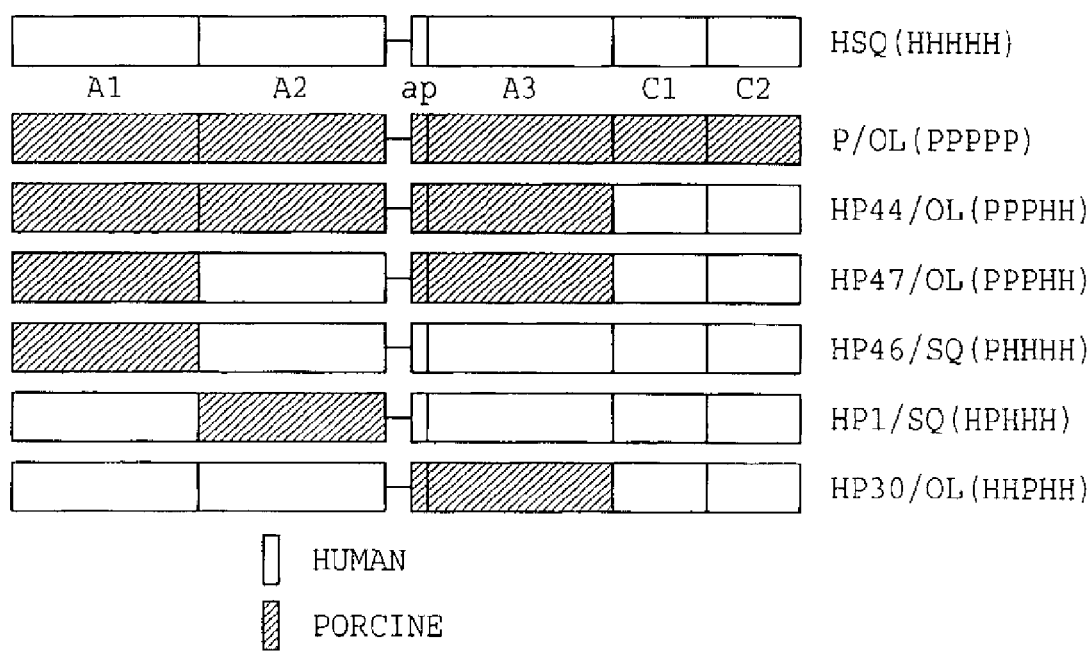
FIG. 2 provides a schematic of B domain-deleted human, porcine, and hybrid human/porcine factor VIII constructs. The solid line between the A2 and ap domains represents linker sequences.

The present invention provides methods and compositions that allow for high-level expression of the factor VIII polypeptide. The factor VIII polypeptide contains homology-defined proteins domains having the following nomenclature: A1-A2-B-ap-A3-C1-C2. The present invention has identified regions within the domains of a non-human factor VIII polypeptide that promote high-level expression of the factor VIII polypeptide. More particularly, regions of the porcine factor VIII polypeptide that comprises the A1 and ap-A3 regions, and variants and fragments thereof, have been identified which impart high-level expression to both the porcine and human factor VIII polypeptide. The present invention thus provides methods and compositions that use the non-human factor VIII polypeptide sequences which impart high-level expression, and active variants or fragments of these sequences, to construct nucleic acid and polypeptide sequences encoding a modified factor VIII polypeptide that results in high-level expression of the encoded factor VIII polypeptide. The modified factor VIII polypeptides characterized by high-level expression are referred to herein as "factor VIII$_{SEP}$" (Super Expression).

By "high-level expression" is intended the production of a polypeptide at increased levels when compared to the expression levels of the corresponding human factor VIII polypeptide expressed under the same conditions. An increase in polypeptide levels (i.e., high-level expression) comprises at least about 0.5, 1, 2, 3, 4, 5, 6, 7, 8, 9, 10, 11, 12, 13, 14, 15, 20 fold or greater expression of the factor VIII$_{SEP}$ polypeptide compared to the expression levels of the corresponding human factor VIII polypeptide. Alternatively, "high-level expression" can comprise an increase in polypeptide expression levels of at least 1-25 fold, 1-5 fold, 5-10 fold, 10-15 fold, 15-20 fold, 20-25 fold or greater expression levels of the factor VIII$_{SEP}$ when compared to the corresponding human factor VIII polypeptide. Methods for assaying "high-level expression" are routine in the art and are outlined in more detail below.

By "corresponding" factor VIII polypeptide is intended a factor VIII polypeptide that comprises an equivalent amino acid sequence. For instance, when a modified factor VIII polypeptide comprising the A1-A2-ap-A3-C1-C2 domains is tested for high-level expression, a human or porcine factor VIII polypeptide containing corresponding domains will be used (i.e., A1-A2-ap-A3-C1-C2). When a fragment of a modified factor VIII polypeptide is tested for high-level expression (i.e., A1-A2-ap-A3), a human or porcine factor VIII polypeptide having the corresponding domains will be tested (i.e., A1-A2-ap-A3).

Compositions

Compositions of the invention include the nucleic acid molecules encoding factor VIII polypeptides characterized by high-level expression. As outlined in further detail below, the A1 domain of porcine factor VIII (amino acid residues 20-391 of SEQ ID NO:19) and the ap-A3 domain of porcine factor VIII (amino acids 1450-1820 of SEQ ID NO:19) allow for high-level expression of factor VIII. The present invention thus provides methods and compositions comprising factor VIII$_{SEP}$ polypeptides and active variant and active fragments of factor VIII$_{SEP}$ polypeptides characterized by high-level expression.

In particular, the present invention provides for isolated nucleic acid molecules comprising nucleotide sequences encoding the amino acid sequence shown in SEQ ID NOS:15, 17, or 19 and active fragments or active variants thereof. Also provided are isolated nucleic acid molecules comprising nucleotide sequences set forth in SEQ ID NOS:14, 16, or 18 and active fragments or active variants thereof. Further provided are polypeptides having an amino acid sequence encoded by a nucleic acid molecule described herein, for example, those set forth in SEQ ID NOS:15, 17, and 19 and active fragments and active variants thereof.

Table 1 provides a summary of structure of the sequences provided in SEQ ID NOS:14-19, where the subscript "P" designates a domain from porcine factor VIII and the subscript "H" designates a domain from human factor VIII.

TABLE 1

Summary of Sequence Structure

| SEQ ID NO | Factor VIII domains |
|---|---|
| 14 and 15 | A1$_P$-A2$_P$-ap$_P$-A3$_P$-C1$_H$-C2$_H$ |
| 16 and 17 | A1$_P$-A2$_H$-ap$_H$-A3$_H$-C1$_H$-C2$_H$ |
| 18 and 19 | A1$_P$-A2$_H$-ap$_P$-A3$_P$-C1$_H$-C2$_H$ |

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed factor VIII$_{SEP}$ nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the polypeptides set forth in SEQ ID NO:15, 17, or 19 and hence are characterized by high-level expression of the factor VIII polypeptide. Thus, fragments of a nucleotide sequence may range from at least about 10 nucleotides, about 20 nucleotides, about 50 nucleotides, about 100 nucleotides, about 500 nucleotides, about 1000 nucleotides, about 2000 nucleotides, about 3000 nucleotides, about 4000 nucleotides, about 5000 nucleotides, about 6000 nucleotides, about 7000 nucleotides, about 8000 nucleotides, and up to the full-length nucleotide sequence encoding the factor VIII polypeptide of the invention about 9000 nucleotides.

A fragment of a nucleotide sequence of the present invention that encodes a biologically active portion of a factor VIII$_{SEP}$ protein of the invention will encode at least 12, 25, 30, 50, 100, 150, 200, 300, 400, 500, 600, 700, 800, 900, 1000, 1100, 1200, 1300, 1400, 1500, 1600, 1700, 1800, 1900, 2000, 2100, 2200, 2300 contiguous amino acids, or up to the total number of amino acids present in a full-length factor VIII protein of the invention (for example, 1457, 1467, or 1467 amino acids for SEQ ID NO:15, 17, or 19 respectively) and will allow high-level expression of the factor VIII polypeptide.

By "variant" is intended substantially similar sequences. For nucleotide sequences, conservative variants include those sequences that, because of the degeneracy of the genetic code, encode the amino acid sequence of one of the polypeptides of the invention. Variant nucleotide sequences include synthetically derived nucleotide sequences, such as those generated, for example, by using site-directed mutagenesis but which still encode a factor VIII$_{SEP}$ protein characterized by high-level expression. Generally, variants of a particular nucleotide sequence of the invention will have at least at least 75%, 80%, 85%, 86%, 87%, 88%, 89%, preferably about 90%, 91%, 92%, 93%, 94%, 95%, 96%, 97%, and more preferably about 98%, 99%, or more sequence identity to that particular nucleotide sequence as determined by sequence alignment programs described elsewhere herein.

By "variant" protein is intended a protein derived from the polypeptide of SEQ ID NO:15, 17, or 19 by deletion (so-called truncation) or addition of one or more amino acids to the N-terminal and/or C-terminal end of the protein; deletion or addition of one or more amino acids at one or more sites in the protein; or substitution of one or more amino acids at one or more sites in the protein. Variant proteins encompassed by the present invention are biologically active, that is they continue to possess the desired biological activity of SEQ ID NO:15, 17, or 19, hence they will continue to allow for the high-level expression of the factor VIII polypeptide. Such variants may result from, for example, genetic polymorphism or from human manipulation. Biologically active variants of a polypeptide of the invention will have at least 75%, 80%, 85%, 86%, 87%, 88%, 89%, preferably about 90%, 91%, 92%, 93%, 94%, 95%, 96%, 97%, 98%, 99% or more sequence identity to the amino acid sequence for SEQ ID NO:15, 17, or 19 as determined by sequence alignment programs described elsewhere herein using default parameters. A biologically active variant of a protein of the invention may differ from that protein by as few as 1-100, 1-50, 1-25, 1-15 amino acid residues, as few as 1-10, such as 6-10, as few as 5, as few as 4, 3, 2, or even 1 amino acid residue.

Biological activity of the factor VIII$_{SEP}$ polypeptides of the present invention can be assayed by any method known in the art. As discussed above, the factor VIII$_{SEP}$ polypeptides of the invention are characterized by high-level expression. Assays to measure high-level expression are known in the art. For example, the level of expression of the factor VIII$_{SEP}$ polypeptide can be measured by Western blot analysis or ELISA. Other methods include, for example, labeling cell lines expressing the factor VIII polypeptide with $^{35}$S-ethionine, followed by immunoprecipitation of radiolabeled factor VIII molecules. Alternatively, the level of expression of the factor VIII$_{SEP}$ polypeptide can be assayed for by measuring the activity of the factor VIII polypeptide. For example, increased factor VIII expression could be assayed by measuring factor VIII activity using standard assays known in the art, including a one-stage coagulation assay or a two-stage activity assay. See, for example, U.S. Pat. No. 6,458,561 and the Experimental section below.

Briefly, coagulation assays are based on the ability of factor VIII to shorten the clotting time of plasma derived from a patient with hemophilia A. For example, in the one-stage assay, 0.1 ml hemophilia A plasma (George King Biomedical, Inc.) is incubated with 0.1 ml activated partial thromboplastin reagent (APTT) (Organon Teknika) and 0.01 ml sample or standard, consisting of diluted, citrated normal human plasma, for 5 min at 37° C. in a water bath. Incubation is followed by addition of 0.1 ml 20 mM CaCl$_2$, and the time for development of a fibrin clot is determined by visual inspection. A unit of factor VIII is defined as the amount present in 1 ml of citrated normal human plasma.

The one-stage assay relies on endogenous activation of factor VIII by activators formed in the hemophilia A plasma, whereas the two-stage assay measures the procoagulant activity of preactivated factor VIII. In the two-stage assay, samples containing factor VIII that are reacted with thrombin are added to a mixture of activated partial thromboplastin and human hemophilia A plasma that is preincubated for 5 min at 37° C. The resulting clotting times are converted to units/ml, based on the same human standard curve described above. See, for example, U.S. Pat. No. 6,376,463.

The factor VIII$_{SEP}$ polypeptides of the invention may be altered in various ways including amino acid substitutions, deletions, truncations, and insertions. Methods for such manipulations are generally known in the art. For example, amino acid sequence variants of the factor VIII$_{SEP}$ proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity (i.e., high-level expression) of the factor VIII$_{SEP}$ may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred. Alternatively, methods to minimize the number of porcine amino acids in the A$_1$ and ap-A$_3$ domains of factor VIII$_{SEP}$ and still continue to retain the high-level expression of the factor VIII$_{SEP}$ are known in the art and include, for example, established site-directed mutagenesis such as by splicing overlap extension as described elsewhere herein. Obviously, the mutations that will be made in the DNA encoding the variant must not place the sequence out of reading frame and preferably will not create complementary regions that could produce secondary mRNA structure. See, EP Patent Application Publication No. 75,444.

When it is difficult to predict the exact effect of the substitution, deletion, or insertion in advance of doing so, one skilled in the art will appreciate that the effect will be evaluated by routine screening assays. That is, the activity can be evaluated by high-level expression of the factor VIII polypeptide as discussed in detail elsewhere herein.

By "sequence identity" is intended the same nucleotides or amino acid residues are found within the variant sequence and a reference sequence when a specified, contiguous segment of the nucleotide sequence or amino acid sequence of the variant is aligned and compared to the nucleotide sequence or amino acid sequence of the reference sequence. Methods for sequence alignment and for determining identity between sequences are well known in the art. See, for example, Ausubel et al., eds. (1995) *Current Protocols in Molecular Biology,* Chapter 19 (Greene Publishing and Wiley-Interscience, New York); and the ALIGN program (Dayhoff (1978) in *Atlas of Polypeptide Sequence and Structure* 5: Suppl. 3 (National Biomedical Research Foundation, Washington, D.C.)). With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. The contiguous segment used for comparison to the reference nucleotide sequence or reference amino acid sequence will comprise at least 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are well known in the art.

The determination of percent identity between two sequences is accomplished using a mathematical algorithm. Specifically, for the purpose of the present invention percent identity of an amino acid sequence is determined using the Smith-Waterman homology search algorithm using an affine 6 gap search with a gap open penalty of 12 and a gap extension penalty of 2, BLOSUM matrix 62. The Smith-Waterman homology search algorithm is taught in Smith and Waterman (1981) *Adv. Appl. Math* 2:482-489, herein incorporated by reference. Alternatively, for the purposes of the present invention percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic.

It is further recognized that when considering percentage of amino acid identity, some amino acid positions may differ as a result of conservative amino acid substitutions, which do not effect the properties of polynucleotide function. In these instances, percent sequence identity may be adjusted upwards to account for the similarity in conservatively substituted amino acids. Such adjustments are well known in the art. See, for example, Meyers et al. (1988) *Computer Applic. Biol. Sci.* 4:11-17.

It is recognized that variants of sequences of the invention may encode factor VIII$_{SEP}$ polypeptides that contain only the amino acid residues of the $A1_P$ and ap-$A3_P$ domains that confer the high-level expression to the factor VIII polypeptide. Consequently, the $A1_P$ and $A3_P$ domains can be progressively humanized such that only the residues required to retain high-level expression are retained in the factor $VIII_{SEP}$ polypeptide. Such methods are known by those skilled in the art and also discussed in more detail below. See also, for example, U.S. Pat. Nos. 6,376,463; 6,458,563; 5,744,466; 5,888,974; 5,663,060; 5,364,771; 5,859,204; and, 6,180,371; all of which are herein incorporated by reference. In addition, it is recognized that a three-dimensional model of the human factor VIII A1-A2-A3 domains can be used to identify regions away from the domain interface. One of skill will be able to use this model to identify target amino acids residues for humanization.

It is recognized that the variant factor $VIII_{SEP}$ or fragments thereof can be made (1) by substitution of isolated, plasma-derived animal subunits or human subunits (heavy or light chains) for corresponding human subunits or animal subunits; (2) by substitution of human domains or animal domains (A1, A2, A3, B, C1, and C2) for corresponding animal domains or human domains; (3) by substitution of parts of human domains or animal domains for parts of animal domains or human domains; (4) by substitution of at least one specific sequence including one or more unique human or animal amino acid(s) for the corresponding animal or human amino acid(s); or (5) by substitution of amino acid sequence that has no known sequence identity to factor VIII for at least one sequence including one or more specific amino acid residue(s) in human, animal, or variant factor VIII or fragments thereof. Individual amino acid replacements can be obtained by site-directed mutagenesis of the corresponding segment coding DNA.

In a factor VIII molecule, a "domain", as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO:6): A1, residues A1al-Arg372; A2, residues Ser373-Arg740; B, residues Ser741-Arg1648; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. Factor VIII is proteolytically activated by thrombin or factor Xa, which dissociates it from von Willebrand factor, forming factor VIII, which has procoagulant function. The biological function of factor VIIIa is to increase the catalytic efficiency of factor 1Xa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes. A "partial domain" as used herein is a continuous sequence of amino acids forming part of a domain. "Subunits" of human or animal (i.e., mouse, pig, dog etc.) factor VIII, as used herein, are the heavy and light chains of the protein. The heavy chain of factor VIII contains three domains, A1, A2, and B. The light chain of factor VIII also contains three domains, A3, C1, and C2. A "unique" amino acid residue or sequence, as used herein, refers to an amino acid sequence or residue in the factor VIII molecule of one species that is different from the homologous residue or sequence in the factor VIII molecule of another species. As used herein, "mammalian factor VIII" includes factor VIII with amino acid sequence derived from any non-human mammal, unless otherwise specified. "Animal", as used herein, refers to pig and other non-human mammals.

Since current information indicates that the B domain has no inhibitory epitope and has no known effect on factor VIII function, factor $VIII_{SEP}$ variants of the present invention may have a B domain or a portion thereof. In addition, factor $VIII_{SEP}$ variants may also have the factor VIII B-domain with the B-domain from porcine or human factor V. See, for example, U.S. Pat. No. 5,004,803. A "B-domainless" variant factor $VIII_{SEP}$ or fragment thereof, as used herein, refers to any one of the variant factor $VIII_{SEP}$ constructs described herein that lacks the B domain, or a portion thereof.

One of skill in the art will be aware of techniques that allow individual subunits, domains, or continuous parts of domains of animal or human factor VIII cDNA to be cloned and substituted for the corresponding human or porcine subunits, domains, or parts of domains by established mutagenesis techniques and thereby generate a factor $VIII_{SEP}$ or variant or fragment thereof. For example, Lubin et al. (1994) *J. Biol. Chem.* 269(12):8639-8641 describes techniques for substituting the porcine A2 domain for the human domain using convenient restriction sites. Other methods for substituting a region of the factor VIII cDNA of one species for the factor VIII cDNA of another species include splicing by overlap extension ("SOE"), as described by Horton et al. (1993) *Meth. Enzymol* 217:270-279.

DNA Constructs and Vectors

The nucleotide sequence encoding the factor $VIII_{SEP}$ polypeptides or active variants or fragments thereof can be contained in a DNA construct. The DNA construct can include a variety of enhancers/promoters from both viral and mammalian sources that drive expression of the factor $VIII_{SEP}$ polypeptide in the desired cell type. The DNA construct can further contain 3' regulatory sequences and nucleic acid sequences that facilitate subcloning and recovery of the DNA.

The transcriptional promoter and, if desired, the transcriptional enhancer element are operably linked to the nucleic acid sequence of the factor VIII polypeptide. A "promoter" is defined as a minimal DNA sequence that is sufficient to direct transcription of a nucleic acid sequence. A "transcriptional enhancer element" refers to a regulatory DNA sequence that stimulates the transcription of the adjacent gene. The nucleic acid sequence encoding the factor VIII polypeptide is operably linked to the promoter sequence. See, for example, Goeddel (1990) *Gene Expression Technology: Methods in Enzymology* 185 (Academic Press, San Diego, Calif.).

By "operably linked" is intended a functional linkage between the regulatory promoter and the nucleic acid sequence encoding the factor VIII polypeptide. The functional linkage permits gene expression of factor VIII when the appropriate transcription activator proteins are present.

Thus, the DNA construct can include a promoter that may be native or foreign. By "foreign" it is meant a sequence not found in the native organism. Furthermore, the transcription regulatory elements may be heterologous to the nucleotide sequence encoding factor VIII. By "heterologous" is intended any nucleotide sequence not naturally found upstream of the sequence encoding the factor VIII polypeptide. The promoter may be a natural sequence or a synthetic sequence. In addition, the promoter may be constitutively active, tissue-specific, or inducible. A tissue-specific promoter is preferentially activated in a given tissue and results in expression of a gene product in the tissue where activated.

For use in mammalian cells, the promoters may be derived from a virus. For example, commonly used promoters are derived from polyoma, Simian Virus 40 (SV40) and Adenovirus 2. The early and late promoters of SV40 virus are useful as is the major late promoter of adenovirus. Further, it is also possible, and often desirable, to utilize promoter or control sequences normally associated with the desired gene sequence, provided such control sequences are compatible with the host cell system.

In certain embodiments, the introduction of the nucleotide sequence encoding factor VIII into a cell can be identified in vitro or in vivo by including a marker in the DNA construct. The marker will result in an identifiable change in the genetically transformed cell. Drug selection markers include for example neomycin, puromycin, hygromycin, DHFR, GPT, zeocin and histidinol. Alternatively, enzymes such as herpes simplex virus thymidine kinase (TK) or immunological markers can be used. Further examples of selectable markers are well known in the art.

It is recognized that multiple alterations can be envisioned for the design of the DNA construct used in the methods of the present invention. For instance, the construct may be designed for the insertion of the nucleotide sequence encoding the factor VIII$_{SEP}$ polypeptide using homologous or site-specific recombination systems (i.e., Cre or FLP recombination systems).

The DNA construct may also contain at least one additional gene to be co-introduced into the host cells.

The nucleotide sequences of the present invention can be contained in an expression vector. An "expression vector" is a DNA element, often of circular structure, having the ability to replicate autonomously in a desired host cell, or to integrate into a host cell genome and also possessing certain well-known features which, for example, permit expression of a coding DNA inserted into the vector sequence at the proper site and in proper orientation. Such features can include, but are not limited to, one or more promoter sequences to direct transcription initiation of the coding DNA and other DNA elements such as enhancers, polyadenylation sites and the like, all as well known in the art.

Other vectors, including both plasmid and eukaryotic viral vectors, may be used to express a recombinant gene construct in eukaryotic cells depending on the preference and judgment of the skilled practitioner (see, for example, Sambrook et al., Chapter 16). For example, many viral vectors are known in the art including, for example, retroviruses, adeno-associated viruses, and adenoviruses. Other viruses useful for introduction of a gene into a cell include, but are not limited to, herpes virus, mumps virus, poliovirus, Sindbis virus, and vaccinia virus, such as, canary pox virus. The methods for producing replication-deficient viral particles and for manipulating the viral genomes are well known. See, for examples, Rosenfeld et al. (1991) *Science* 252:431-434, Rosenfeld et al. (1992) *Cell* 68:143-155, and U.S. Pat. No. 5,882,877 (adenovirus); U.S. Pat. No. 5,139,941 (adeno-associated virus); U.S. Pat. No. 4,861,719, U.S. Pat. No. 5,681,746, and Miller et al. (1993) *Methods in Enzymology* 217:581 (retrovirus), all of which are herein incorporated by reference. Therefore, given the knowledge in the art, viral vectors can be readily constructed for use in the introduction of the factor VIII sequences into a cell. Other vectors and expression systems, including bacterial, yeast, and insect cell systems, can be used but are not preferred due to differences in, or lack of, glycosylation.

Factor VIII polypeptides of the invention can be expressed in a variety of cells commonly used for culture and recombinant mammalian protein expression. In particular, a number of rodent cell lines have been found to be especially useful hosts for expression of large proteins. Preferred cell lines, available from the American Type Culture Collection, Rockville, Md., include, but are not limited to, baby hamster kidney cells, and chinese hamster ovary (CHO) cells which are cultured using routine procedures and media. Additional cells of interest can include vertebrate cells such as VERO, HeLa cells, W138, COS-7, and MDCK cell lines. For other suitable expression systems see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology Methods in Enzymology* 185 (Academic Press, San Diego, Calif.).

Methods of Expression and Isolation

The DNA construct of the present invention may be introduced into a cell (prokaryotic or eukaryotic) by standard methods. As used herein, the terms "transformation" and "transfection" are intended to refer to a variety of art recognized techniques to introduce a DNA into a host cell. Such methods include, for example, transfection, including, but not limited to, liposome-polybrene, DEAE dextranmediated transfection, electroporation, calcium phosphate precipitation, microinjection, or velocity driven microprojectiles ("biolistics"). Such techniques are well known by one skilled in the art. See, Sambrook et al. (1989) *Molecular Cloning: A Laboratory Manaual* (2 ed. Cold Spring Harbor Lab Press, Plainview, N.Y.). Alternatively, one could use a system that delivers the DNA construct in a gene delivery vehicle. The gene delivery vehicle may be viral or chemical. Various viral gene delivery vehicles can be used with the present invention. In general, viral vectors are composed of viral particles derived from naturally occurring viruses. The naturally occurring virus has been genetically modified to be replication defective and does not generate additional infectious viruses. The viral vector also contains a DNA construct capable of expressing the factor VIII protein.

The DNA construct containing nucleic acid sequences encoding the factor VIII$_{SEP}$ polypeptide may also be administered to cell by a non-viral gene delivery vehicle. Such chemical gene delivery vehicles include, for example, a DNA- or RNA-liposome complex formulation or a naked DNA. See, for example, Wang et al. (1987) *Proc. Natl. Acad. Sci. U.S.A.* 84:7851, U.S. Pat. No. 5,844,107, U.S. Pat. No. 5,108,921, and Wagner et al. (1991) *Proc. Natl. Acad. Sci. U.S.A.* 88:4255-4259, all of which are herein incorporated by reference.

It is recognized that the method of introducing the factor VIII$_{SEP}$ polypeptide or variant or fragment thereof into a cell can result in either stable integration into the cell genome or transient, episomal expression.

As defined herein, the "expression product" of a DNA encoding a factor VIII$_{SEP}$ polypeptide or a fragment or variant thereof is the product obtained from expression of the referenced DNA in a suitable host cell, including such features of pre- or post-translational modification of protein encoded by the referenced DNA, including but not limited to glycosylation, proteolytic cleavage and the like. It is known in the art that such modifications can occur and can differ somewhat depending upon host cell type and other factors, and can result in molecular isoforms of the product, with retention of procoagulant activity. See, for example, Lind et al, (1995) *Eur. J. Biochem.* 232:1927 incorporated herein by reference.

In a one embodiment, cDNA encoding factor VIII$_{SEP}$ or a variant or fragment thereof, is inserted in a mammalian expression vector, such as ReNeo. Preliminary characterization of the factor VIII$_{SEP}$ is accomplished by transient expression in the ReNeo expression vector containing the factor VIII$_{SEP}$ construct in COS-7 cells. A determination of whether active factor VIII$_{SEP}$ protein is expressed can then be made. The expression vector construct is used further to stably transfect cells in culture, such as baby hamster kidney cells, using methods that are routine in the art, such as liposome-mediated transfection (Lipofectin™, Life Technologies, Inc.). Expression of the factor VIII$_{SEP}$ protein can be confirmed, for example, by sequencing, Northern and Western blotting, or polymerase chain reaction (PCR).

Factor VIII$_{SEP}$ polypeptides or fragments or variants thereof in the culture media in which the transfected cells stably expressing the protein are maintained can be precipitated, pelleted, washed, and resuspended in an appropriate buffer, and the factor VIII$_{SEP}$ protein or variant or fragment thereof is purified by standard techniques, including immunoaffinity chromatography using, for example, monoclonal anti-A2-Sepharose™.

A "fusion protein" or "fusion factor VIII$_{SEP}$ or fragment thereof", as used herein, is the product of a hybrid gene in which the coding sequence for one protein is extensively altered, for example, by fusing part of it to the coding sequence for a second protein from a different gene to produce a hybrid gene that encodes the fusion protein.

In a further embodiment, the factor VIII$_{SEP}$ or variant or fragment thereof is expressed as a fusion protein from a recombinant molecule in which sequence encoding a protein or peptide that enhances, for example, stability, secretion, detection, isolation, or the like is inserted in place adjacent to the factor VIII encoding sequence. See, for example, U.S. Pat. No. 4,965,199 which discloses a recombinant DNA method for producing factor VIII in mammalian host cells and purification of human factor VIII. Human factor VIII expression on CHO (Chinese hamster ovary) cells and BHKC (baby hamster kidney cells) has been reported. Established protocols for use of homologous or heterologous species expression control sequences including, for example, promoters, operators, and regulators, in the preparation of fusion proteins are known and routinely used in the art. See, Ausubel et al. *Current Protocols in Molecular Biology*, Wiley Interscience, N.Y., herein incorporated by reference. It is further noted that expression is enhanced by including portions of the B-domain. In particular, the inclusion of those parts of the B domain designated "SQ" (Lind et al. (1995) *Eur. J. Biochem.* 232:1927, herein incorporated herein by reference) results in favorable expression. "SQ" constructs lack all of the human B domain except for 5 amino acids of the B domain N-terminus and 9 amino acids of the B domain C-terminus.

It is further recognized that the factor VIII$_{SEP}$ polypeptide or variant or fragment thereof of the invention may be prepared via reconstitution methods. In this embodiment factor VIII$_{SEP}$, variants or fragments thereof are made by isolation of subunits, domains, or continuous parts of domains of plasma-derived factor VIII, followed by reconstitution and purification to produce a factor VIII$_{SEP}$ polypeptide of the invention. Alternatively, the factor VIII$_{SEP}$, variant or fragment thereof can be made by recombinant DNA methods, followed by reconstitution and purification.

More particularly, the method of preparing a factor VIII$_{SEP}$ by reconstitution methods can be performed via a modification of procedures reported by Fay et al. (1990) *J. Biol. Chem.* 265:6197; and Lollar et al. (1988) *J. Biol. Chem.* 263:10451, which involves the isolation of subunits (heavy and light chains) of human and animal factor VIII, followed by recombination of human heavy chain and animal light chain or by recombination of human light chain and animal heavy chain.

Isolation of both human and animal individual subunits involves dissociation of the light chain/heavy chain dimer. This is accomplished, for example, by chelation of calcium with ethylenediaminetetraacetic acid (EDTA), followed by monoS™ HPLC (Pharmacia-LKB, Piscataway, N.J.). Hybrid human/animal factor VIII molecules are reconstituted from isolated subunits in the presence of calcium. Hybrid human light chain/animal heavy chain or animal light chain/human heavy chain factor VIII is isolated from unreacted heavy chains by monoS™ HPLC by procedures for the isolation of porcine factor VIII, such as described by Lollar et al. (1988) *Blood* 71:137-143 and in U.S. Pat. No. 6,376,463, both of which is herein incorporated by reference.

Diagnostic Assays

As used herein, "diagnostic assays" include assays that in some manner utilize the antigen-antibody interaction to detect and/or quantify the amount of a particular antibody that is present in a test sample to assist in the selection of medical therapies. There are many such assays known to those of skill in the art. As used herein, however, the factor VIII$_{SEP}$ DNA or variant or fragment thereof and protein expressed therefrom, in whole or in part, can be substituted for the corresponding reagents in the otherwise known assays, whereby the modified assays may be used to detect and/or quantify antibodies to factor VIII. It is the use of these reagents, the factor VIII$_{SEP}$ DNA or variants or fragments thereof or protein expressed therefrom, that permits modification of known assays for detection of antibodies to human or animal factor VIII or to hybrid human/animal factor VIII. As used herein, the factor VIII$_{SEP}$ or variants or fragment thereof that includes at least one epitope of the protein can be used as the diagnostic reagent.

The DNA or amino acid sequence of the factor VIII$_{SEP}$ or variant or fragment thereof can be used in assays as diagnostic reagents for the detection of inhibitory antibodies to human or animal factor VIII, including, for example, samples of serum and body fluids of human patients with factor VIII deficiency. These antibody assays include assays such as ELISA assays, immunoblots, radioimmunoassays, immunodiffusion assays, and assay of factor VIII biological activity (e.g., by coagulation assay). Examples of other assays in which the factor VIII$_{SEP}$ or variant or fragment thereof can be used include the Bethesda assay and anticoagulation assays.

Techniques for preparing these reagents and methods for use thereof are known to those skilled in the art. For example, an immunoassay for detection of inhibitory antibodies in a patient serum sample can include reacting the test sample with a sufficient amount of the factor VIII$_{SEP}$ that contains at least one antigenic site, wherein the amount is sufficient to form a detectable complex with the inhibitory antibodies in the sample.

Nucleic acid and amino acid probes can be prepared based on the sequence of the factor VIII$_{SEP}$ DNA or protein molecule or fragments or variants thereof. In some embodiments, these can be labeled using dyes or enzymatic, fluorescent, chemiluminescent, or radioactive labels that are commercially available. The amino acid probes can be used, for example, to screen sera or other body fluids where the presence of inhibitors to human, animal, or hybrid human/animal factor VIII is suspected. Levels of inhibitors can be quantitated in patients and compared to healthy controls, and can be used, for example, to determine whether a patient with a factor VIII deficiency can be treated with a factor VIII$_{SEP}$ or active fragment or variant thereof. The cDNA probes can be used, for example, for research purposes in screening DNA libraries.

Pharmaceutical Compositions

The present invention further provides pharmaceutical compositions comprising the nucleic acid molecules and the polypeptides encoding the high-level expression factor VII-I$_{SEP}$ of the present invention or variants and fragments thereof. Such compositions can comprise nucleic acids and polypeptides of the invention either alone or in combination with appropriate pharmaceutical stabilization compounds, delivery vehicles, and/or carrier vehicles, are prepared according to known methods, as described in Martin et al. *Remington's Pharmaceutical Sciences*, herein incorporated by reference.

In one embodiment, the preferred carriers or delivery vehicles for intravenous infusion are physiological saline or phosphate buffered saline.

In another embodiment, suitable stabilization compounds, delivery vehicles, and carrier vehicles include but are not limited to other human or animal proteins such as albumin.

Phospholipid vesicles or liposomal suspensions may also be used as pharmaceutically acceptable carriers or delivery vehicles. These can be prepared according to methods known to those skilled in the art and can contain, for example, phosphatidylserine-phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the factor VIII$_{SEP}$ of the present invention is then introduced into the container. The container is then swirled by hand to free lipid material from the sides of the container and to disperse lipid aggregates, thereby forming the liposomal suspension.

The factor VIII$_{SEP}$ molecules of the invention can be combined with other suitable stabilization compounds, delivery vehicles, and/or carrier vehicles, including vitamin K dependent clotting factors, tissue factor, and von Willebrand factor (vWf) or a fragment of vWf that contains the factor VIII binding site, and polysaccharides such as sucrose.

Factor VIII$_{SEP}$ molecules of the invention can also be delivered by gene therapy using delivery means such as retroviral vectors. This method consists of incorporation of a nucleotide sequence encoding desired factor VIII$_{SEP}$ polypeptide of the invention into human cells that are transplanted directly into a factor VIII$_{SEP}$ deficient patient or that are placed in an implantable device, permeable to the factor VIII molecules but impermeable to cells, that is then transplanted.

In one embodiment, the method will be retroviral-mediated gene transfer. In this method, a nucleotide sequence encoding a factor VIII polypeptide of the invention is cloned into the genome of a modified retrovirus. The gene is inserted into the genome of the host cell by viral machinery where it will be expressed by the cell. The retroviral vector is modified so that it will not produce virus, preventing viral infection of the host. The general principles for this type of therapy are known to those skilled in the art and have been reviewed in the literature (Kohn et al. (1989) *Transfusion* 29:812-820).

The factor VIII$_{SEP}$ polypeptide of the invention can be stored bound to vWf to increase the half-life and shelf-life of the polypeptide molecule. Additionally, lyophilization of factor VIII$_{SEP}$ can improve the yields of active molecules in the presence of vWf. Current methods for storage of human and animal factor VIII used by commercial suppliers can be employed for storage of recombinant factor VIII. These methods include: (1) lyophilization of factor VIII$_{SEP}$ in a partially-purified state (as a factor VIII "concentrate" that is infused without further purification); (2) immunoaffinity-purification of factor VIII$_{SEP}$ by the Zimmerman method and lyophilization in the presence of albumin, which stabilizes the factor VIII; (3) lyophilization of recombinant factor VIII$_{SEP}$ in the presence of albumin.

Additionally, the factor VIII polypeptides can be stored at 4° C. in 0.6 M NaCl, mM MES, and 5 mM CaCl$_2$ at pH 6.0. The polypeptides can also be stored frozen in these buffers and thawed with minimal loss of activity.

Methods of Treatment

Factor VIII$_{SEP}$ or fragments and variant thereof can be used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. The active materials are preferably administered intravenously.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

Additionally, factor VIII$_{SEP}$ or fragments and variant thereof can be administered by transplantation of cells genetically engineered to produce the factor VIII$_{SEP}$ or by implantation of a device containing such cells, as described above.

In one embodiment, pharmaceutical compositions of factor VIII$_{SEP}$ or fragments and variants thereof alone or in combination with stabilizers, delivery vehicles, and/or carriers are infused into patients intravenously according to the same procedure that is used for infusion of factor VIII$_{SEP}$.

The treatment dosages of the factor VIII$_{SEP}$ composition or variants or fragments thereof that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the factor VIII$_{SEP}$ or variants or fragments thereof is included in the pharmaceutically acceptable carrier, delivery vehicle, or stabilizer in an amount sufficient to deliver to a patient a therapeutically effective amount of the hybrid to stop bleeding, as measured by standard clotting assays.

"Specific activity" as used herein, refers to the activity that will correct the coagulation defect of human factor VIII deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed. The specific activity of the factor VIII polypeptides, variant or fragments thereof, may be less than, equal to, or greater than that of either plasma-derived or recombinant human factor VIII.

Factor VIII is classically defined as that substance present in normal blood plasma that corrects the clotting defect in plasma derived from individuals with hemophilia A. The coagulant activity in vitro of purified and partially-purified forms of factor VIII$_{SEP}$ is used to calculate the dose of factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher et al. *New Engl. J. Med.* 328: 453-459; Pittman et al. (1992) *Blood* 79:389-397; and Brinkhous et al. (1985) *Proc. Natl. Acad. Sci.* 82:8752-8755.

The increase of factor VIII$_{SEP}$ in the plasma will be sufficient to produce a therapeutic effect. A "therapeutic effect" is defined as an increase in the blood coagulation activity in the plasma of patients that is greater than the coagulation activity observed in the subject before administration of the factor VIII$_{SEP}$ molecule. In a standard blood clotting assay, the shorter time for clot formation, the greater the activity of factor VIII being assayed. An increase in factor VIII activity in the factor VIII deficient plasma of at least 1% or higher will be therapeutically beneficial.

Usually, the desired plasma factor VIII level to be achieved in the patient through administration of the factor VIII$_{SEP}$ or variant or fragment thereof is in the range of 30-100% of normal. In a one mode of administration of the factor VIII$_{SEP}$ or fragment or variant thereof, the composition is given intravenously at a preferred dosage in the range from about 5 to 50 units/kg body weight, more preferably in a range of 10-50 units/kg body weight, and most preferably at a dosage of 20-40 units/kg body weight; the interval frequency is in the range from about 8 to 24 hours (in severely affected hemophiliacs); and the duration of treatment in days is in the range from 1 to 10 days or until the bleeding episode is resolved. See, for example, Roberts et al. (1990) *Hematology*, Williams et al. ed. Ch. 153, 1453-1474, herein incorporated by reference. Patients with inhibitors may require more factor VIII$_{SEP}$ or variants or fragments thereof, or patients may require less factor VIII$_{SEP}$ or fragments or variants thereof. As in treatment with human or porcine factor VIII, the amount of factor VIII$_{SEP}$ or fragments or variants infused is defamed by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

Treatment can take the form of a single intravenous administration of the composition or periodic or continuous administration over an extended period of time, as required. Alternatively, factor VIII$_{SEP}$ or fragments or variants thereof can be administered subcutaneously or orally with liposomes in one or several doses at varying intervals of time.

Factor VIII$_{SEP}$ or fragments or variants thereof can also be used to treat uncontrolled bleeding due to factor VIII deficiency in hemophiliacs who have developed antibodies to human factor VIII.

EXPERIMENTAL

Example 1

Sequence Characterization of Factor VIII

Both porcine and human factor VIII are isolated from plasma as a two subunit protein. The subunits, known as the heavy chain and light chain, are held together by a non-covalent bond that requires calcium or other divalent metal ions. The heavy chain of factor VIII contains three domains, A1, A2, and B, which are linked covalently. The light chain of factor VIII also contains three domains, designated A3, C1, and C2. The B domain has no known biological function and can be removed, or partially removed from the molecule proteolytically or by recombinant DNA technology methods without significant alteration in any measurable parameter of factor VIII. Human recombinant factor VIII has a similar structure and function to plasma-derived factor VIII, though it is not glycosylated unless expressed in mammalian cells. Both human and porcine activated factor VIII ("factor VIIIa") have three subunits due to cleavage of the heavy chain between the A1 and A2 domains. This structure is designated A1/A2/A3-C1-C2.

The cDNA sequence of porcine factor VIII corresponding the signal peptide coding region, the A1, B, light chain activity peptide region A3, C1, and C2 domains is provided in SEQ ID NO:1. The translation of the porcine cDNA is provided in SEQ ID NO:2.

The alignment of the predicted amino acid sequence of full-length porcine factor VIII (SEQ ID NO:2) with the published human (Wood et al. (1984) *Nature* 312:330-337) (SEQ ID NO:6) and murine (Elder et al. (1993) supra) (SEQ ID NO:8) sequences are shown in FIGS. 1A-1H along with sites for post-translational modification, proteolytic cleavage, and recognition by other macromolecules.

Potential N-linked glycosylation sites (NXS/T where X is not proline) can be seen in FIGS. 1A-1H. There are eight conserved N-linked glycosylation sites: one in the A1 domain, one in the A2 domain, four in the B domain, one in the A3 domain, and one in the C1 domain. The 19 A and C domain cysteines are conserved, whereas there is divergence of B domain cysteines. Six of the seven disulfide linkages in factor VIII are found at homologous sites in factor V and Ceruloplasmin, and both C domain disulfide linkages are found in factor V (McMullen et al. (1995) *Protein Sci.* 4:740-746). Human factor VIII contains sulfated tyrosines at positions 346, 718, 719, 723, 1664, and 1680 (Pittman et al. (1992) *Biochemistry* 31:3315-3325; Michnick et al. (1994) *J. Biol. Chem.* 269:20095-20102). These residues are conserved in mouse factor VIII and porcine factor VIII (FIG. 1), although the CLUSTALW program failed to align the mouse tyrosine corresponding to Tyr346 in human factor VIII. Epitopes of the various domain of the factor VIII polypeptide are outlined in FIG. 1.

Example 2

Summary

Human factor VIII expression levels are significantly lower than levels of other coagulation proteins in vivo and in heterologous expression systems in vitro. Low-level expression of recombinant human factor VIII has constrained the treatment of hemophilia A using recombinant protein infusion and gene therapy protocols. However, recombinant B-domain-deleted porcine factor VIII is expressed at levels 10-14 fold greater than recombinant B-domain-deleted human factor VIII in vitro. To identify sequences of porcine factor VIII necessary for this property, B-domain-deleted human/porcine hybrid factor VIII cDNAs were produced that contained substitution of human sequences with the corresponding porcine sequences. These cDNAs were transiently transfected into COS-7 cells or stably transfected into BHK-derived cells and factor VIII expression into the extracellular media was measured by one-stage coagulation assay. Human/porcine hybrid factor VIII cDNAs containing 1) the A1, A2 and A3 domains of porcine factor VIII and the C1 and C2 domains of human factor VIII, or 2) the A1 and A3 domains of porcine factor VIII and the A2, C1, and C2 domains of human factor VIII demonstrated factor VIII expression levels comparable to porcine factor VIII. A human/porcine hybrid factor VIII molecule demonstrating high-level expression may be valuable for improving factor VIII production for intravenous infusion or for somatic cell gene therapy of hemophilia A.

Materials

Dulbecco's phosphate-buffered saline, fetal bovine serum (FBS), penicillin, streptomycin, DMEM:F12, serum-free AIM V culture media, Lipofectin, Lipofectamine 2000 and geneticin were purchased from Invitrogen. Baby hamster kidney-derived cells, designated BHK-M cells (Funk et al. (1990) *Biochemistry* 29:1654-1660), were a gift from Dr. Ross Macgillivray, University of British Columbia. Transient transfections were controlled for transfection efficiency using the RL-CMV vector and Dual-Luciferase Assay Kit (Promega, Madison, Wis.). Citrated factor VIII-deficient plasma and pooled citrated normal human plasma (FACT) were purchased from George King Biomedical (Overland Park, Kans.). Activated partial thromboplastin reagent (aPTT) was purchased from Organon Teknika (Durham, N.C.). Oligonucleotide primers were synthesized by Life Technologies. Pfu DNA polymerase and *E. coli* XL-1 Blue cells were purchased from Stratagene (La Jolla, Calif.).

Construction of Factor VIII Expression Vectors

All of the factor VIII expression vectors in this study were contained in the ReNeo mammalian expression plasmid (Lind et al. (1995) *Eur. J. Biochem.* 232: 1927). The factor VIII cDNA inserts lack endogenous factor VIII 5'-UTR sequence and contain the first 749 of the 1805 nt human factor VIII 3'-UTR.

A human B domain-deleted factor VIII cDNA designed HSQ (FIG. 2) was created by cloning the human factor VIII cDNA into the mammalian expression vector ReNeo as described previously (Doering et al. (2002) *J. Biol. Chem.* 277: 38345-38349). The HSQ cDNA encodes an S F S Q N P P V L K R H Q R (SEQ ID NO:9) linker sequence between the A2 and ap domains. This linker includes the R H Q R (SEQ ID NO:10) recognition sequence for intracellular proteolytic processing by PACE/furin (Seidah et al. (1997) *Current Opinion in Biotechnology* 8:602-607). This cleavage event converts single chain factor VIII into a heterodimer (Lind et al. (1995) *Eur. J. Biochem.* 232:19-27). Heterodimeric factor VIII is considered the physiologic form of factor VIII (Fass et al. (1982) *Blood* 59:594-600).

A B-domain-deleted form of porcine factor VIII cDNA was ligated into ReNeo as described previously (Doering et al. (2002) *J. Biol. Chem.* 277: 38345-38349). The cDNA, designated P/OL (FIG. 2), encodes a porcine-derived linker sequence S FA Q N S R P P S A S A P K P P V L R R H Q R (SEQ ID NO:11) between the A2 and ap domains for PACE/furin recognition.

A B-domainless hybrid human/porcine factor VIII molecule designated HP1, which contains the porcine A2 domain and human A1, ap-A3, C1 and C2 domains, was prepared as described previously (Lubin et al. (1994) *J. Biol. Chem.* 269: 8639-8641). The cDNA encoding the human-derived linker sequence S F S Q N P P V L K R H Q R (SEQ ID NO:9) was inserted between the A2 and ap domains of HP1 by splicing-by-overlap extension (SOE) mutagenesis (Horton et al. (1993) *Methods Enzymol.* 217:270-279), producing HP1/SQ (FIG. 2).

HP30, which contains the porcine ap-A3 domain and human A1, A2, C1 and C2 domains, was prepared as described previously (Barrow et al. (2000) *Blood* 95:557-561). The cDNA encoding the porcine-derived linker sequence S F A Q N S R P P S A S A P K P P V L R R H Q R(SEQ ID NO:11) was inserted between the A2 and ap domains of HP30 by SOE mutagenesis, producing HP30/OL (FIG. 2).

HP44/OL, which contains the porcine A1, A2, ap-A3 domains, the porcine-derived linker sequence S F A Q N S R P P S A S A P K P P V L R R H Q R (SEQ ID NO:11) and the human C1 and C2 domains (FIG. 2), was prepared as follows. P/OL ReNeo was digested with AvrII and the fragment containing A1, A2 and ReNeo sequence was gel purified. HP30/OL was digested with AvrII and the fragment containing porcine ap-A3 and human C1 and C2 sequences was gel purified. Ligation of the products, transformation of *E. coli* XL-1 cells and plasmid purification were performed as described previously (Healey et al. (1998) *Blood* 92:3701-3709).

HP46/SQ, which contains the porcine A1 domain and human A2, ap-A3, C1 and C2 domains and the human S F S Q N P P V L K R H Q R (SEQ ID NO:11) linker sequence (FIG. 2), was prepared by SOE mutagenesis. P/OL in ReNeo and HSQ in ReNeo were used as templates in the first round SOE reactions. The 5' primer in the P/OL reaction was complementary to ReNeo sequence 5' to the factor VIII cDNA. The 3' primer flanked the porcine A1 domain. The 5' primer in the HSQ reaction was partially complementary to the 3' primer used in the first reaction. The 3' primer was complementary to human A2 sequence. Following gel purification of the products from the first round reactions, the second SOE reaction was performed, yielding a product containing ReNeo sequence 5' to the factor VIII cDNA insert, the porcine A1 domain, and part of the human A2 domain. This product was digested with XhoI, at the junction of ReNeo and the factor VIII insert, and MluI, in the human A2 domain, and ligated into XhoI/MluI digested HSQ/ReNeo. The resulting plasmid was amplified by transformation into *E. coli* XL-1 Blue cells as described above.

HP47/OL, which contains the porcine A1, ap-A3 domains, porcine-derived linker sequence S F A Q N S R P P S A S A P K P P V L R R H Q R (SEQ ID NO:11) and human A2, C1 and C2 domains (FIG. 2) was prepared as follows. HP46/SQ in ReNeo was digested with AvrII, which cleaves the plasmid in the ReNeo sequence 5 to the factor VIII insert and at the A2-ap junction. The fragment containing the A1 and A2 domains was gel purified ligated to a fragment of HP30/OL in ReNeo produced by AvrII digestion.

Sequences produced by SOE mutagenesis were confirmed by dideoxy DNA sequencing.

Transient Expression of Factor VIII from COS-7 Cells

COS-7 cells were grown to 70-80% confluence in 2 $cm^2$ wells containing 1 ml DMEM:F12 supplemented with 10% FBS, 100 units/ml penicillin and 100 µg/ml streptomycin. Cells were transfected with a 2000:1 mass ratio of factor VIII plasmid:luciferase plasmid DNA using Lipofectamine 2000. Twenty-four hours after transfection the cells were rinsed twice with 1 ml of PBS and 0.5 ml of serum-free AIM V medium was added to each well. Cells were cultured 24 hr before the conditioned media was harvested and factor VIII activity was measured as described below.

Stable Expression of Factor VIII from Baby Hamster Kidney-Derived (BHK-M) Cells BHK-M cells were transfected using Lipofectin along with an ReNeo plasmid containing factor VIII cDNA and cultured in the presence of DMEM:F12 containing 10% FBS, 100 units/ml penicillin, 100 µg/ml streptomycin and 500 µg/ml geneticin for 10 days. The ReNeo vector contains the neomycin phosphotransferase gene for resistance to the antibiotic geneticin. Twenty-four to 72 geneticin resistant clones were screened for factor VIII production. The clone from each cDNA construct that displayed the highest level of factor VIII activity was transferred into a 75 $cm^2$ flask, grown to 90-95% confluence and then switched to 25 ml serum-free AIM V media. After 24 hr, the conditioned media was replaced with 25 ml fresh serum-free media AIM V and cultured for an additional 24 hr. Harvested media from each time point was assayed for factor VIII activity as described below.

Factor VIII Assay

Factor VIII activity was measured by one-stage coagulation assay using a ST art Coagulation Instrument (Diagnostica Stago, Asnieres, France). Five µl of sample or standard was added to 50 µl of factor VIII-deficient plasma, followed by addition of 50 µl aPTT reagent and incubation for 3 min at 37° C. Fifty microliters of 20 mM $CaCl_2$ was added to initiate the reaction, and the time required to develop a fibrin clot was measured viscometrically. Standard curves were generated using several dilutions of pooled normal human plasma and subjected to linear regression analysis of the clotting time versus the logarithm of the reciprocal plasma dilution. For determination of factor VIII activity, samples were diluted in HEPES buffered saline to a concentration within the range of the standard curve.

Results

Figure 3:
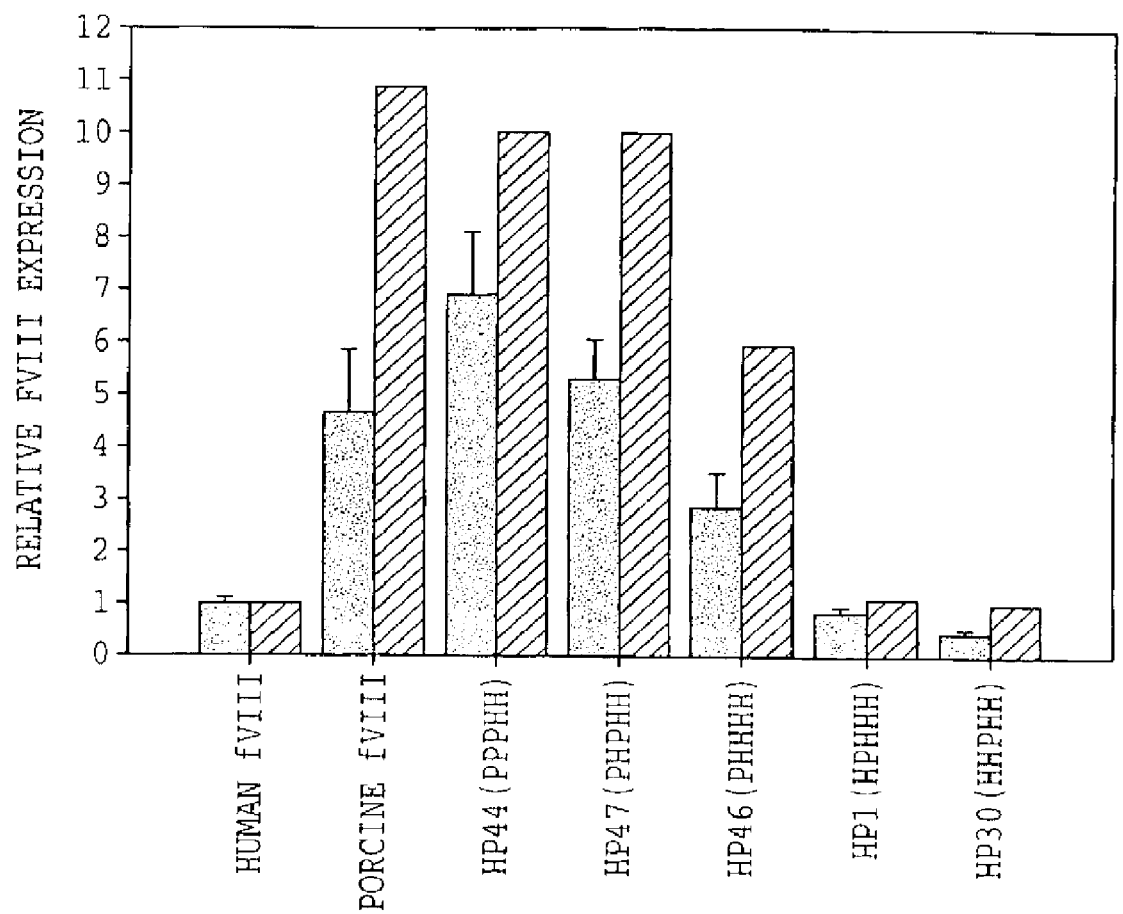
FIG. 3 provides graphical data showing heterologous expression of a recombinant B domain-deleted porcine factor VIII protein, designated P/OL, recombinant B domain-deleted human factor VIII protein, and five recombinant B domain-deleted hybrid human/porcine factor VIII proteins, designated HP1, HP30, HP44, HP46, and HP47. COS-7 cells (solid bars) and baby hamster kidney-derived cells, designated BMK-M cells, (hatched bars) were transfected with the individual factor VIII expression constructs and luciferase plasmid DNA and cultured in serum-free media for 24 hr. The data illustrates that there is a significant increase in expression of P/OL, HP44, HP47, and HP46 compared to HSQ. In contrast, expression of HP1 and HP30 were not increased compared to HSQ.

To identify regions in porcine factor VIII that confer high-level expression, human/porcine hybrid factor VIII molecules shown in FIG. 2 were constructed and their expression levels in COS-7 and BHK-M cells were measured. After COS-7 cell transfection, the expression plasmid is not integrated into genomic DNA, but is present transiently as an episomal DNA. Expression levels from COS-7 cells represent an average of the cell population. FIG. 3 shows the results of COS-7 wells transfected in quadruplicate. There is a significant increase in expression of P/OL, HP44, HP47, and HP46 compared to HSQ. In contrast, expression of HP1 and HP30 were not increased compared to HSQ.

Expression of factor VIII from BHK-M cells was consistent with the results in COS-7 cells. After BHK-M cell transfection, clones containing plasmid DNA that is stably incorporated into the genome are selected using the antibiotic geneticin. Cells that do not contain the neomycin phosphotransferase gene contained in the plasmid do not survive in the presence of geneticin. Approximately 50% of the clones resulting from transfection of BHK-M cells with the constructs shown in FIG. 2 did not express detectable levels of factor VIII (data not shown). This is consistent with previous results with HSQ and P/OL (Doering et al. (2002) *J. Biol. Chem.* 277: 38345-38349) and is expected because factor VIII expression per se is not selected for during geneticin selection. Average expression levels for factor VIII-producing clones were significantly higher for the P/OL, HP44, HP47, and HP46, but not the HP1 and HP30 constructs, compared to HSQ (data not shown). For each factor VIII cDNA construct, the clone producing the highest levels of factor VIII was expanded and switched to serum-free AIM V medium. Consistent with the above results, factor VIII levels for the HP44, HP47, and HP46, but not the HP1 and HP30, were comparable to P/OL (FIG. 3).

FIG. 3 shows heterologous expression of recombinant porcine factor VIII OL and recombinant human factor VIII SQ. COS-7 cells (solid bars) were transfected with the individual factor VIII expression constructs and luciferase plasmid DNA and cultured in serum-free media for 24 hr as described in Experimental Procedures. Conditioned media was assayed for factor VIII activity by one-stage coagulation assay. After media harvest, cells were lysed and assayed for luciferase activity. Data are presented as the ratio of factor VIII activity: luciferase activity (mean+/−standard deviation of four wells of transfected cells for each sample) normalized to the mean HSQ level. Data shown are representative of experiments involving three separate cultures of COS-7 cells. BHK-M cells (hatched bars) were transfected with the individual factor VIII expression constructs and selected for stable transgene integration. The top producing clone for each construct was split to a 75 $cm^2$ flask, grown to greater than 90% confluence, rinsed twice with PBS and cultured 24 hr in serum-free media. After 24 hr, the media was harvested and assayed for factor VIII activity. The data are expressed relative to HSQ expression, which was 2.8 units/$10^6$ cells/24 h in BHK-M cells.

Discussion

Recombinant B domain-deleted porcine factor VIII is expressed at levels up to 14-fold greater than recombinant human factor VIII (Doering et al. (2002) *J. Biol. Chem.* 277: 38345-38349). The levels are substantially greater than in previously published reports of factor VIII expression (Table II). The mechanism for the high expression phenomenon has not been established. However, high-level expression is due to a difference between human and porcine B domain-deleted factor VIII in translated sequence because the P/OL and HSQ expression cassettes do not contain endogenous factor VIII 5'-UTR sequence, while both possess the first 749 nt (of 1805 nt) of the human factor VIII 3'UTR. Furthermore, the effect occurs at the post-transcriptional level, because there is no difference in P/OL and HSQ mRNA levels in BHK-M cells (Doering et al. (2002) *J. Biol. Chem.* 277:38345-38349).

TABLE II

Previous Reports of FACTOR VIII Expression.

| FACTOR VIII Construct | FVIII Level | Assay | Serum | vWf | Cell Line | Reference |
|---|---|---|---|---|---|---|
| Human, full length | $0.07^a$ | Coatest | + | − | BHK | Wood et al. (1984) *Nature* 312: 330-337 |
| Human, full length | $0.16^a$ $0.33^a$ | Coatest Coagulation | + | − | COS | Toole et al. (1986) *Proc. Natl. Acad. Sci. U.S.A.* 83: 5939-5942 |
| Human, B domain-deleted | $0.34^a$ | Coatest | − | − | $CHO^c$ | Kaufman et al. (1988) *J. Biol. Chem.* 263: 6352-6362 |
| Human, full length | $1.4^b$ | Coatest | − | + | CHO | Kaufman et al. (1989) *Mol. Cell Biol.* 9: 1233-1242 |
| Human, B domain-deleted | $5^a$ | Coatest | − | + | CHO | Pittman et al. (1993) *Blood* 81: 2925-2935 |
| Human, B domain-deleted | $1.5^a$ | Coatest | − | − | CHO | Lind et al (1995) *Eur. J. Biochem.* 232: 19-27 |

TABLE II-continued

Previous Reports of FACTOR VIII Expression.

| FACTOR VIII Construct | FVIII Level | Assay | Serum | vWf | Cell Line | Reference |
|---|---|---|---|---|---|---|
| Human, B domain-deleted | 2.5[b] | Coagulation | + | − | CHO | Plantier et al. (2001) Thromb. Haemost. 86: 596-603 |
| Human, B domain-deleted | 3.1[a] 10[b] | Coagulation | − | − | BHK | Deering et al. (2002) J. Biol. Chem. 277, 38345-38349 |
| Porcine, B domain-deleted | 41[a] 140[b] | Coagulation | − | − | BHK | Deering et al. (2002) J. Biol. Chem. 277, 38345-38349 |

[a]units/milliliter/24 hours
[b]units/10$^6$ cells/24 hours
[c]Chinese hamster ovary

Example 3

Figure 12:
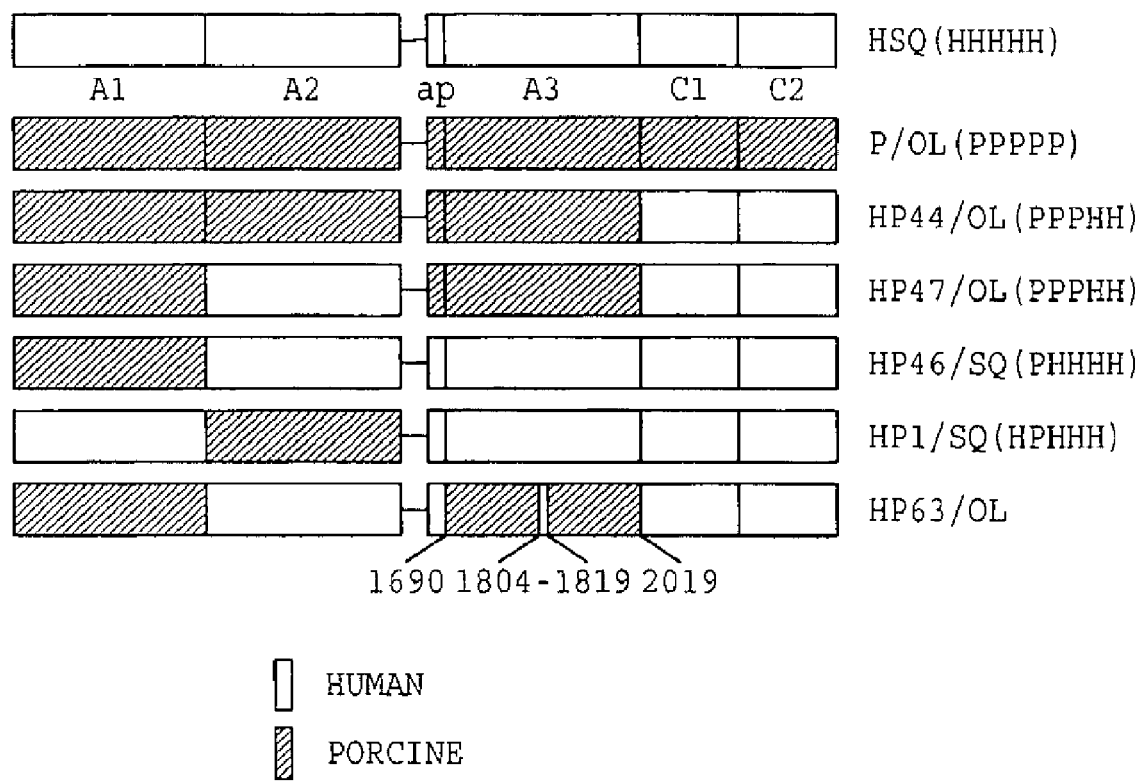
FIG. 12 provides a schematic representation of one possible factor VIII$_{SEP}$ variant of the present invention. The variant, referred to as HP63/OL, contains the porcine A1 domain and a partially humanized ap-A3 domain that comprises porcine amino acids from about 1690 to about 1804 and from about 1819 to about 2019.

Variants of the factor VIII$_{SEP}$ sequences of the invention may be generated. For example, the HP63/OL factor VIII$_{SEP}$ may be generated. See FIGS. 12-14.

Two major human factor VIII epitopes that are recognized by inhibitory antibodies have been identified: in the A2 domain in a segment bound by residues 484-508 (Healey et al. (1995) *J. Biol. Chem.* 270:14505-14509) and in the C2 domain in a segment bounded by residues 2181-2252 (Healey et al. (1998) *Blood* 92:3701-3709 and Barrow et al. (2001) *Blood* 97:169-174, all of which are herein incorporated by reference). The sequence numbering refers to the full-length, mature human factor VIII according to standard convention (Vehar et al. (1984) *Nature* 312:337-342). Antibodies also have been identified that recognize the light chain activation peptide, ap, (Barrow et al. (2000) *Blood* 95:557-561) and the A3 domain in a region bounded by residues 1804-1819 (Zhong et al. (1998) *Blood* 92:136-142), but they are less common (Prescott et al. (1997) *Blood* 89:3663-3671). Other epitopes occasionally have been identified, but they are considered unusual.

A variant of a factor VIII$_{SEP}$ molecule can be generated to contain the human A2, ap, and C2 domains, human sequence 1804-1819 and the porcine A1 domain and porcine A3 sequences from about 1690 to 1803 and from about 1820 to 2019. This factor VIII$_{SEP}$ variant is diagramed in FIG. 12 as HP63. The amino acid and nucleotide sequences are provided in SEQ ID NO: 20 and 21. Such a molecule is predicted to be a super-expresser that has the antigenic characteristics of human factor VIII. Assays to measure the high-level expression activity of the HP63 variant are disclosed elsewhere herein.

TABLE III

Sequence ID Listing

| SEQ ID NO | Type | Species | Description |
|---|---|---|---|
| 1 | NT | *Sus scrofa* | Factor VIII |
| 2 | AA | *Sus scrofa* | Factor VIII |
| 3 | NT | *Sus scrofa* | Factor VIII - B-domain deleted (retains first 12 and last 12 amino acids of B-domain) |
| 4 | AA | *Sus scrofa* | Factor VIII - B domain deleted (retains first 12 and last 12 amino acids of B-domain) |
| 5 | NT | *Homo sapiens* | Factor VIII with 5' and 3' UTR sequences |
| 6 | AA | *Homo sapiens* | Factor VIII |
| 7 | NT | *Homo sapiens* | Factor VIII cDNA |
| 8 | AA | *Mus musculus* | Factor VIII |
| 9 | AA | *Homo sapiens* | Linker sequence between A2 and ap domains |
| 10 | AA | *Homo sapiens* | Recognition sequence for PACE/furin |
| 11 | AA | *Sus scrofa* | Linker sequence between A2 and ap domains |
| 12 | NT | *Homo sapiens* | Factor VIII - B-domain deleted |
| 13 | AA | *Homo sapiens* | Factor VIII - B-domain deleted |
| 14 | NT | Artificial | HP44/OL Factor VIII which has the following domains: $A1_P$-$A2_P$-$ap_P$-$A3_P$-$C1_H$-$C2_H$ |
| 15 | AA | Artificial | HP44/OL Factor VIII which has the following domains: $A1_P$-$A2_P$-$ap_P$-$A3_P$-$C1_H$-$C2_H$ |
| 16 | NT | Artificial | HP46/SQ Factor VIII which has the following domains: $A1_P$-$A2_H$-$ap_H$-$A3_H$-$C1_H$-$C2_H$ |
| 17 | AA | Artificial | HP46/SQ Factor VIII which has the following domains: $A1_P$-$A2_H$-$ap_H$-$A3_H$-$C1_H$-$C2_H$ |
| 18 | NT | Artificial | HP47/OL Factor VIII which has the following domains: $A1_P$-$A2_H$-$ap_P$-$A3_P$-$C1_H$-$C2_H$ |
| 19 | AA | Artificial | HP47/OL Factor VIII which has the following domains: $A1_P$-$A2_H$-$ap_P$-$A3_P$-$C1_H$-$C2_H$ |
| 20 | NT | Artificial | HP63/OL |
| 21 | AA | Artificial | HP63/OL |

The present invention has been described above with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

---

What is claimed is:

1. An isolated polypeptide comprising an amino acid sequence having at least 95% sequence identity to SEQ ID NO: 19.

2. An isolated polypeptide of claim 1, wherein said polypeptide comprises the amino acid sequence set forth in set forth in SEQ ID NO: 19.

3. A method of increasing the level of expression of a factor VIII polypeptide in a cell comprising:
   a) introducing into said cell a nucleic acid molecule comprising a nucleotide sequence having at least 95% sequence identity to SEQ ID NO: 18, wherein said sequence encodes said factor VIII polypeptide and said factor VIII polypeptide is characterized by high expression; and
   b) culturing said cell under conditions that allow expression of said nucleic acid molecule.

4. The method of claim 3, wherein said nucleic acid molecule comprises a nucleotide sequence selected from the group consisting of:
   a) a nucleotide sequence comprising a sequence encoding a polypeptide comprising the amino acid sequence set forth in SEQ ID NO: 19; and,
   b) a nucleotide sequence comprising the sequence set forth in SEQ ID NO: 18.

5. The method of claim 3 further comprising isolating said polypeptide.

6. The method of claim 4 further comprising isolating said polypeptide.

7. A method of treating a factor VIII deficiency comprising administering to a subject in need thereof a composition comprising a therapeutically effective amount of a polypeptide, wherein said polypeptide comprises an amino acid sequence having at least 95% sequence identity to SEQ ID NO: 19 and said polypeptide is characterized by high-level expression.

8. The method of claim 7, wherein said polypeptide comprises an amino acid sequence set forth in SEQ ID NO: 19.

9. An isolated polypeptide comprising an amino acid sequence having at least 95% sequence identity to SEQ ID NO: 19, wherein said polypeptide is characterized by high-level expression as compared to a corresponding human factor VIII polypeptide expressed under the same conditions.

10. A composition comprising a polypeptide according to claim 1 and a pharmaceutically acceptable carrier.

11. The composition according to claim 10, wherein the composition treats a factor VIII deficiency.

* * * * *

SEQUENCE LISTING

```
<160> NUMBER OF SEQ ID NOS: 21

<210> SEQ ID NO 1
<211> LENGTH: 6402
<212> TYPE: DNA
<213> ORGANISM: Sus scrofa
<220> FEATURE:
<221> NAME/KEY: gene
<222> LOCATION: (1)...(6399)
<223> OTHER INFORMATION: Factor VIII-- Full Length
<221> NAME/KEY: CDS
<222> LOCATION: (1)...(6399)

<400> SEQUENCE: 1 atg cag cta gag ctc tcc acc tgt gtc ttt ctg tgt ctc ttg cca ctc      48
Met Gln Leu Glu Leu Ser Thr Cys Val Phe Leu Cys Leu Leu Pro Leu
1               5                   10                  15 ggc ttt agt gcc atc agg aga tac tac ctg ggc gca gtg gaa ctg tcc      96
Gly Phe Ser Ala Ile Arg Arg Tyr Tyr Leu Gly Ala Val Glu Leu Ser
            20                  25                  30 tgg gac tac cgg caa agt gaa ctc ctc cgt gag ctg cac gtg gac acc     144
Trp Asp Tyr Arg Gln Ser Glu Leu Leu Arg Glu Leu His Val Asp Thr
        35                  40                  45 aga ttt cct gct aca gcg cca gga gct ctt ccg ttg ggc ccg tca gtc     192
Arg Phe Pro Ala Thr Ala Pro Gly Ala Leu Pro Leu Gly Pro Ser Val
    50                  55                  60 ctg tac aaa aag act gtg ttc gta gag ttc acg gat caa ctt ttc agc     240
Leu Tyr Lys Lys Thr Val Phe Val Glu Phe Thr Asp Gln Leu Phe Ser
65                  70                  75                  80 gtt gcc agg ccc agg cca cca tgg atg ggt ctg ctg ggt cct acc atc     288
Val Ala Arg Pro Arg Pro Pro Trp Met Gly Leu Leu Gly Pro Thr Ile
                85                  90                  95 cag gct gag gtt tac gac acg gtg gtc gtt acc ctg aag aac atg gct     336
Gln Ala Glu Val Tyr Asp Thr Val Val Val Thr Leu Lys Asn Met Ala
            100                 105                 110 tct cat ccc gtt agt ctt cac gct gtc ggc gtc tcc ttc tgg aaa tct     384
Ser His Pro Val Ser Leu His Ala Val Gly Val Ser Phe Trp Lys Ser
        115                 120                 125 tcc gaa ggc gct gaa tat gag gat cac acc agc caa agg gag aag gaa     432
Ser Glu Gly Ala Glu Tyr Glu Asp His Thr Ser Gln Arg Glu Lys Glu
    130                 135                 140 gac gat aaa gtc ctt ccc ggt aaa agc caa acc tac gtc tgg cag gtc     480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctc acc tac     528
Leu Lys Glu Asn Gly Pro Thr Ala Ser Asp Pro Pro Cys Leu Thr Tyr
                165                 170                 175 tca tac ctg tct cac gtg gac ctg gtg aaa gac ctg aat tcg ggc ctc     576
```

```
Ser Tyr Leu Ser His Val Asp Leu Val Lys Asp Leu Asn Ser Gly Leu
            180                 185                 190 att gga gcc ctg ctg gtt tgt aga gaa ggg agt ctg acc aga gaa agg    624
Ile Gly Ala Leu Leu Val Cys Arg Glu Gly Ser Leu Thr Arg Glu Arg
            195                 200                 205 acc cag aac ctg cac gaa ttt gta cta ctt ttt gct gtc ttt gat gaa    672
Thr Gln Asn Leu His Glu Phe Val Leu Leu Phe Ala Val Phe Asp Glu
            210                 215                 220 ggg aaa agt tgg cac tca gca aga aat gac tcc tgg aca cgg gcc atg    720
Gly Lys Ser Trp His Ser Ala Arg Asn Asp Ser Trp Thr Arg Ala Met
225                 230                 235                 240 gat ccc gca cct gcc agg gcc cag cct gca atg cac aca gtc aat ggc    768
Asp Pro Ala Pro Ala Arg Ala Gln Pro Ala Met His Thr Val Asn Gly
            245                 250                 255 tat gtc aac agg tct ctg cca ggt ctg atc gga tgt cat aag aaa tca    816
Tyr Val Asn Arg Ser Leu Pro Gly Leu Ile Gly Cys His Lys Lys Ser
            260                 265                 270 gtc tac tgg cac gtg att gga atg ggc acc agc ccg gaa gtg cac tcc    864
Val Tyr Trp His Val Ile Gly Met Gly Thr Ser Pro Glu Val His Ser
            275                 280                 285 att ttt ctt gaa ggc cac acg ttt ctc gtg agg cac cat cgc cag gct    912
Ile Phe Leu Glu Gly His Thr Phe Leu Val Arg His His Arg Gln Ala
            290                 295                 300 tcc ttg gag atc tcg cca cta act ttc ctc act gct cag aca ttc ctg    960
Ser Leu Glu Ile Ser Pro Leu Thr Phe Leu Thr Ala Gln Thr Phe Leu
305                 310                 315                 320 atg gac ctt ggc cag ttc cta ctg ttt tgt cat atc tct tcc cac cac    1008
Met Asp Leu Gly Gln Phe Leu Leu Phe Cys His Ile Ser Ser His His
            325                 330                 335 cat ggt ggc atg gag gct cac gtc aga gta gaa agc tgc gcc gag gag    1056
His Gly Gly Met Glu Ala His Val Arg Val Glu Ser Cys Ala Glu Glu
            340                 345                 350 ccc cag ctg cgg agg aaa gct gat gaa gag gaa gat tat gat gac aat    1104
Pro Gln Leu Arg Arg Lys Ala Asp Glu Glu Glu Asp Tyr Asp Asp Asn
            355                 360                 365 ttg tac gac tcg gac atg gac gtg gtc cgg ctc gat ggt gac gac gtg    1152
Leu Tyr Asp Ser Asp Met Asp Val Val Arg Leu Asp Gly Asp Asp Val
            370                 375                 380 tct ccc ttt atc caa atc cgc tcg gtt gcc aag aag cat ccc aaa acc    1200
Ser Pro Phe Ile Gln Ile Arg Ser Val Ala Lys Lys His Pro Lys Thr
385                 390                 395                 400 tgg gtg cac tac atc tct gca gag gag gag gac tgg gac tac gcc ccc    1248
Trp Val His Tyr Ile Ser Ala Glu Glu Glu Asp Trp Asp Tyr Ala Pro
            405                 410                 415 gcg gtc ccc agc ccc agt gac aga agt tat aaa agt ctc tac ttg aac    1296
Ala Val Pro Ser Pro Ser Asp Arg Ser Tyr Lys Ser Leu Tyr Leu Asn
            420                 425                 430 agt ggt cct cag cga att ggt agg aaa tac aaa aaa gct cga ttc gtc    1344
Ser Gly Pro Gln Arg Ile Gly Arg Lys Tyr Lys Lys Ala Arg Phe Val
            435                 440                 445 gct tac acg gat gta aca ttt aag act cgt aaa gct att ccg tat gaa    1392
Ala Tyr Thr Asp Val Thr Phe Lys Thr Arg Lys Ala Ile Pro Tyr Glu
450                 455                 460 tca gga atc ctg gga cct tta ctt tat gga gaa gtt gga gac aca ctt    1440
Ser Gly Ile Leu Gly Pro Leu Leu Tyr Gly Glu Val Gly Asp Thr Leu
465                 470                 475                 480 ttg att ata ttt aag aat aaa gcg agc cga cca tat aac atc tac cct    1488
Leu Ile Ile Phe Lys Asn Lys Ala Ser Arg Pro Tyr Asn Ile Tyr Pro
            485                 490                 495 cat gga atc act gat gtc agc gct ttg cac cca ggg aga ctt cta aaa    1536
```

```
                His Gly Ile Thr Asp Val Ser Ala Leu His Pro Gly Arg Leu Leu Lys
                            500                 505                 510 ggt tgg aaa cat ttg aaa gac atg cca att ctg cca gga gag act ttc        1584
Gly Trp Lys His Leu Lys Asp Met Pro Ile Leu Pro Gly Glu Thr Phe
            515                 520                 525 aag tat aaa tgg aca gtg act gtg gaa gat ggg cca acc aag tcc gat        1632
Lys Tyr Lys Trp Thr Val Thr Val Glu Asp Gly Pro Thr Lys Ser Asp
            530                 535                 540 cct cgg tgc ctg acc cgc tac tac tcg agc tcc att aat cta gag aaa        1680
Pro Arg Cys Leu Thr Arg Tyr Tyr Ser Ser Ser Ile Asn Leu Glu Lys
545                 550                 555                 560 gat ctg gct tcg gga ctc att ggc cct ctc ctc atc tgc tac aaa gaa        1728
Asp Leu Ala Ser Gly Leu Ile Gly Pro Leu Leu Ile Cys Tyr Lys Glu
                565                 570                 575 tct gta gac caa aga gga aac cag atg atg tca gac aag aga aac gtc        1776
Ser Val Asp Gln Arg Gly Asn Gln Met Met Ser Asp Lys Arg Asn Val
                580                 585                 590 atc ctg ttt tct gta ttc gat gag aat caa agc tgg tac ctc gca gag        1824
Ile Leu Phe Ser Val Phe Asp Glu Asn Gln Ser Trp Tyr Leu Ala Glu
                595                 600                 605 aat att cag cgc ttc ctc ccc aat ccg gat gga tta cag ccc cag gat        1872
Asn Ile Gln Arg Phe Leu Pro Asn Pro Asp Gly Leu Gln Pro Gln Asp
610                 615                 620 cca gag ttc caa gct tct aac atc atg cac agc atc aat ggc tat gtt        1920
Pro Glu Phe Gln Ala Ser Asn Ile Met His Ser Ile Asn Gly Tyr Val
625                 630                 635                 640 ttt gat agc ttg cag ctg tcg gtt tgt ttg cac gag gtg gca tac tgg        1968
Phe Asp Ser Leu Gln Leu Ser Val Cys Leu His Glu Val Ala Tyr Trp
                645                 650                 655 tac att cta agt gtt gga gca cag acg gac ttc ctc tcc gtc ttc ttc        2016
Tyr Ile Leu Ser Val Gly Ala Gln Thr Asp Phe Leu Ser Val Phe Phe
                660                 665                 670 tct ggc tac acc ttc aaa cac aaa atg gtc tat gaa gac aca ctc acc        2064
Ser Gly Tyr Thr Phe Lys His Lys Met Val Tyr Glu Asp Thr Leu Thr
                675                 680                 685 ctg ttc ccc ttc tca gga gaa acg gtc ttc atg tca atg gaa aac cca        2112
Leu Phe Pro Phe Ser Gly Glu Thr Val Phe Met Ser Met Glu Asn Pro
690                 695                 700 ggt ctc tgg gtc cta ggg tgc cac aac tca gac ttg cgg aac aga ggg        2160
Gly Leu Trp Val Leu Gly Cys His Asn Ser Asp Leu Arg Asn Arg Gly
705                 710                 715                 720 atg aca gcc tta ctg aag gtg tat agt tgt gac agg gac att ggt gat        2208
Met Thr Ala Leu Leu Lys Val Tyr Ser Cys Asp Arg Asp Ile Gly Asp
                725                 730                 735 tat tat gac aac act tat gaa gat att cca ggc ttc ttg ctg agt gga        2256
Tyr Tyr Asp Asn Thr Tyr Glu Asp Ile Pro Gly Phe Leu Leu Ser Gly
                740                 745                 750 aag aat gtc att gaa ccc aga agc ttt gcc cag aat tca aga ccc cct        2304
Lys Asn Val Ile Glu Pro Arg Ser Phe Ala Gln Asn Ser Arg Pro Pro
                755                 760                 765 agt gcg agc caa aag caa ttc caa acc atc aca agt cca gaa gat gac        2352
Ser Ala Ser Gln Lys Gln Phe Gln Thr Ile Thr Ser Pro Glu Asp Asp
770                 775                 780 gtg gag ctt gac ccg cag tct gga gag aga acc caa gca ctg gaa gaa        2400
Val Glu Leu Asp Pro Gln Ser Gly Glu Arg Thr Gln Ala Leu Glu Glu
785                 790                 795                 800 cta agt gtc ccc tct ggt gat ggg tcg atg ctc ttg gga cag aat cct        2448
Leu Ser Val Pro Ser Gly Asp Gly Ser Met Leu Leu Gly Gln Asn Pro
                805                 810                 815 gct cca cat ggc tca tcc tca tct gat ctt caa gaa gcc agg aat gag        2496
```

|  |  |
|---|---|
| Ala Pro His Gly Ser Ser Ser Asp Leu Gln Glu Ala Arg Asn Glu<br>820                   825                830 |  |
| gct gat gat tat tta cct gga gca aga gaa aga ggc acg gcc cca tcc<br>Ala Asp Asp Tyr Leu Pro Gly Ala Arg Glu Arg Gly Thr Ala Pro Ser<br>            835                840                845 | 2544 |
| gca gcg gca cgt ctc aga cca gag ctg cat cac agt gcc gaa aga gta<br>Ala Ala Arg Leu Arg Pro Glu Leu His His Ser Ala Glu Arg Val<br>850                   855                860 | 2592 |
| ctt act cct gag cca gag aaa gag ttg aag aaa ctt gat tca aaa atg<br>Leu Thr Pro Glu Pro Glu Lys Glu Leu Lys Lys Leu Asp Ser Lys Met<br>865                   870               875              880 | 2640 |
| tct agt tca tca gac ctt cta aag act tcg cca aca att cca tca gac<br>Ser Ser Ser Ser Asp Leu Leu Lys Thr Ser Pro Thr Ile Pro Ser Asp<br>                  885                890              895 | 2688 |
| acg ttg tca gcg gag act gaa agg aca cat tcc tta ggc ccc cca cac<br>Thr Leu Ser Ala Glu Thr Glu Arg Thr His Ser Leu Gly Pro Pro His<br>            900                905                910 | 2736 |
| ccg cag gtt aat ttc agg agt caa tta ggt gcc att gta ctt ggc aaa<br>Pro Gln Val Asn Phe Arg Ser Gln Leu Gly Ala Ile Val Leu Gly Lys<br>                915                920              925 | 2784 |
| aat tca tct cac ttt att ggg gct ggt gtc cct ttg ggc tcg act gag<br>Asn Ser Ser His Phe Ile Gly Ala Gly Val Pro Leu Gly Ser Thr Glu<br>930                   935                940 | 2832 |
| gag gat cat gaa agc tcc ctg gga gaa aat gta tca cca gtg gag agt<br>Glu Asp His Glu Ser Ser Leu Gly Glu Asn Val Ser Pro Val Glu Ser<br>945                   950               955              960 | 2880 |
| gac ggg ata ttt gaa aag gaa aga gct cat gga cct gct tca ctg acc<br>Asp Gly Ile Phe Glu Lys Glu Arg Ala His Gly Pro Ala Ser Leu Thr<br>                  965                970              975 | 2928 |
| aaa gac gat gtt tta ttt aaa gtt aat atc tct ttg gta aag aca aac<br>Lys Asp Asp Val Leu Phe Lys Val Asn Ile Ser Leu Val Lys Thr Asn<br>            980                985                990 | 2976 |
| aag gca cga gtt tac tta aaa act aat aga aag att cac att gat gac<br>Lys Ala Arg Val Tyr Leu Lys Thr Asn Arg Lys Ile His Ile Asp Asp<br>                995                1000              1005 | 3024 |
| gca gct tta tta act gag aat agg gca tct gca acg ttt atg gac aaa<br>Ala Ala Leu Leu Thr Glu Asn Arg Ala Ser Ala Thr Phe Met Asp Lys<br>1010                    1015                1020 | 3072 |
| aat act aca gct tcg gga tta aat cat gtg tca aat tgg ata aaa ggg<br>Asn Thr Thr Ala Ser Gly Leu Asn His Val Ser Asn Trp Ile Lys Gly<br>1025                    1030                1035              1040 | 3120 |
| ccc ctt ggc aag aac ccc cta agc tcg gag cga ggc ccc agt cca gag<br>Pro Leu Gly Lys Asn Pro Leu Ser Ser Glu Arg Gly Pro Ser Pro Glu<br>                    1045                1050              1055 | 3168 |
| ctt ctg aca tct tca gga tca gga aaa tct gtg aaa ggt cag agt tct<br>Leu Leu Thr Ser Ser Gly Ser Gly Lys Ser Val Lys Gly Gln Ser Ser<br>                    1060                1065              1070 | 3216 |
| ggg cag ggg aga ata cgg gtg gca gtg gaa gag gaa gaa ctg agc aaa<br>Gly Gln Gly Arg Ile Arg Val Ala Val Glu Glu Glu Glu Leu Ser Lys<br>                  1075                1080              1085 | 3264 |
| ggc aaa gag atg atg ctt ccc aac agc gag ctc acc ttt ctc act aac<br>Gly Lys Glu Met Met Leu Pro Asn Ser Glu Leu Thr Phe Leu Thr Asn<br>1090                    1095                1100 | 3312 |
| tcg gct gat gtc caa gga aac gat aca cac agt caa gga aaa aag tct<br>Ser Ala Asp Val Gln Gly Asn Asp Thr His Ser Gln Gly Lys Lys Ser<br>1105                    1110                1115              1120 | 3360 |
| cgg gaa gag atg gaa agg aga gaa aaa tta gtc caa gaa aaa gtc gac<br>Arg Glu Glu Met Glu Arg Arg Glu Lys Leu Val Gln Glu Lys Val Asp<br>                    1125                1130              1135 | 3408 |
| ttg cct cag gtg tat aca gcg act gga act aag aat ttc ctg aga aac | 3456 |

```
                                                         -continued

Leu Pro Gln Val Tyr Thr Ala Thr Gly Thr Lys Asn Phe Leu Arg Asn
            1140                1145                1150 att ttt cac caa agc act gag ccc agt gta gaa ggg ttt gat ggg ggg       3504
Ile Phe His Gln Ser Thr Glu Pro Ser Val Glu Gly Phe Asp Gly Gly
            1155                1160                1165 tca cat gcg ccg gtg cct caa gac agc agg tca tta aat gat tcg gca       3552
Ser His Ala Pro Val Pro Gln Asp Ser Arg Ser Leu Asn Asp Ser Ala
            1170                1175                1180 gag aga gca gag act cac ata gcc cat ttc tca gca att agg gaa gag       3600
Glu Arg Ala Glu Thr His Ile Ala His Phe Ser Ala Ile Arg Glu Glu
1185            1190                1195                1200 gca ccc ttg gaa gcc ccg gga aat cga aca ggt cca ggt ccg agg agt       3648
Ala Pro Leu Glu Ala Pro Gly Asn Arg Thr Gly Pro Gly Pro Arg Ser
                1205                1210                1215 gcg gtt ccc cgc cgc gtt aag cag agc ttg aaa cag atc aga ctc ccg       3696
Ala Val Pro Arg Arg Val Lys Gln Ser Leu Lys Gln Ile Arg Leu Pro
                1220                1225                1230 cta gaa gaa ata aag cct gaa agg ggg gtg gtt ctg aat gcc acc tca       3744
Leu Glu Glu Ile Lys Pro Glu Arg Gly Val Val Leu Asn Ala Thr Ser
                1235                1240                1245 acc cgg tgg tct gaa agc agt cct atc tta caa gga gcc aaa aga aat       3792
Thr Arg Trp Ser Glu Ser Ser Pro Ile Leu Gln Gly Ala Lys Arg Asn
            1250                1255                1260 aac ctt tct tta cct ttc ctg acc ttg gaa atg gcc gga ggt caa gga       3840
Asn Leu Ser Leu Pro Phe Leu Thr Leu Glu Met Ala Gly Gly Gln Gly
1265            1270                1275                1280 aag atc agc gcc ctg ggg aaa agt gcc gca ggc ccg ctg gcg tcc ggg       3888
Lys Ile Ser Ala Leu Gly Lys Ser Ala Ala Gly Pro Leu Ala Ser Gly
                1285                1290                1295 aag ctg gag aag gct gtt ctc tct tca gca ggc ttg tct gaa gca tct       3936
Lys Leu Glu Lys Ala Val Leu Ser Ser Ala Gly Leu Ser Glu Ala Ser
                1300                1305                1310 ggc aaa gct gag ttt ctt cct aaa gtt cga gtt cat cgg gaa gac ctg       3984
Gly Lys Ala Glu Phe Leu Pro Lys Val Arg Val His Arg Glu Asp Leu
                1315                1320                1325 ttg cct caa aaa acc agc aat gtt tct tgc gca cac ggg gat ctc ggc       4032
Leu Pro Gln Lys Thr Ser Asn Val Ser Cys Ala His Gly Asp Leu Gly
            1330                1335                1340 cag gag atc ttc ctg cag aaa aca cgg gga cct gtt aac ctg aac aaa       4080
Gln Glu Ile Phe Leu Gln Lys Thr Arg Gly Pro Val Asn Leu Asn Lys
1345            1350                1355                1360 gta aat aga cct gga agg act ccc tcc aag ctt ctg ggt ccc ccg atg       4128
Val Asn Arg Pro Gly Arg Thr Pro Ser Lys Leu Leu Gly Pro Pro Met
                1365                1370                1375 ccc aaa gag tgg gaa tcc cta gag aag tca cca aaa agc aca gct ctc       4176
Pro Lys Glu Trp Glu Ser Leu Glu Lys Ser Pro Lys Ser Thr Ala Leu
            1380                1385                1390 agg acg aaa gac atc atc agt tta ccc ctg gac cgt cac gaa agc aat       4224
Arg Thr Lys Asp Ile Ile Ser Leu Pro Leu Asp Arg His Glu Ser Asn
            1395                1400                1405 cat tca ata gca gca aaa aat gaa gga caa gcc gag acc caa aga gaa       4272
His Ser Ile Ala Ala Lys Asn Glu Gly Gln Ala Glu Thr Gln Arg Glu
            1410                1415                1420 gcc gcc tgg acg aag cag gga ggg cct gga agg ctg tgc gct cca aag       4320
Ala Ala Trp Thr Lys Gln Gly Gly Pro Gly Arg Leu Cys Ala Pro Lys
1425            1430                1435                1440 cct ccg gtc ctg cga cgg cat cag agg gac ata agc ctt cct act ttt       4368
Pro Pro Val Leu Arg Arg His Gln Arg Asp Ile Ser Leu Pro Thr Phe
                1445                1450                1455 cag ccg gag gaa gac aaa atg gac tat gat gat atc ttc tca act gaa       4416
```

```
                        Gln Pro Glu Glu Asp Lys Met Asp Tyr Asp Asp Ile Phe Ser Thr Glu
                                1460                1465                1470 acg aag gga gaa gat ttt gac att tac ggt gag gat gaa aat cag gac         4464
Thr Lys Gly Glu Asp Phe Asp Ile Tyr Gly Glu Asp Glu Asn Gln Asp
        1475                1480                1485 cct cgc agc ttt cag aag aga acc cga cac tat ttc att gct gcg gtg         4512
Pro Arg Ser Phe Gln Lys Arg Thr Arg His Tyr Phe Ile Ala Ala Val
        1490                1495                1500 gag cag ctc tgg gat tac ggg atg agc gaa tcc ccc cgg gcg cta aga         4560
Glu Gln Leu Trp Asp Tyr Gly Met Ser Glu Ser Pro Arg Ala Leu Arg
1505                1510                1515                1520 aac agg gct cag aac gga gag gtg cct cgg ttc aag aag gtg gtc ttc         4608
Asn Arg Ala Gln Asn Gly Glu Val Pro Arg Phe Lys Lys Val Val Phe
                1525                1530                1535 cgg gaa ttt gct gac ggc tcc ttc acg cag ccg tcg tac cgc ggg gaa         4656
Arg Glu Phe Ala Asp Gly Ser Phe Thr Gln Pro Ser Tyr Arg Gly Glu
        1540                1545                1550 ctc aac aaa cac ttg ggg ctc ttg gga ccc tac atc aga gcg gaa gtt         4704
Leu Asn Lys His Leu Gly Leu Leu Gly Pro Tyr Ile Arg Ala Glu Val
        1555                1560                1565 gaa gac aac atc atg gta act ttc aaa aac cag gcg tct cgt ccc tat         4752
Glu Asp Asn Ile Met Val Thr Phe Lys Asn Gln Ala Ser Arg Pro Tyr
        1570                1575                1580 tcc ttc tac tcg agc ctt att tct tat ccg gat gat cag gag caa ggg         4800
Ser Phe Tyr Ser Ser Leu Ile Ser Tyr Pro Asp Asp Gln Glu Gln Gly
1585                1590                1595                1600 gca gaa cct cga cac aac ttc gtc cag cca aat gaa acc aga act tac         4848
Ala Glu Pro Arg His Asn Phe Val Gln Pro Asn Glu Thr Arg Thr Tyr
        1605                1610                1615 ttt tgg aaa gtg cag cat cac atg gca ccc aca gaa gac gag ttt gac         4896
Phe Trp Lys Val Gln His His Met Ala Pro Thr Glu Asp Glu Phe Asp
        1620                1625                1630 tgc aaa gcc tgg gcc tac ttt tct gat gtt gac ctg gaa aaa gat gtg         4944
Cys Lys Ala Trp Ala Tyr Phe Ser Asp Val Asp Leu Glu Lys Asp Val
        1635                1640                1645 cac tca ggc ttg atc ggc ccc ctt ctg atc tgc cgc gcc aac acc ctg         4992
His Ser Gly Leu Ile Gly Pro Leu Leu Ile Cys Arg Ala Asn Thr Leu
        1650                1655                1660 aac gct gct cac ggt aga caa gtg acc gtg caa gaa ttt gct ctg ttt         5040
Asn Ala Ala His Gly Arg Gln Val Thr Val Gln Glu Phe Ala Leu Phe
1665                1670                1675                1680 ttc act att ttt gat gag aca aag agc tgg tac ttc act gaa aat gtg         5088
Phe Thr Ile Phe Asp Glu Thr Lys Ser Trp Tyr Phe Thr Glu Asn Val
                1685                1690                1695 gaa agg aac tgc cgg gcc ccc tgc cac ctg cag atg gag gac ccc act         5136
Glu Arg Asn Cys Arg Ala Pro Cys His Leu Gln Met Glu Asp Pro Thr
        1700                1705                1710 ctg aaa gaa aac tat cgc ttc cat gca atc aat ggc tat gtg atg gat         5184
Leu Lys Glu Asn Tyr Arg Phe His Ala Ile Asn Gly Tyr Val Met Asp
        1715                1720                1725 aca ctc cct ggc tta gta atg gct cag aat caa agg atc cga tgg tat         5232
Thr Leu Pro Gly Leu Val Met Ala Gln Asn Gln Arg Ile Arg Trp Tyr
        1730                1735                1740 ctg ctc agc atg ggc agc aat gaa aat atc cat tcg att cat ttt agc         5280
Leu Leu Ser Met Gly Ser Asn Glu Asn Ile His Ser Ile His Phe Ser
1745                1750                1755                1760 gga cac gtg ttc agt gta cgg aaa aag gag gag tat aaa atg gcc gtg         5328
Gly His Val Phe Ser Val Arg Lys Lys Glu Glu Tyr Lys Met Ala Val
        1765                1770                1775 tac aat ctc tat ccg ggt gtc ttt gag aca gtg gaa atg cta ccg tcc         5376
```

-continued

| | |
|---|---|
| Tyr Asn Leu Tyr Pro Gly Val Phe Glu Thr Val Glu Met Leu Pro Ser<br>            1780                        1785                        1790 | |
| aaa gtt gga att tgg cga ata gaa tgc ctg att ggc gag cac ctg caa<br>Lys Val Gly Ile Trp Arg Ile Glu Cys Leu Ile Gly Glu His Leu Gln<br>            1795                        1800                        1805 | 5424 |
| gct ggg atg agc acg act ttc ctg gtg tac agc aag gag tgt cag gct<br>Ala Gly Met Ser Thr Thr Phe Leu Val Tyr Ser Lys Glu Cys Gln Ala<br>            1810                        1815                        1820 | 5472 |
| cca ctg gga atg gct tct gga cgc att aga gat ttt cag atc aca gct<br>Pro Leu Gly Met Ala Ser Gly Arg Ile Arg Asp Phe Gln Ile Thr Ala<br>1825                        1830                        1835                        1840 | 5520 |
| tca gga cag tat gga cag tgg gcc cca aag ctg gcc aga ctt cat tat<br>Ser Gly Gln Tyr Gly Gln Trp Ala Pro Lys Leu Ala Arg Leu His Tyr<br>            1845                        1850                        1855 | 5568 |
| tcc gga tca atc aat gcc tgg agc acc aag gat ccc cac tcc tgg atc<br>Ser Gly Ser Ile Asn Ala Trp Ser Thr Lys Asp Pro His Ser Trp Ile<br>            1860                        1865                        1870 | 5616 |
| aag gtg gat ctg ttg gca cca atg atc att cac ggc atc atg acc cag<br>Lys Val Asp Leu Leu Ala Pro Met Ile Ile His Gly Ile Met Thr Gln<br>            1875                        1880                        1885 | 5664 |
| ggt gcc cgt cag aag ttt tcc agc ctc tac atc tcc cag ttt atc atc<br>Gly Ala Arg Gln Lys Phe Ser Ser Leu Tyr Ile Ser Gln Phe Ile Ile<br>            1890                        1895                        1900 | 5712 |
| atg tac agt ctt gac ggg agg aac tgg cag agt tac cga ggg aat tcc<br>Met Tyr Ser Leu Asp Gly Arg Asn Trp Gln Ser Tyr Arg Gly Asn Ser<br>1905                        1910                        1915                        1920 | 5760 |
| acg ggc acc tta atg gtc ttc ttt ggc aat gtg gac gca tct ggg att<br>Thr Gly Thr Leu Met Val Phe Phe Gly Asn Val Asp Ala Ser Gly Ile<br>            1925                        1930                        1935 | 5808 |
| aaa cac aat att ttt aac cct ccg att gtg gct cgg tac atc cgt ttg<br>Lys His Asn Ile Phe Asn Pro Pro Ile Val Ala Arg Tyr Ile Arg Leu<br>            1940                        1945                        1950 | 5856 |
| cac cca aca cat tac agc atc cgc agc act ctt cgc atg gag ttg atg<br>His Pro Thr His Tyr Ser Ile Arg Ser Thr Leu Arg Met Glu Leu Met<br>            1955                        1960                        1965 | 5904 |
| ggc tgt gat tta aac agt tgc agc atg ccc ctg gga atg cag aat aaa<br>Gly Cys Asp Leu Asn Ser Cys Ser Met Pro Leu Gly Met Gln Asn Lys<br>1970                        1975                        1980 | 5952 |
| gcg ata tca gac tca cag atc acg gcc tcc tcc cac cta agc aat ata<br>Ala Ile Ser Asp Ser Gln Ile Thr Ala Ser Ser His Leu Ser Asn Ile<br>1985                        1990                        1995                        2000 | 6000 |
| ttt gcc acc tgg tct cct tca caa gcc cga ctt cac ctc cag ggg cgg<br>Phe Ala Thr Trp Ser Pro Ser Gln Ala Arg Leu His Leu Gln Gly Arg<br>            2005                        2010                        2015 | 6048 |
| acg aat gcc tgg cga ccc cgg gtg agc agc gca gag gag tgg ctg cag<br>Thr Asn Ala Trp Arg Pro Arg Val Ser Ser Ala Glu Glu Trp Leu Gln<br>            2020                        2025                        2030 | 6096 |
| gtg gac ctg cag aag acg gtg aag gtc aca ggc atc acc acc cag ggc<br>Val Asp Leu Gln Lys Thr Val Lys Val Thr Gly Ile Thr Thr Gln Gly<br>            2035                        2040                        2045 | 6144 |
| gtg aag tcc ctg ctc agc agc atg tat gtg aag gag ttc ctc gtg tcc<br>Val Lys Ser Leu Leu Ser Ser Met Tyr Val Lys Glu Phe Leu Val Ser<br>            2050                        2055                        2060 | 6192 |
| agt agt cag gac ggc cgc cgc tgg acc ctg ttt ctt cag gac ggc cac<br>Ser Ser Gln Asp Gly Arg Arg Trp Thr Leu Phe Leu Gln Asp Gly His<br>2065                        2070                        2075                        2080 | 6240 |
| acg aag gtt ttt cag ggc aat cag gac tcc tcc acc ccc gtg gtg aac<br>Thr Lys Val Phe Gln Gly Asn Gln Asp Ser Ser Thr Pro Val Val Asn<br>            2085                        2090                        2095 | 6288 |
| gct ctg gac ccc ccg ctg ttc acg cgc tac ctg agg atc cac ccc acg | 6336 |

```
Ala Leu Asp Pro Pro Leu Phe Thr Arg Tyr Leu Arg Ile His Pro Thr
                2100                2105                2110 agc tgg gcg cag cac atc gcc ctg agg ctc gag gtt cta gga tgt gag    6384
Ser Trp Ala Gln His Ile Ala Leu Arg Leu Glu Val Leu Gly Cys Glu
            2115                2120                2125 gca cag gat ctc tac tga                                            6402
Ala Gln Asp Leu Tyr
            2130

<210> SEQ ID NO 2
<211> LENGTH: 2133
<212> TYPE: PRT
<213> ORGANISM: Sus scrofa

<400> SEQUENCE: 2

Met Gln Leu Glu Leu Ser Thr Cys Val Phe Leu Cys Leu Leu Pro Leu
 1               5                  10                  15

Gly Phe Ser Ala Ile Arg Arg Tyr Tyr Leu Gly Ala Val Glu Leu Ser
                20                  25                  30

Trp Asp Tyr Arg Gln Ser Glu Leu Leu Arg Glu Leu His Val Asp Thr
            35                  40                  45

Arg Phe Pro Ala Thr Ala Pro Gly Ala Leu Pro Leu Gly Pro Ser Val
        50                  55                  60

Leu Tyr Lys Lys Thr Val Phe Val Glu Phe Thr Asp Gln Leu Phe Ser
65                  70                  75                  80

Val Ala Arg Pro Arg Pro Pro Trp Met Gly Leu Leu Gly Pro Thr Ile
                85                  90                  95

Gln Ala Glu Val Tyr Asp Thr Val Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
    290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
```

```
                    325                 330                 335
His Gly Gly Met Glu Ala His Val Arg Val Glu Ser Cys Ala Glu Glu
                340                 345                 350

Pro Gln Leu Arg Arg Lys Ala Asp Glu Glu Asp Tyr Asp Asp Asn
            355                 360                 365

Leu Tyr Asp Ser Asp Met Asp Val Val Arg Leu Asp Gly Asp Asp Val
            370                 375                 380

Ser Pro Phe Ile Gln Ile Arg Ser Val Ala Lys Lys His Pro Lys Thr
385                 390                 395                 400

Trp Val His Tyr Ile Ser Ala Glu Glu Glu Asp Trp Asp Tyr Ala Pro
                405                 410                 415

Ala Val Pro Ser Pro Ser Asp Arg Ser Tyr Lys Ser Leu Tyr Leu Asn
                420                 425                 430

Ser Gly Pro Gln Arg Ile Gly Arg Lys Tyr Lys Lys Ala Arg Phe Val
            435                 440                 445

Ala Tyr Thr Asp Val Thr Phe Lys Thr Arg Lys Ala Ile Pro Tyr Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Lys Ala Ser Arg Pro Tyr Asn Ile Tyr Pro
                485                 490                 495

His Gly Ile Thr Asp Val Ser Ala Leu His Pro Gly Arg Leu Leu Lys
                500                 505                 510

Gly Trp Lys His Leu Lys Asp Met Pro Ile Leu Pro Gly Glu Thr Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Ile Asn Leu Glu Lys
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Met Met Ser Asp Lys Arg Asn Val
            580                 585                 590

Ile Leu Phe Ser Val Phe Asp Glu Asn Gln Ser Trp Tyr Leu Ala Glu
            595                 600                 605

Asn Ile Gln Arg Phe Leu Pro Asn Pro Asp Gly Leu Gln Pro Gln Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Val Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Val Leu Gly Cys His Asn Ser Asp Leu Arg Asn Arg Gly
705                 710                 715                 720

Met Thr Ala Leu Leu Lys Val Tyr Ser Cys Asp Arg Asp Ile Gly Asp
                725                 730                 735

Tyr Tyr Asp Asn Thr Tyr Glu Asp Ile Pro Gly Phe Leu Leu Ser Gly
            740                 745                 750
```

```
Lys Asn Val Ile Glu Pro Arg Ser Phe Ala Gln Asn Ser Arg Pro Pro
        755                 760                 765

Ser Ala Ser Gln Lys Gln Phe Gln Thr Ile Thr Ser Pro Glu Asp Asp
    770                 775                 780

Val Glu Leu Asp Pro Gln Ser Gly Glu Arg Thr Gln Ala Leu Glu Glu
785                 790                 795                 800

Leu Ser Val Pro Ser Gly Asp Gly Ser Met Leu Leu Gly Gln Asn Pro
                805                 810                 815

Ala Pro His Gly Ser Ser Ser Asp Leu Gln Glu Ala Arg Asn Glu
                820                 825                 830

Ala Asp Asp Tyr Leu Pro Gly Ala Arg Glu Arg Gly Thr Ala Pro Ser
            835                 840                 845

Ala Ala Ala Arg Leu Arg Pro Glu Leu His His Ser Ala Glu Arg Val
    850                 855                 860

Leu Thr Pro Glu Pro Glu Lys Glu Leu Lys Lys Leu Asp Ser Lys Met
865                 870                 875                 880

Ser Ser Ser Ser Asp Leu Leu Lys Thr Ser Pro Thr Ile Pro Ser Asp
                885                 890                 895

Thr Leu Ser Ala Glu Thr Glu Arg Thr His Ser Leu Gly Pro Pro His
            900                 905                 910

Pro Gln Val Asn Phe Arg Ser Gln Leu Gly Ala Ile Val Leu Gly Lys
            915                 920                 925

Asn Ser Ser His Phe Ile Gly Ala Gly Val Pro Leu Gly Ser Thr Glu
930                 935                 940

Glu Asp His Glu Ser Ser Leu Gly Glu Asn Val Ser Pro Val Glu Ser
945                 950                 955                 960

Asp Gly Ile Phe Glu Lys Glu Arg Ala His Gly Pro Ala Ser Leu Thr
            965                 970                 975

Lys Asp Asp Val Leu Phe Lys Val Asn Ile Ser Leu Val Lys Thr Asn
            980                 985                 990

Lys Ala Arg Val Tyr Leu Lys Thr Asn Arg Lys Ile His Ile Asp Asp
        995                 1000                1005

Ala Ala Leu Leu Thr Glu Asn Arg Ala Ser Ala Thr Phe Met Asp Lys
    1010                1015                1020

Asn Thr Thr Ala Ser Gly Leu Asn His Val Ser Asn Trp Ile Lys Gly
1025                1030                1035                1040

Pro Leu Gly Lys Asn Pro Leu Ser Ser Glu Arg Gly Pro Ser Pro Glu
                1045                1050                1055

Leu Leu Thr Ser Ser Gly Ser Gly Lys Ser Val Lys Gly Gln Ser Ser
            1060                1065                1070

Gly Gln Gly Arg Ile Arg Val Ala Val Glu Glu Glu Leu Ser Lys
        1075                1080                1085

Gly Lys Glu Met Met Leu Pro Asn Ser Glu Leu Thr Phe Leu Thr Asn
    1090                1095                1100

Ser Ala Asp Val Gln Gly Asn Asp Thr His Ser Gln Gly Lys Lys Ser
1105                1110                1115                1120

Arg Glu Glu Met Glu Arg Arg Glu Lys Leu Val Gln Glu Lys Val Asp
            1125                1130                1135

Leu Pro Gln Val Tyr Thr Ala Thr Gly Thr Lys Asn Phe Leu Arg Asn
            1140                1145                1150

Ile Phe His Gln Ser Thr Glu Pro Ser Val Glu Gly Phe Asp Gly Gly
        1155                1160                1165

Ser His Ala Pro Val Pro Gln Asp Ser Arg Ser Leu Asn Asp Ser Ala
    1170                1175                1180
```

```
Glu Arg Ala Glu Thr His Ile Ala His Phe Ser Ala Ile Arg Glu Glu
1185                1190                1195                1200

Ala Pro Leu Glu Ala Pro Gly Asn Arg Thr Gly Pro Gly Pro Arg Ser
            1205                1210                1215

Ala Val Pro Arg Arg Val Lys Gln Ser Leu Lys Gln Ile Arg Leu Pro
        1220                1225                1230

Leu Glu Glu Ile Lys Pro Glu Arg Gly Val Val Leu Asn Ala Thr Ser
    1235                1240                1245

Thr Arg Trp Ser Glu Ser Ser Pro Ile Leu Gln Gly Ala Lys Arg Asn
1250                1255                1260

Asn Leu Ser Leu Pro Phe Leu Thr Leu Glu Met Ala Gly Gly Gln Gly
1265                1270                1275                1280

Lys Ile Ser Ala Leu Gly Lys Ser Ala Ala Gly Pro Leu Ala Ser Gly
            1285                1290                1295

Lys Leu Glu Lys Ala Val Leu Ser Ser Ala Gly Leu Ser Glu Ala Ser
        1300                1305                1310

Gly Lys Ala Glu Phe Leu Pro Lys Val Arg Val His Arg Glu Asp Leu
    1315                1320                1325

Leu Pro Gln Lys Thr Ser Asn Val Ser Cys Ala His Gly Asp Leu Gly
    1330                1335                1340

Gln Glu Ile Phe Leu Gln Lys Thr Arg Gly Pro Val Asn Leu Asn Lys
1345                1350                1355                1360

Val Asn Arg Pro Gly Arg Thr Pro Ser Lys Leu Leu Gly Pro Pro Met
            1365                1370                1375

Pro Lys Glu Trp Glu Ser Leu Glu Lys Ser Pro Lys Ser Thr Ala Leu
        1380                1385                1390

Arg Thr Lys Asp Ile Ile Ser Leu Pro Leu Asp Arg His Glu Ser Asn
    1395                1400                1405

His Ser Ile Ala Ala Lys Asn Glu Gly Gln Ala Glu Thr Gln Arg Glu
    1410                1415                1420

Ala Ala Trp Thr Lys Gln Gly Gly Pro Gly Arg Leu Cys Ala Pro Lys
1425                1430                1435                1440

Pro Pro Val Leu Arg Arg His Gln Arg Asp Ile Ser Leu Pro Thr Phe
            1445                1450                1455

Gln Pro Glu Glu Asp Lys Met Asp Tyr Asp Asp Ile Phe Ser Thr Glu
        1460                1465                1470

Thr Lys Gly Glu Asp Phe Asp Ile Tyr Gly Glu Asp Glu Asn Gln Asp
    1475                1480                1485

Pro Arg Ser Phe Gln Lys Arg Thr Arg His Tyr Phe Ile Ala Ala Val
    1490                1495                1500

Glu Gln Leu Trp Asp Tyr Gly Met Ser Glu Ser Pro Arg Ala Leu Arg
1505                1510                1515                1520

Asn Arg Ala Gln Asn Gly Glu Val Pro Arg Phe Lys Lys Val Val Phe
            1525                1530                1535

Arg Glu Phe Ala Asp Gly Ser Phe Thr Gln Pro Ser Tyr Arg Gly Glu
        1540                1545                1550

Leu Asn Lys His Leu Gly Leu Leu Gly Pro Tyr Ile Arg Ala Glu Val
    1555                1560                1565

Glu Asp Asn Ile Met Val Thr Phe Lys Asn Gln Ala Ser Arg Pro Tyr
    1570                1575                1580

Ser Phe Tyr Ser Ser Leu Ile Ser Tyr Pro Asp Asp Gln Glu Gln Gly
1585                1590                1595                1600

Ala Glu Pro Arg His Asn Phe Val Gln Pro Asn Glu Thr Arg Thr Tyr
```

```
                    1605                1610                1615
        Phe Trp Lys Val Gln His His Met Ala Pro Thr Glu Asp Glu Phe Asp
                        1620                1625                1630

Cys Lys Ala Trp Ala Tyr Phe Ser Asp Val Asp Leu Glu Lys Asp Val
                        1635                1640                1645

His Ser Gly Leu Ile Gly Pro Leu Leu Ile Cys Arg Ala Asn Thr Leu
                        1650                1655                1660

Asn Ala Ala His Gly Arg Gln Val Thr Val Gln Glu Phe Ala Leu Phe
        1665                1670                1675                1680

Phe Thr Ile Phe Asp Glu Thr Lys Ser Trp Tyr Phe Thr Glu Asn Val
                        1685                1690                1695

Glu Arg Asn Cys Arg Ala Pro Cys His Leu Gln Met Glu Asp Pro Thr
                        1700                1705                1710

Leu Lys Glu Asn Tyr Arg Phe His Ala Ile Asn Gly Tyr Val Met Asp
                        1715                1720                1725

Thr Leu Pro Gly Leu Val Met Ala Gln Asn Gln Arg Ile Arg Trp Tyr
                        1730                1735                1740

Leu Leu Ser Met Gly Ser Asn Glu Asn Ile His Ser Ile His Phe Ser
        1745                1750                1755                1760

Gly His Val Phe Ser Val Arg Lys Lys Glu Glu Tyr Lys Met Ala Val
                        1765                1770                1775

Tyr Asn Leu Tyr Pro Gly Val Phe Glu Thr Val Glu Met Leu Pro Ser
                        1780                1785                1790

Lys Val Gly Ile Trp Arg Ile Glu Cys Leu Ile Gly Glu His Leu Gln
                        1795                1800                1805

Ala Gly Met Ser Thr Thr Phe Leu Val Tyr Ser Lys Glu Cys Gln Ala
                        1810                1815                1820

Pro Leu Gly Met Ala Ser Gly Arg Ile Arg Asp Phe Gln Ile Thr Ala
        1825                1830                1835                1840

Ser Gly Gln Tyr Gly Gln Trp Ala Pro Lys Leu Ala Arg Leu His Tyr
                        1845                1850                1855

Ser Gly Ser Ile Asn Ala Trp Ser Thr Lys Asp Pro His Ser Trp Ile
                        1860                1865                1870

Lys Val Asp Leu Leu Ala Pro Met Ile Ile His Gly Ile Met Thr Gln
                        1875                1880                1885

Gly Ala Arg Gln Lys Phe Ser Ser Leu Tyr Ile Ser Gln Phe Ile Ile
        1890                1895                1900

Met Tyr Ser Leu Asp Gly Arg Asn Trp Gln Ser Tyr Arg Gly Asn Ser
        1905                1910                1915                1920

Thr Gly Thr Leu Met Val Phe Phe Gly Asn Val Asp Ala Ser Gly Ile
                        1925                1930                1935

Lys His Asn Ile Phe Asn Pro Pro Ile Val Ala Arg Tyr Ile Arg Leu
                        1940                1945                1950

His Pro Thr His Tyr Ser Ile Arg Ser Thr Leu Arg Met Glu Leu Met
                        1955                1960                1965

Gly Cys Asp Leu Asn Ser Cys Ser Met Pro Leu Gly Met Gln Asn Lys
        1970                1975                1980

Ala Ile Ser Asp Ser Gln Ile Thr Ala Ser Ser His Leu Ser Asn Ile
        1985                1990                1995                2000

Phe Ala Thr Trp Ser Pro Ser Gln Ala Arg Leu His Leu Gln Gly Arg
                        2005                2010                2015

Thr Asn Ala Trp Arg Pro Arg Val Ser Ser Ala Glu Glu Trp Leu Gln
                        2020                2025                2030
```

```
Val Asp Leu Gln Lys Thr Val Lys Val Thr Gly Ile Thr Thr Gln Gly
        2035                2040                2045

Val Lys Ser Leu Leu Ser Ser Met Tyr Val Lys Glu Phe Leu Val Ser
    2050                2055                2060

Ser Ser Gln Asp Gly Arg Arg Trp Thr Leu Phe Leu Gln Asp Gly His
2065                2070                2075                2080

Thr Lys Val Phe Gln Gly Asn Gln Asp Ser Ser Thr Pro Val Val Asn
            2085                2090                2095

Ala Leu Asp Pro Pro Leu Phe Thr Arg Tyr Leu Arg Ile His Pro Thr
        2100                2105                2110

Ser Trp Ala Gln His Ile Ala Leu Arg Leu Glu Val Leu Gly Cys Glu
        2115                2120                2125

Ala Gln Asp Leu Tyr
        2130

<210> SEQ ID NO 3
<211> LENGTH: 4404
<212> TYPE: DNA
<213> ORGANISM: Sus scrofa
<220> FEATURE:
<221> NAME/KEY: gene
<222> LOCATION: (1)...(4401)
<223> OTHER INFORMATION: Factor VIII-- B-domain deleted
<221> NAME/KEY: CDS
<222> LOCATION: (1)...(4401)

<400> SEQUENCE: 3 atg cag cta gag ctc tcc acc tgt gtc ttt ctg tgt ctc ttg cca ctc     48
Met Gln Leu Glu Leu Ser Thr Cys Val Phe Leu Cys Leu Leu Pro Leu
1               5                   10                  15 ggc ttt agt gcc atc agg aga tac tac ctg ggc gca gtg gaa ctg tcc     96
Gly Phe Ser Ala Ile Arg Arg Tyr Tyr Leu Gly Ala Val Glu Leu Ser
                20                  25                  30 tgg gac tac cgg caa agt gaa ctc ctc gtg gag ctg cac gtg gac acc    144
Trp Asp Tyr Arg Gln Ser Glu Leu Leu Arg Glu Leu His Val Asp Thr
            35                  40                  45 aga ttt cct gct aca gcg cca gga gct ctt ccg ttg ggc ccg tca gtc    192
Arg Phe Pro Ala Thr Ala Pro Gly Ala Leu Pro Leu Gly Pro Ser Val
        50                  55                  60 ctg tac aaa aag act gtg ttc gta gag ttc acg gat caa ctt ttc agc    240
Leu Tyr Lys Lys Thr Val Phe Val Glu Phe Thr Asp Gln Leu Phe Ser
65                  70                  75                  80 gtt gcc agg ccc agg cca cca tgg atg ggt ctg ctg ggt cct acc atc    288
Val Ala Arg Pro Arg Pro Pro Trp Met Gly Leu Leu Gly Pro Thr Ile
                85                  90                  95 cag gct gag gtt tac gac acg gtg gtc gtt acc ctg aag aac atg gct    336
Gln Ala Glu Val Tyr Asp Thr Val Val Val Thr Leu Lys Asn Met Ala
                100                 105                 110 tct cat ccc gtt agt ctt cac gct gtc ggc gtc tcc ttc tgg aaa tct    384
Ser His Pro Val Ser Leu His Ala Val Gly Val Ser Phe Trp Lys Ser
            115                 120                 125 tcc gaa ggc gct gaa tat gag gat cac acc agc caa agg gag aag gaa    432
Ser Glu Gly Ala Glu Tyr Glu Asp His Thr Ser Gln Arg Glu Lys Glu
        130                 135                 140 gac gat aaa gtc ctt ccc ggt aaa agc caa acc tac gtc tgg cag gtc    480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctt acc tac    528
Leu Lys Glu Asn Gly Pro Thr Ala Ser Asp Pro Pro Cys Leu Thr Tyr
                165                 170                 175 tca tac ctg tct cac gtg gac ctg gtg aaa gac ctg aat tcg ggc ctc    576
```

```
                Ser Tyr Leu Ser His Val Asp Leu Val Lys Asp Leu Asn Ser Gly Leu
                            180                 185                 190 att gga gcc ctg ctg gtt tgt aga gaa ggg agt ctg acc aga gaa agg         624
Ile Gly Ala Leu Leu Val Cys Arg Glu Gly Ser Leu Thr Arg Glu Arg
            195                 200                 205 acc cag aac ctg cac gaa ttt gta cta ctt ttt gct gtc ttt gat gaa         672
Thr Gln Asn Leu His Glu Phe Val Leu Leu Phe Ala Val Phe Asp Glu
            210                 215                 220 ggg aaa agt tgg cac tca gca aga aat gac tcc tgg aca cgg gcc atg         720
Gly Lys Ser Trp His Ser Ala Arg Asn Asp Ser Trp Thr Arg Ala Met
225                 230                 235                 240 gat ccc gca cct gcc agg gcc cag cct gca atg cac aca gtc aat ggc         768
Asp Pro Ala Pro Ala Arg Ala Gln Pro Ala Met His Thr Val Asn Gly
            245                 250                 255 tat gtc aac agg tct ctg cca ggt ctg atc gga tgt cat aag aaa tca         816
Tyr Val Asn Arg Ser Leu Pro Gly Leu Ile Gly Cys His Lys Lys Ser
            260                 265                 270 gtc tac tgg cac gtg att gga atg ggc acc agc ccg gaa gtg cac tcc         864
Val Tyr Trp His Val Ile Gly Met Gly Thr Ser Pro Glu Val His Ser
            275                 280                 285 att ttt ctt gaa ggc cac acg ttt ctc gtg agg cac cat cgc cag gct         912
Ile Phe Leu Glu Gly His Thr Phe Leu Val Arg His His Arg Gln Ala
            290                 295                 300 tcc ttg gag atc tcg cca cta act ttc ctc act gct cag aca ttc ctg         960
Ser Leu Glu Ile Ser Pro Leu Thr Phe Leu Thr Ala Gln Thr Phe Leu
305                 310                 315                 320 atg gac ctt ggc cag ttc cta ctg ttt tgt cat atc tct tcc cac cac        1008
Met Asp Leu Gly Gln Phe Leu Leu Phe Cys His Ile Ser Ser His His
            325                 330                 335 cat ggt ggc atg gag gct cac gtc aga gta gaa agc tgc gcc gag gag        1056
His Gly Gly Met Glu Ala His Val Arg Val Glu Ser Cys Ala Glu Glu
            340                 345                 350 ccc cag ctg cgg agg aaa gct gat gaa gag gaa gat tat gat gac aat        1104
Pro Gln Leu Arg Arg Lys Ala Asp Glu Glu Glu Asp Tyr Asp Asp Asn
            355                 360                 365 ttg tac gac tcg gac atg gac gtg gtc cgg ctc gat ggt gac gac gtg        1152
Leu Tyr Asp Ser Asp Met Asp Val Val Arg Leu Asp Gly Asp Asp Val
            370                 375                 380 tct ccc ttt atc caa atc cgc tcg gtt gcc aag aag cat ccc aaa acc        1200
Ser Pro Phe Ile Gln Ile Arg Ser Val Ala Lys Lys His Pro Lys Thr
385                 390                 395                 400 tgg gtg cac tac atc tct gca gag gag gag gac tgg gac tac gcc ccc        1248
Trp Val His Tyr Ile Ser Ala Glu Glu Glu Asp Trp Asp Tyr Ala Pro
            405                 410                 415 gcg gtc ccc agc ccc agt gac aga agt tat aaa agt ctc tac ttg aac        1296
Ala Val Pro Ser Pro Ser Asp Arg Ser Tyr Lys Ser Leu Tyr Leu Asn
            420                 425                 430 agt ggt cct cag cga att ggt agg aaa tac aaa aaa gct cga ttc gtc        1344
Ser Gly Pro Gln Arg Ile Gly Arg Lys Tyr Lys Lys Ala Arg Phe Val
            435                 440                 445 gct tac acg gat gta aca ttt aag act cgt aaa gct att ccg tat gaa        1392
Ala Tyr Thr Asp Val Thr Phe Lys Thr Arg Lys Ala Ile Pro Tyr Glu
450                 455                 460 tca gga atc ctg gga cct tta ctt tat gga gaa gtt gga gac aca ctt        1440
Ser Gly Ile Leu Gly Pro Leu Leu Tyr Gly Glu Val Gly Asp Thr Leu
465                 470                 475                 480 ttg att ata ttt aag aat aaa gcg agc cga cca tat aac atc tac cct        1488
Leu Ile Ile Phe Lys Asn Lys Ala Ser Arg Pro Tyr Asn Ile Tyr Pro
            485                 490                 495 cat gga atc act gat gtc agc gct ttg cac cca ggg aga ctt cta aaa        1536
```

```
            His Gly Ile Thr Asp Val Ser Ala Leu His Pro Gly Arg Leu Leu Lys
                        500                 505                 510 ggt tgg aaa cat ttg aaa gac atg cca att ctg cca gga gag act ttc        1584
Gly Trp Lys His Leu Lys Asp Met Pro Ile Leu Pro Gly Glu Thr Phe
            515                 520                 525 aag tat aaa tgg aca gtg act gtg gaa gat ggg cca acc aag tcc gat        1632
Lys Tyr Lys Trp Thr Val Thr Val Glu Asp Gly Pro Thr Lys Ser Asp
            530                 535                 540 cct cgg tgc ctg acc cgc tac tac tcg agc tcc att aat cta gag aaa        1680
Pro Arg Cys Leu Thr Arg Tyr Tyr Ser Ser Ser Ile Asn Leu Glu Lys
545                 550                 555                 560 gat ctg gct tcg gga ctc att ggc cct ctc ctc atc tgc tac aaa gaa        1728
Asp Leu Ala Ser Gly Leu Ile Gly Pro Leu Leu Ile Cys Tyr Lys Glu
                565                 570                 575 tct gta gac caa aga gga aac cag atg atg tca gac aag aga aac gtc        1776
Ser Val Asp Gln Arg Gly Asn Gln Met Met Ser Asp Lys Arg Asn Val
                580                 585                 590 atc ctg ttt tct gta ttc gat gag aat caa agc tgg tac ctc gca gag        1824
Ile Leu Phe Ser Val Phe Asp Glu Asn Gln Ser Trp Tyr Leu Ala Glu
                595                 600                 605 aat att cag cgc ttc ctc ccc aat ccg gat gga tta cag ccc cag gat        1872
Asn Ile Gln Arg Phe Leu Pro Asn Pro Asp Gly Leu Gln Pro Gln Asp
        610                 615                 620 cca gag ttc caa gct tct aac atc atg cac agc atc aat ggc tat gtt        1920
Pro Glu Phe Gln Ala Ser Asn Ile Met His Ser Ile Asn Gly Tyr Val
625                 630                 635                 640 ttt gat agc ttg cag ctg tcg gtt tgt ttg cac gag gtg gca tac tgg        1968
Phe Asp Ser Leu Gln Leu Ser Val Cys Leu His Glu Val Ala Tyr Trp
                645                 650                 655 tac att cta agt gtt gga gca cag acg gac ttc ctc tcc gtc ttc ttc        2016
Tyr Ile Leu Ser Val Gly Ala Gln Thr Asp Phe Leu Ser Val Phe Phe
                660                 665                 670 tct ggc tac acc ttc aaa cac aaa atg gtc tat gaa gac aca ctc acc        2064
Ser Gly Tyr Thr Phe Lys His Lys Met Val Tyr Glu Asp Thr Leu Thr
                675                 680                 685 ctg ttc ccc ttc tca gga gaa acg gtc ttc atg tca atg gaa aac cca        2112
Leu Phe Pro Phe Ser Gly Glu Thr Val Phe Met Ser Met Glu Asn Pro
        690                 695                 700 ggt ctc tgg gtc ctt ggg tgc cac aac tca gac ttg cgg aac aga ggg        2160
Gly Leu Trp Val Leu Gly Cys His Asn Ser Asp Leu Arg Asn Arg Gly
705                 710                 715                 720 atg aca gcc tta ctg aag gtg tat agt tgt gac agg gac att ggt gat        2208
Met Thr Ala Leu Leu Lys Val Tyr Ser Cys Asp Arg Asp Ile Gly Asp
                725                 730                 735 tat tat gac aac act tat gaa gat att cca ggc ttc ttg ctg agt gga        2256
Tyr Tyr Asp Asn Thr Tyr Glu Asp Ile Pro Gly Phe Leu Leu Ser Gly
                740                 745                 750 aag aat gtc att gaa cct agg agc ttt gcc cag aat tca aga ccc cct        2304
Lys Asn Val Ile Glu Pro Arg Ser Phe Ala Gln Asn Ser Arg Pro Pro
            755                 760                 765 agt gcg agc gct cca aag cct ccg gtc ctg cga cgg cat cag agg gac        2352
Ser Ala Ser Ala Pro Lys Pro Pro Val Leu Arg Arg His Gln Arg Asp
            770                 775                 780 ata agc ctt cct act ttt cag ccg gag gaa gac aaa atg gac tat gat        2400
Ile Ser Leu Pro Thr Phe Gln Pro Glu Glu Asp Lys Met Asp Tyr Asp
785                 790                 795                 800 gat ate ttc tca act gaa acg aag gga gaa gat ttt gac att tac ggt        2448
Asp Ile Phe Ser Thr Glu Thr Lys Gly Glu Asp Phe Asp Ile Tyr Gly
                805                 810                 815 gag gat gaa aat cag gac cct cgc agc ttt cag aag aga acc cga cac        2496
```

```
Glu Asp Glu Asn Gln Asp Pro Arg Ser Phe Gln Lys Arg Thr Arg His
            820                 825                 830 tat ttc att gct gcg gtg gag cag ctc tgg gat tac ggg atg agc gaa      2544
Tyr Phe Ile Ala Ala Val Glu Gln Leu Trp Asp Tyr Gly Met Ser Glu
            835                 840                 845 tcc ccc cgg gcg cta aga aac agg gct cag aac gga gag gtg cct cgg      2592
Ser Pro Arg Ala Leu Arg Asn Arg Ala Gln Asn Gly Glu Val Pro Arg
    850                 855                 860 ttc aag aag gtg gtc ttc cgg gaa ttt gct gac ggc tcc ttc acg cag      2640
Phe Lys Lys Val Val Phe Arg Glu Phe Ala Asp Gly Ser Phe Thr Gln
865                 870                 875                 880 ccg tcg tac cgc ggg gaa ctc aac aaa cac ttg ggg ctc ttg gga ccc      2688
Pro Ser Tyr Arg Gly Glu Leu Asn Lys His Leu Gly Leu Leu Gly Pro
                885                 890                 895 tac atc aga gcg gaa gtt gaa gac aac atc atg gta act ttc aaa aac      2736
Tyr Ile Arg Ala Glu Val Glu Asp Asn Ile Met Val Thr Phe Lys Asn
            900                 905                 910 cag gcg tct cgt ccc tat tcc ttc tac tcg agc ctt att tct tat ccg      2784
Gln Ala Ser Arg Pro Tyr Ser Phe Tyr Ser Ser Leu Ile Ser Tyr Pro
            915                 920                 925 gat gat cag gag caa ggg gca gaa cct cga cac aac ttc gtc cag cca      2832
Asp Asp Gln Glu Gln Gly Ala Glu Pro Arg His Asn Phe Val Gln Pro
930                 935                 940 aat gaa acc aga act tac ttt tgg aaa gtg cag cat cac atg gca ccc      2880
Asn Glu Thr Arg Thr Tyr Phe Trp Lys Val Gln His His Met Ala Pro
945                 950                 955                 960 aca gaa gac gag ttt gac tgc aaa gcc tgg gcc tac ttt tct gat gtt      2928
Thr Glu Asp Glu Phe Asp Cys Lys Ala Trp Ala Tyr Phe Ser Asp Val
                965                 970                 975 gac ctg gaa aaa gat gtg cac tca ggc ttg atc ggc ccc ctt ctg atc      2976
Asp Leu Glu Lys Asp Val His Ser Gly Leu Ile Gly Pro Leu Leu Ile
            980                 985                 990 tgc cgc gcc aac acc ctg aac gct gct cac ggt aga caa gtg acc gtg      3024
Cys Arg Ala Asn Thr Leu Asn Ala Ala His Gly Arg Gln Val Thr Val
            995                 1000                1005 caa gaa ttt gct ctg ttt ttc act att ttt gat gag aca aag agc tgg      3072
Gln Glu Phe Ala Leu Phe Phe Thr Ile Phe Asp Glu Thr Lys Ser Trp
    1010                1015                1020 tac ttc act gaa aat gtg gaa agg aac tgc cgg gcc ccc tgc cat ctg      3120
Tyr Phe Thr Glu Asn Val Glu Arg Asn Cys Arg Ala Pro Cys His Leu
1025                1030                1035                1040 cag atg gag gac ccc act ctg aaa gaa aac tat cgc ttc cat gca atc      3168
Gln Met Glu Asp Pro Thr Leu Lys Glu Asn Tyr Arg Phe His Ala Ile
                1045                1050                1055 aat ggc tat gtg atg gat aca ctc cct ggc tta gta atg gct cag aat      3216
Asn Gly Tyr Val Met Asp Thr Leu Pro Gly Leu Val Met Ala Gln Asn
            1060                1065                1070 caa agg atc cga tgg tat ctg ctc agc atg ggc agc aat gaa aat atc      3264
Gln Arg Ile Arg Trp Tyr Leu Leu Ser Met Gly Ser Asn Glu Asn Ile
            1075                1080                1085 cat tcg att cat ttt agc gga cac gtg ttc agt gta cgg aaa aag gag      3312
His Ser Ile His Phe Ser Gly His Val Phe Ser Val Arg Lys Lys Glu
    1090                1095                1100 gag tat aaa atg gcc gtg tac aat ctc tat ccg ggt gtc ttt gag aca      3360
Glu Tyr Lys Met Ala Val Tyr Asn Leu Tyr Pro Gly Val Phe Glu Thr
1105                1110                1115                1120 gtg gaa atg cta ccg tcc aaa gtt gga att tgg cga ata gaa tgc ctg      3408
Val Glu Met Leu Pro Ser Lys Val Gly Ile Trp Arg Ile Glu Cys Leu
                1125                1130                1135 att ggc gag cac ctg caa gct ggg atg agc acg act ttc ctg gtg tac      3456
```

```
                   Ile Gly Glu His Leu Gln Ala Gly Met Ser Thr Thr Phe Leu Val Tyr
                                1140                1145                1150 agc aag gag tgt cag gct cca ctg gga atg gct tct gga cgc att aga             3504
Ser Lys Glu Cys Gln Ala Pro Leu Gly Met Ala Ser Gly Arg Ile Arg
        1155                1160                1165 gat ttt cag atc aca gct tca gga cag tat gga cag tgg gcc cca aag             3552
Asp Phe Gln Ile Thr Ala Ser Gly Gln Tyr Gly Gln Trp Ala Pro Lys
    1170                1175                1180 ctg gcc aga ctt cat tat tcc gga tca atc aat gcc tgg agc acc aag             3600
Leu Ala Arg Leu His Tyr Ser Gly Ser Ile Asn Ala Trp Ser Thr Lys
1185                1190                1195                1200 gat ccc cac tcc tgg atc aag gtg gat ctg ttg gca cca atg atc att             3648
Asp Pro His Ser Trp Ile Lys Val Asp Leu Leu Ala Pro Met Ile Ile
            1205                1210                1215 cac ggc atc atg acc cag ggt gcc cgt cag aag ttt tcc agc ctc tac             3696
His Gly Ile Met Thr Gln Gly Ala Arg Gln Lys Phe Ser Ser Leu Tyr
                1220                1225                1230 atc tcc cag ttt atc atc atg tac agt ctt gac ggg agg aac tgg cag             3744
Ile Ser Gln Phe Ile Ile Met Tyr Ser Leu Asp Gly Arg Asn Trp Gln
        1235                1240                1245 agt tac cga ggg aat tcc acg ggc acc tta atg gtc ttc ttt ggc aat             3792
Ser Tyr Arg Gly Asn Ser Thr Gly Thr Leu Met Val Phe Phe Gly Asn
    1250                1255                1260 gtg gac gca tct ggg att aaa cac aat att ttt aac cct ccg att gtg             3840
Val Asp Ala Ser Gly Ile Lys His Asn Ile Phe Asn Pro Pro Ile Val
1265                1270                1275                1280 gct cgg tac atc cgt ttg cac cca aca cat tac agc atc cgc agc act             3888
Ala Arg Tyr Ile Arg Leu His Pro Thr His Tyr Ser Ile Arg Ser Thr
            1285                1290                1295 ctt cgc atg gag ttg atg ggc tgt gat tta aac agt tgc agc atg ccc             3936
Leu Arg Met Glu Leu Met Gly Cys Asp Leu Asn Ser Cys Ser Met Pro
                1300                1305                1310 ctg gga atg cag aat aaa gcg ata tca gac tca cag atc acg gcc tcc             3984
Leu Gly Met Gln Asn Lys Ala Ile Ser Asp Ser Gln Ile Thr Ala Ser
        1315                1320                1325 tcc cac cta agc aat ata ttt gcc acc tgg tct cct tca caa gcc cga             4032
Ser His Leu Ser Asn Ile Phe Ala Thr Trp Ser Pro Ser Gln Ala Arg
    1330                1335                1340 ctt cac ctc cag ggg cgg acg aat gcc tgg cga ccc cgg gtg agc agc             4080
Leu His Leu Gln Gly Arg Thr Asn Ala Trp Arg Pro Arg Val Ser Ser
1345                1350                1355                1360 gca gag gag tgg ctg cag gtg gac ctg cag aag acg gtg aag gtc aca             4128
Ala Glu Glu Trp Leu Gln Val Asp Leu Gln Lys Thr Val Lys Val Thr
            1365                1370                1375 ggc atc acc acc cag ggc gtg aag tcc ctg ctc agc agc atg tat gtg             4176
Gly Ile Thr Thr Gln Gly Val Lys Ser Leu Leu Ser Ser Met Tyr Val
                1380                1385                1390 aag gag ttc ctc gtg tcc agt agt cag gac ggc cgc cgc tgg acc ctg             4224
Lys Glu Phe Leu Val Ser Ser Ser Gln Asp Gly Arg Arg Trp Thr Leu
        1395                1400                1405 ttt ctt cag gac ggc cac acg aag gtt ttt cag ggc aat cag gac tcc             4272
Phe Leu Gln Asp Gly His Thr Lys Val Phe Gln Gly Asn Gln Asp Ser
    1410                1415                1420 tcc acc ccc gtg gtg aac gct ctg gac ccc ccg ctg ttc acg cgc tac             4320
Ser Thr Pro Val Val Asn Ala Leu Asp Pro Pro Leu Phe Thr Arg Tyr
1425                1430                1435                1440 ctg agg atc cac ccc acg agc tgg gcg cag cac atc gcc ctg agg ctc             4368
Leu Arg Ile His Pro Thr Ser Trp Ala Gln His Ile Ala Leu Arg Leu
            1445                1450                1455 gag gtt cta gga tgt gag gca cag gat ctc tac tga                             4404
Glu Val Leu Gly Cys Glu Ala Gln Asp Leu Tyr
```

```
Glu Val Leu Gly Cys Glu Ala Gln Asp Leu Tyr
            1460                1465
```

<210> SEQ ID NO 4
<211> LENGTH: 1467
<212> TYPE: PRT
<213> ORGANISM: Sus scrofa

<400> SEQUENCE: 4

```
Met Gln Leu Glu Leu Ser Thr Cys Val Phe Leu Cys Leu Leu Pro Leu
 1               5                  10                  15

Gly Phe Ser Ala Ile Arg Arg Tyr Tyr Leu Gly Ala Val Glu Leu Ser
            20                  25                  30

Trp Asp Tyr Arg Gln Ser Glu Leu Leu Arg Glu Leu His Val Asp Thr
        35                  40                  45

Arg Phe Pro Ala Thr Ala Pro Gly Ala Leu Pro Leu Gly Pro Ser Val
    50                  55                  60

Leu Tyr Lys Lys Thr Val Phe Val Glu Phe Thr Asp Gln Leu Phe Ser
65                  70                  75                  80

Val Ala Arg Pro Arg Pro Pro Trp Met Gly Leu Leu Gly Pro Thr Ile
                85                  90                  95

Gln Ala Glu Val Tyr Asp Thr Val Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
    290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
            340                 345                 350

Pro Gln Leu Arg Arg Lys Ala Asp Glu Glu Glu Asp Tyr Asp Asp Asn
        355                 360                 365
```

-continued

```
Leu Tyr Asp Ser Asp Met Asp Val Arg Leu Asp Gly Asp Val
    370                 375                 380

Ser Pro Phe Ile Gln Ile Arg Ser Val Ala Lys Lys His Pro Lys Thr
385                 390                 395                 400

Trp Val His Tyr Ile Ser Ala Glu Glu Glu Asp Trp Asp Tyr Ala Pro
                405                 410                 415

Ala Val Pro Ser Pro Ser Asp Arg Ser Tyr Lys Ser Leu Tyr Leu Asn
            420                 425                 430

Ser Gly Pro Gln Arg Ile Gly Arg Lys Tyr Lys Lys Ala Arg Phe Val
        435                 440                 445

Ala Tyr Thr Asp Val Thr Phe Lys Thr Arg Lys Ala Ile Pro Tyr Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Lys Ala Ser Arg Pro Tyr Asn Ile Tyr Pro
                485                 490                 495

His Gly Ile Thr Asp Val Ser Ala Leu His Pro Gly Arg Leu Leu Lys
            500                 505                 510

Gly Trp Lys His Leu Lys Asp Met Pro Ile Leu Pro Gly Glu Thr Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Ile Asn Leu Glu Lys
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Met Met Ser Asp Lys Arg Asn Val
            580                 585                 590

Ile Leu Phe Ser Val Phe Asp Glu Asn Gln Ser Trp Tyr Leu Ala Glu
        595                 600                 605

Asn Ile Gln Arg Phe Leu Pro Asn Pro Asp Gly Leu Gln Pro Gln Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Val Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Val Leu Gly Cys His Asn Ser Asp Leu Arg Asn Arg Gly
705                 710                 715                 720

Met Thr Ala Leu Leu Lys Val Tyr Ser Cys Asp Arg Asp Ile Gly Asp
                725                 730                 735

Tyr Tyr Asp Asn Thr Tyr Glu Asp Ile Pro Gly Phe Leu Leu Ser Gly
            740                 745                 750

Lys Asn Val Ile Glu Pro Arg Ser Phe Ala Gln Asn Ser Arg Pro Pro
        755                 760                 765

Ser Ala Ser Ala Pro Lys Pro Pro Val Leu Arg Arg His Gln Arg Asp
    770                 775                 780

Ile Ser Leu Pro Thr Phe Gln Pro Glu Glu Asp Lys Met Asp Tyr Asp
785                 790                 795                 800
```

-continued

Asp Ile Phe Ser Thr Glu Thr Lys Gly Glu Asp Phe Asp Ile Tyr Gly
                805                 810                 815
Glu Asp Glu Asn Gln Asp Pro Arg Ser Phe Gln Lys Arg Thr Arg His
            820                 825                 830
Tyr Phe Ile Ala Ala Val Glu Gln Leu Trp Asp Tyr Gly Met Ser Glu
            835                 840                 845
Ser Pro Arg Ala Leu Arg Asn Arg Ala Gln Asn Gly Glu Val Pro Arg
        850                 855                 860
Phe Lys Lys Val Val Phe Arg Glu Phe Ala Asp Gly Ser Phe Thr Gln
865                 870                 875                 880
Pro Ser Tyr Arg Gly Glu Leu Asn Lys His Leu Gly Leu Leu Gly Pro
                885                 890                 895
Tyr Ile Arg Ala Glu Val Glu Asp Asn Ile Met Val Thr Phe Lys Asn
            900                 905                 910
Gln Ala Ser Arg Pro Tyr Ser Phe Tyr Ser Ser Leu Ile Ser Tyr Pro
        915                 920                 925
Asp Asp Gln Glu Gln Gly Ala Glu Pro Arg His Asn Phe Val Gln Pro
    930                 935                 940
Asn Glu Thr Arg Thr Tyr Phe Trp Lys Val Gln His His Met Ala Pro
945                 950                 955                 960
Thr Glu Asp Glu Phe Asp Cys Lys Ala Trp Ala Tyr Phe Ser Asp Val
                965                 970                 975
Asp Leu Glu Lys Asp Val His Ser Gly Leu Ile Gly Pro Leu Leu Ile
            980                 985                 990
Cys Arg Ala Asn Thr Leu Asn Ala Ala His Gly Arg Gln Val Thr Val
        995                 1000                1005
Gln Glu Phe Ala Leu Phe Phe Thr Ile Phe Asp Glu Thr Lys Ser Trp
    1010                1015                1020
Tyr Phe Thr Glu Asn Val Glu Arg Asn Cys Arg Ala Pro Cys His Leu
1025                1030                1035                1040
Gln Met Glu Asp Pro Thr Leu Lys Glu Asn Tyr Arg Phe His Ala Ile
                1045                1050                1055
Asn Gly Tyr Val Met Asp Thr Leu Pro Gly Leu Val Met Ala Gln Asn
            1060                1065                1070
Gln Arg Ile Arg Trp Tyr Leu Leu Ser Met Gly Ser Asn Glu Asn Ile
        1075                1080                1085
His Ser Ile His Phe Ser Gly His Val Phe Ser Val Arg Lys Lys Glu
    1090                1095                1100
Glu Tyr Lys Met Ala Val Tyr Asn Leu Tyr Pro Gly Val Phe Glu Thr
1105                1110                1115                1120
Val Glu Met Leu Pro Ser Lys Val Gly Ile Trp Arg Ile Glu Cys Leu
                1125                1130                1135
Ile Gly Glu His Leu Gln Ala Gly Met Ser Thr Thr Phe Leu Val Tyr
            1140                1145                1150
Ser Lys Glu Cys Gln Ala Pro Leu Gly Met Ala Ser Gly Arg Ile Arg
        1155                1160                1165
Asp Phe Gln Ile Thr Ala Ser Gly Gln Tyr Gly Gln Trp Ala Pro Lys
    1170                1175                1180
Leu Ala Arg Leu His Tyr Ser Gly Ser Ile Asn Ala Trp Ser Thr Lys
1185                1190                1195                1200
Asp Pro His Ser Trp Ile Lys Val Asp Leu Leu Ala Pro Met Ile Ile
                1205                1210                1215
His Gly Ile Met Thr Gln Gly Ala Arg Gln Lys Phe Ser Ser Leu Tyr

```
              1220              1225             1230
    Ile Ser Gln Phe Ile Ile Met Tyr Ser Leu Asp Gly Arg Asn Trp Gln
            1235             1240             1245
    Ser Tyr Arg Gly Asn Ser Thr Gly Thr Leu Met Val Phe Phe Gly Asn
            1250             1255             1260
    Val Asp Ala Ser Gly Ile Lys His Asn Ile Phe Asn Pro Pro Ile Val
    1265             1270             1275             1280
    Ala Arg Tyr Ile Arg Leu His Pro Thr His Tyr Ser Ile Arg Ser Thr
                1285             1290             1295
    Leu Arg Met Glu Leu Met Gly Cys Asp Leu Asn Ser Cys Ser Met Pro
            1300             1305             1310
    Leu Gly Met Gln Asn Lys Ala Ile Ser Asp Ser Gln Ile Thr Ala Ser
            1315             1320             1325
    Ser His Leu Ser Asn Ile Phe Ala Thr Trp Ser Pro Ser Gln Ala Arg
            1330             1335             1340
    Leu His Leu Gln Gly Arg Thr Asn Ala Trp Arg Pro Arg Val Ser Ser
    1345             1350             1355             1360
    Ala Glu Glu Trp Leu Gln Val Asp Leu Gln Lys Thr Val Lys Val Thr
                1365             1370             1375
    Gly Ile Thr Thr Gln Gly Val Lys Ser Leu Leu Ser Ser Met Tyr Val
            1380             1385             1390
    Lys Glu Phe Leu Val Ser Ser Ser Gln Asp Gly Arg Arg Trp Thr Leu
            1395             1400             1405
    Phe Leu Gln Asp Gly His Thr Lys Val Phe Gln Gly Asn Gln Asp Ser
            1410             1415             1420
    Ser Thr Pro Val Val Asn Ala Leu Asp Pro Pro Leu Phe Thr Arg Tyr
    1425             1430             1435             1440
    Leu Arg Ile His Pro Thr Ser Trp Ala Gln His Ile Ala Leu Arg Leu
                1445             1450             1455
    Glu Val Leu Gly Cys Glu Ala Gln Asp Leu Tyr
            1460             1465

<210> SEQ ID NO 5
<211> LENGTH: 9009
<212> TYPE: DNA
<213> ORGANISM: Homo sapiens
<220> FEATURE:
<221> NAME/KEY: gene
<222> LOCATION: (0)...(0)
<223> OTHER INFORMATION: Factor VIII- Full Length
<221> NAME/KEY: CDS
<222> LOCATION: (208)...(7203)

<400> SEQUENCE: 5
cagtgggtaa gttccttaaa tgctctgcaa agaaattggg acttttcatt aaatcagaaa      60
ttttactttt ttcccctcct gggagctaaa gatattttag agaagaatta accttttgct     120
tctccagttg aacatttgta gcaataagtc atgcaaatag agctctccac ctgcttcttt     180
ctgtgccttt tgcgattctg ctttagt gcc acc aga aga tac tac ctg ggt gca    234
                              Ala Thr Arg Arg Tyr Tyr Leu Gly Ala
                                1               5 gtg gaa ctg tca tgg gac tat atg caa agt gat ctc ggt gag ctg cct      282
Val Glu Leu Ser Trp Asp Tyr Met Gln Ser Asp Leu Gly Glu Leu Pro
 10              15               20              25 gtg gac gca aga ttt cct cct aga gtg cca aaa tct ttt cca ttc aac      330
Val Asp Ala Arg Phe Pro Pro Arg Val Pro Lys Ser Phe Pro Phe Asn
             30               35              40 acc tca gtc gtg tac aaa aag act ctg ttt gta gaa ttc acg gtt cac      378
```

```
                                                              -continued

Thr Ser Val Val Tyr Lys Lys Thr Leu Phe Val Glu Phe Thr Val His
         45                  50                  55 ctt ttc aac atc gct aag cca agg cca ccc tgg atg ggt ctg cta ggt    426
Leu Phe Asn Ile Ala Lys Pro Arg Pro Pro Trp Met Gly Leu Leu Gly
             60                  65                  70 cct acc atc cag gct gag gtt tat gat aca gtg gtc att aca ctt aag    474
Pro Thr Ile Gln Ala Glu Val Tyr Asp Thr Val Val Ile Thr Leu Lys
         75                  80                  85 aac atg gct tcc cat cct gtc agt ctt cat gct gtt ggt gta tcc tac    522
Asn Met Ala Ser His Pro Val Ser Leu His Ala Val Gly Val Ser Tyr
 90                  95                 100                 105 tgg aaa gct tct gag gga gct gaa tat gat gat cag acc agt caa agg    570
Trp Lys Ala Ser Glu Gly Ala Glu Tyr Asp Asp Gln Thr Ser Gln Arg
                110                 115                 120 gag aaa gaa gat gat aaa gtc ttc cct ggt gga agc cat aca tat gtc    618
Glu Lys Glu Asp Asp Lys Val Phe Pro Gly Gly Ser His Thr Tyr Val
            125                 130                 135 tgg cag gtc ctg aaa gag aat ggt cca atg gcc tct gac cca ctg tgc    666
Trp Gln Val Leu Lys Glu Asn Gly Pro Met Ala Ser Asp Pro Leu Cys
        140                 145                 150 ctt acc tac tca tat ctt tct cat gtg gac ctg gta aaa gac ttg aat    714
Leu Thr Tyr Ser Tyr Leu Ser His Val Asp Leu Val Lys Asp Leu Asn
155                 160                 165 tca ggc ctc att gga gcc cta cta gta tgt aga gaa ggg agt ctg gcc    762
Ser Gly Leu Ile Gly Ala Leu Leu Val Cys Arg Glu Gly Ser Leu Ala
170                 175                 180                 185 aag gaa aag aca cag acc ttg cac aaa ttt ata cta ctt ttt gct gta    810
Lys Glu Lys Thr Gln Thr Leu His Lys Phe Ile Leu Leu Phe Ala Val
                190                 195                 200 ttt gat gaa ggg aaa agt tgg cac tca gaa aca aag aac tcc ttg atg    858
Phe Asp Glu Gly Lys Ser Trp His Ser Glu Thr Lys Asn Ser Leu Met
            205                 210                 215 cag gat agg gat gct gca tct gct cgg gcc tgg cct aaa atg cac aca    906
Gln Asp Arg Asp Ala Ala Ser Ala Arg Ala Trp Pro Lys Met His Thr
        220                 225                 230 gtc aat ggt tat gta aac agg tct ctg cca ggt ctg att gga tgc cac    954
Val Asn Gly Tyr Val Asn Arg Ser Leu Pro Gly Leu Ile Gly Cys His
    235                 240                 245 agg aaa tca gtc tat tgg cat gtg att gga atg ggc acc act cct gaa   1002
Arg Lys Ser Val Tyr Trp His Val Ile Gly Met Gly Thr Thr Pro Glu
250                 255                 260                 265 gtg cac tca ata ttc ctc gaa ggt cac aca ttt ctt gtg agg aac cat   1050
Val His Ser Ile Phe Leu Glu Gly His Thr Phe Leu Val Arg Asn His
                270                 275                 280 cgc cag gcg tcc ttg gaa atc tcg cca ata act ttc ctt act gct caa   1098
Arg Gln Ala Ser Leu Glu Ile Ser Pro Ile Thr Phe Leu Thr Ala Gln
            285                 290                 295 aca ctc ttg atg gac ctt gga cag ttt cta ctg ttt tgt cat atc tct   1146
Thr Leu Leu Met Asp Leu Gly Gln Phe Leu Leu Phe Cys His Ile Ser
        300                 305                 310 tcc cac caa cat gat ggc atg gaa gct tat gtc aaa gta gac agc tgt   1194
Ser His Gln His Asp Gly Met Glu Ala Tyr Val Lys Val Asp Ser Cys
    315                 320                 325 cca gag gaa ccc caa cta cga atg aaa aat aat gaa gaa gcg gaa gac   1242
Pro Glu Glu Pro Gln Leu Arg Met Lys Asn Asn Glu Glu Ala Glu Asp
330                 335                 340                 345 tat gat gat gat ctt act gat tct gaa atg gat gtg gtc agg ttt gat   1290
Tyr Asp Asp Asp Leu Thr Asp Ser Glu Met Asp Val Val Arg Phe Asp
                350                 355                 360 gat gac aac tct cct tcc ttt atc caa att cgc tca gtt gcc aag aag   1338
```

```
                        -continued

Asp Asp Asn Ser Pro Ser Phe Ile Gln Ile Arg Ser Val Ala Lys Lys
            365                 370                 375 cat cct aaa act tgg gta cat tac att gct gct gaa gag gag gac tgg      1386
His Pro Lys Thr Trp Val His Tyr Ile Ala Ala Glu Glu Glu Asp Trp
            380                 385                 390 gac tat gct ccc tta gtc ctc gcc ccc gat gac aga agt tat aaa agt      1434
Asp Tyr Ala Pro Leu Val Leu Ala Pro Asp Asp Arg Ser Tyr Lys Ser
    395                 400                 405 caa tat ttg aac aat ggc cct cag cgg att ggt agg aag tac aaa aaa      1482
Gln Tyr Leu Asn Asn Gly Pro Gln Arg Ile Gly Arg Lys Tyr Lys Lys
410                 415                 420                 425 gtc cga ttt atg gca tac aca gat gaa acc ttt aag act cgt gaa gct      1530
Val Arg Phe Met Ala Tyr Thr Asp Glu Thr Phe Lys Thr Arg Glu Ala
                430                 435                 440 att cag cat gaa tca gga atc ttg gga cct tta ctt tat ggg gaa gtt      1578
Ile Gln His Glu Ser Gly Ile Leu Gly Pro Leu Leu Tyr Gly Glu Val
            445                 450                 455 gga gac aca ctg ttg att ata ttt aag aat caa gca agc aga cca tat      1626
Gly Asp Thr Leu Leu Ile Ile Phe Lys Asn Gln Ala Ser Arg Pro Tyr
        460                 465                 470 aac atc tac cct cac gga atc act gat gtc cgt cct ttg tat tca agg      1674
Asn Ile Tyr Pro His Gly Ile Thr Asp Val Arg Pro Leu Tyr Ser Arg
    475                 480                 485 aga tta cca aaa ggt gta aaa cat ttg aag gat ttt cca att ctg cca      1722
Arg Leu Pro Lys Gly Val Lys His Leu Lys Asp Phe Pro Ile Leu Pro
490                 495                 500                 505 gga gaa ata ttc aaa tat aaa tgg aca gtg act gta gaa gat ggg cca      1770
Gly Glu Ile Phe Lys Tyr Lys Trp Thr Val Thr Val Glu Asp Gly Pro
                510                 515                 520 act aaa tca gat cct cgg tgc ctg acc cgc tat tac tct agt ttc gtt      1818
Thr Lys Ser Asp Pro Arg Cys Leu Thr Arg Tyr Tyr Ser Ser Phe Val
            525                 530                 535 aat atg gag aga gat cta gct tca gga ctc att ggc cct ctc ctc atc      1866
Asn Met Glu Arg Asp Leu Ala Ser Gly Leu Ile Gly Pro Leu Leu Ile
        540                 545                 550 tgc tac aaa gaa tct gta gat caa aga gga aac cag ata atg tca gac      1914
Cys Tyr Lys Glu Ser Val Asp Gln Arg Gly Asn Gln Ile Met Ser Asp
    555                 560                 565 aag agg aat gtc atc ctg ttt tct gta ttt gat gag aac cga agc tgg      1962
Lys Arg Asn Val Ile Leu Phe Ser Val Phe Asp Glu Asn Arg Ser Trp
570                 575                 580                 585 tac ctc aca gag aat ata caa cgc ttt ctc ccc aat cca gct gga gtg      2010
Tyr Leu Thr Glu Asn Ile Gln Arg Phe Leu Pro Asn Pro Ala Gly Val
                590                 595                 600 cag ctt gag gat cca gag ttc caa gcc tcc aac atc atg cac agc atc      2058
Gln Leu Glu Asp Pro Glu Phe Gln Ala Ser Asn Ile Met His Ser Ile
            605                 610                 615 aat ggc tat gtt ttt gat agt ttg cag ttg tca gtt tgt ttg cat gag      2106
Asn Gly Tyr Val Phe Asp Ser Leu Gln Leu Ser Val Cys Leu His Glu
        620                 625                 630 gtg gca tac tgg tac att cta agc att gga gca cag act gac ttc ctt      2154
Val Ala Tyr Trp Tyr Ile Leu Ser Ile Gly Ala Gln Thr Asp Phe Leu
    635                 640                 645 tct gtc ttc ttc tct gga tat acc ttc aaa cac aaa atg gtc tat gaa      2202
Ser Val Phe Phe Ser Gly Tyr Thr Phe Lys His Lys Met Val Tyr Glu
650                 655                 660                 665 gac aca ctc acc cta ttc cca ttc tca gga gaa act gtc ttc atg tcg      2250
Asp Thr Leu Thr Leu Phe Pro Phe Ser Gly Glu Thr Val Phe Met Ser
                670                 675                 680 atg gaa aac cca ggt cta tgg att ctg ggg tgc cac aac tca gac ttt      2298
```

```
            Met Glu Asn Pro Gly Leu Trp Ile Leu Gly Cys His Asn Ser Asp Phe
                        685                 690                 695 cgg aac aga ggc atg acc gcc tta ctg aag gtt tct agt tgt gac aag         2346
Arg Asn Arg Gly Met Thr Ala Leu Leu Lys Val Ser Ser Cys Asp Lys
            700                 705                 710 aac act ggt gat tat tac gag gac agt tat gaa gat att tca gca tac         2394
Asn Thr Gly Asp Tyr Tyr Glu Asp Ser Tyr Glu Asp Ile Ser Ala Tyr
            715                 720                 725 ttg ctg agt aaa aac aat gcc att gaa cca aga agc ttc tcc cag aat         2442
Leu Leu Ser Lys Asn Asn Ala Ile Glu Pro Arg Ser Phe Ser Gln Asn
730                 735                 740                 745 tca aga cac cct agc act agg caa aag caa ttt aat gcc acc aca att         2490
Ser Arg His Pro Ser Thr Arg Gln Lys Gln Phe Asn Ala Thr Thr Ile
                750                 755                 760 cca gaa aat gac ata gag aag act gac cct tgg ttt gca cac aga aca         2538
Pro Glu Asn Asp Ile Glu Lys Thr Asp Pro Trp Phe Ala His Arg Thr
            765                 770                 775 cct atg cct aaa ata caa aat gtc tcc tct agt gat ttg ttg atg ctc         2586
Pro Met Pro Lys Ile Gln Asn Val Ser Ser Ser Asp Leu Leu Met Leu
            780                 785                 790 ttg cga cag agt cct act cca cat ggg cta tcc tta tct gat ctc caa         2634
Leu Arg Gln Ser Pro Thr Pro His Gly Leu Ser Leu Ser Asp Leu Gln
795                 800                 805 gaa gcc aaa tat gag act ttt tct gat gat cca tca cct gga gca ata         2682
Glu Ala Lys Tyr Glu Thr Phe Ser Asp Asp Pro Ser Pro Gly Ala Ile
810                 815                 820                 825 gac agt aat aac agc ctg tct gaa atg aca cac ttc agg cca cag ctc         2730
Asp Ser Asn Asn Ser Leu Ser Glu Met Thr His Phe Arg Pro Gln Leu
                830                 835                 840 cat cac agt ggg gac atg gta ttt acc cct gag tca ggc ctc caa tta         2778
His His Ser Gly Asp Met Val Phe Thr Pro Glu Ser Gly Leu Gln Leu
            845                 850                 855 aga tta aat gag aaa ctg gga aca act gca gca aca gag ttg aag aaa         2826
Arg Leu Asn Glu Lys Leu Gly Thr Thr Ala Ala Thr Glu Leu Lys Lys
            860                 865                 870 ctt gat ttc aaa gtt tct agt aca tca aat aat ctg att tca aca att         2874
Leu Asp Phe Lys Val Ser Ser Thr Ser Asn Asn Leu Ile Ser Thr Ile
875                 880                 885 cca tca gac aat ttg gca gca ggt act gat aat aca agt tcc tta gga         2922
Pro Ser Asp Asn Leu Ala Ala Gly Thr Asp Asn Thr Ser Ser Leu Gly
890                 895                 900                 905 ccc cca agt atg cca gtt cat tat gat agt caa tta gat acc act cta         2970
Pro Pro Ser Met Pro Val His Tyr Asp Ser Gln Leu Asp Thr Thr Leu
                910                 915                 920 ttt ggc aaa aag tca tct ccc ctt act gag tct ggt gga cct ctg agc         3018
Phe Gly Lys Lys Ser Ser Pro Leu Thr Glu Ser Gly Gly Pro Leu Ser
            925                 930                 935 ttg agt gaa gaa aat aat gat tca aag ttg tta gaa tca ggt tta atg         3066
Leu Ser Glu Glu Asn Asn Asp Ser Lys Leu Leu Glu Ser Gly Leu Met
            940                 945                 950 aat agc caa gaa agt tca tgg gga aaa aat gta tcg tca aca gag agt         3114
Asn Ser Gln Glu Ser Ser Trp Gly Lys Asn Val Ser Ser Thr Glu Ser
955                 960                 965 ggt agg tta ttt aaa ggg aaa aga gct cat gga cct gct ttg ttg act         3162
Gly Arg Leu Phe Lys Gly Lys Arg Ala His Gly Pro Ala Leu Leu Thr
970                 975                 980                 985 aaa gat aat gcc tta ttc aaa gtt agc atc tct ttg tta aag aca aac         3210
Lys Asp Asn Ala Leu Phe Lys Val Ser Ile Ser Leu Leu Lys Thr Asn
                990                 995                 1000 aaa act tcc aat aat tca gca act aat aga aag act cac att gat ggc         3258
```

-continued

```
Lys Thr Ser Asn Asn Ser Ala Thr Asn Arg Lys Thr His Ile Asp Gly
            1005                1010                1015 cca tca tta tta att gag aat agt cca tca gtc tgg caa aat ata tta    3306
Pro Ser Leu Leu Ile Glu Asn Ser Pro Ser Val Trp Gln Asn Ile Leu
            1020                1025                1030 gaa agt gac act gag ttt aaa aaa gtg aca cct ttg att cat gac aga    3354
Glu Ser Asp Thr Glu Phe Lys Lys Val Thr Pro Leu Ile His Asp Arg
            1035                1040                1045 atg ctt atg gac aaa aat gct aca gct ttg agg cta aat cat atg tca    3402
Met Leu Met Asp Lys Asn Ala Thr Ala Leu Arg Leu Asn His Met Ser
1050                1055                1060                1065 aat aaa act act tca tca aaa aac atg gaa atg gtc caa cag aaa aaa    3450
Asn Lys Thr Thr Ser Ser Lys Asn Met Glu Met Val Gln Gln Lys Lys
            1070                1075                1080 gag ggc ccc att cca cca gat gca caa aat cca gat atg tcg ttc ttt    3498
Glu Gly Pro Ile Pro Pro Asp Ala Gln Asn Pro Asp Met Ser Phe Phe
            1085                1090                1095 aag atg cta ttc ttg cca gaa tca gca agg tgg ata caa agg act cat    3546
Lys Met Leu Phe Leu Pro Glu Ser Ala Arg Trp Ile Gln Arg Thr His
            1100                1105                1110 gga aag aac tct ctg aac tct ggg caa ggc ccc agt cca aag caa tta    3594
Gly Lys Asn Ser Leu Asn Ser Gly Gln Gly Pro Ser Pro Lys Gln Leu
            1115                1120                1125 gta tcc tta gga cca gaa aaa tct gtg gaa ggt cag aat ttc ttg tct    3642
Val Ser Leu Gly Pro Glu Lys Ser Val Glu Gly Gln Asn Phe Leu Ser
1130                1135                1140                1145 gag aaa aac aaa gtg gta gta gga aag ggt gaa ttt aca aag gac gta    3690
Glu Lys Asn Lys Val Val Val Gly Lys Gly Glu Phe Thr Lys Asp Val
            1150                1155                1160 gga ctc aaa gag atg gtt ttt cca agc agc aga aac cta ttt ctt act    3738
Gly Leu Lys Glu Met Val Phe Pro Ser Ser Arg Asn Leu Phe Leu Thr
            1165                1170                1175 aac ttg gat aat tta cat gaa aat aat aca cac aat caa gaa aaa aaa    3786
Asn Leu Asp Asn Leu His Glu Asn Asn Thr His Asn Gln Glu Lys Lys
            1180                1185                1190 att cag gaa gaa ata gaa aag aag gaa aca tta atc caa gag aat gta    3834
Ile Gln Glu Glu Ile Glu Lys Lys Glu Thr Leu Ile Gln Glu Asn Val
            1195                1200                1205 gtt ttg cct cag ata cat aca gtg act ggc act aag aat ttc atg aag    3882
Val Leu Pro Gln Ile His Thr Val Thr Gly Thr Lys Asn Phe Met Lys
1210                1215                1220                1225 aac ctt ttc tta ctg agc act agg caa aat gta gaa ggt tca tat gag    3930
Asn Leu Phe Leu Leu Ser Thr Arg Gln Asn Val Glu Gly Ser Tyr Glu
            1230                1235                1240 ggg gca tat gct cca gta ctt caa gat ttt agg tca tta aat gat tca    3978
Gly Ala Tyr Ala Pro Val Leu Gln Asp Phe Arg Ser Leu Asn Asp Ser
            1245                1250                1255 aca aat aga aca aag aaa cac aca gct cat ttc tca aaa aaa ggg gag    4026
Thr Asn Arg Thr Lys Lys His Thr Ala His Phe Ser Lys Lys Gly Glu
            1260                1265                1270 gaa gaa aac ttg gaa ggc ttg gga aat caa acc aag caa att gta gag    4074
Glu Glu Asn Leu Glu Gly Leu Gly Asn Gln Thr Lys Gln Ile Val Glu
            1275                1280                1285 aaa tat gca tgc acc aca agg ata tct cct aat aca agc cag cag aat    4122
Lys Tyr Ala Cys Thr Thr Arg Ile Ser Pro Asn Thr Ser Gln Gln Asn
1290                1295                1300                1305 ttt gtc acg caa cgt agt aag aga gct ttg aaa caa ttc aga ctc cca    4170
Phe Val Thr Gln Arg Ser Lys Arg Ala Leu Lys Gln Phe Arg Leu Pro
            1310                1315                1320 cta gaa gaa aca gaa ctt gaa aaa agg ata att gtg gat gac acc tca    4218
```

|  |  |
|---|---:|
| Leu Glu Glu Thr Glu Leu Glu Lys Arg Ile Ile Val Asp Asp Thr Ser<br>               1325                  1330               1335 |  |
| acc cag tgg tcc aaa aac atg aaa cat ttg acc ccg agc acc ctc aca<br>Thr Gln Trp Ser Lys Asn Met Lys His Leu Thr Pro Ser Thr Leu Thr<br>            1340                  1345               1350 | 4266 |
| cag ata gac tac aat gag aag gag aaa ggg gcc att act cag tct ccc<br>Gln Ile Asp Tyr Asn Glu Lys Glu Lys Gly Ala Ile Thr Gln Ser Pro<br>            1355                  1360               1365 | 4314 |
| tta tca gat tgc ctt acg agg agt cat agc atc cct caa gca aat aga<br>Leu Ser Asp Cys Leu Thr Arg Ser His Ser Ile Pro Gln Ala Asn Arg<br>1370                 1375                  1380               1385 | 4362 |
| tct cca tta ccc att gca aag gta tca tca ttt cca tct att aga cct<br>Ser Pro Leu Pro Ile Ala Lys Val Ser Ser Phe Pro Ser Ile Arg Pro<br>            1390                  1395               1400 | 4410 |
| ata tat ctg acc agg gtc cta ttc caa gac aac tct tct cat ctt cca<br>Ile Tyr Leu Thr Arg Val Leu Phe Gln Asp Asn Ser Ser His Leu Pro<br>            1405                  1410               1415 | 4458 |
| gca gca tct tat aga aag aaa gat tct ggg gtc caa gaa agc agt cat<br>Ala Ala Ser Tyr Arg Lys Lys Asp Ser Gly Val Gln Glu Ser Ser His<br>            1420                  1425               1430 | 4506 |
| ttc tta caa gga gcc aaa aaa aat aac ctt tct tta gcc att cta acc<br>Phe Leu Gln Gly Ala Lys Lys Asn Asn Leu Ser Leu Ala Ile Leu Thr<br>            1435                  1440               1445 | 4554 |
| ttg gag atg act ggt gat caa aga gag gtt ggc tcc ctg ggg aca agt<br>Leu Glu Met Thr Gly Asp Gln Arg Glu Val Gly Ser Leu Gly Thr Ser<br>1450                 1455                  1460               1465 | 4602 |
| gcc aca aat tca gtc aca tac aag aaa gtt gag aac act gtt ctc ccg<br>Ala Thr Asn Ser Val Thr Tyr Lys Lys Val Glu Asn Thr Val Leu Pro<br>            1470                  1475               1480 | 4650 |
| aaa cca gac ttg ccc aaa aca tct ggc aaa gtt gaa ttg ctt cca aaa<br>Lys Pro Asp Leu Pro Lys Thr Ser Gly Lys Val Glu Leu Leu Pro Lys<br>            1485                  1490               1495 | 4698 |
| gtt cac att tat cag aag gac cta ttc cct acg gaa act agc aat ggg<br>Val His Ile Tyr Gln Lys Asp Leu Phe Pro Thr Glu Thr Ser Asn Gly<br>            1500                  1505               1510 | 4746 |
| tct cct ggc cat ctg gat ctc gtg gaa ggg agc ctt ctt cag gga aca<br>Ser Pro Gly His Leu Asp Leu Val Glu Gly Ser Leu Leu Gln Gly Thr<br>            1515                  1520               1525 | 4794 |
| gag gga gcg att aag tgg aat gaa gca aac aga cct gga aaa gtt ccc<br>Glu Gly Ala Ile Lys Trp Asn Glu Ala Asn Arg Pro Gly Lys Val Pro<br>1530                 1535                  1540               1545 | 4842 |
| ttt ctg aga gta gca aca gaa agc tct gca aag act ccc tcc aag cta<br>Phe Leu Arg Val Ala Thr Glu Ser Ser Ala Lys Thr Pro Ser Lys Leu<br>            1550                  1555               1560 | 4890 |
| ttg gat cct ctt gct tgg gat aac cac tat ggt act cag ata cca aaa<br>Leu Asp Pro Leu Ala Trp Asp Asn His Tyr Gly Thr Gln Ile Pro Lys<br>            1565                  1570               1575 | 4938 |
| gaa gag tgg aaa tcc caa gag aag tca cca gaa aaa aca gct ttt aag<br>Glu Glu Trp Lys Ser Gln Glu Lys Ser Pro Glu Lys Thr Ala Phe Lys<br>            1580                  1585               1590 | 4986 |
| aaa aag gat acc att ttg tcc ctg aac gct tgt gaa agc aat cat gca<br>Lys Lys Asp Thr Ile Leu Ser Leu Asn Ala Cys Glu Ser Asn His Ala<br>            1595                  1600               1605 | 5034 |
| ata gca gca ata aat gag gga caa aat aag ccc gaa ata gaa gtc acc<br>Ile Ala Ala Ile Asn Glu Gly Gln Asn Lys Pro Glu Ile Glu Val Thr<br>1610                 1615                  1620               1625 | 5082 |
| tgg gca aag caa ggt agg act gaa agg ctg tgc tct caa aac cca cca<br>Trp Ala Lys Gln Gly Arg Thr Glu Arg Leu Cys Ser Gln Asn Pro Pro<br>            1630                  1635               1640 | 5130 |
| gtc ttg aaa cgc cat caa cgg gaa ata act cgt act act ctt cag tca | 5178 |

-continued

```
                Val Leu Lys Arg His Gln Arg Glu Ile Thr Arg Thr Thr Leu Gln Ser
                                1645                1650                1655 gat caa gag gaa att gac tat gat gat acc ata tca gtt gaa atg aag         5226
Asp Gln Glu Glu Ile Asp Tyr Asp Asp Thr Ile Ser Val Glu Met Lys
                1660                1665                1670 aag gaa gat ttt gac att tat gat gag gat gaa aat cag agc ccc cgc         5274
Lys Glu Asp Phe Asp Ile Tyr Asp Glu Asp Glu Asn Gln Ser Pro Arg
                1675                1680                1685 agc ttt caa aag aaa aca cga cac tat ttt att gct gca gtg gag agg         5322
Ser Phe Gln Lys Lys Thr Arg His Tyr Phe Ile Ala Ala Val Glu Arg
        1690                1695                1700                1705 ctc tgg gat tat ggg atg agt agc tcc cca cat gtt cta aga aac agg         5370
Leu Trp Asp Tyr Gly Met Ser Ser Ser Pro His Val Leu Arg Asn Arg
                    1710                1715                1720 gct cag agt ggc agt gtc cct cag ttc aag aaa gtt gtt ttc cag gaa         5418
Ala Gln Ser Gly Ser Val Pro Gln Phe Lys Lys Val Val Phe Gln Glu
                1725                1730                1735 ttt act gat ggc tcc ttt act cag ccc tta tac cgt gga gaa cta aat         5466
Phe Thr Asp Gly Ser Phe Thr Gln Pro Leu Tyr Arg Gly Glu Leu Asn
                1740                1745                1750 gaa cat ttg gga ctc ctg ggg cca tat ata aga gca gaa gtt gaa gat         5514
Glu His Leu Gly Leu Leu Gly Pro Tyr Ile Arg Ala Glu Val Glu Asp
                1755                1760                1765 aat atc atg gta act ttc aga aat cag gcc tct cgt ccc tat tcc ttc         5562
Asn Ile Met Val Thr Phe Arg Asn Gln Ala Ser Arg Pro Tyr Ser Phe
1770                1775                1780                1785 tat tct agc ctt att tct tat gag gaa gat cag agg caa gga gca gaa         5610
Tyr Ser Ser Leu Ile Ser Tyr Glu Glu Asp Gln Arg Gln Gly Ala Glu
                    1790                1795                1800 cct aga aaa aac ttt gtc aag cct aat gaa acc aaa act tac ttt tgg         5658
Pro Arg Lys Asn Phe Val Lys Pro Asn Glu Thr Lys Thr Tyr Phe Trp
                1805                1810                1815 aaa gtg caa cat cat atg gca ccc act aaa gat gag ttt gac tgc aaa         5706
Lys Val Gln His His Met Ala Pro Thr Lys Asp Glu Phe Asp Cys Lys
                1820                1825                1830 gcc tgg gct tat ttc tct gat gtt gac ctg gaa aaa gat gtg cac tca         5754
Ala Trp Ala Tyr Phe Ser Asp Val Asp Leu Glu Lys Asp Val His Ser
                1835                1840                1845 ggc ctg att gga ccc ctt ctg gtc tgc cac act aac aca ctg aac cct         5802
Gly Leu Ile Gly Pro Leu Leu Val Cys His Thr Asn Thr Leu Asn Pro
1850                1855                1860                1865 gct cat ggg aga caa gtg aca gta cag gaa ttt gct ctg ttt ttc acc         5850
Ala His Gly Arg Gln Val Thr Val Gln Glu Phe Ala Leu Phe Phe Thr
                    1870                1875                1880 atc ttt gat gag acc aaa agc tgg tac ttc act gaa aat atg gaa aga         5898
Ile Phe Asp Glu Thr Lys Ser Trp Tyr Phe Thr Glu Asn Met Glu Arg
                1885                1890                1895 aac tgc agg gct ccc tgc aat atc cag atg gaa gat ccc act ttt aaa         5946
Asn Cys Arg Ala Pro Cys Asn Ile Gln Met Glu Asp Pro Thr Phe Lys
                1900                1905                1910 gag aat tat cgc ttc cat gca atc aat ggc tac ata atg gat aca cta         5994
Glu Asn Tyr Arg Phe His Ala Ile Asn Gly Tyr Ile Met Asp Thr Leu
        1915                1920                1925 cct ggc tta gta atg gct cag gat caa agg att cga tgg tat ctg ctc         6042
Pro Gly Leu Val Met Ala Gln Asp Gln Arg Ile Arg Trp Tyr Leu Leu
1930                1935                1940                1945 agc atg ggc agc aat gaa aac atc cat tct att cat ttc agt gga cat         6090
Ser Met Gly Ser Asn Glu Asn Ile His Ser Ile His Phe Ser Gly His
                    1950                1955                1960 gtg ttc act gta cga aaa aaa gag gag tat aaa atg gca ctg tac aat         6138
```

```
Val Phe Thr Val Arg Lys Lys Glu Glu Tyr Lys Met Ala Leu Tyr Asn
            1965                1970                1975 ctc tat cca ggt gtt ttt gag aca gtg gaa atg tta cca tcc aaa gct      6186
Leu Tyr Pro Gly Val Phe Glu Thr Val Glu Met Leu Pro Ser Lys Ala
        1980                1985                1990 gga att tgg cgg gtg gaa tgc ctt att ggc gag cat cta cat gct ggg      6234
Gly Ile Trp Arg Val Glu Cys Leu Ile Gly Glu His Leu His Ala Gly
        1995                2000                2005 atg agc aca ctt ttt ctg gtg tac agc aat aag tgt cag act ccc ctg      6282
Met Ser Thr Leu Phe Leu Val Tyr Ser Asn Lys Cys Gln Thr Pro Leu
2010                2015                2020                2025 gga atg gct tct gga cac att aga gat ttt cag att aca gct tca gga      6330
Gly Met Ala Ser Gly His Ile Arg Asp Phe Gln Ile Thr Ala Ser Gly
        2030                2035                2040 caa tat gga cag tgg gcc cca aag ctg gcc aga ctt cat tat tcc gga      6378
Gln Tyr Gly Gln Trp Ala Pro Lys Leu Ala Arg Leu His Tyr Ser Gly
        2045                2050                2055 tca atc aat gcc tgg agc acc aag gag ccc ttt tct tgg atc aag gtg      6426
Ser Ile Asn Ala Trp Ser Thr Lys Glu Pro Phe Ser Trp Ile Lys Val
        2060                2065                2070 gat ctg ttg gca cca atg att att cac ggc atc aag acc cag ggt gcc      6474
Asp Leu Leu Ala Pro Met Ile Ile His Gly Ile Lys Thr Gln Gly Ala
        2075                2080                2085 cgt cag aag ttc tcc agc ctc tac atc tct cag ttt atc atc atg tat      6522
Arg Gln Lys Phe Ser Ser Leu Tyr Ile Ser Gln Phe Ile Ile Met Tyr
2090                2095                2100                2105 agt ctt gat ggg aag aag tgg cag act tat cga gga aat tcc act gga      6570
Ser Leu Asp Gly Lys Lys Trp Gln Thr Tyr Arg Gly Asn Ser Thr Gly
        2110                2115                2120 acc tta atg gtc ttc ttt ggc aat gtg gat tca tct ggg ata aaa cac      6618
Thr Leu Met Val Phe Phe Gly Asn Val Asp Ser Ser Gly Ile Lys His
        2125                2130                2135 aat att ttt aac cct cca att att gct cga tac atc cgt ttg cac cca      6666
Asn Ile Phe Asn Pro Pro Ile Ile Ala Arg Tyr Ile Arg Leu His Pro
        2140                2145                2150 act cat tat agc att cgc agc act ctt cgc atg gag ttg atg ggc tgt      6714
Thr His Tyr Ser Ile Arg Ser Thr Leu Arg Met Glu Leu Met Gly Cys
        2155                2160                2165 gat tta aat agt tgc agc atg cca ttg gga atg gag agt aaa gca ata      6762
Asp Leu Asn Ser Cys Ser Met Pro Leu Gly Met Glu Ser Lys Ala Ile
2170                2175                2180                2185 tca gat gca cag att act gct tca tcc tac ttt acc aat atg ttt gcc      6810
Ser Asp Ala Gln Ile Thr Ala Ser Ser Tyr Phe Thr Asn Met Phe Ala
        2190                2195                2200 acc tgg tct cct tca aaa gct cga ctt cac ctc caa ggg agg agt aat      6858
Thr Trp Ser Pro Ser Lys Ala Arg Leu His Leu Gln Gly Arg Ser Asn
        2205                2210                2215 gcc tgg aga cct cag gtg aat aat cca aaa gag tgg ctg caa gtg gac      6906
Ala Trp Arg Pro Gln Val Asn Asn Pro Lys Glu Trp Leu Gln Val Asp
        2220                2225                2230 ttc cag aag aca atg aaa gtc aca gga gta act act cag gga gta aaa      6954
Phe Gln Lys Thr Met Lys Val Thr Gly Val Thr Thr Gln Gly Val Lys
        2235                2240                2245 tct ctg ctt acc agc atg tat gtg aag gag ttc ctc atc tcc agc agt      7002
Ser Leu Leu Thr Ser Met Tyr Val Lys Glu Phe Leu Ile Ser Ser Ser
2250                2255                2260                2265 caa gat ggc cat cag tgg act ctc ttt ttt cag aat ggc aaa gta aag      7050
Gln Asp Gly His Gln Trp Thr Leu Phe Phe Gln Asn Gly Lys Val Lys
        2270                2275                2280 gtt ttt cag gga aat caa gac tcc ttc aca cct gtg gtg aac tct cta      7098
```

| | | |
|---|---|---|
| Val Phe Gln Gly Asn Gln Asp Ser Phe Thr Pro Val Val Asn Ser Leu<br>                        2285                         2290                        2295 | | |
| gac cca ccg tta ctg act cgc tac ctt cga att cac ccc cag agt tgg<br>Asp Pro Pro Leu Leu Thr Arg Tyr Leu Arg Ile His Pro Gln Ser Trp<br>                    2300                        2305                        2310 | 7146 | |
| gtg cac cag att gcc ctg agg atg gag gtt ctg ggc tgc gag gca cag<br>Val His Gln Ile Ala Leu Arg Met Glu Val Leu Gly Cys Glu Ala Gln<br>                    2315                        2320                        2325 | 7194 | |
| gac ctc tac tgagggtggc cactgcagca cctgccactg ccgtcacctc<br>Asp Leu Tyr<br>2330 | 7243 | |
| tccctcctca gctccagggc agtgtccctc cctggcttgc cttctacctt tgtgctaaat | 7303 | |
| cctagcagac actgccttga agcctcctga attaactatc atcagtcctg catttctttg | 7363 | |
| gtgggggggcc aggagggtgc atccaattta acttaactct tacctatttt ctgcagctgc | 7423 | |
| tcccagatta ctccttcctt ccaatataac taggcaaaaa gaagtgagga gaaacctgca | 7483 | |
| tgaaagcatt cttccctgaa aagttaggcc tctcagagtc accacttcct ctgttgtaga | 7543 | |
| aaaactatgt gatgaaactt tgaaaaagat atttatgatg ttaacatttc aggttaagcc | 7603 | |
| tcatcgtttt aaaataaaac tctcagttgt ttattatcct gatcaagcat ggaacaaagc | 7663 | |
| atgtttcagg atcagatcaa tacaatcttg gagtcaaaag gcaaatcatt tggacaatct | 7723 | |
| gcaaaatgga gagaatacaa taactactac agtaaagtct gtttctgctt ccttacacat | 7783 | |
| agatataatt atgttattta gtcattatga ggggcacatt cttatctcca aaactagcat | 7843 | |
| tcttaaactg agaattatag atggggttca agaatcccta agtccctga aattatataa | 7903 | |
| ggcattctgt ataaatgcaa atgtgcattt ttctgacgag tgtccataga tataaagcca | 7963 | |
| ttggtcttaa ttctgaccaa taaaaaaata agtcaggagg atgcaattgt tgaaagcttt | 8023 | |
| gaaataaaat aacatgtctt cttgaaattt gtgatggcca agaaagaaaa tgatgatgac | 8083 | |
| attaggcttc taaaggacat acatttaata tttctgtgga aatatgagga aaatccatgg | 8143 | |
| ttatctgaga taggagatac aaactttgta attctaataa tgcactcagt ttactctctc | 8203 | |
| cctctactaa tttcctgctg aaaataacac aacaaaaatg taacagggga aattatatac | 8263 | |
| cgtgactgaa aactagagtc ctacttacat agttgaaata tcaaggaggt cagaagaaaa | 8323 | |
| ttggactggt gaaaacagaa aaaacactcc agtctgccat atcaccacac aataggatcc | 8383 | |
| cccttcttgc cctccacccc cataagattg tgaagggttt actgctcctt ccatctgcct | 8443 | |
| gcacccttc actatgacta cacagaactc tcctgatagt aaaggggggct ggaggcaagg | 8503 | |
| ataagttata gagcagttgg aggaagcatc caaagactgc aacccagggc aaatggaaaa | 8563 | |
| caggagatcc taatatgaaa gaaaaatgga tcccaatctg agaaaaggca aaagaatggc | 8623 | |
| tactttttc tatgctggag tattttctaa taatcctgct tgacccttat ctgacctctt | 8683 | |
| tggaaactat aacatagctg tcacagtata gtcacaatcc acaaatgatg caggtgcaaa | 8743 | |
| tggtttatag ccctgtgaag ttcttaaagt ttagaggcta acttacagaa atgaataagt | 8803 | |
| tgttttgttt tatagcccgg tagaggagtt aaccccaaag gtgatatggt tttatttcct | 8863 | |
| gttatgttta acttgataat cttattttgg cattcttttc ccattgacta tatacatctc | 8923 | |
| tatttctcaa atgttcatgg aactagctct tttattttcc tgctggtttc ttcagtaatg | 8983 | |
| agttaaaataa aacattgaca cataca | 9009 | |

<210> SEQ ID NO 6
<211> LENGTH: 2351
<212> TYPE: PRT
<213> ORGANISM: Homo sapiens

```
<400> SEQUENCE: 6

Met Gln Ile Glu Leu Ser Thr Cys Phe Phe Leu Cys Leu Leu Arg Phe
 1               5                  10                  15

Cys Phe Ser Ala Thr Arg Arg Tyr Tyr Leu Gly Ala Val Glu Leu Ser
             20                  25                  30

Trp Asp Tyr Met Gln Ser Asp Leu Gly Glu Leu Pro Val Asp Ala Arg
         35                  40                  45

Phe Pro Pro Arg Val Pro Lys Ser Phe Pro Phe Asn Thr Ser Val Val
 50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
             85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415
```

```
Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
                435                 440                 445

Ala Tyr Thr Asp Glu Thr Phe Lys Thr Arg Glu Ala Ile Gln His Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
        770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
```

-continued

```
                835                 840                845
Ser Leu Ser Glu Met Thr His Phe Arg Pro Gln Leu His His Ser Gly
850                 855                860
Asp Met Val Phe Thr Pro Glu Ser Gly Leu Gln Leu Arg Leu Asn Glu
865                 870                875                880
Lys Leu Gly Thr Thr Ala Ala Thr Glu Leu Lys Lys Leu Asp Phe Lys
                885                890                895
Val Ser Ser Thr Ser Asn Asn Leu Ile Ser Thr Ile Pro Ser Asp Asn
                900                905                910
Leu Ala Ala Gly Thr Asp Asn Thr Ser Ser Leu Gly Pro Pro Ser Met
                915                920                925
Pro Val His Tyr Asp Ser Gln Leu Asp Thr Thr Leu Phe Gly Lys Lys
930                 935                940
Ser Ser Pro Leu Thr Glu Ser Gly Gly Pro Leu Ser Leu Ser Glu Glu
945                 950                955                960
Asn Asn Asp Ser Lys Leu Leu Glu Ser Gly Leu Met Asn Ser Gln Glu
                965                970                975
Ser Ser Trp Gly Lys Asn Val Ser Ser Thr Glu Ser Gly Arg Leu Phe
                980                985                990
Lys Gly Lys Arg Ala His Gly Pro Ala Leu Leu Thr Lys Asp Asn Ala
                995                1000               1005
Leu Phe Lys Val Ser Ile Ser Leu Leu Lys Thr Asn Lys Thr Ser
1010                1015                1020
Asn Asn Ser Ala Thr Asn Arg Lys Thr His Ile Asp Gly Pro Ser
1025                1030                1035
Leu Leu Ile Glu Asn Ser Pro Ser Val Trp Gln Asn Ile Leu Glu
1040                1045                1050
Ser Asp Thr Glu Phe Lys Lys Val Thr Pro Leu Ile His Asp Arg
1055                1060                1065
Met Leu Met Asp Lys Asn Ala Thr Ala Leu Arg Leu Asn His Met
1070                1075                1080
Ser Asn Lys Thr Thr Ser Ser Lys Asn Met Glu Met Val Gln Gln
1085                1090                1095
Lys Lys Glu Gly Pro Ile Pro Pro Asp Ala Gln Asn Pro Asp Met
1100                1105                1110
Ser Phe Phe Lys Met Leu Phe Leu Pro Glu Ser Ala Arg Trp Ile
1115                1120                1125
Gln Arg Thr His Gly Lys Asn Ser Leu Asn Ser Gly Gln Gly Pro
1130                1135                1140
Ser Pro Lys Gln Leu Val Ser Leu Gly Pro Glu Lys Ser Val Glu
1145                1150                1155
Gly Gln Asn Phe Leu Ser Glu Lys Asn Lys Val Val Val Gly Lys
1160                1165                1170
Gly Glu Phe Thr Lys Asp Val Gly Leu Lys Glu Met Val Phe Pro
1175                1180                1185
Ser Ser Arg Asn Leu Phe Leu Thr Asn Leu Asp Asn Leu His Glu
1190                1195                1200
Asn Asn Thr His Asn Gln Glu Lys Lys Ile Gln Glu Glu Ile Glu
1205                1210                1215
Lys Lys Glu Thr Leu Ile Gln Glu Asn Val Val Leu Pro Gln Ile
1220                1225                1230
His Thr Val Thr Gly Thr Lys Asn Phe Met Lys Asn Leu Phe Leu
1235                1240                1245
```

```
Leu Ser Thr Arg Gln Asn Val Glu Gly Ser Tyr Glu Gly Ala Tyr
    1250            1255                1260

Ala Pro Val Leu Gln Asp Phe Arg Ser Leu Asn Asp Ser Thr Asn
    1265            1270                1275

Arg Thr Lys Lys His Thr Ala His Phe Ser Lys Lys Gly Glu Glu
    1280            1285                1290

Glu Asn Leu Glu Gly Leu Gly Asn Gln Thr Lys Gln Ile Val Glu
    1295            1300                1305

Lys Tyr Ala Cys Thr Thr Arg Ile Ser Pro Asn Thr Ser Gln Gln
    1310            1315                1320

Asn Phe Val Thr Gln Arg Ser Lys Arg Ala Leu Lys Gln Phe Arg
    1325            1330                1335

Leu Pro Leu Glu Glu Thr Glu Leu Glu Lys Arg Ile Ile Val Asp
    1340            1345                1350

Asp Thr Ser Thr Gln Trp Ser Lys Asn Met Lys His Leu Thr Pro
    1355            1360                1365

Ser Thr Leu Thr Gln Ile Asp Tyr Asn Glu Lys Glu Lys Gly Ala
    1370            1375                1380

Ile Thr Gln Ser Pro Leu Ser Asp Cys Leu Thr Arg Ser His Ser
    1385            1390                1395

Ile Pro Gln Ala Asn Arg Ser Pro Leu Pro Ile Ala Lys Val Ser
    1400            1405                1410

Ser Phe Pro Ser Ile Arg Pro Ile Tyr Leu Thr Arg Val Leu Phe
    1415            1420                1425

Gln Asp Asn Ser Ser His Leu Pro Ala Ala Ser Tyr Arg Lys Lys
    1430            1435                1440

Asp Ser Gly Val Gln Glu Ser Ser His Phe Leu Gln Gly Ala Lys
    1445            1450                1455

Lys Asn Asn Leu Ser Leu Ala Ile Leu Thr Leu Glu Met Thr Gly
    1460            1465                1470

Asp Gln Arg Glu Val Gly Ser Leu Gly Thr Ser Ala Thr Asn Ser
    1475            1480                1485

Val Thr Tyr Lys Lys Val Glu Asn Thr Val Leu Pro Lys Pro Asp
    1490            1495                1500

Leu Pro Lys Thr Ser Gly Lys Val Glu Leu Leu Pro Lys Val His
    1505            1510                1515

Ile Tyr Gln Lys Asp Leu Phe Pro Thr Glu Thr Ser Asn Gly Ser
    1520            1525                1530

Pro Gly His Leu Asp Leu Val Glu Gly Ser Leu Leu Gln Gly Thr
    1535            1540                1545

Glu Gly Ala Ile Lys Trp Asn Glu Ala Asn Arg Pro Gly Lys Val
    1550            1555                1560

Pro Phe Leu Arg Val Ala Thr Glu Ser Ser Ala Lys Thr Pro Ser
    1565            1570                1575

Lys Leu Leu Asp Pro Leu Ala Trp Asp Asn His Tyr Gly Thr Gln
    1580            1585                1590

Ile Pro Lys Glu Glu Trp Lys Ser Gln Glu Lys Ser Pro Glu Lys
    1595            1600                1605

Thr Ala Phe Lys Lys Lys Asp Thr Ile Leu Ser Leu Asn Ala Cys
    1610            1615                1620

Glu Ser Asn His Ala Ile Ala Ala Ile Asn Glu Gly Gln Asn Lys
    1625            1630                1635

Pro Glu Ile Glu Val Thr Trp Ala Lys Gln Gly Arg Thr Glu Arg
    1640            1645                1650
```

-continued

```
Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Val Cys His
    1865                1870                1875

Thr Asn Thr Leu Asn Pro Ala His Gly Arg Gln Val Thr Val Gln
    1880                1885                1890

Glu Phe Ala Leu Phe Phe Thr Ile Phe Asp Glu Thr Lys Ser Trp
    1895                1900                1905

Tyr Phe Thr Glu Asn Met Glu Arg Asn Cys Arg Ala Pro Cys Asn
    1910                1915                1920

Ile Gln Met Glu Asp Pro Thr Phe Lys Glu Asn Tyr Arg Phe His
    1925                1930                1935

Ala Ile Asn Gly Tyr Ile Met Asp Thr Leu Pro Gly Leu Val Met
    1940                1945                1950

Ala Gln Asp Gln Arg Ile Arg Trp Tyr Leu Leu Ser Met Gly Ser
    1955                1960                1965

Asn Glu Asn Ile His Ser Ile His Phe Ser Gly His Val Phe Thr
    1970                1975                1980

Val Arg Lys Lys Glu Glu Tyr Lys Met Ala Leu Tyr Asn Leu Tyr
    1985                1990                1995

Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
```

```
            2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
    2075                2080                2085

Trp Ile Lys Val Asp Leu Leu Ala Pro Met Ile Ile His Gly Ile
    2090                2095                2100

Lys Thr Gln Gly Ala Arg Gln Lys Phe Ser Ser Leu Tyr Ile Ser
    2105                2110                2115

Gln Phe Ile Ile Met Tyr Ser Leu Asp Gly Lys Lys Trp Gln Thr
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190

Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser
    2210                2215                2220

Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250

Gln Lys Thr Met Lys Val Thr Gly Val Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr
    2345                2350

<210> SEQ ID NO 7
<211> LENGTH: 6996
<212> TYPE: DNA
<213> ORGANISM: Homo sapiens
<220> FEATURE:
<221> NAME/KEY: gene
<222> LOCATION: (0)...(0)
<223> OTHER INFORMATION: Factor VIII- Full Length coding sequence

<400> SEQUENCE: 7
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggttca ccttttcaac     180
```

```
atcgctaagc caaggccacc ctggatgggt ctgctaggtc ctaccatcca ggctgaggtt    240
tatgatacag tggtcattac acttaagaac atggcttccc atcctgtcag tcttcatgct    300
gttggtgtat cctactggaa agcttctgag ggagctgaat atgatgatca gaccagtcaa    360
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg gagccctact agtatgtaga    540
gaagggagtc tggccaagga aaagacacag accttgcaca aatttatact acttttttgct    600 gtatttgatg aagggaaaag ttggcactca gaaacaaaga actccttgat gcaggatagg    660
gatgctgcat ctgctcgggc ctggcctaaa atgcacacag tcaatggtta tgtaaacagg    720
tctctgccag gtctgattgg atgccacagg aaatcagtct attggcatgt gattggaatg    780
ggcaccactc ctgaagtgca ctcaatattc ctcgaaggtc acacatttct tgtgaggaac    840
catcgccagg cgtccttgga aatctcgcca ataactttcc ttactgctca aacactcttg    900
atggaccttg acagtttcct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca ctctcccttc ctttatccaa attcgctcag ttgccaagaa gcatcctaaa   1140
acttgggtac attacattgc tgctgaagag gaggactggg actatgctcc cttagtcctc   1200
gcccccgatg acagaagtta taaaagtcaa tatttgaaca atggccctca gcggattggt   1260
aggaagtaca aaaagtccg atttatggca tacacagatg aaacctttaa gactcgtgaa   1320
gctattcagc atgaatcagg aatcttggga ccctttacttt atggggaagt tggagacaca   1380
ctgttgatta tatttaagaa tcaagcaagc agaccatata acatctaccc tcacggaatc   1440
actgatgtcc gtccttttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctgtagat   1680
caaagaggaa accagataat gtcagacaag aggaatgtca tcctgttttc tgtatttgat   1740
gagaaccgaa gctggtacct cacagagaat atacaacgct tctctcccaa tccagctgga   1800
gtgcagcttg aggatccaga gttccaagcc tccaacatca tgcacagcat caatggctat   1860
gtttttgata gtttgcagtt gtcagtttgt ttgcatgagg tggcatactg gtacattcta   1920
agcattggag cacagactga cttccttttct gtcttcttct ctggatatac cttcaaacac   1980
aaaatggtct atgaagacac actcacccta ttcccattct caggagaaac tgtcttcatg   2040
tcgatggaaa acccaggtct atggattctg ggtgccaca actcagactt tcggaacaga   2100
ggcatgaccg ccttactgaa ggtttctagt tgtgacaaga acactggtga ttattacgag   2160
gacagttatg aagatatttc agcatacttg ctgagtaaaa acaatgccat tgaaccaaga   2220
agcttctccc agaattcaag acaccctagc actaggcaaa agcaatttaa tgccaccaca   2280
attccagaaa atgacataga gaagactgac ccttggtttg cacacagaac acctatgcct   2340
aaaatacaaa atgtctcctc tagtgatttg ttgatgctct gcgacagag tcctactcca   2400 catgggctat ccttatctga tctccaagaa gccaaatatg agacttttttc tgatgatcca   2460 tcacctggag caatagacag taataacagc ctgtctgaaa tgacacactt caggccacag   2520
ctccatcaca gtggggacat ggtatttacc cctgagtcag gcctccaatt aagattaaat   2580
```

```
gagaaactgg ggacaactgc agcaacagag ttgaagaaac ttgatttcaa agtttctagt    2640
acatcaaata atctgatttc aacaattcca tcagacaatt tggcagcagg tactgataat    2700
acaagttcct taggacccccc aagtatgcca gttcattatg atagtcaatt agataccact   2760
ctatttggca aaaagtcatc tccccttact gagtctggtg gacctctgag cttgagtgaa    2820 gaaataatg attcaaagtt gttagaatca ggtttaatga atagccaaga aagttcatgg     2880
ggaaaaaatg tatcgtcaac agagagtggt aggttattta aagggaaaag agctcatgga    2940
cctgctttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagtttaaa    3120
aaagtgacac ctttgattca tgacagaatg cttatggaca aaaatgctac agcttttgagg  3180 ctaaatcata tgtcaaataa aactacttca tcaaaaaaca tggaaatggt ccaacagaaa    3240
aaagagggcc ccattccacc agatgcacaa atcccagata tgtcgttctt taagatgcta    3300
ttcttgccag aatcagcaag gtggatacaa aggactcatg gaaagaactc tctgaactct    3360
gggcaaggcc ccagtccaaa gcaattagta tccttaggac cagaaaaatc tgtggaaggt    3420
cagaatttct tgtctgagaa aaacaaagtg gtagtaggaa agggtgaatt tacaaaggac    3480
gtaggactca aagagatggt ttttccaagc agcagaaacc tatttcttac taacttggat    3540
aatttacatg aaaataatac acacaatcaa gaaaaaaaaa ttcaggaaga aatagaaaag    3600
aaggaaacat taatccaaga gaatgtagtt ttgcctcaga tacatacagt gactggcact    3660
aagaatttca tgaagaacct tttcttactg agcactaggc aaaatgtaga aggttcatat    3720 gaggggggcat atgctccagt acttcaagat tttaggtcat taaatgattc aacaaataga    3780
acaaagaaac acacagctca tttctcaaaa aaggggagg aagaaaactt ggaaggcttg    3840
ggaaatcaaa ccaagcaaat tgtagagaaa tatgcatgca ccacaaggat atctcctaat    3900
acaagccagc agaattttgt cacgcaacgt agtaagagag ctttgaaaca attcagactc    3960
ccactagaag aaacagaact tgaaaaaagg ataattgtgg atgacacctc aacccagtgg    4020
tccaaaaaca tgaaacattt gaccccgagc accctcacac agatagacta caatgagaag    4080
gagaaagggg ccattactca gtctcccttta tcagattgcc ttacgaggag tcatagcatc    4140
cctcaagcaa atagatctcc attacccatt gcaaaggtat catcatttcc atctattaga    4200
cctatatatc tgaccagggt cctattccaa gacaactctt ctcatcttcc agcagcatct    4260
tatagaaaga aagattctgg ggtccaagaa agcagtcatt tcttacaagg agccaaaaaa    4320
aataaccttt ctttagccat tctaaccttg gagatgactg gtgatcaaag agaggttggc    4380
tccctgggga caagtgccac aaattcagtc acatacaaga aagttgagaa cactgttctc    4440
ccgaaaccag acttgcccaa aacatctggc aaagttgaat tgcttccaaa agttcacatt    4500
tatcagaagg acctattccc tacgaaaact agcaatgggt ctcctggcca tctggatctc    4560
gtggaaggga gccttcttca gggaacagag ggagcgatta agtggaatga agcaaacaga    4620
cctgaaaaag ttccctttct gagagtagca acagaaagct ctgcaaagac tcctccaag    4680 ctattggatc ctcttgcttg ggataaccac tatggtactc agataccaaa agaagagtgg    4740
aaatcccaag agaagtcacc agaaaaaaca gcttttaaga aaaaggatac cattttgtcc    4800
ctgaacgctt gtgaaagcaa tcatgcaata gcagcaataa atgagggaca aaataagccc    4860
gaaatagaag tcacctgggc aaagcaaggt aggactgaaa ggctgtgctc tcaaaaccca    4920
ccagtcttga aacgccatca acgggaaata actcgtacta ctcttcagtc agatcaagag    4980
```

```
gaaattgact atgatgatac catatcagtt gaaatgaaga aggaagattt tgacatttat    5040
gatgaggatg aaaatcagag ccccccgcagc tttcaaaaga aaacacgaca ctattttat    5100
gctgcagtgg agaggctctg ggattatggg atgagtagct ccccacatgt tctaagaaac    5160
agggctcaga gtggcagtgt ccctcagttc aagaaagttg ttttccagga atttactgat    5220
ggctccttta ctcagccctt ataccgtgga gaactaaatg aacatttggg actcctgggg    5280
ccatatataa gagcagaagt tgaagataat atcatggtaa ctttcagaaa tcaggcctct    5340
cgtccctatt ccttctattc tagccttatt tcttatgagg aagatcagag gcaaggagca    5400
gaacctagaa aaaactttgt caagcctaat gaaaccaaaa cttacttttg gaaagtgcaa    5460
catcatatgg cacccactaa agatgagttt gactgcaaag cctgggctta tttctctgat    5520
gttgacctgg aaaagatgt gcactcaggc ctgattggac cccttctggt ctgccacact    5580
aacacactga accctgctca tgggagacaa gtgacagtac aggaatttgc tctgtttttc    5640
accatctttg atgagaccaa aagctggtac ttcactgaaa atatggaaag aaactgcagg    5700
gctccctgca atatccagat ggaagatccc acttttaaag agaattatcg cttccatgca    5760
atcaatggct acataatgga tacactacct ggcttagtaa tggctcagga tcaaaggatt    5820
cgatggtatc tgctcagcat gggcagcaat gaaaacatcc attctattca tttcagtgga    5880
catgtgttca ctgtacgaaa aaagaggag tataaaatgg cactgtacaa tctctatcca    5940
ggtgtttttg agacagtgga atgttacca tccaaagctg gaatttggcg ggtggaatgc    6000
cttattggcg agcatctaca tgctgggatg agcacacttt ttctggtgta cagcaataag    6060
tgtcagactc ccctgggaat ggcttctgga cacattagag attttcagat tacagcttca    6120
ggacaatatg gacagtgggc cccaaagctg gccagacttc attattccgg atcaatcaat    6180
gcctggagca ccaaggagcc ctttcttgg atcaaggtgg atctgttggc accaatgatt    6240
attcacggca tcaagaccca gggtgcccgt cagaagttct ccagcctcta catctctcag    6300
tttatcatca tgtatagtct tgatgggaag aagtggcaga cttatcgagg aaattccact    6360
ggaaccttaa tggtcttctt tggcaatgtg gattcatctg gataaaaca caatattttt    6420
aaccctccaa ttattgctcg atacatccgt ttgcacccaa ctcattatag cattcgcagc    6480
actcttcgca tggagttgat gggctgtgat ttaaatagtt gcagcatgcc attgggaatg    6540
gagagtaaag caatatcaga tgcacagatt actgcttcat cctactttac caatatgttt    6600
gccacctggt ctccttcaaa agctcgactt cacctccaag ggaggagtaa tgcctggaga    6660
cctcaggtga ataatccaaa agagtggctg caagtggact tccagaagac aatgaaagtc    6720
acaggagtaa ctactcaggg agtaaaatct ctgcttacca gcatgtatgt gaaggagttc    6780
ctcatctcca gcagtcaaga tggccatcag tggactctct tttttcagaa tggcaaagta    6840
aaggtttttc agggaaatca agactccttc acacctgtgg tgaactctct agacccaccg    6900
ttactgactc gctaccttcg aattcacccc cagagttggg tgcaccagat tgccctgagg    6960
atggaggttc tgggctgcga ggcacaggac ctctac                               6996
```

<210> SEQ ID NO 8
<211> LENGTH: 2319
<212> TYPE: PRT
<213> ORGANISM: Mus musculus

<400> SEQUENCE: 8

Met Gln Ile Ala Leu Phe Ala Cys Phe Phe Leu Ser Leu Phe Asn Phe
 1               5                  10                  15

Cys Ser Ser Ala Ile Arg Arg Tyr Tyr Leu Gly Ala Val Glu Leu Ser

```
                 20                  25                  30
Trp Asn Tyr Ile Gln Ser Asp Leu Leu Ser Val Leu His Thr Asp Ser
             35                  40                  45

Arg Phe Leu Pro Arg Met Ser Thr Ser Phe Pro Phe Asn Thr Ser Ile
 50                  55                  60

Met Tyr Lys Lys Thr Val Phe Val Glu Tyr Lys Asp Gln Leu Phe Asn
 65                  70                  75                  80

Ile Ala Lys Pro Arg Pro Pro Trp Met Gly Leu Leu Gly Pro Thr Ile
                 85                  90                  95

Trp Thr Glu Val His Asp Thr Val Val Ile Thr Leu Lys Asn Met Ala
                100                 105                 110

Ser His Pro Val Ser Leu His Ala Val Gly Val Ser Tyr Trp Lys Ala
                115                 120                 125

Ser Glu Gly Asp Glu Tyr Glu Asp Gln Thr Ser Gln Met Glu Lys Glu
            130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Met Ser His Val Asp Leu Val Lys Asp Leu Asn Ser Gly Leu
                180                 185                 190

Ile Gly Ala Leu Leu Val Cys Lys Glu Gly Ser Leu Ser Lys Glu Arg
                195                 200                 205

Thr Gln Met Leu Tyr Gln Phe Val Leu Leu Phe Ala Val Phe Asp Glu
                210                 215                 220

Gly Lys Ser Trp His Ser Glu Thr Asn Asp Ser Tyr Thr Gln Ser Met
225                 230                 235                 240

Asp Ser Ala Ser Ala Arg Asp Trp Pro Lys Met His Thr Val Asn Gly
                245                 250                 255

Tyr Val Asn Arg Ser Leu Pro Gly Leu Ile Gly Cys His Arg Lys Ser
                260                 265                 270

Val Tyr Trp His Val Ile Gly Met Gly Thr Thr Pro Glu Ile His Ser
                275                 280                 285

Ile Phe Leu Glu Gly His Thr Phe Phe Val Arg Asn His Arg Gln Ala
                290                 295                 300

Ser Leu Glu Ile Ser Pro Ile Thr Phe Leu Thr Ala Gln Thr Leu Leu
305                 310                 315                 320

Ile Asp Leu Gly Gln Phe Leu Leu Phe Cys His Ile Ser Ser His Lys
                325                 330                 335

His Asp Gly Met Glu Ala Tyr Val Lys Val Asp Ser Cys Pro Glu Glu
                340                 345                 350

Ser Gln Trp Gln Lys Asn Asn Asn Glu Glu Met Glu Asp Tyr Asp Asp
                355                 360                 365

Asp Asp Leu Tyr Ser Glu Met Asp Met Phe Thr Leu Asp Tyr Asp Ser
                370                 375                 380

Ser Pro Phe Ile Gln Ile Arg Ser Val Ala Lys Lys Tyr Pro Lys Thr
385                 390                 395                 400

Trp Ile His Tyr Ile Ser Ala Glu Glu Glu Asp Trp Asp Tyr Ala Pro
                405                 410                 415

Ser Val Pro Thr Ser Asp Asn Gly Ser Tyr Lys Ser Gln Tyr Leu Ser
                420                 425                 430

Asn Gly Pro His Arg Ile Gly Arg Lys Tyr Lys Lys Val Arg Phe Ile
                435                 440                 445
```

Ala Tyr Thr Asp Glu Thr Phe Lys Thr Arg Glu Thr Ile Gln His Glu
        450                 455                 460

Ser Gly Leu Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Ser Pro Leu His Ala Arg Arg Leu Pro Arg
                500                 505                 510

Gly Ile Lys His Val Lys Asp Leu Pro Ile His Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Ile Asn Pro Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Met Met Ser Asp Lys Arg Asn Val
                580                 585                 590

Ile Leu Phe Ser Ile Phe Asp Glu Asn Gln Ser Trp Tyr Ile Thr Glu
            595                 600                 605

Asn Met Gln Arg Phe Leu Pro Asn Ala Ala Lys Thr Gln Pro Gln Asp
        610                 615                 620

Pro Gly Phe Gln Ala Ser Asn Ile Met His Ser Ile Asn Gly Tyr Val
625                 630                 635                 640

Phe Asp Ser Leu Glu Leu Thr Val Cys Leu His Glu Val Ala Tyr Trp
                645                 650                 655

His Ile Leu Ser Val Gly Ala Gln Thr Asp Phe Leu Ser Ile Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
        690                 695                 700

Gly Leu Trp Val Leu Gly Cys His Asn Ser Asp Phe Arg Lys Arg Gly
705                 710                 715                 720

Met Thr Ala Leu Leu Lys Val Ser Ser Cys Asp Lys Ser Thr Ser Asp
                725                 730                 735

Tyr Tyr Glu Glu Ile Tyr Glu Asp Ile Pro Thr Gln Leu Val Asn Glu
                740                 745                 750

Asn Asn Val Ile Asp Pro Arg Ser Phe Phe Gln Asn Thr Asn His Pro
            755                 760                 765

Asn Thr Arg Lys Lys Lys Phe Lys Asp Ser Thr Ile Pro Lys Asn Asp
770                 775                 780

Met Glu Lys Ile Glu Pro Gln Phe Glu Glu Ile Ala Glu Met Leu Lys
785                 790                 795                 800

Val Gln Ser Val Ser Val Ser Asp Met Leu Met Leu Leu Gly Gln Ser
                805                 810                 815

His Pro Thr Pro His Gly Leu Phe Leu Ser Asp Gly Gln Glu Ala Ile
            820                 825                 830

Tyr Glu Ala Ile His Asp Asp His Ser Pro Asn Ala Ile Asp Ser Asn
        835                 840                 845

Glu Gly Pro Ser Lys Val Thr Gln Leu Arg Pro Glu Ser His His Ser
        850                 855                 860

Glu Lys Ile Val Phe Thr Pro Gln Pro Gly Leu Gln Leu Arg Ser Asn
865                 870                 875                 880

```
Lys Ser Leu Glu Thr Thr Ile Glu Val Lys Trp Lys Lys Leu Gly Leu
            885                 890                 895
Gln Val Ser Ser Leu Pro Ser Asn Leu Met Thr Thr Ile Leu Ser
            900                 905                 910
Asp Asn Leu Lys Ala Thr Phe Glu Lys Thr Asp Ser Ser Gly Phe Pro
            915                 920                 925
Asp Met Pro Val His Ser Ser Lys Leu Ser Thr Thr Ala Phe Gly
            930                 935                 940
Lys Lys Ala Tyr Ser Leu Val Gly Ser His Val Pro Leu Asn Ala Ser
945                 950                 955                 960
Glu Glu Asn Ser Asp Ser Asn Ile Leu Asp Ser Thr Leu Met Tyr Ser
            965                 970                 975
Gln Glu Ser Leu Pro Arg Asp Asn Ile Leu Ser Ile Glu Asn Asp Arg
            980                 985                 990
Leu Leu Arg Glu Lys Arg Phe His Gly Ile Ala Leu Leu Thr Lys Asp
            995                 1000                1005
Asn Thr Leu Phe Lys Asp Asn Val Ser Leu Met Lys Thr Asn Lys Thr
            1010                1015                1020
Tyr Asn His Ser Thr Thr Asn Glu Lys Leu His Thr Glu Ser Pro Thr
1025                1030                1035                1040
Ser Ile Glu Asn Ser Thr Thr Asp Leu Gln Asp Ala Ile Leu Lys Val
            1045                1050                1055
Asn Ser Glu Ile Gln Glu Val Thr Ala Leu Ile His Asp Gly Thr Leu
            1060                1065                1070
Leu Gly Lys Asn Ser Thr Tyr Leu Arg Leu Asn His Met Leu Asn Arg
            1075                1080                1085
Thr Thr Ser Thr Lys Asn Lys Asp Ile Phe His Arg Lys Asp Glu Asp
            1090                1095                1100
Pro Ile Pro Gln Asp Glu Glu Asn Thr Ile Met Pro Phe Ser Lys Met
1105                1110                1115                1120
Leu Phe Leu Ser Glu Ser Ser Asn Trp Phe Lys Lys Thr Asn Gly Asn
            1125                1130                1135
Asn Ser Leu Asn Ser Glu Gln Glu His Ser Pro Lys Gln Leu Val Tyr
            1140                1145                1150
Leu Met Phe Lys Lys Tyr Val Lys Asn Gln Ser Phe Leu Ser Glu Lys
            1155                1160                1165
Asn Lys Val Thr Val Glu Gln Asp Gly Phe Thr Lys Asn Ile Gly Leu
            1170                1175                1180
Lys Asp Met Ala Phe Pro His Asn Met Ser Ile Phe Leu Thr Thr Leu
1185                1190                1195                1200
Ser Asn Val His Glu Asn Gly Arg His Asn Gln Glu Lys Asn Ile Gln
            1205                1210                1215
Glu Glu Ile Glu Lys Glu Ala Leu Ile Glu Glu Lys Val Val Leu Pro
            1220                1225                1230
Gln Val His Glu Ala Thr Gly Ser Lys Asn Phe Leu Lys Asp Ile Leu
            1235                1240                1245
Ile Leu Gly Thr Arg Gln Asn Ile Ser Leu Tyr Glu Val His Val Pro
            1250                1255                1260
Val Leu Gln Asn Ile Thr Ser Ile Asn Asn Ser Thr Asn Thr Val Gln
1265                1270                1275                1280
Ile His Met Glu His Phe Phe Lys Arg Arg Lys Asp Lys Glu Thr Asn
            1285                1290                1295
Ser Glu Gly Leu Val Asn Lys Thr Arg Glu Met Val Lys Asn Tyr Pro
```

-continued

```
              1300                1305                1310
Ser Gln Lys Asn Ile Thr Thr Gln Arg Ser Lys Arg Ala Leu Gly Gln
            1315                1320                1325

Phe Arg Leu Ser Thr Gln Trp Leu Lys Thr Ile Asn Cys Ser Thr Gln
        1330                1335                1340

Cys Ile Ile Lys Gln Ile Asp His Ser Lys Glu Met Lys Lys Phe Ile
1345                1350                1355                1360

Thr Lys Ser Ser Leu Ser Asp Ser Val Ile Lys Ser Thr Thr Gln
            1365                1370                1375

Thr Asn Ser Ser Asp Ser His Ile Val Lys Thr Ser Ala Phe Pro Pro
        1380                1385                1390

Ile Asp Leu Lys Arg Ser Pro Phe Gln Asn Lys Phe Ser His Val Gln
            1395                1400                1405

Ala Ser Ser Tyr Ile Tyr Asp Phe Lys Thr Lys Ser Ser Arg Ile Gln
        1410                1415                1420

Glu Ser Asn Asn Phe Leu Lys Glu Thr Lys Ile Asn Asn Pro Ser Leu
1425                1430                1435                1440

Ala Ile Leu Pro Trp Asn Met Phe Ile Asp Gln Gly Lys Phe Thr Ser
            1445                1450                1455

Pro Gly Lys Ser Asn Thr Asn Ser Val Thr Tyr Lys Lys Arg Glu Asn
        1460                1465                1470

Ile Ile Phe Leu Lys Pro Thr Leu Pro Glu Glu Ser Gly Lys Ile Glu
            1475                1480                1485

Leu Leu Pro Gln Val Ser Ile Gln Glu Glu Ile Leu Pro Thr Glu
        1490                1495                1500

Thr Ser His Gly Ser Pro Gly His Leu Asn Leu Met Lys Glu Val Phe
1505                1510                1515                1520

Leu Gln Lys Ile Gln Gly Pro Thr Lys Trp Asn Lys Ala Lys Arg His
            1525                1530                1535

Gly Glu Ser Ile Lys Gly Lys Thr Glu Ser Ser Lys Asn Thr Arg Ser
        1540                1545                1550

Lys Leu Leu Asn His His Ala Trp Asp Tyr His Tyr Ala Ala Gln Ile
            1555                1560                1565

Pro Lys Asp Met Trp Lys Ser Lys Glu Lys Ser Pro Glu Ile Ile Ser
        1570                1575                1580

Ile Lys Gln Glu Asp Thr Ile Leu Ser Leu Arg Pro His Gly Asn Ser
1585                1590                1595                1600

His Ser Ile Gly Ala Asn Glu Lys Gln Asn Trp Pro Gln Arg Glu Thr
            1605                1610                1615

Thr Trp Val Lys Gln Gly Gln Thr Gln Arg Thr Cys Ser Gln Ile Pro
        1620                1625                1630

Pro Val Leu Lys Arg His Gln Arg Glu Leu Ser Ala Phe Gln Ser Glu
            1635                1640                1645

Gln Glu Ala Thr Asp Tyr Asp Asp Ala Ile Thr Ile Glu Thr Ile Glu
        1650                1655                1660

Asp Phe Asp Ile Tyr Ser Glu Asp Ile Lys Gln Gly Pro Arg Ser Phe
1665                1670                1675                1680

Gln Gln Lys Thr Arg His Tyr Phe Ile Ala Ala Val Glu Arg Leu Trp
            1685                1690                1695

Asp Tyr Gly Met Ser Thr Ser His Val Leu Arg Asn Arg Tyr Gln Ser
        1700                1705                1710

Asp Asn Val Pro Gln Phe Lys Lys Val Val Phe Gln Glu Phe Thr Asp
            1715                1720                1725
```

```
Gly Ser Phe Ser Gln Pro Leu Tyr Arg Gly Glu Leu Asn Glu His Leu
        1730                1735                1740

Gly Leu Leu Gly Pro Tyr Ile Arg Ala Glu Val Glu Asp Asn Ile Met
1745                1750                1755                1760

Val Thr Phe Lys Asn Gln Ala Ser Arg Pro Tyr Ser Phe Tyr Ser Ser
                1765                1770                1775

Leu Ile Ser Tyr Lys Glu Asp Gln Arg Gly Glu Glu Pro Arg Arg Asn
                1780                1785                1790

Phe Val Lys Pro Asn Glu Thr Lys Ile Tyr Phe Trp Lys Val Gln His
                1795                1800                1805

His Met Ala Pro Thr Glu Asp Glu Phe Asp Cys Lys Ala Trp Ala Tyr
        1810                1815                1820

Phe Ser Asp Val Asp Leu Glu Arg Asp Met His Ser Gly Leu Ile Gly
1825                1830                1835                1840

Pro Leu Leu Ile Cys His Ala Asn Thr Leu Asn Pro Ala His Gly Arg
                1845                1850                1855

Gln Val Ser Val Gln Glu Phe Ala Leu Leu Phe Thr Ile Phe Asp Glu
                1860                1865                1870

Thr Lys Ser Trp Tyr Phe Thr Glu Asn Val Lys Arg Asn Cys Lys Thr
                1875                1880                1885

Pro Cys Asn Phe Gln Met Glu Asp Pro Thr Leu Lys Glu Asn Tyr Arg
        1890                1895                1900

Phe His Ala Ile Asn Gly Tyr Val Met Asp Thr Leu Pro Gly Leu Val
1905                1910                1915                1920

Met Ala Gln Asp Gln Arg Ile Arg Trp Tyr Leu Leu Ser Met Gly Asn
                1925                1930                1935

Asn Glu Asn Ile Gln Ser Ile His Phe Ser Gly His Val Phe Thr Val
                1940                1945                1950

Arg Lys Lys Glu Glu Tyr Lys Met Ala Val Tyr Asn Leu Tyr Pro Gly
                1955                1960                1965

Val Phe Glu Thr Leu Glu Met Ile Pro Ser Arg Ala Gly Ile Trp Arg
        1970                1975                1980

Val Glu Cys Leu Ile Gly Glu His Leu Gln Ala Gly Met Ser Thr Leu
1985                1990                1995                2000

Phe Leu Val Tyr Ser Lys Gln Cys Gln Ile Pro Leu Gly Met Ala Ser
                2005                2010                2015

Gly Ser Ile Arg Asp Phe Gln Ile Thr Ala Ser Gly His Tyr Gly Gln
                2020                2025                2030

Trp Ala Pro Asn Leu Ala Arg Leu His Tyr Ser Gly Ser Ile Asn Ala
                2035                2040                2045

Trp Ser Thr Lys Glu Pro Phe Ser Trp Ile Lys Val Asp Leu Leu Ala
                2050                2055                2060

Pro Met Ile Val His Gly Ile Lys Thr Gln Gly Ala Arg Gln Lys Phe
2065                2070                2075                2080

Ser Ser Leu Tyr Ile Ser Gln Phe Ile Ile Met Tyr Ser Leu Asp Gly
                2085                2090                2095

Lys Lys Trp Leu Ser Tyr Gln Gly Asn Ser Thr Gly Thr Leu Met Val
                2100                2105                2110

Phe Phe Gly Asn Val Asp Ser Ser Gly Ile Lys His Asn Ser Phe Asn
                2115                2120                2125

Pro Pro Ile Ile Ala Arg Tyr Ile Arg Leu His Pro Thr His Ser Ser
        2130                2135                2140

Ile Arg Ser Thr Leu Arg Met Glu Leu Met Gly Cys Asp Leu Asn Ser
2145                2150                2155                2160
```

-continued

Cys Ser Ile Pro Leu Gly Met Glu Ser Lys Val Ile Ser Asp Thr Gln
            2165                2170                2175

Ile Thr Ala Ser Ser Tyr Phe Thr Asn Met Phe Ala Thr Trp Ser Pro
            2180                2185                2190

Ser Gln Ala Arg Leu His Leu Gln Gly Arg Thr Asn Ala Trp Arg Pro
            2195                2200                2205

Gln Val Asn Asp Pro Lys Gln Trp Leu Gln Val Asp Leu Gln Lys Thr
            2210                2215                2220

Met Lys Val Thr Gly Ile Ile Thr Gln Gly Val Lys Ser Leu Phe Thr
2225                2230                2235                2240

Ser Met Phe Val Lys Glu Phe Leu Ile Ser Ser Ser Gln Asp Gly His
            2245                2250                2255

His Trp Thr Gln Ile Leu Tyr Asn Gly Lys Val Lys Val Phe Gln Gly
            2260                2265                2270

Asn Gln Asp Ser Ser Thr Pro Met Met Asn Ser Leu Asp Pro Pro Leu
            2275                2280                2285

Leu Thr Arg Tyr Leu Arg Ile His Pro Gln Ile Trp Glu His Gln Ile
            2290                2295                2300

Ala Leu Arg Leu Glu Ile Leu Gly Cys Glu Ala Gln Gln Gln Tyr
2305                2310                2315

```
<210> SEQ ID NO 9
<211> LENGTH: 14
<212> TYPE: PRT
<213> ORGANISM: Homo sapeins
<220> FEATURE:
<221> NAME/KEY: DOMAIN
<222> LOCATION: (1)...(14)
<223> OTHER INFORMATION: Linker sequence

<400> SEQUENCE: 9
```

Ser Phe Ser Gln Asn Pro Pro Val Leu Lys Arg His Gln Arg
1               5                   10

```
<210> SEQ ID NO 10
<211> LENGTH: 4
<212> TYPE: PRT
<213> ORGANISM: Homo sapiens

<400> SEQUENCE: 10
```

Arg His Gln Arg
1

```
<210> SEQ ID NO 11
<211> LENGTH: 24
<212> TYPE: PRT
<213> ORGANISM: Sus Scrofa
<220> FEATURE:
<221> NAME/KEY: DOMAIN
<222> LOCATION: (1)...(24)
<223> OTHER INFORMATION: Linker sequence

<400> SEQUENCE: 11
```

Ser Phe Ala Gln Asn Ser Arg Pro Pro Ser Ala Ser Ala Pro Lys Pro
1               5                   10                  15

Pro Val Leu Arg Arg His Gln Arg
            20

```
<210> SEQ ID NO 12
<211> LENGTH: 4371
<212> TYPE: DNA
<213> ORGANISM: Homo sapiens
```

```
<220> FEATURE:
<221> NAME/KEY: CDS
<222> LOCATION: (1)...(4371)
<223> OTHER INFORMATION: B domain-deleted factor VIII
      (HSQ)

<400> SEQUENCE: 12 atg caa ata gag ctc tcc acc tgc ttc ttt ctg tgc ctt ttg cga ttc        48
Met Gln Ile Glu Leu Ser Thr Cys Phe Phe Leu Cys Leu Leu Arg Phe
1               5                   10                  15 tgc ttt agt gcc acc aga aga tac tac ctg ggt gca gtg gaa ctg tca        96
Cys Phe Ser Ala Thr Arg Arg Tyr Tyr Leu Gly Ala Val Glu Leu Ser
            20                  25                  30 tgg gac tat atg caa agt gat ctc ggt gag ctg cct gtg gac gca aga       144
Trp Asp Tyr Met Gln Ser Asp Leu Gly Glu Leu Pro Val Asp Ala Arg
        35                  40                  45 ttt cct cct aga gtg cca aaa tct ttt cca ttc aac acc tca gtc gtg       192
Phe Pro Pro Arg Val Pro Lys Ser Phe Pro Phe Asn Thr Ser Val Val
    50                  55                  60 tac aaa aag act ctg ttt gta gaa ttc acg gtt cac ctt ttc aac atc       240
Tyr Lys Lys Thr Leu Phe Val Glu Phe Thr Val His Leu Phe Asn Ile
65                  70                  75                  80 gct aag cca agg cca ccc tgg atg ggt ctg cta ggt cct acc atc cag       288
Ala Lys Pro Arg Pro Pro Trp Met Gly Leu Leu Gly Pro Thr Ile Gln
                85                  90                  95 gct gag gtt tat gat aca gtg gtc att aca ctt aag aac atg gct tcc       336
Ala Glu Val Tyr Asp Thr Val Val Ile Thr Leu Lys Asn Met Ala Ser
            100                 105                 110 cat cct gtc agt ctt cat gct gtt ggt gta tcc tac tgg aaa gct tct       384
His Pro Val Ser Leu His Ala Val Gly Val Ser Tyr Trp Lys Ala Ser
        115                 120                 125 gag gga gct gaa tat gat gat cag acc agt caa agg gag aaa gaa gat       432
Glu Gly Ala Glu Tyr Asp Asp Gln Thr Ser Gln Arg Glu Lys Glu Asp
    130                 135                 140 gat aaa gtc ttc cct ggt gga agc cat aca tat gtc tgg cag gtc ctg       480
Asp Lys Val Phe Pro Gly Gly Ser His Thr Tyr Val Trp Gln Val Leu
145                 150                 155                 160 aaa gag aat ggt cca atg gcc tct gac cca ctg tgc ctt acc tac tca       528
Lys Glu Asn Gly Pro Met Ala Ser Asp Pro Leu Cys Leu Thr Tyr Ser
                165                 170                 175 tat ctt tct cat gtg gac ctg gta aaa gac ttg aat tca ggc ctc att       576
Tyr Leu Ser His Val Asp Leu Val Lys Asp Leu Asn Ser Gly Leu Ile
            180                 185                 190 gga gcc cta cta gta tgt aga gaa ggg agt ctg gcc aag gaa aag aca       624
Gly Ala Leu Leu Val Cys Arg Glu Gly Ser Leu Ala Lys Glu Lys Thr
        195                 200                 205 cag acc ttg cac aaa ttt ata cta ctt ttt gct gta ttt gat gaa ggg       672
Gln Thr Leu His Lys Phe Ile Leu Leu Phe Ala Val Phe Asp Glu Gly
    210                 215                 220 aaa agt tgg cac tca gaa aca aag aac tcc ttg atg cag gat agg gat       720
Lys Ser Trp His Ser Glu Thr Lys Asn Ser Leu Met Gln Asp Arg Asp
225                 230                 235                 240 gct gca tct gct cgg gcc tgg cct aaa atg cac aca gtc aat ggt tat       768
Ala Ala Ser Ala Arg Ala Trp Pro Lys Met His Thr Val Asn Gly Tyr
                245                 250                 255 gta aac agg tct ctg cca ggt ctg att gga tgc cac agg aaa tca gtc       816
Val Asn Arg Ser Leu Pro Gly Leu Ile Gly Cys His Arg Lys Ser Val
            260                 265                 270 tat tgg cat gtg att gga atg ggc acc act cct gaa gtg cac tca ata       864
Tyr Trp His Val Ile Gly Met Gly Thr Thr Pro Glu Val His Ser Ile
        275                 280                 285
```

| | | |
|---|---|---|
| ttc ctc gaa ggt cac aca ttt ctt gtg agg aac cat cgc cag gcg tcc<br>Phe Leu Glu Gly His Thr Phe Leu Val Arg Asn His Arg Gln Ala Ser<br>290                            295                         300 | | 912 |
| ttg gaa atc tcg cca ata act ttc ctt act gct caa aca ctc ttg atg<br>Leu Glu Ile Ser Pro Ile Thr Phe Leu Thr Ala Gln Thr Leu Leu Met<br>305                            310                         315                    320 | | 960 |
| gac ctt gga cag ttt cta ctg ttt tgt cat atc tct tcc cac caa cat<br>Asp Leu Gly Gln Phe Leu Leu Phe Cys His Ile Ser Ser His Gln His<br>                      325                         330                    335 | | 1008 |
| gat ggc atg gaa gct tat gtc aaa gta gac agc tgt cca gag gaa ccc<br>Asp Gly Met Glu Ala Tyr Val Lys Val Asp Ser Cys Pro Glu Glu Pro<br>           340                        345                         350 | | 1056 |
| caa cta cga atg aaa aat aat gaa gaa gcg gaa gac tat gat gat gat<br>Gln Leu Arg Met Lys Asn Asn Glu Glu Ala Glu Asp Tyr Asp Asp Asp<br>                 355                         360                    365 | | 1104 |
| ctt act gat tct gaa atg gat gtg gtc agg ttt gat gat gac aac tct<br>Leu Thr Asp Ser Glu Met Asp Val Val Arg Phe Asp Asp Asp Asn Ser<br>370                            375                         380 | | 1152 |
| cct tcc ttt atc caa att cgc tca gtt gcc aag aag cat cct aaa act<br>Pro Ser Phe Ile Gln Ile Arg Ser Val Ala Lys Lys His Pro Lys Thr<br>385                            390                         395                    400 | | 1200 |
| tgg gta cat tac att gct gct gaa gag gag gac tgg gac tat gct ccc<br>Trp Val His Tyr Ile Ala Ala Glu Glu Glu Asp Trp Asp Tyr Ala Pro<br>                                  405                         410                    415 | | 1248 |
| tta gtc ctc gcc ccc gat gac aga agt tat aaa agt caa tat ttg aac<br>Leu Val Leu Ala Pro Asp Asp Arg Ser Tyr Lys Ser Gln Tyr Leu Asn<br>           420                        425                         430 | | 1296 |
| aat ggc cct cag cgg att ggt agg aag tac aaa aaa gtc cga ttt atg<br>Asn Gly Pro Gln Arg Ile Gly Arg Lys Tyr Lys Lys Val Arg Phe Met<br>                 435                         440                    445 | | 1344 |
| gca tac aca gat gaa acc ttt aag acg cgt gaa gct att cag cat gaa<br>Ala Tyr Thr Asp Glu Thr Phe Lys Thr Arg Glu Ala Ile Gln His Glu<br>450                            455                         460 | | 1392 |
| tca gga atc ttg gga cct tta ctt tat ggg gaa gtt gga gac aca ctg<br>Ser Gly Ile Leu Gly Pro Leu Leu Tyr Gly Glu Val Gly Asp Thr Leu<br>465                            470                         475                    480 | | 1440 |
| ttg att ata ttt aag aat caa gca agc aga cca tat aac atc tac cct<br>Leu Ile Ile Phe Lys Asn Gln Ala Ser Arg Pro Tyr Asn Ile Tyr Pro<br>                                  485                         490                    495 | | 1488 |
| cac gga atc act gat gtc cgt cct ttg tat tca agg aga tta cca aaa<br>His Gly Ile Thr Asp Val Arg Pro Leu Tyr Ser Arg Arg Leu Pro Lys<br>                 500                         505                    510 | | 1536 |
| ggt gta aaa cat ttg aag gat ttt cca att ctg cca gga gaa ata ttc<br>Gly Val Lys His Leu Lys Asp Phe Pro Ile Leu Pro Gly Glu Ile Phe<br>                      515                         520                    525 | | 1584 |
| aaa tat aaa tgg aca gtg act gta gaa gat ggg cca act aaa tca gat<br>Lys Tyr Lys Trp Thr Val Thr Val Glu Asp Gly Pro Thr Lys Ser Asp<br>530                            535                         540 | | 1632 |
| ccg cgg tgc ctg acc cgc tat tac tct agt ttc gtt aat atg gag aga<br>Pro Arg Cys Leu Thr Arg Tyr Tyr Ser Ser Phe Val Asn Met Glu Arg<br>545                            550                         555                    560 | | 1680 |
| gat cta gct tca gga ctc att ggc cct ctc ctc atc tgc tac aaa gaa<br>Asp Leu Ala Ser Gly Leu Ile Gly Pro Leu Leu Ile Cys Tyr Lys Glu<br>                                 565                         570                    575 | | 1728 |
| tct gta gat caa aga gga aac cag ata atg tca gac aag agg aat gtc<br>Ser Val Asp Gln Arg Gly Asn Gln Ile Met Ser Asp Lys Arg Asn Val<br>                 580                         585                    590 | | 1776 |
| atc ctg ttt tct gta ttt gat gag aac cga agc tgg tac ctc aca gag<br>Ile Leu Phe Ser Val Phe Asp Glu Asn Arg Ser Trp Tyr Leu Thr Glu<br>                      595                         600                    605 | | 1824 |

```
aat ata caa cgc ttt ctc ccc aat cca gct gga gtg cag ctt gag gat    1872
Asn Ile Gln Arg Phe Leu Pro Asn Pro Ala Gly Val Gln Leu Glu Asp
    610             615                 620 cca gag ttc caa gcc tcc aac atc atg cac agc atc aat ggc tat gtt    1920
Pro Glu Phe Gln Ala Ser Asn Ile Met His Ser Ile Asn Gly Tyr Val
625             630                 635                 640 ttt gat agt ttg cag ttg tca gtt tgt ttg cat gag gtg gca tac tgg    1968
Phe Asp Ser Leu Gln Leu Ser Val Cys Leu His Glu Val Ala Tyr Trp
                645                 650                 655 tac att cta agc att gga gca cag act gac ttc ctt tct gtc ttc ttc    2016
Tyr Ile Leu Ser Ile Gly Ala Gln Thr Asp Phe Leu Ser Val Phe Phe
            660                 665                 670 tct gga tat acc ttc aaa cac aaa atg gtc tat gaa gac aca ctc acc    2064
Ser Gly Tyr Thr Phe Lys His Lys Met Val Tyr Glu Asp Thr Leu Thr
        675                 680                 685 cta ttc cca ttc tca gga gaa act gtc ttc atg tcg atg gaa aac cca    2112
Leu Phe Pro Phe Ser Gly Glu Thr Val Phe Met Ser Met Glu Asn Pro
    690                 695                 700 ggt cta tgg att ctg ggg tgc cac aac tca gac ttt cgg aac aga ggc    2160
Gly Leu Trp Ile Leu Gly Cys His Asn Ser Asp Phe Arg Asn Arg Gly
705             710                 715                 720 atg acc gcc tta ctg aag gtt tct agt tgt gac aag aac act ggt gat    2208
Met Thr Ala Leu Leu Lys Val Ser Ser Cys Asp Lys Asn Thr Gly Asp
                725                 730                 735 tat tac gag gac agt tat gaa gat att tca gca tac ttg ctg agt aaa    2256
Tyr Tyr Glu Asp Ser Tyr Glu Asp Ile Ser Ala Tyr Leu Leu Ser Lys
            740                 745                 750 aac aat gcc att gaa cct agg agc ttc tct cag aat cca cca gtc ttg    2304
Asn Asn Ala Ile Glu Pro Arg Ser Phe Ser Gln Asn Pro Pro Val Leu
        755                 760                 765 aaa cgc cat caa cgg gaa ata act cgt act act ctt cag tca gat caa    2352
Lys Arg His Gln Arg Glu Ile Thr Arg Thr Thr Leu Gln Ser Asp Gln
    770                 775                 780 gag gaa att gac tat gat gat acc ata tca gtt gaa atg aag aag gaa    2400
Glu Glu Ile Asp Tyr Asp Asp Thr Ile Ser Val Glu Met Lys Lys Glu
785             790                 795                 800 gat ttt gac att tat gat gag gat gaa aat cag agc ccc cgc agc ttt    2448
Asp Phe Asp Ile Tyr Asp Glu Asp Glu Asn Gln Ser Pro Arg Ser Phe
                805                 810                 815 caa aag aaa aca cga cac tat ttt att gct gca gtg gag agg ctc tgg    2496
Gln Lys Lys Thr Arg His Tyr Phe Ile Ala Ala Val Glu Arg Leu Trp
            820                 825                 830 gat tat ggg atg agt agc tcc cca cat gtt cta aga aac agg gct cag    2544
Asp Tyr Gly Met Ser Ser Ser Pro His Val Leu Arg Asn Arg Ala Gln
        835                 840                 845 agt ggc agt gtc cct cag ttc aag aaa gtt gtt ttc cag gaa ttt act    2592
Ser Gly Ser Val Pro Gln Phe Lys Lys Val Val Phe Gln Glu Phe Thr
    850                 855                 860 gat ggc tcc ttt act cag ccc tta tac cgt gga gaa cta aat gaa cat    2640
Asp Gly Ser Phe Thr Gln Pro Leu Tyr Arg Gly Glu Leu Asn Glu His
865             870                 875                 880 ttg gga ctc ctg ggg cca tat ata aga gca gaa gtt gaa gat aat atc    2688
Leu Gly Leu Leu Gly Pro Tyr Ile Arg Ala Glu Val Glu Asp Asn Ile
                885                 890                 895 atg gta act ttc aga aat cag gcc tct cgt ccc tat tcc ttc tat tct    2736
Met Val Thr Phe Arg Asn Gln Ala Ser Arg Pro Tyr Ser Phe Tyr Ser
            900                 905                 910 agc ctt att tct tat gag gaa gat cag agg caa gga gca gaa cct aga    2784
Ser Leu Ile Ser Tyr Glu Glu Asp Gln Arg Gln Gly Ala Glu Pro Arg
        915                 920                 925
```

```
aaa aac ttt gtc aag cct aat gaa acc aaa act tac ttt tgg aaa gtg    2832
Lys Asn Phe Val Lys Pro Asn Glu Thr Lys Thr Tyr Phe Trp Lys Val
930                 935                 940 caa cat cat atg gca ccc act aaa gat gag ttt gac tgc aaa gcc tgg    2880
Gln His His Met Ala Pro Thr Lys Asp Glu Phe Asp Cys Lys Ala Trp
945                 950                 955                 960 gct tat ttc tct gat gtt gac ctg gaa aaa gat gtg cac tca ggc ctg    2928
Ala Tyr Phe Ser Asp Val Asp Leu Glu Lys Asp Val His Ser Gly Leu
                965                 970                 975 att gga ccc ctt ctg gtc tgc cac act aac aca ctg aac cct gct cat    2976
Ile Gly Pro Leu Leu Val Cys His Thr Asn Thr Leu Asn Pro Ala His
            980                 985                 990 ggg aga caa gtg aca gta cag gaa ttt gct ctg ttt ttc acc atc ttt    3024
Gly Arg Gln Val Thr Val Gln Glu Phe Ala Leu Phe Phe Thr Ile Phe
        995                 1000                1005 gat gag acc aaa agc tgg tac ttc act gaa aat atg gaa aga aac tgc    3072
Asp Glu Thr Lys Ser Trp Tyr Phe Thr Glu Asn Met Glu Arg Asn Cys
    1010                1015                1020 agg gct ccc tgc aat atc cag atg gaa gat ccc act ttt aaa gag aat    3120
Arg Ala Pro Cys Asn Ile Gln Met Glu Asp Pro Thr Phe Lys Glu Asn
1025                1030                1035                1040 tat cgc ttc cat gca atc aat ggc tac ata atg gat aca cta cct ggc    3168
Tyr Arg Phe His Ala Ile Asn Gly Tyr Ile Met Asp Thr Leu Pro Gly
                1045                1050                1055 tta gta atg gct cag gat caa agg att cga tgg tat ctg ctc agc atg    3216
Leu Val Met Ala Gln Asp Gln Arg Ile Arg Trp Tyr Leu Leu Ser Met
            1060                1065                1070 ggc agc aat gaa aac atc cat tct att cat ttc agt gga cat gtg ttc    3264
Gly Ser Asn Glu Asn Ile His Ser Ile His Phe Ser Gly His Val Phe
        1075                1080                1085 act gta cga aaa aaa gag gag tat aaa atg gca ctg tac aat ctc tat    3312
Thr Val Arg Lys Lys Glu Glu Tyr Lys Met Ala Leu Tyr Asn Leu Tyr
    1090                1095                1100 cca ggt gtt ttt gag aca gtg gaa atg tta cca tcc aaa gct gga att    3360
Pro Gly Val Phe Glu Thr Val Glu Met Leu Pro Ser Lys Ala Gly Ile
1105                1110                1115                1120 tgg cgg gtg gaa tgc ctt att ggc gag cat cta cat gct ggg atg agc    3408
Trp Arg Val Glu Cys Leu Ile Gly Glu His Leu His Ala Gly Met Ser
                1125                1130                1135 aca ctt ttt ctg gtg tac agc aat aag tgt cag act ccc ctg gga atg    3456
Thr Leu Phe Leu Val Tyr Ser Asn Lys Cys Gln Thr Pro Leu Gly Met
            1140                1145                1150 gct tct gga cac att aga gat ttt cag att aca gct tca gga caa tat    3504
Ala Ser Gly His Ile Arg Asp Phe Gln Ile Thr Ala Ser Gly Gln Tyr
        1155                1160                1165 gga cag tgg gcc cca aag ctg gcc aga ctt cat tat tcc gga tca atc    3552
Gly Gln Trp Ala Pro Lys Leu Ala Arg Leu His Tyr Ser Gly Ser Ile
    1170                1175                1180 aat gcc tgg agc acc aag gag ccc ttt tct tgg atc aag gtg gat ctg    3600
Asn Ala Trp Ser Thr Lys Glu Pro Phe Ser Trp Ile Lys Val Asp Leu
1185                1190                1195                1200 ttg gca cca atg att att cac ggc atc aag acc cag ggt gcc cgt cag    3648
Leu Ala Pro Met Ile Ile His Gly Ile Lys Thr Gln Gly Ala Arg Gln
                1205                1210                1215 aag ttc tcc agc ctc tac atc tct cag ttt atc atc atg tat agt ctt    3696
Lys Phe Ser Ser Leu Tyr Ile Ser Gln Phe Ile Ile Met Tyr Ser Leu
            1220                1225                1230 gat ggg aag aag tgg cag act tat cga gga aat tcc act gga acc tta    3744
Asp Gly Lys Lys Trp Gln Thr Tyr Arg Gly Asn Ser Thr Gly Thr Leu
        1235                1240                1245
```

```
atg gtc ttc ttt ggc aat gtg gat tca tct ggg ata aaa cac aat att    3792
Met Val Phe Phe Gly Asn Val Asp Ser Ser Gly Ile Lys His Asn Ile
    1250                1255                1260 ttt aac cct cca att att gct cga tac atc cgt ttg cac cca act cat    3840
Phe Asn Pro Pro Ile Ile Ala Arg Tyr Ile Arg Leu His Pro Thr His
1265                1270                1275                1280 tat agc att cgc agc act ctt cgc atg gag ttg atg ggc tgt gat tta    3888
Tyr Ser Ile Arg Ser Thr Leu Arg Met Glu Leu Met Gly Cys Asp Leu
                1285                1290                1295 aat agt tgc agc atg cca ttg gga atg gag agt aaa gca ata tca gat    3936
Asn Ser Cys Ser Met Pro Leu Gly Met Glu Ser Lys Ala Ile Ser Asp
            1300                1305                1310 gca cag att act gct tca tcc tac ttt acc aat atg ttt gcc acc tgg    3984
Ala Gln Ile Thr Ala Ser Ser Tyr Phe Thr Asn Met Phe Ala Thr Trp
        1315                1320                1325 tct cct tca aaa gct cga ctt cac ctc caa ggg agg agt aat gcc tgg    4032
Ser Pro Ser Lys Ala Arg Leu His Leu Gln Gly Arg Ser Asn Ala Trp
    1330                1335                1340 aga cct cag gtg aat aat cca aaa gag tgg ctg caa gtg gac ttc cag    4080
Arg Pro Gln Val Asn Asn Pro Lys Glu Trp Leu Gln Val Asp Phe Gln
1345                1350                1355                1360 aag aca atg aaa gtc aca gga gta act act cag gga gta aaa tct ctg    4128
Lys Thr Met Lys Val Thr Gly Val Thr Thr Gln Gly Val Lys Ser Leu
                1365                1370                1375 ctt acc agc atg tat gtg aag gag ttc ctc atc tcc agc agt caa gat    4176
Leu Thr Ser Met Tyr Val Lys Glu Phe Leu Ile Ser Ser Ser Gln Asp
            1380                1385                1390 ggc cat cag tgg act ctc ttt ttt cag aat ggc aaa gta aag gtt ttt    4224
Gly His Gln Trp Thr Leu Phe Phe Gln Asn Gly Lys Val Lys Val Phe
        1395                1400                1405 cag gga aat caa gac tcc ttc aca cct gtg gtg aac tct cta gac cca    4272
Gln Gly Asn Gln Asp Ser Phe Thr Pro Val Val Asn Ser Leu Asp Pro
    1410                1415                1420 ccg tta ctg act cgc tac ctt cga att cac ccc cag agt tgg gtg cac    4320
Pro Leu Leu Thr Arg Tyr Leu Arg Ile His Pro Gln Ser Trp Val His
1425                1430                1435                1440 cag att gcc ctg agg atg gag gtt ctg ggc tgc gag gca cag gac ctc    4368
Gln Ile Ala Leu Arg Met Glu Val Leu Gly Cys Glu Ala Gln Asp Leu
                1445                1450                1455 tac                                                                4371
Tyr

<210> SEQ ID NO 13
<211> LENGTH: 1457
<212> TYPE: PRT
<213> ORGANISM: Homo sapiens

<400> SEQUENCE: 13

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Asn Thr Ser Val Val
        50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
                85                  90                  95
```

```
Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
            130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
            165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
            210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
            245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
            290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
            325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
            405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
```

```
                515                 520                 525
Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
            565                 570                 575

Ser Val Asp Gln Arg Gly Asn Gln Ile Met Ser Asp Lys Arg Asn Val
        580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
        690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
        740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
            805                 810                 815

Gln Lys Lys Thr Arg His Tyr Phe Ile Ala Ala Val Glu Arg Leu Trp
        820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
        850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
            885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
        930                 935                 940
```

-continued

```
Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
        995                 1000                1005

Asp Glu Thr Lys Ser Trp Tyr Phe Thr Glu Asn Met Glu Arg Asn Cys
    1010                1015                1020

Arg Ala Pro Cys Asn Ile Gln Met Glu Asp Pro Thr Phe Lys Glu Asn
1025                1030                1035                1040

Tyr Arg Phe His Ala Ile Asn Gly Tyr Ile Met Asp Thr Leu Pro Gly
                1045                1050                1055

Leu Val Met Ala Gln Asp Gln Arg Ile Arg Trp Tyr Leu Leu Ser Met
            1060                1065                1070

Gly Ser Asn Glu Asn Ile His Ser Ile His Phe Ser Gly His Val Phe
        1075                1080                1085

Thr Val Arg Lys Lys Glu Glu Tyr Lys Met Ala Leu Tyr Asn Leu Tyr
    1090                1095                1100

Pro Gly Val Phe Glu Thr Val Glu Met Leu Pro Ser Lys Ala Gly Ile
1105                1110                1115                1120

Trp Arg Val Glu Cys Leu Ile Gly Glu His Leu His Ala Gly Met Ser
                1125                1130                1135

Thr Leu Phe Leu Val Tyr Ser Asn Lys Cys Gln Thr Pro Leu Gly Met
            1140                1145                1150

Ala Ser Gly His Ile Arg Asp Phe Gln Ile Thr Ala Ser Gly Gln Tyr
        1155                1160                1165

Gly Gln Trp Ala Pro Lys Leu Ala Arg Leu His Tyr Ser Gly Ser Ile
    1170                1175                1180

Asn Ala Trp Ser Thr Lys Glu Pro Phe Ser Trp Ile Lys Val Asp Leu
1185                1190                1195                1200

Leu Ala Pro Met Ile Ile His Gly Ile Lys Thr Gln Gly Ala Arg Gln
                1205                1210                1215

Lys Phe Ser Ser Leu Tyr Ile Ser Gln Phe Ile Ile Met Tyr Ser Leu
            1220                1225                1230

Asp Gly Lys Lys Trp Gln Thr Tyr Arg Gly Asn Ser Thr Gly Thr Leu
        1235                1240                1245

Met Val Phe Phe Gly Asn Val Asp Ser Ser Gly Ile Lys His Asn Ile
    1250                1255                1260

Phe Asn Pro Pro Ile Ile Ala Arg Tyr Ile Arg Leu His Pro Thr His
1265                1270                1275                1280

Tyr Ser Ile Arg Ser Thr Leu Arg Met Glu Leu Met Gly Cys Asp Leu
                1285                1290                1295

Asn Ser Cys Ser Met Pro Leu Gly Met Glu Ser Lys Ala Ile Ser Asp
            1300                1305                1310

Ala Gln Ile Thr Ala Ser Ser Tyr Phe Thr Asn Met Phe Ala Thr Trp
        1315                1320                1325

Ser Pro Ser Lys Ala Arg Leu His Leu Gln Gly Arg Ser Asn Ala Trp
    1330                1335                1340

Arg Pro Gln Val Asn Asn Pro Lys Glu Trp Leu Gln Val Asp Phe Gln
1345                1350                1355                1360

Lys Thr Met Lys Val Thr Gly Val Thr Thr Gln Gly Val Lys Ser Leu
                1365                1370                1375
```

```
Leu Thr Ser Met Tyr Val Lys Glu Phe Leu Ile Ser Ser Ser Gln Asp
            1380                1385                1390
Gly His Gln Trp Thr Leu Phe Phe Gln Asn Gly Lys Val Lys Val Phe
        1395                1400                1405
Gln Gly Asn Gln Asp Ser Phe Thr Pro Val Val Asn Ser Leu Asp Pro
    1410                1415                1420
Pro Leu Leu Thr Arg Tyr Leu Arg Ile His Pro Gln Ser Trp Val His
1425                1430                1435                1440
Gln Ile Ala Leu Arg Met Glu Val Leu Gly Cys Glu Ala Gln Asp Leu
                1445                1450                1455
Tyr

<210> SEQ ID NO 14
<211> LENGTH: 4401
<212> TYPE: DNA
<213> ORGANISM: Artificial Sequence
<220> FEATURE:
<223> OTHER INFORMATION: hybrid human and porcine factor VIII sequence
<221> NAME/KEY: CDS
<222> LOCATION: (1)...(4401)
<223> OTHER INFORMATION: HP44/OL-- factor VIII having the following
      domains: A1p-A2p-app-A3p-C1h-C2h

<400> SEQUENCE: 14 atg cag cta gag ctc tcc acc tgt gtc ttt ctg tgt ctc ttg cca ctc      48
Met Gln Leu Glu Leu Ser Thr Cys Val Phe Leu Cys Leu Leu Pro Leu
1               5                   10                  15 ggc ttt agt gcc atc agg aga tac tac ctg ggc gca gtg gaa ctg tcc     96
Gly Phe Ser Ala Ile Arg Arg Tyr Tyr Leu Gly Ala Val Glu Leu Ser
                20                  25                  30 tgg gac tac cgg caa agt gaa ctc ctc cgt gag ctg cac gtg gac acc    144
Trp Asp Tyr Arg Gln Ser Glu Leu Leu Arg Glu Leu His Val Asp Thr
            35                  40                  45 aga ttt cct gct aca gcg cca gga gct ctt ccg ttg ggc ccg tca gtc    192
Arg Phe Pro Ala Thr Ala Pro Gly Ala Leu Pro Leu Gly Pro Ser Val
        50                  55                  60 ctg tac aaa aag act gtg ttc gta gag ttc acg gat caa ctt ttc agc    240
Leu Tyr Lys Lys Thr Val Phe Val Glu Phe Thr Asp Gln Leu Phe Ser
65                  70                  75                  80 gtt gcc agg ccc agg cca cca tgg atg ggt ctg ctg ggt cct acc atc    288
Val Ala Arg Pro Arg Pro Pro Trp Met Gly Leu Leu Gly Pro Thr Ile
                    85                  90                  95 cag gct gag gtt tac gac acg gtg gtc gtt acc ctg aag aac atg gct    336
Gln Ala Glu Val Tyr Asp Thr Val Val Val Thr Leu Lys Asn Met Ala
                100                 105                 110 tct cat ccc gtt agt ctt cac gct gtc ggc gtc tcc ttc tgg aaa tct    384
Ser His Pro Val Ser Leu His Ala Val Gly Val Ser Phe Trp Lys Ser
            115                 120                 125 tcc gaa ggc gct gaa tat gag gat cac acc agc caa agg gag aag gaa    432
Ser Glu Gly Ala Glu Tyr Glu Asp His Thr Ser Gln Arg Glu Lys Glu
        130                 135                 140 gac gat aaa gtc ctt ccc ggt aaa agc caa acc tac gtc tgg cag gtc    480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctt acc tac    528
Leu Lys Glu Asn Gly Pro Thr Ala Ser Asp Pro Pro Cys Leu Thr Tyr
                165                 170                 175 tca tac ctg tct cac gtg gac ctg gtg aaa gac ctg aat tcg ggc ctc    576
Ser Tyr Leu Ser His Val Asp Leu Val Lys Asp Leu Asn Ser Gly Leu
                180                 185                 190
```

-continued

| | | |
|---|---|---|
| att gga gcc ctg ctg gtt tgt aga gaa ggg agt ctg acc aga gaa agg<br>Ile Gly Ala Leu Leu Val Cys Arg Glu Gly Ser Leu Thr Arg Glu Arg<br>     195                   200                  205 | 624 | |
| acc cag aac ctg cac gaa ttt gta cta ctt ttt gct gtc ttt gat gaa<br>Thr Gln Asn Leu His Glu Phe Val Leu Leu Phe Ala Val Phe Asp Glu<br>210                   215                   220 | 672 | |
| ggg aaa agt tgg cac tca gca aga aat gac tcc tgg aca cgg gcc atg<br>Gly Lys Ser Trp His Ser Ala Arg Asn Asp Ser Trp Thr Arg Ala Met<br>225                   230                   235               240 | 720 | |
| gat ccc gca cct gcc agg gcc cag cct gca atg cac aca gtc aat ggc<br>Asp Pro Ala Pro Ala Arg Ala Gln Pro Ala Met His Thr Val Asn Gly<br>                 245                   250               255 | 768 | |
| tat gtc aac agg tct ctg cca ggt ctg atc gga tgt cat aag aaa tca<br>Tyr Val Asn Arg Ser Leu Pro Gly Leu Ile Gly Cys His Lys Lys Ser<br>             260                   265               270 | 816 | |
| gtc tac tgg cac gtg att gga atg ggc acc agc ccg gaa gtg cac tcc<br>Val Tyr Trp His Val Ile Gly Met Gly Thr Ser Pro Glu Val His Ser<br>     275                   280                   285 | 864 | |
| att ttt ctt gaa ggc cac acg ttt ctc gtg agg cac cat cgc cag gct<br>Ile Phe Leu Glu Gly His Thr Phe Leu Val Arg His His Arg Gln Ala<br>     290                   295                   300 | 912 | |
| tcc ttg gag atc tcg cca cta act ttc ctc act gct cag aca ttc ctg<br>Ser Leu Glu Ile Ser Pro Leu Thr Phe Leu Thr Ala Gln Thr Phe Leu<br>305                   310                   315               320 | 960 | |
| atg gac ctt ggc cag ttc cta ctg ttt tgt cat atc tcc tcc cac cac<br>Met Asp Leu Gly Gln Phe Leu Leu Phe Cys His Ile Ser Ser His His<br>                 325                   330               335 | 1008 | |
| cat ggt ggc atg gag gct cac gtc aga gta gaa agc tgc gcc gag gag<br>His Gly Gly Met Glu Ala His Val Arg Val Glu Ser Cys Ala Glu Glu<br>             340                   345               350 | 1056 | |
| ccc cag ctg cgg agg aaa gct gat gaa gag gaa gat tat gat gac aat<br>Pro Gln Leu Arg Arg Lys Ala Asp Glu Glu Glu Asp Tyr Asp Asp Asn<br>                 355                   360               365 | 1104 | |
| ttg tac gac tcg gac atg gac gtg gtc cgg ctc gat ggt gac gac gtg<br>Leu Tyr Asp Ser Asp Met Asp Val Val Arg Leu Asp Gly Asp Asp Val<br>370                   375                   380 | 1152 | |
| tct ccc ttt atc caa atc cgc tcg gtt gcc aag aag cat ccc aaa acc<br>Ser Pro Phe Ile Gln Ile Arg Ser Val Ala Lys Lys His Pro Lys Thr<br>385                   390                   395               400 | 1200 | |
| tgg gtg cac tac atc tct gca gag gag gag gac tgg gac tac gcc ccc<br>Trp Val His Tyr Ile Ser Ala Glu Glu Glu Asp Trp Asp Tyr Ala Pro<br>                 405                   410               415 | 1248 | |
| gcg gtc ccc agc ccc agt gac aga agt tat aaa agt ctc tac ttg aac<br>Ala Val Pro Ser Pro Ser Asp Arg Ser Tyr Lys Ser Leu Tyr Leu Asn<br>             420                   425               430 | 1296 | |
| agt ggt cct cag cga att ggt agg aaa tac aaa aaa gct cga ttc gtc<br>Ser Gly Pro Gln Arg Ile Gly Arg Lys Tyr Lys Lys Ala Arg Phe Val<br>                 435                   440               445 | 1344 | |
| gct tac acg gat gta aca ttt aag act cgt aaa gct att ccg tat gaa<br>Ala Tyr Thr Asp Val Thr Phe Lys Thr Arg Lys Ala Ile Pro Tyr Glu<br>450                   455                   460 | 1392 | |
| tca gga atc ctg gga cct tta ctt tat gga gaa gtt gga gac aca ctt<br>Ser Gly Ile Leu Gly Pro Leu Leu Tyr Gly Glu Val Gly Asp Thr Leu<br>465                   470                   475               480 | 1440 | |
| ttg att ata ttt aag aat aaa gcg agc cga cca tat aac atc tac cct<br>Leu Ile Ile Phe Lys Asn Lys Ala Ser Arg Pro Tyr Asn Ile Tyr Pro<br>                 485                   490               495 | 1488 | |
| cat gga atc act gat gtc agc gct ttg cac cca ggg aga ctt cta aaa<br>His Gly Ile Thr Asp Val Ser Ala Leu His Pro Gly Arg Leu Leu Lys<br>             500                   505               510 | 1536 | |

```
ggt tgg aaa cat ttg aaa gac atg cca att ctg cca gga gag act ttc      1584
Gly Trp Lys His Leu Lys Asp Met Pro Ile Leu Pro Gly Glu Thr Phe
        515                 520                 525 aag tat aaa tgg aca gtg act gtg gaa gat ggg cca acc aag tcc gat      1632
Lys Tyr Lys Trp Thr Val Thr Val Glu Asp Gly Pro Thr Lys Ser Asp
    530                 535                 540 cct cgg tgc ctg acc cgc tac tac tcg agc tcc att aat cta gag aaa      1680
Pro Arg Cys Leu Thr Arg Tyr Tyr Ser Ser Ser Ile Asn Leu Glu Lys
545                 550                 555                 560 gat ctg gct tcg gga ctc att ggc cct ctc ctc atc tgc tac aaa gaa      1728
Asp Leu Ala Ser Gly Leu Ile Gly Pro Leu Leu Ile Cys Tyr Lys Glu
                565                 570                 575 tct gta gac caa aga gga aac cag atg atg tca gac aag aga aac gtc      1776
Ser Val Asp Gln Arg Gly Asn Gln Met Met Ser Asp Lys Arg Asn Val
            580                 585                 590 atc ctg ttt tct gta ttc gat gag aat caa agc tgg tac ctc gca gag      1824
Ile Leu Phe Ser Val Phe Asp Glu Asn Gln Ser Trp Tyr Leu Ala Glu
        595                 600                 605 aat att cag cgc ttc ctc ccc aat ccg gat gga tta cag ccc cag gat      1872
Asn Ile Gln Arg Phe Leu Pro Asn Pro Asp Gly Leu Gln Pro Gln Asp
    610                 615                 620 cca gag ttc caa gct tct aac atc atg cac agc atc aat ggc tat gtt      1920
Pro Glu Phe Gln Ala Ser Asn Ile Met His Ser Ile Asn Gly Tyr Val
625                 630                 635                 640 ttt gat agc ttg cag ctg tcg gtt tgt ttg cac gag gtg gca tac tgg      1968
Phe Asp Ser Leu Gln Leu Ser Val Cys Leu His Glu Val Ala Tyr Trp
                645                 650                 655 tac att cta agt gtt gga gca cag acg gac ttc ctc tcc gtc ttc ttc      2016
Tyr Ile Leu Ser Val Gly Ala Gln Thr Asp Phe Leu Ser Val Phe Phe
            660                 665                 670 tct ggc tac acc ttc aaa cac aaa atg gtc tat gaa gac aca ctc acc      2064
Ser Gly Tyr Thr Phe Lys His Lys Met Val Tyr Glu Asp Thr Leu Thr
        675                 680                 685 ctg ttc ccc ttc tca gga gaa acg gtc ttc atg tca atg gaa aac cca      2112
Leu Phe Pro Phe Ser Gly Glu Thr Val Phe Met Ser Met Glu Asn Pro
    690                 695                 700 ggt ctc tgg gtc ctt ggg tgc cac aac tca gac ttg cgg aac aga ggg      2160
Gly Leu Trp Val Leu Gly Cys His Asn Ser Asp Leu Arg Asn Arg Gly
705                 710                 715                 720 atg aca gcc tta ctg aag gtg tat agt tgt gac agg gac att ggt gat      2208
Met Thr Ala Leu Leu Lys Val Tyr Ser Cys Asp Arg Asp Ile Gly Asp
                725                 730                 735 tat tat gac aac act tat gaa gat att cca ggc ttc ttg ctg agt gga      2256
Tyr Tyr Asp Asn Thr Tyr Glu Asp Ile Pro Gly Phe Leu Leu Ser Gly
            740                 745                 750 aag aat gtc att gaa cct agg agc ttt gcc cag aat tca aga ccc cct      2304
Lys Asn Val Ile Glu Pro Arg Ser Phe Ala Gln Asn Ser Arg Pro Pro
        755                 760                 765 agt gcg agc gct cca aag cct ccg gtc ctg cga cgg cat cag agg gac      2352
Ser Ala Ser Ala Pro Lys Pro Pro Val Leu Arg Arg His Gln Arg Asp
    770                 775                 780 ata agc ctt cct act ttt cag ccg gag gaa gac aaa atg gac tat gat      2400
Ile Ser Leu Pro Thr Phe Gln Pro Glu Glu Asp Lys Met Asp Tyr Asp
785                 790                 795                 800 gat atc ttc tca act gaa acg aag gga gaa gat ttt gac att tac ggt      2448
Asp Ile Phe Ser Thr Glu Thr Lys Gly Glu Asp Phe Asp Ile Tyr Gly
                805                 810                 815 gag gat gaa aat cag gac cct cgc agc ttt cag aag aga acc cga cac      2496
Glu Asp Glu Asn Gln Asp Pro Arg Ser Phe Gln Lys Arg Thr Arg His
            820                 825                 830
```

```
tat ttc att gct gcg gtg gag cag ctc tgg gat tac ggg atg agc gaa    2544
Tyr Phe Ile Ala Ala Val Glu Gln Leu Trp Asp Tyr Gly Met Ser Glu
        835                 840                 845 tcc ccc cgg gcg cta aga aac agg gct cag aac gga gag gtg cct cgg    2592
Ser Pro Arg Ala Leu Arg Asn Arg Ala Gln Asn Gly Glu Val Pro Arg
850                 855                 860 ttc aag aag gtg gtc ttc cgg gaa ttt gct gac ggc tcc ttc acg cag    2640
Phe Lys Lys Val Val Phe Arg Glu Phe Ala Asp Gly Ser Phe Thr Gln
865                 870                 875                 880 ccg tcg tac cgc ggg gaa ctc aac aaa cac ttg ggg ctc ttg gga ccc    2688
Pro Ser Tyr Arg Gly Glu Leu Asn Lys His Leu Gly Leu Leu Gly Pro
                885                 890                 895 tac atc aga gcg gaa gtt gaa gac aac atc atg gta act ttc aaa aac    2736
Tyr Ile Arg Ala Glu Val Glu Asp Asn Ile Met Val Thr Phe Lys Asn
            900                 905                 910 cag gcg tct cgt ccc tat tcc ttc tac tcg agc ctt att tct tat ccg    2784
Gln Ala Ser Arg Pro Tyr Ser Phe Tyr Ser Ser Leu Ile Ser Tyr Pro
        915                 920                 925 gat gat cag gag caa ggg gca gaa cct cga cac aac ttc gtc cag cca    2832
Asp Asp Gln Glu Gln Gly Ala Glu Pro Arg His Asn Phe Val Gln Pro
930                 935                 940 aat gaa acc aga act tac ttt tgg aaa gtg cag cat cac atg gca ccc    2880
Asn Glu Thr Arg Thr Tyr Phe Trp Lys Val Gln His His Met Ala Pro
945                 950                 955                 960 aca gaa gac gag ttt gac tgc aaa gcc tgg gcc tac ttt tct gat gtt    2928
Thr Glu Asp Glu Phe Asp Cys Lys Ala Trp Ala Tyr Phe Ser Asp Val
                965                 970                 975 gac ctg gaa aaa gat gtg cac tca ggc ttg atc ggc ccc ctt ctg atc    2976
Asp Leu Glu Lys Asp Val His Ser Gly Leu Ile Gly Pro Leu Leu Ile
            980                 985                 990 tgc cgc gcc aac acc ctg aac gct gct cac ggt aga caa gtg acc gtg    3024
Cys Arg Ala Asn Thr Leu Asn Ala Ala His Gly Arg Gln Val Thr Val
        995                 1000                1005 caa gaa ttt gct ctg ttt ttc act att ttt gat gag aca aag agc tgg    3072
Gln Glu Phe Ala Leu Phe Phe Thr Ile Phe Asp Glu Thr Lys Ser Trp
    1010                1015                1020 tac ttc act gaa aat gtg gaa agg aac tgc cgg gcc ccc tgc cat ctg    3120
Tyr Phe Thr Glu Asn Val Glu Arg Asn Cys Arg Ala Pro Cys His Leu
1025                1030                1035                1040 cag atg gag gac ccc act ctg aaa gaa aac tat cgc ttc cat gca atc    3168
Gln Met Glu Asp Pro Thr Leu Lys Glu Asn Tyr Arg Phe His Ala Ile
                1045                1050                1055 aat ggc tat gtg atg gat aca ctc cct ggc tta gta atg gct cag aat    3216
Asn Gly Tyr Val Met Asp Thr Leu Pro Gly Leu Val Met Ala Gln Asn
            1060                1065                1070 caa agg atc cga tgg tat ctg ctc agc atg ggc agc aat gaa aat atc    3264
Gln Arg Ile Arg Trp Tyr Leu Leu Ser Met Gly Ser Asn Glu Asn Ile
        1075                1080                1085 cat tcg att cat ttt agc gga cac gtg ttc agt gta cgg aaa aag gag    3312
His Ser Ile His Phe Ser Gly His Val Phe Ser Val Arg Lys Lys Glu
    1090                1095                1100 gag tat aaa atg gcc gtg tac aat ctc tat ccg ggt gtc ttt gag aca    3360
Glu Tyr Lys Met Ala Val Tyr Asn Leu Tyr Pro Gly Val Phe Glu Thr
1105                1110                1115                1120 gtg gaa atg cta ccg tcc aaa gtt gga att tgg cga ata gaa tgc ctg    3408
Val Glu Met Leu Pro Ser Lys Val Gly Ile Trp Arg Ile Glu Cys Leu
                1125                1130                1135 att ggc gag cac ctg caa gct ggg atg agc acg act ttc ctg gtg tac    3456
Ile Gly Glu His Leu Gln Ala Gly Met Ser Thr Thr Phe Leu Val Tyr
            1140                1145                1150
```

```
agc aag aag tgt cag act ccc ctg gga atg gct tct gga cac att aga    3504
Ser Lys Lys Cys Gln Thr Pro Leu Gly Met Ala Ser Gly His Ile Arg
        1155                1160                1165 gat ttt cag att aca gct tca gga caa tat gga cag tgg gcc cca aag    3552
Asp Phe Gln Ile Thr Ala Ser Gly Gln Tyr Gly Gln Trp Ala Pro Lys
    1170                1175                1180 ctg gcc aga ctt cat tat tcc gga tca atc aat gcc tgg agc acc aag    3600
Leu Ala Arg Leu His Tyr Ser Gly Ser Ile Asn Ala Trp Ser Thr Lys
1185                1190                1195                1200 gag ccc ttt tct tgg atc aag gtg gat ctg ttg gca cca atg att att    3648
Glu Pro Phe Ser Trp Ile Lys Val Asp Leu Leu Ala Pro Met Ile Ile
                1205                1210                1215 cac ggc atc aag acc cag ggt gcc cgt cag aag ttc tcc agc ctc tac    3696
His Gly Ile Lys Thr Gln Gly Ala Arg Gln Lys Phe Ser Ser Leu Tyr
            1220                1225                1230 atc tct cag ttt atc atc atg tat agt ctt gat ggg aag aag tgg cag    3744
Ile Ser Gln Phe Ile Ile Met Tyr Ser Leu Asp Gly Lys Lys Trp Gln
        1235                1240                1245 act tat cga gga aat tcc act gga acc tta atg gtc ttc ttt ggc aat    3792
Thr Tyr Arg Gly Asn Ser Thr Gly Thr Leu Met Val Phe Phe Gly Asn
    1250                1255                1260 gtg gat tca tct ggg ata aaa cac aat att ttt aac cct cca att att    3840
Val Asp Ser Ser Gly Ile Lys His Asn Ile Phe Asn Pro Pro Ile Ile
1265                1270                1275                1280 gct cga tac atc cgt ttg cac cca act cat tat agc att cgc agc act    3888
Ala Arg Tyr Ile Arg Leu His Pro Thr His Tyr Ser Ile Arg Ser Thr
                1285                1290                1295 ctt cgc atg gag ttg atg ggc tgt gat tta aat agt tgc agc atg cca    3936
Leu Arg Met Glu Leu Met Gly Cys Asp Leu Asn Ser Cys Ser Met Pro
            1300                1305                1310 ttg gga atg gag agt aaa gca ata tca gat gca cag att act gct tca    3984
Leu Gly Met Glu Ser Lys Ala Ile Ser Asp Ala Gln Ile Thr Ala Ser
        1315                1320                1325 tcc tac ttt acc aat atg ttt gcc acc tgg tct cct tca aaa gct cga    4032
Ser Tyr Phe Thr Asn Met Phe Ala Thr Trp Ser Pro Ser Lys Ala Arg
    1330                1335                1340 ctt cac ctc caa ggg agg agt aat gcc tgg aga cct cag gtg aat aat    4080
Leu His Leu Gln Gly Arg Ser Asn Ala Trp Arg Pro Gln Val Asn Asn
1345                1350                1355                1360 cca aaa gag tgg ctg caa gtg gac ttc cag aag aca atg aaa gtc aca    4128
Pro Lys Glu Trp Leu Gln Val Asp Phe Gln Lys Thr Met Lys Val Thr
                1365                1370                1375 gga gta act act cag gga gta aaa tct ctg ctt acc agc atg tat gtg    4176
Gly Val Thr Thr Gln Gly Val Lys Ser Leu Leu Thr Ser Met Tyr Val
            1380                1385                1390 aag gag ttc ctc atc tcc agc agt caa gat ggc cat cag tgg act ctc    4224
Lys Glu Phe Leu Ile Ser Ser Ser Gln Asp Gly His Gln Trp Thr Leu
        1395                1400                1405 ttt ttt cag aat ggc aaa gta aag gtt ttt cag gga aat caa gac tcc    4272
Phe Phe Gln Asn Gly Lys Val Lys Val Phe Gln Gly Asn Gln Asp Ser
    1410                1415                1420 ttc aca cct gtg gtg aac tct cta gac cca ccg tta ctg act cgc tac    4320
Phe Thr Pro Val Val Asn Ser Leu Asp Pro Pro Leu Leu Thr Arg Tyr
1425                1430                1435                1440 ctt cga att cac ccc cag agt tgg gtg cac cag att gcc ctg agg atg    4368
Leu Arg Ile His Pro Gln Ser Trp Val His Gln Ile Ala Leu Arg Met
                1445                1450                1455 gag gtt ctg ggc tgc gag gca cag gac ctc tac                        4401
Glu Val Leu Gly Cys Glu Ala Gln Asp Leu Tyr
            1460                1465
```

<210> SEQ ID NO 15
<211> LENGTH: 1467
<212> TYPE: PRT
<213> ORGANISM: Artificial Sequence
<220> FEATURE:
<223> OTHER INFORMATION: HP44/OL-- factor VIII having the following
      domains: A1p-A2p-app-A3p-C1h-C2h

<400> SEQUENCE: 15

```
Met Gln Leu Glu Leu Ser Thr Cys Val Phe Leu Cys Leu Leu Pro Leu
 1               5                  10                  15

Gly Phe Ser Ala Ile Arg Arg Tyr Tyr Leu Gly Ala Val Glu Leu Ser
            20                  25                  30

Trp Asp Tyr Arg Gln Ser Glu Leu Leu Arg Glu Leu His Val Asp Thr
        35                  40                  45

Arg Phe Pro Ala Thr Ala Pro Gly Ala Leu Pro Leu Gly Pro Ser Val
    50                  55                  60

Leu Tyr Lys Lys Thr Val Phe Val Glu Phe Thr Asp Gln Leu Phe Ser
65                  70                  75                  80

Val Ala Arg Pro Arg Pro Pro Trp Met Gly Leu Leu Gly Pro Thr Ile
                85                  90                  95

Gln Ala Glu Val Tyr Asp Thr Val Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
    290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
            340                 345                 350

Pro Gln Leu Arg Arg Lys Ala Asp Glu Glu Asp Tyr Asp Asp Asn
        355                 360                 365
```

```
Leu Tyr Asp Ser Asp Met Asp Val Arg Leu Asp Gly Asp Val
    370                 375                 380

Ser Pro Phe Ile Gln Ile Arg Ser Val Ala Lys Lys His Pro Lys Thr
385                 390                 395                 400

Trp Val His Tyr Ile Ser Ala Glu Glu Asp Trp Asp Tyr Ala Pro
                405                 410                 415

Ala Val Pro Ser Pro Ser Asp Arg Ser Tyr Lys Ser Leu Tyr Leu Asn
            420                 425                 430

Ser Gly Pro Gln Arg Ile Gly Arg Lys Tyr Lys Lys Ala Arg Phe Val
            435                 440                 445

Ala Tyr Thr Asp Val Thr Phe Lys Thr Arg Lys Ala Ile Pro Tyr Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Lys Ala Ser Arg Pro Tyr Asn Ile Tyr Pro
                485                 490                 495

His Gly Ile Thr Asp Val Ser Ala Leu His Pro Gly Arg Leu Leu Lys
            500                 505                 510

Gly Trp Lys His Leu Lys Asp Met Pro Ile Leu Pro Gly Glu Thr Phe
    515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Ile Asn Leu Glu Lys
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Met Met Ser Asp Lys Arg Asn Val
            580                 585                 590

Ile Leu Phe Ser Val Phe Asp Glu Asn Gln Ser Trp Tyr Leu Ala Glu
    595                 600                 605

Asn Ile Gln Arg Phe Leu Pro Asn Pro Asp Gly Leu Gln Pro Gln Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Val Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
    690                 695                 700

Gly Leu Trp Val Leu Gly Cys His Asn Ser Asp Leu Arg Asn Arg Gly
705                 710                 715                 720

Met Thr Ala Leu Leu Lys Val Tyr Ser Cys Asp Arg Asp Ile Gly Asp
                725                 730                 735

Tyr Tyr Asp Asn Thr Tyr Glu Asp Ile Pro Gly Phe Leu Leu Ser Gly
            740                 745                 750

Lys Asn Val Ile Glu Pro Arg Ser Phe Ala Gln Asn Ser Arg Pro Pro
            755                 760                 765

Ser Ala Ser Ala Pro Lys Pro Pro Val Leu Arg Arg His Gln Arg Asp
    770                 775                 780

Ile Ser Leu Pro Thr Phe Gln Pro Glu Glu Asp Lys Met Asp Tyr Asp
785                 790                 795                 800
```

```
Asp Ile Phe Ser Thr Glu Thr Lys Gly Glu Asp Phe Asp Ile Tyr Gly
                805                 810                 815

Glu Asp Glu Asn Gln Asp Pro Arg Ser Phe Gln Lys Arg Thr Arg His
        820                 825                 830

Tyr Phe Ile Ala Ala Val Glu Gln Leu Trp Asp Tyr Gly Met Ser Glu
            835                 840                 845

Ser Pro Arg Ala Leu Arg Asn Arg Ala Gln Asn Gly Glu Val Pro Arg
    850                 855                 860

Phe Lys Lys Val Val Phe Arg Glu Phe Ala Asp Gly Ser Phe Thr Gln
865                 870                 875                 880

Pro Ser Tyr Arg Gly Glu Leu Asn Lys His Leu Gly Leu Leu Gly Pro
                885                 890                 895

Tyr Ile Arg Ala Glu Val Glu Asp Asn Ile Met Val Thr Phe Lys Asn
            900                 905                 910

Gln Ala Ser Arg Pro Tyr Ser Phe Tyr Ser Ser Leu Ile Ser Tyr Pro
        915                 920                 925

Asp Asp Gln Glu Gln Gly Ala Glu Pro Arg His Asn Phe Val Gln Pro
    930                 935                 940

Asn Glu Thr Arg Thr Tyr Phe Trp Lys Val Gln His His Met Ala Pro
945                 950                 955                 960

Thr Glu Asp Glu Phe Asp Cys Lys Ala Trp Ala Tyr Phe Ser Asp Val
                965                 970                 975

Asp Leu Glu Lys Asp Val His Ser Gly Leu Ile Gly Pro Leu Leu Ile
            980                 985                 990

Cys Arg Ala Asn Thr Leu Asn Ala Ala His Gly Arg Gln Val Thr Val
        995                 1000                1005

Gln Glu Phe Ala Leu Phe Phe Thr Ile Phe Asp Glu Thr Lys Ser Trp
    1010                1015                1020

Tyr Phe Thr Glu Asn Val Glu Arg Asn Cys Arg Ala Pro Cys His Leu
1025                1030                1035                1040

Gln Met Glu Asp Pro Thr Leu Lys Glu Asn Tyr Arg Phe His Ala Ile
                1045                1050                1055

Asn Gly Tyr Val Met Asp Thr Leu Pro Gly Leu Val Met Ala Gln Asn
            1060                1065                1070

Gln Arg Ile Arg Trp Tyr Leu Leu Ser Met Gly Ser Asn Glu Asn Ile
        1075                1080                1085

His Ser Ile His Phe Ser Gly His Val Phe Ser Val Arg Lys Lys Glu
    1090                1095                1100

Glu Tyr Lys Met Ala Val Tyr Asn Leu Tyr Pro Gly Val Phe Glu Thr
1105                1110                1115                1120

Val Glu Met Leu Pro Ser Lys Val Gly Ile Trp Arg Ile Glu Cys Leu
                1125                1130                1135

Ile Gly Glu His Leu Gln Ala Gly Met Ser Thr Thr Phe Leu Val Tyr
            1140                1145                1150

Ser Lys Lys Cys Gln Thr Pro Leu Gly Met Ala Ser Gly His Ile Arg
        1155                1160                1165

Asp Phe Gln Ile Thr Ala Ser Gly Gln Tyr Gly Gln Trp Ala Pro Lys
    1170                1175                1180

Leu Ala Arg Leu His Tyr Ser Gly Ser Ile Asn Ala Trp Ser Thr Lys
1185                1190                1195                1200

Glu Pro Phe Ser Trp Ile Lys Val Asp Leu Leu Ala Pro Met Ile Ile
                1205                1210                1215

His Gly Ile Lys Thr Gln Gly Ala Arg Gln Lys Phe Ser Ser Leu Tyr
```

```
                  1220              1225              1230
Ile Ser Gln Phe Ile Ile Met Tyr Ser Leu Asp Gly Lys Lys Trp Gln
            1235              1240              1245

Thr Tyr Arg Gly Asn Ser Thr Gly Thr Leu Met Val Phe Phe Gly Asn
        1250              1255              1260

Val Asp Ser Ser Gly Ile Lys His Asn Ile Phe Asn Pro Pro Ile Ile
1265              1270              1275              1280

Ala Arg Tyr Ile Arg Leu His Pro Thr His Tyr Ser Ile Arg Ser Thr
            1285              1290              1295

Leu Arg Met Glu Leu Met Gly Cys Asp Leu Asn Ser Cys Ser Met Pro
            1300              1305              1310

Leu Gly Met Glu Ser Lys Ala Ile Ser Asp Ala Gln Ile Thr Ala Ser
            1315              1320              1325

Ser Tyr Phe Thr Asn Met Phe Ala Thr Trp Ser Pro Ser Lys Ala Arg
            1330              1335              1340

Leu His Leu Gln Gly Arg Ser Asn Ala Trp Arg Pro Gln Val Asn Asn
1345              1350              1355              1360

Pro Lys Glu Trp Leu Gln Val Asp Phe Gln Lys Thr Met Lys Val Thr
            1365              1370              1375

Gly Val Thr Thr Gln Gly Val Lys Ser Leu Leu Thr Ser Met Tyr Val
            1380              1385              1390

Lys Glu Phe Leu Ile Ser Ser Ser Gln Asp Gly His Gln Trp Thr Leu
            1395              1400              1405

Phe Phe Gln Asn Gly Lys Val Lys Val Phe Gln Gly Asn Gln Asp Ser
            1410              1415              1420

Phe Thr Pro Val Val Asn Ser Leu Asp Pro Pro Leu Leu Thr Arg Tyr
1425              1430              1435              1440

Leu Arg Ile His Pro Gln Ser Trp Val His Gln Ile Ala Leu Arg Met
            1445              1450              1455

Glu Val Leu Gly Cys Glu Ala Gln Asp Leu Tyr
            1460              1465

<210> SEQ ID NO 16
<211> LENGTH: 4371
<212> TYPE: DNA
<213> ORGANISM: Artificial Sequence
<220> FEATURE:
<223> OTHER INFORMATION: hybrid human and porcine factor VIII sequence
<221> NAME/KEY: CDS
<222> LOCATION: (1)...(4371)
<223> OTHER INFORMATION: HP46/SQ-- factor VIII having the following
      domains: A1p-A2h-aph-A3h-C1h-C2h

<400> SEQUENCE: 16 atg cag cta gag ctc tcc acc tgt gtc ttt ctg tgt ctc ttg cca ctc      48
Met Gln Leu Glu Leu Ser Thr Cys Val Phe Leu Cys Leu Leu Pro Leu
 1               5                  10                  15 ggc ttt agt gcc atc agg aga tac tac ctg ggc gca gtg gaa ctg tcc      96
Gly Phe Ser Ala Ile Arg Arg Tyr Tyr Leu Gly Ala Val Glu Leu Ser
             20                  25                  30 tgg gac tac cgg caa agt gaa ctc ctc cgt gag ctg cac gtg gac acc    144
Trp Asp Tyr Arg Gln Ser Glu Leu Leu Arg Glu Leu His Val Asp Thr
         35                  40                  45 aga ttt cct gct aca gcg cca gga gct ctt ccg ttg ggc ccg tca gtc    192
Arg Phe Pro Ala Thr Ala Pro Gly Ala Leu Pro Leu Gly Pro Ser Val
     50                  55                  60 ctg tac aaa aag act gtg ttc gta gag ttc acg gat caa ctt ttc agc    240
Leu Tyr Lys Lys Thr Val Phe Val Glu Phe Thr Asp Gln Leu Phe Ser
 65                  70                  75                  80
```

```
gtt gcc agg ccc agg cca cca tgg atg ggt ctg ctg ggt cct acc atc         288
Val Ala Arg Pro Arg Pro Pro Trp Met Gly Leu Leu Gly Pro Thr Ile
            85                  90                  95 cag gct gag gtt tac gac acg gtg gtc gtt acc ctg aag aac atg gct         336
Gln Ala Glu Val Tyr Asp Thr Val Val Val Thr Leu Lys Asn Met Ala
        100                 105                 110 tct cat ccc gtt agt ctt cac gct gtc ggc gtc tcc ttc tgg aaa tct         384
Ser His Pro Val Ser Leu His Ala Val Gly Val Ser Phe Trp Lys Ser
    115                 120                 125 tcc gaa ggc gct gaa tat gag gat cac acc agc caa agg gag aag gaa         432
Ser Glu Gly Ala Glu Tyr Glu Asp His Thr Ser Gln Arg Glu Lys Glu
130                 135                 140 gac gat aaa gtc ctt ccc ggt aaa agc caa acc tac gtc tgg cag gtc         480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctt acc tac         528
Leu Lys Glu Asn Gly Pro Thr Ala Ser Asp Pro Pro Cys Leu Thr Tyr
                165                 170                 175 tca tac ctg tct cac gtg gac ctg gtg aaa gac ctg aat tcg ggc ctc         576
Ser Tyr Leu Ser His Val Asp Leu Val Lys Asp Leu Asn Ser Gly Leu
            180                 185                 190 att gga gcc ctg ctg gtt tgt aga gaa ggg agt ctg acc aga gaa agg         624
Ile Gly Ala Leu Leu Val Cys Arg Glu Gly Ser Leu Thr Arg Glu Arg
        195                 200                 205 acc cag aac ctg cac gaa ttt gta cta ctt ttt gct gtc ttt gat gaa         672
Thr Gln Asn Leu His Glu Phe Val Leu Leu Phe Ala Val Phe Asp Glu
    210                 215                 220 ggg aaa agt tgg cac tca gca aga aat gac tcc tgg aca cgg gcc atg         720
Gly Lys Ser Trp His Ser Ala Arg Asn Asp Ser Trp Thr Arg Ala Met
225                 230                 235                 240 gat ccc gca cct gcc agg gcc cag cct gca atg cac aca gtc aat ggc         768
Asp Pro Ala Pro Ala Arg Ala Gln Pro Ala Met His Thr Val Asn Gly
                245                 250                 255 tat gtc aac agg tct ctg cca ggt ctg atc gga tgt cat aag aaa tca         816
Tyr Val Asn Arg Ser Leu Pro Gly Leu Ile Gly Cys His Lys Lys Ser
            260                 265                 270 gtc tac tgg cac gtg att gga atg ggc acc agc ccg gaa gtg cac tcc         864
Val Tyr Trp His Val Ile Gly Met Gly Thr Ser Pro Glu Val His Ser
        275                 280                 285 att ttt ctt gaa ggc cac acg ttt ctc gtg agg cac cat cgc cag gct         912
Ile Phe Leu Glu Gly His Thr Phe Leu Val Arg His His Arg Gln Ala
    290                 295                 300 tcc ttg gag atc tcg cca cta act ttc ctc act gct cag aca ttc ctg         960
Ser Leu Glu Ile Ser Pro Leu Thr Phe Leu Thr Ala Gln Thr Phe Leu
305                 310                 315                 320 atg gac ctt ggc cag ttc cta ctg ttt tgt cat atc tct tcc cac cac        1008
Met Asp Leu Gly Gln Phe Leu Leu Phe Cys His Ile Ser Ser His His
                325                 330                 335 cat ggt ggc atg gag gct cac gtc aga gta gaa agc tgc gcc gag gag        1056
His Gly Gly Met Glu Ala His Val Arg Val Glu Ser Cys Ala Glu Glu
            340                 345                 350 ccc cag ctg cgg agg aaa gct gat gaa gag gaa gat tat gat gac aat        1104
Pro Gln Leu Arg Arg Lys Ala Asp Glu Glu Glu Asp Tyr Asp Asp Asn
        355                 360                 365 ttg tac gac tcg gac atg gac gtg gtc cgg ctc gat ggt gac gac gtg        1152
Leu Tyr Asp Ser Asp Met Asp Val Val Arg Leu Asp Gly Asp Asp Val
    370                 375                 380 tct ccc ttt atc caa atc cgc tca gtt gcc aag aag cat cct aaa act        1200
Ser Pro Phe Ile Gln Ile Arg Ser Val Ala Lys Lys His Pro Lys Thr
385                 390                 395                 400
```

| | |
|---|---|
| tgg gta cat tac att gct gct gaa gag gag gac tgg gac tat gct ccc<br>Trp Val His Tyr Ile Ala Ala Glu Glu Glu Asp Trp Asp Tyr Ala Pro<br>                              405                            410                          415 | 1248 |
| tta gtc ctc gcc ccc gat gac aga agt tat aaa agt caa tat ttg aac<br>Leu Val Leu Ala Pro Asp Asp Arg Ser Tyr Lys Ser Gln Tyr Leu Asn<br>             420                            425                          430 | 1296 |
| aat ggc cct cag cgg att ggt agg aag tac aaa aaa gtc cga ttt atg<br>Asn Gly Pro Gln Arg Ile Gly Arg Lys Tyr Lys Lys Val Arg Phe Met<br>             435                            440                          445 | 1344 |
| gca tac aca gat gaa acc ttt aag acg cgt gaa gct att cag cat gaa<br>Ala Tyr Thr Asp Glu Thr Phe Lys Thr Arg Glu Ala Ile Gln His Glu<br>450                            455                          460 | 1392 |
| tca gga atc ttg gga cct tta ctt tat ggg gaa gtt gga gac aca ctg<br>Ser Gly Ile Leu Gly Pro Leu Leu Tyr Gly Glu Val Gly Asp Thr Leu<br>465                            470                          475                      480 | 1440 |
| ttg att ata ttt aag aat caa gca agc aga cca tat aac atc tac cct<br>Leu Ile Ile Phe Lys Asn Gln Ala Ser Arg Pro Tyr Asn Ile Tyr Pro<br>                        485                            490                          495 | 1488 |
| cac gga atc act gat gtc cgt cct ttg tat tca agg aga tta cca aaa<br>His Gly Ile Thr Asp Val Arg Pro Leu Tyr Ser Arg Arg Leu Pro Lys<br>             500                            505                          510 | 1536 |
| ggt gta aaa cat ttg aag gat ttt cca att ctg cca gga gaa ata ttc<br>Gly Val Lys His Leu Lys Asp Phe Pro Ile Leu Pro Gly Glu Ile Phe<br>                        515                            520                          525 | 1584 |
| aaa tat aaa tgg aca gtg act gta gaa gat ggg cca act aaa tca gat<br>Lys Tyr Lys Trp Thr Val Thr Val Glu Asp Gly Pro Thr Lys Ser Asp<br>530                            535                          540 | 1632 |
| ccg cgg tgc ctg acc cgc tat tac tct agt ttc gtt aat atg gag aga<br>Pro Arg Cys Leu Thr Arg Tyr Tyr Ser Ser Phe Val Asn Met Glu Arg<br>545                            550                          555                      560 | 1680 |
| gat cta gct tca gga ctc att ggc cct ctc ctc atc tgc tac aaa gaa<br>Asp Leu Ala Ser Gly Leu Ile Gly Pro Leu Leu Ile Cys Tyr Lys Glu<br>                              565                            570                          575 | 1728 |
| tct gta gat caa aga gga aac cag ata atg tca gac aag agg aat gtc<br>Ser Val Asp Gln Arg Gly Asn Gln Ile Met Ser Asp Lys Arg Asn Val<br>                        580                            585                          590 | 1776 |
| atc ctg ttt tct gta ttt gat gag aac cga agc tgg tac ctc aca gag<br>Ile Leu Phe Ser Val Phe Asp Glu Asn Arg Ser Trp Tyr Leu Thr Glu<br>             595                            600                          605 | 1824 |
| aat ata caa cgc ttt ctc ccc aat cca gct gga gtg cag ctt gag gat<br>Asn Ile Gln Arg Phe Leu Pro Asn Pro Ala Gly Val Gln Leu Glu Asp<br>610                            615                          620 | 1872 |
| cca gag ttc caa gcc tcc aac atc atg cac agc atc aat ggc tat gtt<br>Pro Glu Phe Gln Ala Ser Asn Ile Met His Ser Ile Asn Gly Tyr Val<br>625                            630                          635                      640 | 1920 |
| ttt gat agt ttg cag ttg tca gtt tgt ttg cat gag gtg gca tac tgg<br>Phe Asp Ser Leu Gln Leu Ser Val Cys Leu His Glu Val Ala Tyr Trp<br>                        645                            650                          655 | 1968 |
| tac att cta agc att gga gca cag act gac ttc ctt tct gtc ttc ttc<br>Tyr Ile Leu Ser Ile Gly Ala Gln Thr Asp Phe Leu Ser Val Phe Phe<br>                        660                            665                          670 | 2016 |
| tct gga tat acc ttc aaa cac aaa atg gtc tat gaa gac aca ctc acc<br>Ser Gly Tyr Thr Phe Lys His Lys Met Val Tyr Glu Asp Thr Leu Thr<br>             675                            680                          685 | 2064 |
| cta ttc cca ttc tca gga gaa act gtc ttc atg tcg atg gaa aac cca<br>Leu Phe Pro Phe Ser Gly Glu Thr Val Phe Met Ser Met Glu Asn Pro<br>690                            695                          700 | 2112 |
| ggt cta tgg att ctg ggg tgc cac aac tca gac ttt cgg aac aga ggc<br>Gly Leu Trp Ile Leu Gly Cys His Asn Ser Asp Phe Arg Asn Arg Gly<br>705                            710                          715                      720 | 2160 |

```
atg acc gcc tta ctg aag gtt tct agt tgt gac aag aac act ggt gat    2208
Met Thr Ala Leu Leu Lys Val Ser Ser Cys Asp Lys Asn Thr Gly Asp
            725                 730                 735 tat tac gag gac agt tat gaa gat att tca gca tac ttg ctg agt aaa    2256
Tyr Tyr Glu Asp Ser Tyr Glu Asp Ile Ser Ala Tyr Leu Leu Ser Lys
        740                 745                 750 aac aat gcc att gaa cct agg agc ttc tct cag aat cca cca gtc ttg    2304
Asn Asn Ala Ile Glu Pro Arg Ser Phe Ser Gln Asn Pro Pro Val Leu
    755                 760                 765 aaa cgc cat caa cgg gaa ata act cgt act act ctt cag tca gat caa    2352
Lys Arg His Gln Arg Glu Ile Thr Arg Thr Thr Leu Gln Ser Asp Gln
770                 775                 780 gag gaa att gac tat gat gat acc ata tca gtt gaa atg aag aag gaa    2400
Glu Glu Ile Asp Tyr Asp Asp Thr Ile Ser Val Glu Met Lys Lys Glu
785                 790                 795                 800 gat ttt gac att tat gat gag gat gaa aat cag agc ccc cgc agc ttt    2448
Asp Phe Asp Ile Tyr Asp Glu Asp Glu Asn Gln Ser Pro Arg Ser Phe
            805                 810                 815 caa aag aaa aca cga cac tat ttt att gct gca gtg gag agg ctc tgg    2496
Gln Lys Lys Thr Arg His Tyr Phe Ile Ala Ala Val Glu Arg Leu Trp
        820                 825                 830 gat tat ggg atg agt agc tcc cca cat gtt cta aga aac agg gct cag    2544
Asp Tyr Gly Met Ser Ser Ser Pro His Val Leu Arg Asn Arg Ala Gln
    835                 840                 845 agt ggc agt gtc cct cag ttc aag aaa gtt gtt ttc cag gaa ttt act    2592
Ser Gly Ser Val Pro Gln Phe Lys Lys Val Val Phe Gln Glu Phe Thr
850                 855                 860 gat ggc tcc ttt act cag ccc tta tac cgt gga gaa cta aat gaa cat    2640
Asp Gly Ser Phe Thr Gln Pro Leu Tyr Arg Gly Glu Leu Asn Glu His
865                 870                 875                 880 ttg gga ctc ctg ggg cca tat ata aga gca gaa gtt gaa gat aat atc    2688
Leu Gly Leu Leu Gly Pro Tyr Ile Arg Ala Glu Val Glu Asp Asn Ile
            885                 890                 895 atg gta act ttc aga aat cag gcc tct cgt ccc tat tcc ttc tat tct    2736
Met Val Thr Phe Arg Asn Gln Ala Ser Arg Pro Tyr Ser Phe Tyr Ser
        900                 905                 910 agc ctt att tct tat gag gaa gat cag agg caa gga gca gaa cct aga    2784
Ser Leu Ile Ser Tyr Glu Glu Asp Gln Arg Gln Gly Ala Glu Pro Arg
    915                 920                 925 aaa aac ttt gtc aag cct aat gaa acc aaa act tac ttt tgg aaa gtg    2832
Lys Asn Phe Val Lys Pro Asn Glu Thr Lys Thr Tyr Phe Trp Lys Val
930                 935                 940 caa cat cat atg gca ccc act aaa gat gag ttt gac tgc aaa gcc tgg    2880
Gln His His Met Ala Pro Thr Lys Asp Glu Phe Asp Cys Lys Ala Trp
945                 950                 955                 960 gct tat ttc tct gat gtt gac ctg gaa aaa gat gtg cac tca ggc ctg    2928
Ala Tyr Phe Ser Asp Val Asp Leu Glu Lys Asp Val His Ser Gly Leu
            965                 970                 975 att gga ccc ctt ctg gtc tgc cac act aac aca ctg aac cct gct cat    2976
Ile Gly Pro Leu Leu Val Cys His Thr Asn Thr Leu Asn Pro Ala His
        980                 985                 990 ggg aga caa gtg aca gta cag gaa ttt gct ctg ttt ttc acc atc ttt    3024
Gly Arg Gln Val Thr Val Gln Glu Phe Ala Leu Phe Phe Thr Ile Phe
    995                 1000                1005 gat gag acc aaa agc tgg tac ttc act gaa aat atg gaa aga aac tgc    3072
Asp Glu Thr Lys Ser Trp Tyr Phe Thr Glu Asn Met Glu Arg Asn Cys
1010                1015                1020 agg gct ccc tgc aat atc cag atg gaa gat ccc act ttt aaa gag aat    3120
Arg Ala Pro Cys Asn Ile Gln Met Glu Asp Pro Thr Phe Lys Glu Asn
1025                1030                1035                1040
```

| | | |
|---|---|---|
| tat cgc ttc cat gca atc aat ggc tac ata atg gat aca cta cct ggc<br>Tyr Arg Phe His Ala Ile Asn Gly Tyr Ile Met Asp Thr Leu Pro Gly<br>            1045                    1050                  1055 | 3168 |
| tta gta atg gct cag gat caa agg att cga tgg tat ctg ctc agc atg<br>Leu Val Met Ala Gln Asp Gln Arg Ile Arg Trp Tyr Leu Leu Ser Met<br>    1060                    1065                  1070 | 3216 |
| ggc agc aat gaa aac atc cat tct att cat ttc agt gga cat gtg ttc<br>Gly Ser Asn Glu Asn Ile His Ser Ile His Phe Ser Gly His Val Phe<br>        1075                    1080              1085 | 3264 |
| act gta cga aaa aaa gag gag tat aaa atg gca ctg tac aat ctc tat<br>Thr Val Arg Lys Lys Glu Glu Tyr Lys Met Ala Leu Tyr Asn Leu Tyr<br>            1090                    1095                1100 | 3312 |
| cca ggt gtt ttt gag aca gtg gaa atg tta cca tcc aaa gct gga att<br>Pro Gly Val Phe Glu Thr Val Glu Met Leu Pro Ser Lys Ala Gly Ile<br>1105                    1110                  1115                  1120 | 3360 |
| tgg cgg gtg gaa tgc ctt att ggc gag cat cta cat gct ggg atg agc<br>Trp Arg Val Glu Cys Leu Ile Gly Glu His Leu His Ala Gly Met Ser<br>                1125                    1130                  1135 | 3408 |
| aca ctt ttt ctg gtg tac agc aat aag tgt cag act ccc ctg gga atg<br>Thr Leu Phe Leu Val Tyr Ser Asn Lys Cys Gln Thr Pro Leu Gly Met<br>            1140                    1145                1150 | 3456 |
| gct tct gga cac att aga gat ttt cag att aca gct tca gga caa tat<br>Ala Ser Gly His Ile Arg Asp Phe Gln Ile Thr Ala Ser Gly Gln Tyr<br>    1155                    1160                  1165 | 3504 |
| gga cag tgg gcc cca aag ctg gcc aga ctt cat tat tcc gga tca atc<br>Gly Gln Trp Ala Pro Lys Leu Ala Arg Leu His Tyr Ser Gly Ser Ile<br>        1170                    1175                1180 | 3552 |
| aat gcc tgg agc acc aag gag ccc ttt tct tgg atc aag gtg gat ctg<br>Asn Ala Trp Ser Thr Lys Glu Pro Phe Ser Trp Ile Lys Val Asp Leu<br>1185                    1190                  1195                  1200 | 3600 |
| ttg gca cca atg att att cac ggc atc aag acc cag ggt gcc cgt cag<br>Leu Ala Pro Met Ile Ile His Gly Ile Lys Thr Gln Gly Ala Arg Gln<br>                1205                    1210                  1215 | 3648 |
| aag ttc tcc agc ctc tac atc tct cag ttt atc atc atg tat agt ctt<br>Lys Phe Ser Ser Leu Tyr Ile Ser Gln Phe Ile Ile Met Tyr Ser Leu<br>            1220                    1225                1230 | 3696 |
| gat ggg aag aag tgg cag act tat cga gga aat tcc act gga acc tta<br>Asp Gly Lys Lys Trp Gln Thr Tyr Arg Gly Asn Ser Thr Gly Thr Leu<br>    1235                    1240                  1245 | 3744 |
| atg gtc ttc ttt ggc aat gtg gat tca tct ggg ata aaa cac aat att<br>Met Val Phe Phe Gly Asn Val Asp Ser Ser Gly Ile Lys His Asn Ile<br>        1250                    1255                  1260 | 3792 |
| ttt aac cct cca att att gct cga tac atc cgt ttg cac cca act cat<br>Phe Asn Pro Pro Ile Ile Ala Arg Tyr Ile Arg Leu His Pro Thr His<br>1265                    1270                  1275                  1280 | 3840 |
| tat agc att cgc agc act ctt cgc atg gag ttg atg ggc tgt gat tta<br>Tyr Ser Ile Arg Ser Thr Leu Arg Met Glu Leu Met Gly Cys Asp Leu<br>                1285                    1290                  1295 | 3888 |
| aat agt tgc agc atg cca ttg gga atg gag agt aaa gca ata tca gat<br>Asn Ser Cys Ser Met Pro Leu Gly Met Glu Ser Lys Ala Ile Ser Asp<br>            1300                    1305                1310 | 3936 |
| gca cag att act gct tca tcc tac ttt acc aat atg ttt gcc acc tgg<br>Ala Gln Ile Thr Ala Ser Ser Tyr Phe Thr Asn Met Phe Ala Thr Trp<br>    1315                    1320                  1325 | 3984 |
| tct cct tca aaa gct cga ctt cac ctc caa ggg agg agt aat gcc tgg<br>Ser Pro Ser Lys Ala Arg Leu His Leu Gln Gly Arg Ser Asn Ala Trp<br>        1330                    1335                1340 | 4032 |
| aga cct cag gtg aat aat cca aaa gag tgg ctg caa gtg gac ttc cag<br>Arg Pro Gln Val Asn Asn Pro Lys Glu Trp Leu Gln Val Asp Phe Gln<br>1345                    1350                  1355                  1360 | 4080 |

```
aag aca atg aaa gtc aca gga gta act act cag gga gta aaa tct ctg      4128
Lys Thr Met Lys Val Thr Gly Val Thr Thr Gln Gly Val Lys Ser Leu
            1365                1370                1375 ctt acc agc atg tat gtg aag gag ttc ctc atc tcc agc agt caa gat      4176
Leu Thr Ser Met Tyr Val Lys Glu Phe Leu Ile Ser Ser Ser Gln Asp
        1380                1385                1390 ggc cat cag tgg act ctc ttt ttt cag aat ggc aaa gta aag gtt ttt      4224
Gly His Gln Trp Thr Leu Phe Phe Gln Asn Gly Lys Val Lys Val Phe
    1395                1400                1405 cag gga aat caa gac tcc ttc aca cct gtg gtg aac tct cta gac cca      4272
Gln Gly Asn Gln Asp Ser Phe Thr Pro Val Val Asn Ser Leu Asp Pro
1410                1415                1420 ccg tta ctg act cgc tac ctt cga att cac ccc cag agt tgg gtg cac      4320
Pro Leu Leu Thr Arg Tyr Leu Arg Ile His Pro Gln Ser Trp Val His
1425                1430                1435                1440 cag att gcc ctg agg atg gag gtt ctg ggc tgc gag gca cag gac ctc      4368
Gln Ile Ala Leu Arg Met Glu Val Leu Gly Cys Glu Ala Gln Asp Leu
                1445                1450                1455 tac                                                                  4371
Tyr

<210> SEQ ID NO 17
<211> LENGTH: 1457
<212> TYPE: PRT
<213> ORGANISM: Artificial Sequence
<220> FEATURE:
<223> OTHER INFORMATION: HP46/SQ-- factor VIII having the following
      domains: A1p-A2h-aph-A3h-C1h-C2h

<400> SEQUENCE: 17

Met Gln Leu Glu Leu Ser Thr Cys Val Phe Leu Cys Leu Leu Pro Leu
 1               5                  10                  15

Gly Phe Ser Ala Ile Arg Arg Tyr Tyr Leu Gly Ala Val Glu Leu Ser
            20                  25                  30

Trp Asp Tyr Arg Gln Ser Glu Leu Leu Arg Glu Leu His Val Asp Thr
        35                  40                  45

Arg Phe Pro Ala Thr Ala Pro Gly Ala Leu Pro Leu Gly Pro Ser Val
    50                  55                  60

Leu Tyr Lys Lys Thr Val Phe Val Glu Phe Thr Asp Gln Leu Phe Ser
65                  70                  75                  80

Val Ala Arg Pro Arg Pro Pro Trp Met Gly Leu Leu Gly Pro Thr Ile
                85                  90                  95

Gln Ala Glu Val Tyr Asp Thr Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220
```

-continued

```
Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
            245                 250                 255

Tyr Val Asn Arg Ser Leu Pro Gly Leu Ile Gly Cys His Lys Lys Ser
        260                 265                 270

Val Tyr Trp His Val Ile Gly Met Gly Thr Ser Pro Glu Val His Ser
    275                 280                 285

Ile Phe Leu Glu Gly His Thr Phe Leu Val Arg His Arg Gln Ala
290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
            340                 345                 350

Pro Gln Leu Arg Arg Lys Ala Asp Glu Glu Asp Tyr Asp Asp Asn
        355                 360                 365

Leu Tyr Asp Ser Asp Met Asp Val Val Arg Leu Asp Gly Asp Val
    370                 375                 380

Ser Pro Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
```

```
                    645                 650                 655
Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Pro Pro Val Leu
            755                 760                 765

Lys Arg His Gln Arg Glu Ile Thr Arg Thr Thr Leu Gln Ser Asp Gln
770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
            835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
        995                 1000                1005

Asp Glu Thr Lys Ser Trp Tyr Phe Thr Glu Asn Met Glu Arg Asn Cys
    1010                1015                1020

Arg Ala Pro Cys Asn Ile Gln Met Glu Asp Pro Thr Phe Lys Glu Asn
1025                1030                1035                1040

Tyr Arg Phe His Ala Ile Asn Gly Tyr Ile Met Asp Thr Leu Pro Gly
                1045                1050                1055

Leu Val Met Ala Gln Asp Gln Arg Ile Arg Trp Tyr Leu Leu Ser Met
            1060                1065                1070
```

```
Gly Ser Asn Glu Asn Ile His Ser Ile His Phe Ser Gly His Val Phe
        1075                1080                1085

Thr Val Arg Lys Lys Glu Glu Tyr Lys Met Ala Leu Tyr Asn Leu Tyr
        1090                1095                1100

Pro Gly Val Phe Glu Thr Val Glu Met Leu Pro Ser Lys Ala Gly Ile
1105                1110                1115                1120

Trp Arg Val Glu Cys Leu Ile Gly His Leu His Ala Gly Met Ser
                1125                1130                1135

Thr Leu Phe Leu Val Tyr Ser Asn Lys Cys Gln Thr Pro Leu Gly Met
            1140                1145                1150

Ala Ser Gly His Ile Arg Asp Phe Gln Ile Thr Ala Ser Gly Gln Tyr
        1155                1160                1165

Gly Gln Trp Ala Pro Lys Leu Ala Arg Leu His Tyr Ser Gly Ser Ile
    1170                1175                1180

Asn Ala Trp Ser Thr Lys Glu Pro Phe Ser Trp Ile Lys Val Asp Leu
1185                1190                1195                1200

Leu Ala Pro Met Ile Ile His Gly Ile Lys Thr Gln Gly Ala Arg Gln
                1205                1210                1215

Lys Phe Ser Ser Leu Tyr Ile Ser Gln Phe Ile Ile Met Tyr Ser Leu
        1220                1225                1230

Asp Gly Lys Lys Trp Gln Thr Tyr Arg Gly Asn Ser Thr Gly Thr Leu
            1235                1240                1245

Met Val Phe Phe Gly Asn Val Asp Ser Ser Gly Ile Lys His Asn Ile
        1250                1255                1260

Phe Asn Pro Pro Ile Ile Ala Arg Tyr Ile Arg Leu His Pro Thr His
1265                1270                1275                1280

Tyr Ser Ile Arg Ser Thr Leu Arg Met Glu Leu Met Gly Cys Asp Leu
            1285                1290                1295

Asn Ser Cys Ser Met Pro Leu Gly Met Glu Ser Lys Ala Ile Ser Asp
        1300                1305                1310

Ala Gln Ile Thr Ala Ser Ser Tyr Phe Thr Asn Met Phe Ala Thr Trp
        1315                1320                1325

Ser Pro Ser Lys Ala Arg Leu His Leu Gln Gly Arg Ser Asn Ala Trp
        1330                1335                1340

Arg Pro Gln Val Asn Asn Pro Lys Glu Trp Leu Gln Val Asp Phe Gln
1345                1350                1355                1360

Lys Thr Met Lys Val Thr Gly Val Thr Thr Gln Gly Val Lys Ser Leu
                1365                1370                1375

Leu Thr Ser Met Tyr Val Lys Glu Phe Leu Ile Ser Ser Gln Asp
            1380                1385                1390

Gly His Gln Trp Thr Leu Phe Phe Gln Asn Gly Lys Val Lys Val Phe
        1395                1400                1405

Gln Gly Asn Gln Asp Ser Phe Thr Pro Val Val Asn Ser Leu Asp Pro
    1410                1415                1420

Pro Leu Leu Thr Arg Tyr Leu Arg Ile His Pro Gln Ser Trp Val His
1425                1430                1435                1440

Gln Ile Ala Leu Arg Met Glu Val Leu Gly Cys Glu Ala Gln Asp Leu
                1445                1450                1455

Tyr

<210> SEQ ID NO 18
<211> LENGTH: 4401
<212> TYPE: DNA
<213> ORGANISM: Artificial Sequence
<220> FEATURE:
```

-continued

```
<223> OTHER INFORMATION: hybrid human and porcine factor VIII sequence
<221> NAME/KEY: CDS
<222> LOCATION: (1)...(4401)
<223> OTHER INFORMATION: HP47/OL -- factor VIII having the following
      domains:  A1p-A2h-app-A3p-C1h-C2h

<400> SEQUENCE: 18 atg cag cta gag ctc tcc acc tgt gtc ttt ctg tgt ctc ttg cca ctc        48
Met Gln Leu Glu Leu Ser Thr Cys Val Phe Leu Cys Leu Leu Pro Leu
 1               5                  10                  15 ggc ttt agt gcc atc agg aga tac tac ctg ggc gca gtg gaa ctg tcc        96
Gly Phe Ser Ala Ile Arg Arg Tyr Tyr Leu Gly Ala Val Glu Leu Ser
             20                  25                  30 tgg gac tac cgg caa agt gaa ctc ctc cgt gag ctg cac gtg gac acc       144
Trp Asp Tyr Arg Gln Ser Glu Leu Leu Arg Glu Leu His Val Asp Thr
         35                  40                  45 aga ttt cct gct aca gcg cca gga gct ctt ccg ttg ggc ccg tca gtc       192
Arg Phe Pro Ala Thr Ala Pro Gly Ala Leu Pro Leu Gly Pro Ser Val
     50                  55                  60 ctg tac aaa aag act gtg ttc gta gag ttc acg gat caa ctt ttc agc       240
Leu Tyr Lys Lys Thr Val Phe Val Glu Phe Thr Asp Gln Leu Phe Ser
 65                  70                  75                  80 gtt gcc agg ccc agg cca cca tgg atg ggt ctg ctg ggt cct acc atc       288
Val Ala Arg Pro Arg Pro Pro Trp Met Gly Leu Leu Gly Pro Thr Ile
                 85                  90                  95 cag gct gag gtt tac gac acg gtg gtc gtt acc ctg aag aac atg gct       336
Gln Ala Glu Val Tyr Asp Thr Val Val Val Thr Leu Lys Asn Met Ala
            100                 105                 110 tct cat ccc gtt agt ctt cac gct gtc ggc gtc tcc ttc tgg aaa tct       384
Ser His Pro Val Ser Leu His Ala Val Gly Val Ser Phe Trp Lys Ser
        115                 120                 125 tcc gaa ggc gct gaa tat gag gat cac acc agc caa agg gag aag gaa       432
Ser Glu Gly Ala Glu Tyr Glu Asp His Thr Ser Gln Arg Glu Lys Glu
    130                 135                 140 gac gat aaa gtc ctt ccc ggt aaa agc caa acc tac gtc tgg cag gtc       480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctt acc tac       528
Leu Lys Glu Asn Gly Pro Thr Ala Ser Asp Pro Pro Cys Leu Thr Tyr
                165                 170                 175 tca tac ctg tct cac gtg gac ctg gtg aaa gac ctg aat tcg ggc ctc       576
Ser Tyr Leu Ser His Val Asp Leu Val Lys Asp Leu Asn Ser Gly Leu
            180                 185                 190 att gga gcc ctg ctg gtt tgt aga gaa ggg agt ctg acc aga gaa agg       624
Ile Gly Ala Leu Leu Val Cys Arg Glu Gly Ser Leu Thr Arg Glu Arg
        195                 200                 205 acc cag aac ctg cac gaa ttt gta cta ctt ttt gct gtc ttt gat gaa       672
Thr Gln Asn Leu His Glu Phe Val Leu Leu Phe Ala Val Phe Asp Glu
    210                 215                 220 ggg aaa agt tgg cac tca gca aga aat gac tcc tgg aca cgg gcc atg       720
Gly Lys Ser Trp His Ser Ala Arg Asn Asp Ser Trp Thr Arg Ala Met
225                 230                 235                 240 gat ccc gca cct gcc agg gcc cag cct gca atg cac aca gtc aat ggc       768
Asp Pro Ala Pro Ala Arg Ala Gln Pro Ala Met His Thr Val Asn Gly
                245                 250                 255 tat gtc aac agg tct ctg cca ggt ctg atc gga tgt cat aag aaa tca       816
Tyr Val Asn Arg Ser Leu Pro Gly Leu Ile Gly Cys His Lys Lys Ser
            260                 265                 270 gtc tac tgg cac gtg att gga atg ggc acc agc ccg gaa gtg cac tcc       864
Val Tyr Trp His Val Ile Gly Met Gly Thr Ser Pro Glu Val His Ser
        275                 280                 285
```

```
att ttt ctt gaa ggc cac acg ttt ctc gtg agg cac cat cgc cag gct         912
Ile Phe Leu Glu Gly His Thr Phe Leu Val Arg His His Arg Gln Ala
290                 295                 300 tcc ttg gag atc tcg cca cta act ttc ctc act gct cag aca ttc ctg         960
Ser Leu Glu Ile Ser Pro Leu Thr Phe Leu Thr Ala Gln Thr Phe Leu
305                 310                 315                 320 atg gac ctt ggc cag ttc cta ctg ttt tgt cat atc tct tcc cac cac        1008
Met Asp Leu Gly Gln Phe Leu Leu Phe Cys His Ile Ser Ser His His
            325                 330                 335 cat ggt ggc atg gag gct cac gtc aga gta gaa agc tgc gcc gag gag        1056
His Gly Gly Met Glu Ala His Val Arg Val Glu Ser Cys Ala Glu Glu
        340                 345                 350 ccc cag ctg cgg agg aaa gct gat gaa gag gaa gat tat gat gac aat        1104
Pro Gln Leu Arg Arg Lys Ala Asp Glu Glu Glu Asp Tyr Asp Asp Asn
    355                 360                 365 ttg tac gac tcg gac atg gac gtg gtc cgg ctc gat ggt gac gac gtg        1152
Leu Tyr Asp Ser Asp Met Asp Val Val Arg Leu Asp Gly Asp Asp Val
370                 375                 380 tct ccc ttt atc caa atc cgc tca gtt gcc aag aag cat cct aaa act        1200
Ser Pro Phe Ile Gln Ile Arg Ser Val Ala Lys Lys His Pro Lys Thr
385                 390                 395                 400 tgg gta cat tac att gct gct gaa gag gag gac tgg gac tat gct ccc        1248
Trp Val His Tyr Ile Ala Ala Glu Glu Glu Asp Trp Asp Tyr Ala Pro
            405                 410                 415 tta gtc ctc gcc ccc gat gac aga agt tat aaa agt caa tat ttg aac        1296
Leu Val Leu Ala Pro Asp Asp Arg Ser Tyr Lys Ser Gln Tyr Leu Asn
        420                 425                 430 aat ggc cct cag cgg att ggt agg aag tac aaa aaa gtc cga ttt atg        1344
Asn Gly Pro Gln Arg Ile Gly Arg Lys Tyr Lys Lys Val Arg Phe Met
    435                 440                 445 gca tac aca gat gaa acc ttt aag acg cgt gaa gct att cag cat gaa        1392
Ala Tyr Thr Asp Glu Thr Phe Lys Thr Arg Glu Ala Ile Gln His Glu
450                 455                 460 tca gga atc ttg gga cct tta ctt tat ggg gaa gtt gga gac aca ctg        1440
Ser Gly Ile Leu Gly Pro Leu Leu Tyr Gly Glu Val Gly Asp Thr Leu
465                 470                 475                 480 ttg att ata ttt aag aat caa gca agc aga cca tat aac atc tac cct        1488
Leu Ile Ile Phe Lys Asn Gln Ala Ser Arg Pro Tyr Asn Ile Tyr Pro
            485                 490                 495 cac gga atc act gat gtc cgt cct ttg tat tca agg aga tta cca aaa        1536
His Gly Ile Thr Asp Val Arg Pro Leu Tyr Ser Arg Arg Leu Pro Lys
        500                 505                 510 ggt gta aaa cat ttg aag gat ttt cca att ctg cca gga gaa ata ttc        1584
Gly Val Lys His Leu Lys Asp Phe Pro Ile Leu Pro Gly Glu Ile Phe
    515                 520                 525 aaa tat aaa tgg aca gtg act gta gaa gat ggg cca act aaa tca gat        1632
Lys Tyr Lys Trp Thr Val Thr Val Glu Asp Gly Pro Thr Lys Ser Asp
530                 535                 540 ccg cgg tgc ctg acc cgc tat tac tct agt ttc gtt aat atg gag aga        1680
Pro Arg Cys Leu Thr Arg Tyr Tyr Ser Ser Phe Val Asn Met Glu Arg
545                 550                 555                 560 gat cta gct tca gga ctc att ggc cct ctc ctc atc tgc tac aaa gaa        1728
Asp Leu Ala Ser Gly Leu Ile Gly Pro Leu Leu Ile Cys Tyr Lys Glu
            565                 570                 575 tct gta gat caa aga gga aac cag ata atg tca gac aag agg aat gtc        1776
Ser Val Asp Gln Arg Gly Asn Gln Ile Met Ser Asp Lys Arg Asn Val
        580                 585                 590 atc ctg ttt tct gta ttt gat gag aac cga agc tgg tac ctc aca gag        1824
Ile Leu Phe Ser Val Phe Asp Glu Asn Arg Ser Trp Tyr Leu Thr Glu
    595                 600                 605
```

| | | |
|---|---|---|
| aat ata caa cgc ttt ctc ccc aat cca gct gga gtg cag ctt gag gat<br>Asn Ile Gln Arg Phe Leu Pro Asn Pro Ala Gly Val Gln Leu Glu Asp<br>610                              615                        620 | | 1872 |
| cca gag ttc caa gcc tcc aac atc atg cac agc atc aat ggc tat gtt<br>Pro Glu Phe Gln Ala Ser Asn Ile Met His Ser Ile Asn Gly Tyr Val<br>625                              630                        635                        640 | | 1920 |
| ttt gat agt ttg cag ttg tca gtt tgt ttg cat gag gtg gca tac tgg<br>Phe Asp Ser Leu Gln Leu Ser Val Cys Leu His Glu Val Ala Tyr Trp<br>                          645                        650                        655 | | 1968 |
| tac att cta agc att gga gca cag act gac ttc ctt tct gtc ttc ttc<br>Tyr Ile Leu Ser Ile Gly Ala Gln Thr Asp Phe Leu Ser Val Phe Phe<br>                    660                        665                        670 | | 2016 |
| tct gga tat acc ttc aaa cac aaa atg gtc tat gaa gac aca ctc acc<br>Ser Gly Tyr Thr Phe Lys His Lys Met Val Tyr Glu Asp Thr Leu Thr<br>              675                        680                        685 | | 2064 |
| cta ttc cca ttc tca gga gaa act gtc ttc atg tcg atg gaa aac cca<br>Leu Phe Pro Phe Ser Gly Glu Thr Val Phe Met Ser Met Glu Asn Pro<br>690                              695                        700 | | 2112 |
| ggt cta tgg att ctg ggg tgc cac aac tca gac ttt cgg aac aga ggc<br>Gly Leu Trp Ile Leu Gly Cys His Asn Ser Asp Phe Arg Asn Arg Gly<br>705                              710                        715                        720 | | 2160 |
| atg acc gcc tta ctg aag gtt tct agt tgt gac aag aac act ggt gat<br>Met Thr Ala Leu Leu Lys Val Ser Ser Cys Asp Lys Asn Thr Gly Asp<br>                          725                        730                        735 | | 2208 |
| tat tac gag gac agt tat gaa gat att tca gca tac ttg ctg agt aaa<br>Tyr Tyr Glu Asp Ser Tyr Glu Asp Ile Ser Ala Tyr Leu Leu Ser Lys<br>                    740                        745                        750 | | 2256 |
| aac aat gcc att gaa cct agg agc ttt gcc cag aat tca aga ccc cct<br>Asn Asn Ala Ile Glu Pro Arg Ser Phe Ala Gln Asn Ser Arg Pro Pro<br>              755                        760                        765 | | 2304 |
| agt gcg agc gct cca aag cct ccg gtc ctg cga cgg cat cag agg gac<br>Ser Ala Ser Ala Pro Lys Pro Pro Val Leu Arg Arg His Gln Arg Asp<br>770                              775                        780 | | 2352 |
| ata agc ctt cct act ttt cag ccg gag gaa gac aaa atg gac tat gat<br>Ile Ser Leu Pro Thr Phe Gln Pro Glu Glu Asp Lys Met Asp Tyr Asp<br>785                              790                        795                        800 | | 2400 |
| gat atc ttc tca act gaa acg aag gga gaa gat ttt gac att tac ggt<br>Asp Ile Phe Ser Thr Glu Thr Lys Gly Glu Asp Phe Asp Ile Tyr Gly<br>                          805                        810                        815 | | 2448 |
| gag gat gaa aat cag gac cct cgc agc ttt cag aag aga acc cga cac<br>Glu Asp Glu Asn Gln Asp Pro Arg Ser Phe Gln Lys Arg Thr Arg His<br>                    820                        825                        830 | | 2496 |
| tat ttc att gct gcg gtg gag cag ctc tgg gat tac ggg atg agc gaa<br>Tyr Phe Ile Ala Ala Val Glu Gln Leu Trp Asp Tyr Gly Met Ser Glu<br>              835                        840                        845 | | 2544 |
| tcc ccc cgg gcg cta aga aac agg gct cag aac gga gag gtg cct cgg<br>Ser Pro Arg Ala Leu Arg Asn Arg Ala Gln Asn Gly Glu Val Pro Arg<br>850                              855                        860 | | 2592 |
| ttc aag aag gtg gtc ttc cgg gaa ttt gct gac ggc tcc ttc acg cag<br>Phe Lys Lys Val Val Phe Arg Glu Phe Ala Asp Gly Ser Phe Thr Gln<br>865                              870                        875                        880 | | 2640 |
| ccg tcg tac cgc ggg gaa ctc aac aaa cac ttg ggg ctc ttg gga ccc<br>Pro Ser Tyr Arg Gly Glu Leu Asn Lys His Leu Gly Leu Leu Gly Pro<br>                          885                        890                        895 | | 2688 |
| tac atc aga gcg gaa gtt gaa gac aac atc atg gta act ttc aaa aac<br>Tyr Ile Arg Ala Glu Val Glu Asp Asn Ile Met Val Thr Phe Lys Asn<br>              900                        905                        910 | | 2736 |
| cag gcg tct cgt ccc tat tcc ttc tac tcg agc ctt att tct tat ccg<br>Gln Ala Ser Arg Pro Tyr Ser Phe Tyr Ser Ser Leu Ile Ser Tyr Pro<br>              915                        920                        925 | | 2784 |

```
gat gat cag gag caa ggg gca gaa cct cga cac aac ttc gtc cag cca         2832
Asp Asp Gln Glu Gln Gly Ala Glu Pro Arg His Asn Phe Val Gln Pro
        930                 935                 940 aat gaa acc aga act tac ttt tgg aaa gtg cag cat cac atg gca ccc         2880
Asn Glu Thr Arg Thr Tyr Phe Trp Lys Val Gln His His Met Ala Pro
945                 950                 955                 960 aca gaa gac gag ttt gac tgc aaa gcc tgg gcc tac ttt tct gat gtt         2928
Thr Glu Asp Glu Phe Asp Cys Lys Ala Trp Ala Tyr Phe Ser Asp Val
                965                 970                 975 gac ctg gaa aaa gat gtg cac tca ggc ttg atc ggc ccc ctt ctg atc         2976
Asp Leu Glu Lys Asp Val His Ser Gly Leu Ile Gly Pro Leu Leu Ile
            980                 985                 990 tgc cgc gcc aac acc ctg aac gct gct cac ggt aga caa gtg acc gtg         3024
Cys Arg Ala Asn Thr Leu Asn Ala Ala His Gly Arg Gln Val Thr Val
        995                 1000                1005 caa gaa ttt gct ctg ttt ttc act att ttt gat gag aca aag agc tgg         3072
Gln Glu Phe Ala Leu Phe Phe Thr Ile Phe Asp Glu Thr Lys Ser Trp
    1010                1015                1020 tac ttc act gaa aat gtg gaa agg aac tgc cgg gcc ccc tgc cat ctg         3120
Tyr Phe Thr Glu Asn Val Glu Arg Asn Cys Arg Ala Pro Cys His Leu
1025                1030                1035                1040 cag atg gag gac ccc act ctg aaa gaa aac tat cgc ttc cat gca atc         3168
Gln Met Glu Asp Pro Thr Leu Lys Glu Asn Tyr Arg Phe His Ala Ile
                1045                1050                1055 aat ggc tat gtg atg gat aca ctc cct ggc tta gta atg gct cag aat         3216
Asn Gly Tyr Val Met Asp Thr Leu Pro Gly Leu Val Met Ala Gln Asn
            1060                1065                1070 caa agg atc cga tgg tat ctg ctc agc atg ggc agc aat gaa aat atc         3264
Gln Arg Ile Arg Trp Tyr Leu Leu Ser Met Gly Ser Asn Glu Asn Ile
        1075                1080                1085 cat tcg att cat ttt agc gga cac gtg ttc agt gta cgg aaa aag gag         3312
His Ser Ile His Phe Ser Gly His Val Phe Ser Val Arg Lys Lys Glu
    1090                1095                1100 gag tat aaa atg gcc gtg tac aat ctc tat ccg ggt gtc ttt gag aca         3360
Glu Tyr Lys Met Ala Val Tyr Asn Leu Tyr Pro Gly Val Phe Glu Thr
1105                1110                1115                1120 gtg gaa atg cta ccg tcc aaa gtt gga att tgg cga ata gaa tgc ctg         3408
Val Glu Met Leu Pro Ser Lys Val Gly Ile Trp Arg Ile Glu Cys Leu
                1125                1130                1135 att ggc gag cac ctg caa gct ggg atg agc acg act ttc ctg gtg tac         3456
Ile Gly Glu His Leu Gln Ala Gly Met Ser Thr Thr Phe Leu Val Tyr
            1140                1145                1150 agc aag aag tgt cag act ccc ctg gga atg gct tct gga cac att aga         3504
Ser Lys Lys Cys Gln Thr Pro Leu Gly Met Ala Ser Gly His Ile Arg
        1155                1160                1165 gat ttt cag att aca gct tca gga caa tat gga cag tgg gcc cca aag         3552
Asp Phe Gln Ile Thr Ala Ser Gly Gln Tyr Gly Gln Trp Ala Pro Lys
    1170                1175                1180 ctg gcc aga ctt cat tat tcc gga tca atc aat gcc tgg agc acc aag         3600
Leu Ala Arg Leu His Tyr Ser Gly Ser Ile Asn Ala Trp Ser Thr Lys
1185                1190                1195                1200 gag ccc ttt tct tgg atc aag gtg gat ctg ttg gca cca atg att att         3648
Glu Pro Phe Ser Trp Ile Lys Val Asp Leu Leu Ala Pro Met Ile Ile
                1205                1210                1215 cac ggc atc aag acc cag ggt gcc cgt cag aag ttc tcc agc ctc tac         3696
His Gly Ile Lys Thr Gln Gly Ala Arg Gln Lys Phe Ser Ser Leu Tyr
            1220                1225                1230 atc tct cag ttt atc atc atg tat agt ctt gat ggg aag aag tgg cag         3744
Ile Ser Gln Phe Ile Ile Met Tyr Ser Leu Asp Gly Lys Lys Trp Gln
        1235                1240                1245
```

```
act tat cga gga aat tcc act gga acc tta atg gtc ttc ttt ggc aat      3792
Thr Tyr Arg Gly Asn Ser Thr Gly Thr Leu Met Val Phe Phe Gly Asn
    1250                1255                1260 gtg gat tca tct ggg ata aaa cac aat att ttt aac cct cca att att      3840
Val Asp Ser Ser Gly Ile Lys His Asn Ile Phe Asn Pro Pro Ile Ile
1265                1270                1275                1280 gct cga tac atc cgt ttg cac cca act cat tat agc att cgc agc act      3888
Ala Arg Tyr Ile Arg Leu His Pro Thr His Tyr Ser Ile Arg Ser Thr
            1285                1290                1295 ctt cgc atg gag ttg atg ggc tgt gat tta aat agt tgc agc atg cca      3936
Leu Arg Met Glu Leu Met Gly Cys Asp Leu Asn Ser Cys Ser Met Pro
        1300                1305                1310 ttg gga atg gag agt aaa gca ata tca gat gca cag att act gct tca      3984
Leu Gly Met Glu Ser Lys Ala Ile Ser Asp Ala Gln Ile Thr Ala Ser
    1315                1320                1325 tcc tac ttt acc aat atg ttt gcc acc tgg tct cct tca aaa gct cga      4032
Ser Tyr Phe Thr Asn Met Phe Ala Thr Trp Ser Pro Ser Lys Ala Arg
1330                1335                1340 ctt cac ctc caa ggg agg agt aat gcc tgg aga cct cag gtg aat aat      4080
Leu His Leu Gln Gly Arg Ser Asn Ala Trp Arg Pro Gln Val Asn Asn
1345                1350                1355                1360 cca aaa gag tgg ctg caa gtg gac ttc cag aag aca atg aaa gtc aca      4128
Pro Lys Glu Trp Leu Gln Val Asp Phe Gln Lys Thr Met Lys Val Thr
            1365                1370                1375 gga gta act act cag gga gta aaa tct ctg ctt acc agc atg tat gtg      4176
Gly Val Thr Thr Gln Gly Val Lys Ser Leu Leu Thr Ser Met Tyr Val
        1380                1385                1390 aag gag ttc ctc atc tcc agc agt caa gat ggc cat cag tgg act ctc      4224
Lys Glu Phe Leu Ile Ser Ser Ser Gln Asp Gly His Gln Trp Thr Leu
    1395                1400                1405 ttt ttt cag aat ggc aaa gta aag gtt ttt cag gga aat caa gac tcc      4272
Phe Phe Gln Asn Gly Lys Val Lys Val Phe Gln Gly Asn Gln Asp Ser
1410                1415                1420 ttc aca cct gtg gtg aac tct cta gac cca ccg tta ctg act cgc tac      4320
Phe Thr Pro Val Val Asn Ser Leu Asp Pro Pro Leu Leu Thr Arg Tyr
1425                1430                1435                1440 ctt cga att cac ccc cag agt tgg gtg cac cag att gcc ctg agg atg      4368
Leu Arg Ile His Pro Gln Ser Trp Val His Gln Ile Ala Leu Arg Met
            1445                1450                1455 gag gtt ctg ggc tgc gag gca cag gac ctc tac                          4401
Glu Val Leu Gly Cys Glu Ala Gln Asp Leu Tyr
        1460                1465

<210> SEQ ID NO 19
<211> LENGTH: 1467
<212> TYPE: PRT
<213> ORGANISM: Artificial Sequence
<220> FEATURE:
<223> OTHER INFORMATION: HP47/OL -- factor VIII having the following
      domains:  A1p-A2h-app-A3p-C1h-C2h

<400> SEQUENCE: 19

Met Gln Leu Glu Leu Ser Thr Cys Val Phe Leu Cys Leu Leu Pro Leu
1               5                   10                  15

Gly Phe Ser Ala Ile Arg Arg Tyr Tyr Leu Gly Ala Val Glu Leu Ser
            20                  25                  30

Trp Asp Tyr Arg Gln Ser Glu Leu Leu Arg Glu Leu His Val Asp Thr
        35                  40                  45

Arg Phe Pro Ala Thr Ala Pro Gly Ala Leu Pro Leu Gly Pro Ser Val
    50                  55                  60

Leu Tyr Lys Lys Thr Val Phe Val Glu Phe Thr Asp Gln Leu Phe Ser
```

```
                 65                  70                  75                  80
Val Ala Arg Pro Arg Pro Pro Trp Met Gly Leu Leu Gly Pro Thr Ile
                         85                  90                  95

Gln Ala Glu Val Tyr Asp Thr Val Val Thr Leu Lys Asn Met Ala
                100                 105                 110

Ser His Pro Val Ser Leu His Ala Val Gly Val Ser Phe Trp Lys Ser
                115                 120                 125

Ser Glu Gly Ala Glu Tyr Glu Asp His Thr Ser Gln Arg Glu Lys Glu
                130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                    165                 170                 175

Ser Tyr Leu Ser His Val Asp Leu Val Lys Asp Leu Asn Ser Gly Leu
                180                 185                 190

Ile Gly Ala Leu Leu Val Cys Arg Glu Gly Ser Leu Thr Arg Glu Arg
                195                 200                 205

Thr Gln Asn Leu His Glu Phe Val Leu Leu Phe Ala Val Phe Asp Glu
                210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                    245                 250                 255

Tyr Val Asn Arg Ser Leu Pro Gly Leu Ile Gly Cys His Lys Lys Ser
                260                 265                 270

Val Tyr Trp His Val Ile Gly Met Gly Thr Ser Pro Glu Val His Ser
                275                 280                 285

Ile Phe Leu Glu Gly His Thr Phe Leu Val Arg His His Arg Gln Ala
                290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                    325                 330                 335

His Gly Gly Met Glu Ala His Val Arg Val Glu Ser Cys Ala Glu Glu
                340                 345                 350

Pro Gln Leu Arg Arg Lys Ala Asp Glu Glu Asp Tyr Asp Asp Asn
                355                 360                 365

Leu Tyr Asp Ser Asp Met Asp Val Val Arg Leu Asp Gly Asp Asp Val
                370                 375                 380

Ser Pro Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                    405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
                435                 440                 445

Ala Tyr Thr Asp Glu Thr Phe Lys Thr Arg Glu Ala Ile Gln His Glu
                450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                    485                 490                 495
```

```
His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ala Gln Asn Ser Arg Pro Pro
            755                 760                 765

Ser Ala Ser Ala Pro Lys Pro Pro Val Leu Arg Arg His Gln Arg Asp
            770                 775                 780

Ile Ser Leu Pro Thr Phe Gln Pro Glu Glu Asp Lys Met Asp Tyr Asp
785                 790                 795                 800

Asp Ile Phe Ser Thr Glu Thr Lys Gly Glu Asp Phe Asp Ile Tyr Gly
                805                 810                 815

Glu Asp Glu Asn Gln Asp Pro Arg Ser Phe Gln Lys Arg Thr Arg His
                820                 825                 830

Tyr Phe Ile Ala Ala Val Glu Gln Leu Trp Asp Tyr Gly Met Ser Glu
            835                 840                 845

Ser Pro Arg Ala Leu Arg Asn Arg Ala Gln Asn Gly Glu Val Pro Arg
            850                 855                 860

Phe Lys Lys Val Val Phe Arg Glu Phe Ala Asp Gly Ser Phe Thr Gln
865                 870                 875                 880

Pro Ser Tyr Arg Gly Glu Leu Asn Lys His Leu Gly Leu Leu Gly Pro
                885                 890                 895

Tyr Ile Arg Ala Glu Val Glu Asp Asn Ile Met Val Thr Phe Lys Asn
                900                 905                 910

Gln Ala Ser Arg Pro Tyr Ser Phe Tyr Ser Ser Leu Ile Ser Tyr Pro
            915                 920                 925
```

```
Asp Asp Gln Glu Gln Gly Ala Glu Pro Arg His Asn Phe Val Gln Pro
    930                 935                 940

Asn Glu Thr Arg Thr Tyr Phe Trp Lys Val Gln His His Met Ala Pro
945                 950                 955                 960

Thr Glu Asp Glu Phe Asp Cys Lys Ala Trp Ala Tyr Phe Ser Asp Val
                965                 970                 975

Asp Leu Glu Lys Asp Val His Ser Gly Leu Ile Gly Pro Leu Leu Ile
                980                 985                 990

Cys Arg Ala Asn Thr Leu Asn Ala Ala His Gly Arg Gln Val Thr Val
                995                 1000                1005

Gln Glu Phe Ala Leu Phe Phe Thr Ile Phe Asp Glu Thr Lys Ser Trp
    1010                1015                1020

Tyr Phe Thr Glu Asn Val Glu Arg Asn Cys Arg Ala Pro Cys His Leu
1025                1030                1035                1040

Gln Met Glu Asp Pro Thr Leu Lys Glu Asn Tyr Arg Phe His Ala Ile
                1045                1050                1055

Asn Gly Tyr Val Met Asp Thr Leu Pro Gly Leu Val Met Ala Gln Asn
                1060                1065                1070

Gln Arg Ile Arg Trp Tyr Leu Leu Ser Met Gly Ser Asn Glu Asn Ile
                1075                1080                1085

His Ser Ile His Phe Ser Gly His Val Phe Ser Val Arg Lys Lys Glu
    1090                1095                1100

Glu Tyr Lys Met Ala Val Tyr Asn Leu Tyr Pro Gly Val Phe Glu Thr
1105                1110                1115                1120

Val Glu Met Leu Pro Ser Lys Val Gly Ile Trp Arg Ile Glu Cys Leu
                1125                1130                1135

Ile Gly Glu His Leu Gln Ala Gly Met Ser Thr Thr Phe Leu Val Tyr
                1140                1145                1150

Ser Lys Lys Cys Gln Thr Pro Leu Gly Met Ala Ser Gly His Ile Arg
    1155                1160                1165

Asp Phe Gln Ile Thr Ala Ser Gly Gln Tyr Gly Gln Trp Ala Pro Lys
    1170                1175                1180

Leu Ala Arg Leu His Tyr Ser Gly Ser Ile Asn Ala Trp Ser Thr Lys
1185                1190                1195                1200

Glu Pro Phe Ser Trp Ile Lys Val Asp Leu Leu Ala Pro Met Ile Ile
                1205                1210                1215

His Gly Ile Lys Thr Gln Gly Ala Arg Gln Lys Phe Ser Ser Leu Tyr
    1220                1225                1230

Ile Ser Gln Phe Ile Ile Met Tyr Ser Leu Asp Gly Lys Lys Trp Gln
    1235                1240                1245

Thr Tyr Arg Gly Asn Ser Thr Gly Thr Leu Met Val Phe Phe Gly Asn
    1250                1255                1260

Val Asp Ser Ser Gly Ile Lys His Asn Ile Phe Asn Pro Pro Ile Ile
1265                1270                1275                1280

Ala Arg Tyr Ile Arg Leu His Pro Thr His Tyr Ser Ile Arg Ser Thr
                1285                1290                1295

Leu Arg Met Glu Leu Met Gly Cys Asp Leu Asn Ser Cys Ser Met Pro
                1300                1305                1310

Leu Gly Met Glu Ser Lys Ala Ile Ser Asp Ala Gln Ile Thr Ala Ser
                1315                1320                1325

Ser Tyr Phe Thr Asn Met Phe Ala Thr Trp Ser Pro Ser Lys Ala Arg
                1330                1335                1340

Leu His Leu Gln Gly Arg Ser Asn Ala Trp Arg Pro Gln Val Asn Asn
```

```
                1345           1350           1355           1360

Pro Lys Glu Trp Leu Gln Val Asp Phe Gln Lys Thr Met Lys Val Thr
                    1365               1370               1375

Gly Val Thr Thr Gln Gly Val Lys Ser Leu Leu Thr Ser Met Tyr Val
        1380               1385               1390

Lys Glu Phe Leu Ile Ser Ser Ser Gln Asp Gly His Gln Trp Thr Leu
            1395               1400           1405

Phe Phe Gln Asn Gly Lys Val Lys Val Phe Gln Gly Asn Gln Asp Ser
        1410               1415               1420

Phe Thr Pro Val Val Asn Ser Leu Asp Pro Pro Leu Leu Thr Arg Tyr
1425               1430               1435               1440

Leu Arg Ile His Pro Gln Ser Trp Val His Gln Ile Ala Leu Arg Met
            1445               1450               1455

Glu Val Leu Gly Cys Glu Ala Gln Asp Leu Tyr
            1460               1465

<210> SEQ ID NO 20
<211> LENGTH: 4401
<212> TYPE: DNA
<213> ORGANISM: Artificial Sequence
<220> FEATURE:
<223> OTHER INFORMATION: hybrid human and porcine factor VIII sequence
<221> NAME/KEY: CDS
<222> LOCATION: (1)...(4401)
<223> OTHER INFORMATION: HP63/OL -- factor VIII variant

<400> SEQUENCE: 20 atg cag cta gag ctc tcc acc tgt gtc ttt ctg tgt ctc ttg cca ctc       48
Met Gln Leu Glu Leu Ser Thr Cys Val Phe Leu Cys Leu Leu Pro Leu
  1               5                  10                  15 ggc ttt agt gcc atc agg aga tac tac ctg ggc gca gtg gaa ctg tcc       96
Gly Phe Ser Ala Ile Arg Arg Tyr Tyr Leu Gly Ala Val Glu Leu Ser
             20                  25                  30 tgg gac tac cgg caa agt gaa ctc ctc cgt gag ctg cac gtg gac acc      144
Trp Asp Tyr Arg Gln Ser Glu Leu Leu Arg Glu Leu His Val Asp Thr
         35                  40                  45 aga ttt cct gct aca gcg cca gga gct ctt ccg ttg ggc ccg tca gtc      192
Arg Phe Pro Ala Thr Ala Pro Gly Ala Leu Pro Leu Gly Pro Ser Val
     50                  55                  60 ctg tac aaa aag act gtg ttc gta gag ttc acg gat caa ctt ttc agc      240
Leu Tyr Lys Lys Thr Val Phe Val Glu Phe Thr Asp Gln Leu Phe Ser
 65                  70                  75                  80 gtt gcc agg ccc agg cca cca tgg atg ggt ctg ctg ggt cct acc atc      288
Val Ala Arg Pro Arg Pro Pro Trp Met Gly Leu Leu Gly Pro Thr Ile
                 85                  90                  95 cag gct gag gtt tac gac acg gtg gtc gtt acc ctg aag aac atg gct      336
Gln Ala Glu Val Tyr Asp Thr Val Val Val Thr Leu Lys Asn Met Ala
            100                 105                 110 tct cat ccc gtt agt ctt cac gct gtc ggc gtc tcc ttc tgg aaa tct      384
Ser His Pro Val Ser Leu His Ala Val Gly Val Ser Phe Trp Lys Ser
        115                 120                 125 tcc gaa ggc gct gaa tat gag gat cac acc agc caa agg gag aag gaa      432
Ser Glu Gly Ala Glu Tyr Glu Asp His Thr Ser Gln Arg Glu Lys Glu
    130                 135                 140 gac gat aaa gtc ctt ccc ggt aaa agc caa acc tac gtc tgg cag gtc      480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctt acc tac      528
Leu Lys Glu Asn Gly Pro Thr Ala Ser Asp Pro Pro Cys Leu Thr Tyr
                165                 170                 175
```

```
tca tac ctg tct cac gtg gac ctg gtg aaa gac ctg aat tcg ggc ctc        576
Ser Tyr Leu Ser His Val Asp Leu Val Lys Asp Leu Asn Ser Gly Leu
        180                 185                 190 att gga gcc ctg ctg gtt tgt aga gaa ggg agt ctg acc aga gaa agg        624
Ile Gly Ala Leu Leu Val Cys Arg Glu Gly Ser Leu Thr Arg Glu Arg
    195                 200                 205 acc cag aac ctg cac gaa ttt gta cta ctt ttt gct gtc ttt gat gaa        672
Thr Gln Asn Leu His Glu Phe Val Leu Leu Phe Ala Val Phe Asp Glu
210                 215                 220 ggg aaa agt tgg cac tca gca aga aat gac tcc tgg aca cgg gcc atg        720
Gly Lys Ser Trp His Ser Ala Arg Asn Asp Ser Trp Thr Arg Ala Met
225                 230                 235                 240 gat ccc gca cct gcc agg gcc cag cct gca atg cac aca gtc aat ggc        768
Asp Pro Ala Pro Ala Arg Ala Gln Pro Ala Met His Thr Val Asn Gly
            245                 250                 255 tat gtc aac agg tct ctg cca ggt ctg atc gga tgt cat aag aaa tca        816
Tyr Val Asn Arg Ser Leu Pro Gly Leu Ile Gly Cys His Lys Lys Ser
        260                 265                 270 gtc tac tgg cac gtg att gga atg ggc acc agc ccg gaa gtg cac tcc        864
Val Tyr Trp His Val Ile Gly Met Gly Thr Ser Pro Glu Val His Ser
    275                 280                 285 att ttt ctt gaa ggc cac acg ttt ctc gtg agg cac cat cgc cag gct        912
Ile Phe Leu Glu Gly His Thr Phe Leu Val Arg His His Arg Gln Ala
290                 295                 300 tcc ttg gag atc tcg cca cta act ttc ctc act gct cag aca ttc ctg        960
Ser Leu Glu Ile Ser Pro Leu Thr Phe Leu Thr Ala Gln Thr Phe Leu
305                 310                 315                 320 atg gac ctt ggc cag ttc cta ctg ttt tgt cat atc tct tcc cac cac       1008
Met Asp Leu Gly Gln Phe Leu Leu Phe Cys His Ile Ser Ser His His
            325                 330                 335 cat ggt ggc atg gag gct cac gtc aga gta gaa agc tgc gcc gag gag       1056
His Gly Gly Met Glu Ala His Val Arg Val Glu Ser Cys Ala Glu Glu
        340                 345                 350 ccc cag ctg cgg agg aaa gct gat gaa gag gaa gat tat gat gac aat       1104
Pro Gln Leu Arg Arg Lys Ala Asp Glu Glu Glu Asp Tyr Asp Asp Asn
    355                 360                 365 ttg tac gac tcg gac atg gac gtg gtc cgg ctc gat ggt gac gac gtg       1152
Leu Tyr Asp Ser Asp Met Asp Val Val Arg Leu Asp Gly Asp Asp Val
370                 375                 380 tct ccc ttt atc caa atc cgc tca gtt gcc aag aag cat cct aaa act       1200
Ser Pro Phe Ile Gln Ile Arg Ser Val Ala Lys Lys His Pro Lys Thr
385                 390                 395                 400 tgg gta cat tac att gct gct gaa gag gag gac tgg gac tat gct ccc       1248
Trp Val His Tyr Ile Ala Ala Glu Glu Glu Asp Trp Asp Tyr Ala Pro
            405                 410                 415 tta gtc ctc gcc ccc gat gac aga agt tat aaa agt caa tat ttg aac       1296
Leu Val Leu Ala Pro Asp Asp Arg Ser Tyr Lys Ser Gln Tyr Leu Asn
        420                 425                 430 aat ggc cct cag cgg att ggt agg aag tac aaa aaa gtc cga ttt atg       1344
Asn Gly Pro Gln Arg Ile Gly Arg Lys Tyr Lys Lys Val Arg Phe Met
    435                 440                 445 gca tac aca gat gaa acc ttt aag act cgt gaa gct att cag cat gaa       1392
Ala Tyr Thr Asp Glu Thr Phe Lys Thr Arg Glu Ala Ile Gln His Glu
450                 455                 460 tca gga atc ttg gga cct tta ctt tat ggg gaa gtt gga gac aca ctg       1440
Ser Gly Ile Leu Gly Pro Leu Leu Tyr Gly Glu Val Gly Asp Thr Leu
465                 470                 475                 480 ttg att ata ttt aag aat caa gca agc aga cca tat aac atc tac cct       1488
Leu Ile Ile Phe Lys Asn Gln Ala Ser Arg Pro Tyr Asn Ile Tyr Pro
            485                 490                 495
```

-continued

| | | |
|---|---|---|
| cac gga atc act gat gtc cgt cct ttg tat tca agg aga tta cca aaa<br>His Gly Ile Thr Asp Val Arg Pro Leu Tyr Ser Arg Arg Leu Pro Lys<br>              500                    505                  510 | | 1536 |
| ggt gta aaa cat ttg aag gat ttt cca att ctg cca gga gaa ata ttc<br>Gly Val Lys His Leu Lys Asp Phe Pro Ile Leu Pro Gly Glu Ile Phe<br>              515                    520                  525 | | 1584 |
| aaa tat aaa tgg aca gtg act gta gaa gat ggg cca act aaa tca gat<br>Lys Tyr Lys Trp Thr Val Thr Val Glu Asp Gly Pro Thr Lys Ser Asp<br>530                    535                    540 | | 1632 |
| cct cgg tgc ctg acc cgc tat tac tct agt ttc gtt aat atg gag aga<br>Pro Arg Cys Leu Thr Arg Tyr Tyr Ser Ser Phe Val Asn Met Glu Arg<br>545                    550                    555                  560 | | 1680 |
| gat cta gct tca gga ctc att ggc cct ctc ctc atc tgc tac aaa gaa<br>Asp Leu Ala Ser Gly Leu Ile Gly Pro Leu Leu Ile Cys Tyr Lys Glu<br>              565                    570                  575 | | 1728 |
| tct gta gat caa aga gga aac cag ata atg tca gac aag agg aat gtc<br>Ser Val Asp Gln Arg Gly Asn Gln Ile Met Ser Asp Lys Arg Asn Val<br>                    580                    585                  590 | | 1776 |
| atc ctg ttt tct gta ttt gat gag aac cga agc tgg tac ctc aca gag<br>Ile Leu Phe Ser Val Phe Asp Glu Asn Arg Ser Trp Tyr Leu Thr Glu<br>              595                    600                  605 | | 1824 |
| aat ata caa cgc ttt ctc ccc aat cca gct gga gtg cag ctt gag gat<br>Asn Ile Gln Arg Phe Leu Pro Asn Pro Ala Gly Val Gln Leu Glu Asp<br>610                    615                    620 | | 1872 |
| cca gag ttc caa gcc tcc aac atc atg cac agc atc aat ggc tat gtt<br>Pro Glu Phe Gln Ala Ser Asn Ile Met His Ser Ile Asn Gly Tyr Val<br>625                    630                    635                  640 | | 1920 |
| ttt gat agt ttg cag ttg tca gtt tgt ttg cat gag gtg gca tac tgg<br>Phe Asp Ser Leu Gln Leu Ser Val Cys Leu His Glu Val Ala Tyr Trp<br>              645                    650                  655 | | 1968 |
| tac att cta agc att gga gca cag act gac ttc ctt tct gtc ttc ttc<br>Tyr Ile Leu Ser Ile Gly Ala Gln Thr Asp Phe Leu Ser Val Phe Phe<br>                    660                    665                  670 | | 2016 |
| tct gga tat acc ttc aaa cac aaa atg gtc tat gaa gac aca ctc acc<br>Ser Gly Tyr Thr Phe Lys His Lys Met Val Tyr Glu Asp Thr Leu Thr<br>              675                    680                  685 | | 2064 |
| cta ttc cca ttc tca gga gaa act gtc ttc atg tcg atg gaa aac cca<br>Leu Phe Pro Phe Ser Gly Glu Thr Val Phe Met Ser Met Glu Asn Pro<br>690                    695                    700 | | 2112 |
| ggt cta tgg att ctg ggg tgc cac aac tca gac ttt cgg aac aga ggc<br>Gly Leu Trp Ile Leu Gly Cys His Asn Ser Asp Phe Arg Asn Arg Gly<br>705                    710                    715                  720 | | 2160 |
| atg acc gcc tta ctg aag gtt tct agt tgt gac aag aac act ggt gat<br>Met Thr Ala Leu Leu Lys Val Ser Ser Cys Asp Lys Asn Thr Gly Asp<br>                    725                    730                  735 | | 2208 |
| tat tac gag gac agt tat gaa gat att tca gca tac ttg ctg agt aaa<br>Tyr Tyr Glu Asp Ser Tyr Glu Asp Ile Ser Ala Tyr Leu Leu Ser Lys<br>                    740                    745                  750 | | 2256 |
| aac aat gcc att gaa cct agg agc ttc tcc cag aat tca aga cac cct<br>Asn Asn Ala Ile Glu Pro Arg Ser Phe Ser Gln Asn Ser Arg His Pro<br>              755                    760                  765 | | 2304 |
| agc act agg tct caa aac cca cca gtc ttg aaa cgc cat caa cgg gaa<br>Ser Thr Arg Ser Gln Asn Pro Pro Val Leu Lys Arg His Gln Arg Glu<br>770                    775                    780 | | 2352 |
| ata act cgt act act ctt cag tca gat caa gag gaa att gac tat gat<br>Ile Thr Arg Thr Thr Leu Gln Ser Asp Gln Glu Glu Ile Asp Tyr Asp<br>785                    790                    795                  800 | | 2400 |
| gat acc ata tca gtt gaa atg aag aag gaa gat ttt gac att tat gat<br>Asp Thr Ile Ser Val Glu Met Lys Lys Glu Asp Phe Asp Ile Tyr Asp<br>                    805                    810                  815 | | 2448 |

```
                                              -continued
gag gat gaa aat cag agc ccc cgc agc ttt caa aag aga acc cga cac    2496
Glu Asp Glu Asn Gln Ser Pro Arg Ser Phe Gln Lys Arg Thr Arg His
            820                 825                 830 tat ttc att gct gcg gtg gag cag ctc tgg gat tac ggg atg agc gaa    2544
Tyr Phe Ile Ala Ala Val Glu Gln Leu Trp Asp Tyr Gly Met Ser Glu
                835                 840                 845 tcc ccc cgg gcg cta aga aac agg gct cag aac gga gag gtg cct cgg    2592
Ser Pro Arg Ala Leu Arg Asn Arg Ala Gln Asn Gly Glu Val Pro Arg
850                 855                 860 ttc aag aag gtg gtc ttc cgg gaa ttt gct gac ggc tcc ttc acg cag    2640
Phe Lys Lys Val Val Phe Arg Glu Phe Ala Asp Gly Ser Phe Thr Gln
865                 870                 875                 880 ccg tcg tac cgc ggg gaa ctc aac aaa cac ttg ggg ctc ttg gga ccc    2688
Pro Ser Tyr Arg Gly Glu Leu Asn Lys His Leu Gly Leu Leu Gly Pro
                885                 890                 895 tac atc aga gcg gaa gtt gaa gac aac atc atg gta act ttc aaa aac    2736
Tyr Ile Arg Ala Glu Val Glu Asp Asn Ile Met Val Thr Phe Lys Asn
                900                 905                 910 cag gcg tct cgt ccc tat tcc ttc tac tcg agc ctt att tct tat ccg    2784
Gln Ala Ser Arg Pro Tyr Ser Phe Tyr Ser Ser Leu Ile Ser Tyr Pro
            915                 920                 925 gat gat cag gag caa ggg gca gaa cct cga aaa aac ttt gtc aag cct    2832
Asp Asp Gln Glu Gln Gly Ala Glu Pro Arg Lys Asn Phe Val Lys Pro
930                 935                 940 aat gaa acc aaa act tac ttt tgg aaa gtg cag cat cac atg gca ccc    2880
Asn Glu Thr Lys Thr Tyr Phe Trp Lys Val Gln His His Met Ala Pro
945                 950                 955                 960 aca gaa gac gag ttt gac tgc aaa gcc tgg gcc tac ttt tct gat gtt    2928
Thr Glu Asp Glu Phe Asp Cys Lys Ala Trp Ala Tyr Phe Ser Asp Val
                965                 970                 975 gac ctg gaa aaa gat gtg cac tca ggc ttg atc ggc ccc ctt ctg atc    2976
Asp Leu Glu Lys Asp Val His Ser Gly Leu Ile Gly Pro Leu Leu Ile
            980                 985                 990 tgc cgc gcc aac acc ctg aac gct gct cac ggt aga caa gtg acc gtg    3024
Cys Arg Ala Asn Thr Leu Asn Ala Ala His Gly Arg Gln Val Thr Val
        995                 1000                1005 caa gaa ttt gct ctg ttt ttc act att ttt gat gag aca aag agc tgg    3072
Gln Glu Phe Ala Leu Phe Phe Thr Ile Phe Asp Glu Thr Lys Ser Trp
    1010                1015                1020 tac ttc act gaa aat gtg gaa agg aac tgc cgg gcc ccc tgc cat ctg    3120
Tyr Phe Thr Glu Asn Val Glu Arg Asn Cys Arg Ala Pro Cys His Leu
1025                1030                1035                1040 cag atg gag gac ccc act ctg aaa gaa aac tat cgc ttc cat gca atc    3168
Gln Met Glu Asp Pro Thr Leu Lys Glu Asn Tyr Arg Phe His Ala Ile
                1045                1050                1055 aat ggc tat gtg atg gat aca ctc cct ggc tta gta atg gct cag aat    3216
Asn Gly Tyr Val Met Asp Thr Leu Pro Gly Leu Val Met Ala Gln Asn
            1060                1065                1070 caa agg atc cga tgg tat ctg ctc agc atg ggc agc aat gaa aat atc    3264
Gln Arg Ile Arg Trp Tyr Leu Leu Ser Met Gly Ser Asn Glu Asn Ile
        1075                1080                1085 cat tcg att cat ttt agc gga cac gtg ttc agt gta cgg aaa aag gag    3312
His Ser Ile His Phe Ser Gly His Val Phe Ser Val Arg Lys Lys Glu
    1090                1095                1100 gag tat aaa atg gcc gtg tac aat ctc tat ccg ggt gtc ttt gag aca    3360
Glu Tyr Lys Met Ala Val Tyr Asn Leu Tyr Pro Gly Val Phe Glu Thr
1105                1110                1115                1120 gtg gaa atg cta ccg tcc aaa gtt gga att tgg cgg aat aga tgc ctg    3408
Val Glu Met Leu Pro Ser Lys Val Gly Ile Trp Arg Asn Arg Cys Leu
                1125                1130                1135
```

```
                                        -continued
att ggc gag cac ctg caa gct ggg atg agc acg act ttc ctg gtg tac        3456
Ile Gly Glu His Leu Gln Ala Gly Met Ser Thr Thr Phe Leu Val Tyr
        1140                1145                1150 agc aag aag tgt cag act ccc ctg gga atg gct tct gga cac att aga        3504
Ser Lys Lys Cys Gln Thr Pro Leu Gly Met Ala Ser Gly His Ile Arg
        1155                1160                1165 gat ttt cag att aca gct tca gga caa tat gga cag tgg gcc cca aag        3552
Asp Phe Gln Ile Thr Ala Ser Gly Gln Tyr Gly Gln Trp Ala Pro Lys
        1170                1175                1180 ctg gcc aga ctt cat tat tcc gga tca atc aat gcc tgg agc acc aag        3600
Leu Ala Arg Leu His Tyr Ser Gly Ser Ile Asn Ala Trp Ser Thr Lys
1185                1190                1195                1200 gag ccc ttt tct tgg atc aag gtg gat ctg ttg gca cca atg att att        3648
Glu Pro Phe Ser Trp Ile Lys Val Asp Leu Leu Ala Pro Met Ile Ile
                1205                1210                1215 cac ggc atc aag acc cag ggt gcc cgt cag aag ttc tcc agc ctc tac        3696
His Gly Ile Lys Thr Gln Gly Ala Arg Gln Lys Phe Ser Ser Leu Tyr
        1220                1225                1230 atc tct cag ttt atc atc atg tat agt ctt gat ggg aag aag tgg cag        3744
Ile Ser Gln Phe Ile Ile Met Tyr Ser Leu Asp Gly Lys Lys Trp Gln
        1235                1240                1245 act tat cga gga aat tcc act gga acc tta atg gtc ttc ttt ggc aat        3792
Thr Tyr Arg Gly Asn Ser Thr Gly Thr Leu Met Val Phe Phe Gly Asn
        1250                1255                1260 gtg gat tca tct ggg ata aaa cac aat att ttt aac cct cca att att        3840
Val Asp Ser Ser Gly Ile Lys His Asn Ile Phe Asn Pro Pro Ile Ile
1265                1270                1275                1280 gct cga tac atc cgt ttg cac cca act cat tat agc att cgc agc act        3888
Ala Arg Tyr Ile Arg Leu His Pro Thr His Tyr Ser Ile Arg Ser Thr
                1285                1290                1295 ctt cgc atg gag ttg atg ggc tgt gat tta aat agt tgc agc atg cca        3936
Leu Arg Met Glu Leu Met Gly Cys Asp Leu Asn Ser Cys Ser Met Pro
        1300                1305                1310 ttg gga atg gag agt aaa gca ata tca gat gca cag att act gct tca        3984
Leu Gly Met Glu Ser Lys Ala Ile Ser Asp Ala Gln Ile Thr Ala Ser
        1315                1320                1325 tcc tac ttt acc aat atg ttt gcc acc tgg tct cct tca aaa gct cga        4032
Ser Tyr Phe Thr Asn Met Phe Ala Thr Trp Ser Pro Ser Lys Ala Arg
        1330                1335                1340 ctt cac ctc caa ggg agg agt aat gcc tgg aga cct cag gtg aat aat        4080
Leu His Leu Gln Gly Arg Ser Asn Ala Trp Arg Pro Gln Val Asn Asn
1345                1350                1355                1360 cca aaa gag tgg ctg caa gtg gac ttc cag aag aca atg aaa gtc aca        4128
Pro Lys Glu Trp Leu Gln Val Asp Phe Gln Lys Thr Met Lys Val Thr
                1365                1370                1375 gga gta act act cag gga gta aaa tct ctg ctt acc agc atg tat gtg        4176
Gly Val Thr Thr Gln Gly Val Lys Ser Leu Leu Thr Ser Met Tyr Val
        1380                1385                1390 aag gag ttc ctc atc tcc agc agt caa gat ggc cat cag tgg act ctc        4224
Lys Glu Phe Leu Ile Ser Ser Ser Gln Asp Gly His Gln Trp Thr Leu
        1395                1400                1405 ttt ttt cag aat ggc aaa gta aag gtt ttt cag gga aat caa gac tcc        4272
Phe Phe Gln Asn Gly Lys Val Lys Val Phe Gln Gly Asn Gln Asp Ser
        1410                1415                1420 ttc aca cct gtg gtg aac tct cta gac cca ccg tta ctg act cgc tac        4320
Phe Thr Pro Val Val Asn Ser Leu Asp Pro Pro Leu Leu Thr Arg Tyr
1425                1430                1435                1440 ctt cga att cac ccc cag agt tgg gtg cac cag att gcc ctg agg atg        4368
Leu Arg Ile His Pro Gln Ser Trp Val His Gln Ile Ala Leu Arg Met
                1445                1450                1455
```

```
gag gtt ctg ggc tgc gag gca cag gac ctc tac                          4401
Glu Val Leu Gly Cys Glu Ala Gln Asp Leu Tyr
        1460                1465
```

<210> SEQ ID NO 21
<211> LENGTH: 1467
<212> TYPE: PRT
<213> ORGANISM: Artificial Sequence
<220> FEATURE:
<223> OTHER INFORMATION: HP63/OL -- factor VIII variant

<400> SEQUENCE: 21

```
Met Gln Leu Glu Leu Ser Thr Cys Val Phe Leu Cys Leu Leu Pro Leu
 1               5                  10                  15

Gly Phe Ser Ala Ile Arg Arg Tyr Tyr Leu Gly Ala Val Glu Leu Ser
            20                  25                  30

Trp Asp Tyr Arg Gln Ser Glu Leu Leu Arg Glu Leu His Val Asp Thr
        35                  40                  45

Arg Phe Pro Ala Thr Ala Pro Gly Ala Leu Pro Leu Gly Pro Ser Val
    50                  55                  60

Leu Tyr Lys Lys Thr Val Phe Val Glu Phe Thr Asp Gln Leu Phe Ser
65                  70                  75                  80

Val Ala Arg Pro Arg Pro Pro Trp Met Gly Leu Leu Gly Pro Thr Ile
                85                  90                  95

Gln Ala Glu Val Tyr Asp Thr Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
    290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
            340                 345                 350
```

-continued

```
Pro Gln Leu Arg Arg Lys Ala Asp Glu Glu Asp Tyr Asp Asp Asn
        355                 360                 365

Leu Tyr Asp Ser Asp Met Asp Val Val Arg Leu Asp Gly Asp Val
        370                 375                 380

Ser Pro Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Val Arg Phe Met
                435                 440                 445

Ala Tyr Thr Asp Glu Thr Phe Lys Thr Arg Glu Ala Ile Gln His Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
        690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Ser Arg His Pro
                755                 760                 765

Ser Thr Arg Ser Gln Asn Pro Pro Val Leu Lys Arg His Gln Arg Glu
        770                 775                 780
```

```
Ile Thr Arg Thr Thr Leu Gln Ser Asp Gln Glu Ile Asp Tyr Asp
785                 790                 795                 800

Asp Thr Ile Ser Val Glu Met Lys Lys Glu Asp Phe Asp Ile Tyr Asp
                805                 810                 815

Glu Asp Glu Asn Gln Ser Pro Arg Ser Phe Gln Lys Arg Thr Arg His
            820                 825                 830

Tyr Phe Ile Ala Ala Val Glu Gln Leu Trp Asp Tyr Gly Met Ser Glu
        835                 840                 845

Ser Pro Arg Ala Leu Arg Asn Arg Ala Gln Asn Gly Glu Val Pro Arg
    850                 855                 860

Phe Lys Lys Val Val Phe Arg Glu Phe Ala Asp Gly Ser Phe Thr Gln
865                 870                 875                 880

Pro Ser Tyr Arg Gly Glu Leu Asn Lys His Leu Gly Leu Leu Gly Pro
                885                 890                 895

Tyr Ile Arg Ala Glu Val Glu Asp Asn Ile Met Val Thr Phe Lys Asn
            900                 905                 910

Gln Ala Ser Arg Pro Tyr Ser Phe Tyr Ser Ser Leu Ile Ser Tyr Pro
        915                 920                 925

Asp Asp Gln Glu Gln Gly Ala Glu Pro Arg Lys Asn Phe Val Lys Pro
    930                 935                 940

Asn Glu Thr Lys Thr Tyr Phe Trp Lys Val Gln His His Met Ala Pro
945                 950                 955                 960

Thr Glu Asp Glu Phe Asp Cys Lys Ala Trp Ala Tyr Phe Ser Asp Val
                965                 970                 975

Asp Leu Glu Lys Asp Val His Ser Gly Leu Ile Gly Pro Leu Leu Ile
            980                 985                 990

Cys Arg Ala Asn Thr Leu Asn Ala Ala His Gly Arg Gln Val Thr Val
        995                 1000                1005

Gln Glu Phe Ala Leu Phe Phe Thr Ile Phe Asp Glu Thr Lys Ser Trp
    1010                1015                1020

Tyr Phe Thr Glu Asn Val Glu Arg Asn Cys Arg Ala Pro Cys His Leu
1025                1030                1035                1040

Gln Met Glu Asp Pro Thr Leu Lys Glu Asn Tyr Arg Phe His Ala Ile
                1045                1050                1055

Asn Gly Tyr Val Met Asp Thr Leu Pro Gly Leu Val Met Ala Gln Asn
            1060                1065                1070

Gln Arg Ile Arg Trp Tyr Leu Leu Ser Met Gly Ser Asn Glu Asn Ile
        1075                1080                1085

His Ser Ile His Phe Ser Gly His Val Phe Ser Val Arg Lys Lys Glu
    1090                1095                1100

Glu Tyr Lys Met Ala Val Tyr Asn Leu Tyr Pro Gly Val Phe Glu Thr
1105                1110                1115                1120

Val Glu Met Leu Pro Ser Lys Val Gly Ile Trp Arg Asn Arg Cys Leu
                1125                1130                1135

Ile Gly Glu His Leu Gln Ala Gly Met Ser Thr Thr Phe Leu Val Tyr
            1140                1145                1150

Ser Lys Lys Cys Gln Thr Pro Leu Gly Met Ala Ser Gly His Ile Arg
        1155                1160                1165

Asp Phe Gln Ile Thr Ala Ser Gly Gln Tyr Gly Gln Trp Ala Pro Lys
    1170                1175                1180

Leu Ala Arg Leu His Tyr Ser Gly Ser Ile Asn Ala Trp Ser Thr Lys
1185                1190                1195                1200

Glu Pro Phe Ser Trp Ile Lys Val Asp Leu Leu Ala Pro Met Ile Ile
```

-continued

```
                  1205                1210                1215
His Gly Ile Lys Thr Gln Gly Ala Arg Gln Lys Phe Ser Ser Leu Tyr
                1220                1225                1230
Ile Ser Gln Phe Ile Ile Met Tyr Ser Leu Asp Gly Lys Lys Trp Gln
                1235                1240                1245
Thr Tyr Arg Gly Asn Ser Thr Gly Thr Leu Met Val Phe Phe Gly Asn
                1250                1255                1260
Val Asp Ser Ser Gly Ile Lys His Asn Ile Phe Asn Pro Pro Ile Ile
1265                1270                1275                1280
Ala Arg Tyr Ile Arg Leu His Pro Thr His Tyr Ser Ile Arg Ser Thr
                1285                1290                1295
Leu Arg Met Glu Leu Met Gly Cys Asp Leu Asn Ser Cys Ser Met Pro
                1300                1305                1310
Leu Gly Met Glu Ser Lys Ala Ile Ser Asp Ala Gln Ile Thr Ala Ser
                1315                1320                1325
Ser Tyr Phe Thr Asn Met Phe Ala Thr Trp Ser Pro Ser Lys Ala Arg
                1330                1335                1340
Leu His Leu Gln Gly Arg Ser Asn Ala Trp Arg Pro Gln Val Asn Asn
1345                1350                1355                1360
Pro Lys Glu Trp Leu Gln Val Asp Phe Gln Lys Thr Met Lys Val Thr
                1365                1370                1375
Gly Val Thr Thr Gln Gly Val Lys Ser Leu Leu Thr Ser Met Tyr Val
                1380                1385                1390
Lys Glu Phe Leu Ile Ser Ser Ser Gln Asp Gly His Gln Trp Thr Leu
                1395                1400                1405
Phe Phe Gln Asn Gly Lys Val Lys Val Phe Gln Gly Asn Gln Asp Ser
     1410                1415                1420
Phe Thr Pro Val Val Asn Ser Leu Asp Pro Pro Leu Leu Thr Arg Tyr
1425                1430                1435                1440
Leu Arg Ile His Pro Gln Ser Trp Val His Gln Ile Ala Leu Arg Met
                1445                1450                1455
Glu Val Leu Gly Cys Glu Ala Gln Asp Leu Tyr
                1460                1465
```